US009556121B2

(12) United States Patent
Greul et al.

(10) Patent No.: US 9,556,121 B2
(45) Date of Patent: Jan. 31, 2017

(54) PYRIDYLOXYALKYL CARBOXAMIDES AND USE THEREOF AS ENDOPARASITICIDES AND NEMATICIDES

(71) Applicant: BAYER CROPSCIENCE AG, Monheim (DE)

(72) Inventors: Joerg Nico Greul, Leverkusen (DE); Hans-Georg Schwarz, Dorsten (DE); Bernd Alig, Koenigswinter (DE); Angela Becker, Duesseldorf (DE); Daniela Portz, Vettweiss (DE); Kerstin Ilg, Cologne (DE); Ulrich Goergens, Ratingen (DE); Claudia Welz, Duesseldorf (DE)

(73) Assignee: BAYER CROPSCIENCE AG, Monheim (DE)

( * ) Notice: Subject to any disclaimer, the term of this patent is extended or adjusted under 35 U.S.C. 154(b) by 0 days.

(21) Appl. No.: 14/441,554

(22) PCT Filed: Nov. 8, 2013

(86) PCT No.: PCT/EP2013/073424
§ 371 (c)(1),
(2) Date: May 8, 2015

(87) PCT Pub. No.: WO2014/076015
PCT Pub. Date: May 22, 2014

(65) Prior Publication Data
US 2015/0291524 A1     Oct. 15, 2015

(30) Foreign Application Priority Data
Nov. 13, 2012   (EP) .................................... 12192446

(51) Int. Cl.
| C07D 409/12 | (2006.01) |
| C07D 213/84 | (2006.01) |
| C07D 213/64 | (2006.01) |
| A01N 43/40 | (2006.01) |
| C07D 213/70 | (2006.01) |
| C07D 405/12 | (2006.01) |
| C07D 401/12 | (2006.01) |
| A01N 43/48 | (2006.01) |
| A01N 43/50 | (2006.01) |
| A01N 43/56 | (2006.01) |

(52) U.S. Cl.
CPC ............ C07D 213/64 (2013.01); A01N 43/40 (2013.01); A01N 43/48 (2013.01); A01N 43/50 (2013.01); A01N 43/56 (2013.01); C07D 213/70 (2013.01); C07D 213/84 (2013.01); C07D 401/12 (2013.01); C07D 405/12 (2013.01); C07D 409/12 (2013.01)

(58) Field of Classification Search
CPC ... C07D 213/64; C07D 213/70; C07D 213/84; C07D 401/12; C07D 405/12; C07D 409/12; A01N 43/40; A01N 43/48; A01N 43/50; A01N 43/56

USPC ......................................................... 546/261
See application file for complete search history.

(56) References Cited

U.S. PATENT DOCUMENTS

| 3,535,328 A | * | 10/1970 | Zielinski | ................ A01N 57/24 504/195 |
| 4,579,856 A | * | 4/1986 | Chan | ..................... A01N 43/40 514/242 |
| 6,277,791 B1 | | 8/2001 | Assmann et al. | |
| 6,372,692 B1 | | 4/2002 | Assmann et al. | |
| 6,642,181 B2 | | 11/2003 | Assmann et al. | |
| 6,875,783 B2 | | 4/2005 | Assmann et al. | |
| 7,157,481 B2 | | 1/2007 | Assmann et al. | |
| 7,560,567 B2 | | 7/2009 | Coqueron et al. | |
| 7,572,818 B2 | | 8/2009 | Mansfield et al. | |
| 7,632,865 B2 | * | 12/2009 | Kato | ..................... C07C 233/66 514/599 |
| 7,696,355 B2 | | 4/2010 | Assmann et al. | |
| 7,723,363 B2 | | 5/2010 | Mansfield et al. | |
| 7,754,741 B2 | | 7/2010 | Mansfield et al. | |
| 7,825,068 B2 | | 11/2010 | Mansfield et al. | |
| 7,888,289 B2 | | 2/2011 | Mansfield et al. | |
| 7,951,973 B2 | | 5/2011 | Mansfield et al. | |
| 8,283,349 B2 | | 10/2012 | Coqueron et al. | |
| 8,314,269 B2 | | 11/2012 | Mansfield et al. | |
| 8,318,777 B2 | | 11/2012 | Coqueron et al. | |

(Continued)

FOREIGN PATENT DOCUMENTS

| DE | 10307845 A1 | 9/2004 |
| EP | 1574511 A1 | 9/2005 |

(Continued)

OTHER PUBLICATIONS

Molyneux; Advances in Parasitology 2006, 61, 1-45.*

(Continued)

Primary Examiner — Noble Jarrell
Assistant Examiner — Daniel Carcanague
(74) Attorney, Agent, or Firm — McBee Moore Woodward Vanik IP LLC

(57) ABSTRACT

The present application relates to novel pyridyloxyalkylcarboxamides of the formula (I)

(I)

$(M^1)_k$ — pyridine — $O-L^2-L^3-N(Y)-C(=W)-Q$ with $M^2$ and to their use as endoparasiticides against endoparasites in animals or humans, and to their use as nematicides for controlling phytopathogenic nematodes, and furthermore to endoparasiticides and nematicides comprising pyridyloxyalkylcarboxamides.

11 Claims, No Drawings

(56) References Cited

U.S. PATENT DOCUMENTS

| | | | |
|---|---|---|---|
| 8,999,956 B2 | 4/2015 | Benting et al. | |
| 2006/0052366 A1* | 3/2006 | Mansfield | A01N 43/56 514/217.04 |
| 2006/0173022 A1* | 8/2006 | Schaper | A01N 43/40 514/256 |
| 2006/0246102 A1 | 11/2006 | Mansfield | |
| 2007/0099965 A1* | 5/2007 | Coqueron | A01N 43/40 514/344 |
| 2010/0048647 A1* | 2/2010 | Suwa | A01N 43/40 514/357 |
| 2010/0249193 A1* | 9/2010 | Andersch | A01N 43/40 514/341 |
| 2010/0292239 A1* | 11/2010 | Stierli | C07D 207/34 514/249 |
| 2011/0136831 A1* | 6/2011 | Oda | A01N 37/18 514/255.06 |
| 2014/0088157 A1* | 3/2014 | Kita | A61K 31/166 514/346 |

FOREIGN PATENT DOCUMENTS

| | | |
|---|---|---|
| EP | 1997800 A1 | 12/2008 |
| EP | 2132987 A1 | 12/2009 |
| WO | 9924413 A2 | 5/1999 |
| WO | 0160783 A1 | 8/2001 |
| WO | 2004016088 A2 | 2/2004 |
| WO | 2004074280 A1 | 9/2004 |
| WO | 2005014545 A2 | 2/2005 |
| WO | 2005058828 A1 | 6/2005 |
| WO | 2005058833 A1 | 6/2005 |
| WO | 2005085238 A1 | 9/2005 |
| WO | 2006108791 A | 10/2006 |
| WO | 2006108792 A1 | 10/2006 |
| WO | 2007060162 A1 | 5/2007 |
| WO | 2007060164 A1 | 5/2007 |
| WO | 2007060166 A1 | 5/2007 |
| WO | 2007108483 A | 9/2007 |
| WO | 2008101976 A1 | 8/2008 |
| WO | 2008126922 A | 10/2008 |
| WO | 2008148570 A1 | 12/2008 |
| WO | 2009012998 A1 | 1/2009 |
| WO | 2010063700 A2 | 6/2010 |
| WO | 2011151370 A1 | 12/2011 |
| WO | WO2012038480 * | 3/2012 |
| WO | 2012118139 A | 9/2012 |
| WO | WO2012118139 * | 9/2012 |

OTHER PUBLICATIONS

Fivelman; "Antiprotozoan Drugs" In: Encyclopedia of Life Sciences (ELS). 2009, John Wiley & Sons, Ltd: Chichester, pp. 1-13.*
Chemical Abstracts STN Database Records for 45 resistry numbers entered into the Registry database by Oct. 29 2013.*
National Center for Biotechnology Information. PubChem Compound Database; CID=20242055, Create Date Dec. 5, 2007.*
National Center for Biotechnology Information. PubChem Compound Database; CID=23152112, Create Date Dec. 5, 2007.*
National Center for Biotechnology Information. PubChem Compound Database; CID=23152016, Create Date Dec. 5, 2007.*
National Center for Biotechnology Information. PubChem Compound Database; CID=23151878, Create Date Dec. 5, 2007.*
Veloukas; Pest Manag Sci 2012, 68, 858-864.*
International Search Report from corresponding PCT/EP2013/073424, mailed Dec. 5, 2013.

* cited by examiner

PYRIDYLOXYALKYL CARBOXAMIDES AND USE THEREOF AS ENDOPARASITICIDES AND NEMATICIDES

CROSS REFERENCE TO RELATED APPLICATIONS

This application is a §371 National Stage Application of PCT/EP2013/073424, filed 8 Nov. 2013, which claims priority to EP 12192446.8, filed 13 Nov. 2012.

BACKGROUND

Field of the Invention

The present application relates to novel pyridyloxyalkylcarboxamides and to their use as endoparasiticides against endoparasites in animals or humans, and to their use as nematicides for controlling phytopathogenic nematodes, and furthermore to endoparasiticides and nematicides comprising pyridyloxyalkylcarboxamides.

Description of Related Art

In the field of veterinary medicine, the occurrence of resistances against all commercially available anthelmintics is an increasing problem which requires endoparasiticides having novel molecular mechanisms of action. Such compounds should exhibit excellent efficacy against a broad spectrum of helminths and nematodes and at the same time not cause any toxic effects in the animals treated.

In the field of crop protection, too, nematodes may cause considerable yield losses, and they are therefore also controlled with active chemical compounds having nematicidal activity. To this end, suitable active compounds should have high activity and a broad spectrum of action against various species of nematodes, and at the same time be toxicologically safe for non-target organisms.

WO-A 2001/060783 claims certain phenacylbenzamides for oral use as anthelmintics in veterinary medicine.

Isothiazolecarboxamides are known from WO-A 1999/24413, heterocyclylethylcarboxamide derivatives from WO-A 2006/108791, heterocyclylethylbenzamide derivatives from WO-A 2006/108792, N-(1-methyl-2-phenylethyl)benzamides from WO-A 2007/060162, N-(1-methyl-2-phenylethyl)carboxamides from WO-A 2007/060164, N-phenethylcarboxamide derivatives from WO-A 2007/060166, N-(3-phenylpropyl)carboxamides from WO-A 2008/101976, pyrazolecarboxamides from WO-A 2008/148570 and WO-A 2010/063700, pyrazinylcarboxamides from WO-A 2011/128989, various 2-pyridylethylcarboxamide derivatives from WO-A 2004/016088, WO-A 2004/074280, WO-A 2005/014545, WO-A 2005/058828, WO-A 2005/058833 and WO-A 2005/085238 and pyridyloxyalkylcarboxamides from WO-A 2009/012998 as agrochemical fungicides. WO-A 2011/151370 describes N-[(het)arylalkyl)]pyrazolecarboxamides or -thiocarboxamides as fungicides. Furthermore, WO-A 2007/108483/EP-A 1 997800 describes N-2-(hetero)arylethylcarboxamide derivatives as fungicides and nematicides. WO-A 2008/126922 explicitly claims the use of 2-pyridylethylcarboxamide derivatives for use against nematodes in crop cultivation. WO-A 2012/118139 also embraces phenyl(oxy)ethylcarboxamides and 2-pyridyl(oxy)ethylcarboxamides as endoparasiticides; however, these are only embodied as benzamides. DE 103 07 845 A1 discloses heterocyclic amides as pesticides, the compounds 1009 and 1011 being part of the class of compounds disclosed herein and therefore excluded from the scope of the invention.

Further nematicidal and/or anthelmintic patent applications were published after the priority date of the present application: WO-A 2013/064460 and WO-A 2013/064461 describe pyridylethylcarboxamides and their use as nematicides. WO-A 2013/076230 also claims phenyloxyethylcarboxamides and their use as medicaments for controlling endoparasites in animals or humans.

The use of the pyridyloxyalkylcarboxamides of the prior art as endoparasiticides in the field of veterinary medicine and as nematicides in crop cultivation has hitherto not been described.

In the literature, there are indications that by incorporating oxygen in the vicinity of the heteroaromatic system it may be possible to overcome the disadvantages of the metabolic instability of a benzylic $CH_2$ group. Accordingly, the present application describes novel pyridyloxyalkylcarboxamides and their use as endoparasiticides against endoparasites in animals or humans, and their use as nematicides for controlling phytopathogenic nematodes, and furthermore endoparasiticides and nematicides comprising pyridyloxyalkylcarboxamides.

SUMMARY

The present invention now provides novel compounds of the formula (I)

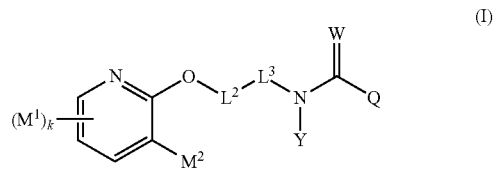

in which

Q represents the structural elements below, where n for each Q is in each case as defined below:

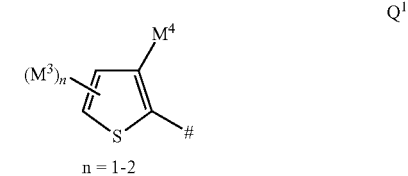

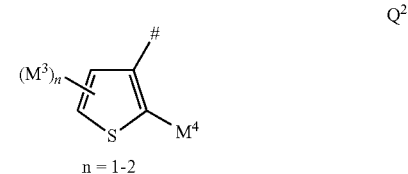

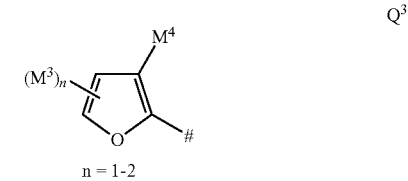

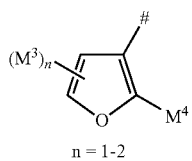
n = 1-2

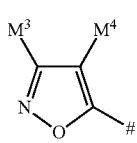

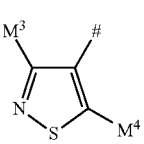

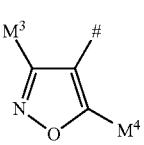

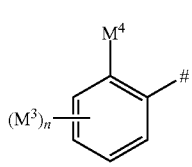
n = 1-4

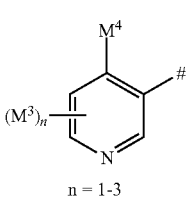
n = 1-3

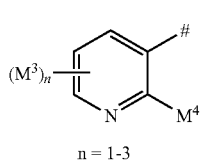
n = 1-3

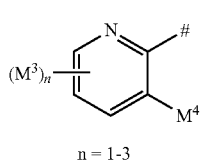
n = 1-3

Q⁴

Q⁵

Q⁶

Q⁷

Q⁸

Q⁹

Q¹⁰

Q¹¹

Q¹²

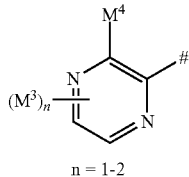
n = 1-2

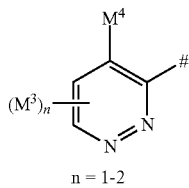
n = 1-2

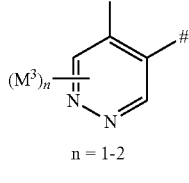
n = 1-2

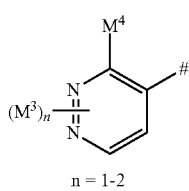
n = 1-2

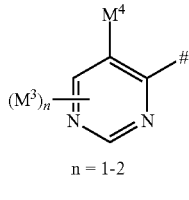
n = 1-2

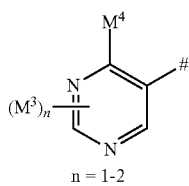
n = 1-2

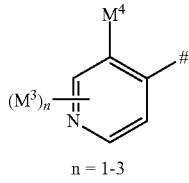
n = 1-3

Q¹³

Q¹⁴

Q¹⁵

Q¹⁶

Q¹⁷

Q¹⁸

Q¹⁹

Y represents hydrogen or represents optionally mono- or poly-$M^2$-substituted ($C_1$-$C_{10}$)-alkyl, ($C_2$-$C_{10}$)-alkenyl, ($C_2$-$C_{10}$)-alkynyl, ($C_1$-$C_{10}$)-haloalkyl, ($C_2$-$C_{10}$)-haloalkenyl, ($C_2$-$C_{10}$)-haloalkynyl, ($C_1$-$C_{10}$)-alkoxy, ($C_2$-$C_{10}$)-alkenyloxy, ($C_3$-$C_{10}$)-alkynyloxy, ($C_3$-$C_{14}$)-cycloalkyl-($C_1$-$C_{10}$)-alkyl or represents an optionally mono- or poly-$M^2$-substituted 3- to 14-membered cyclic group;

W represents oxygen or sulphur;

$L^2$ represents —C($R^{21}$, $R^{22}$)—;

$L^3$ represents —C($R^{31}$, $R^{32}$)—;

$M^1$, $M^2$ and $M^3$ each independently of one another represent hydrogen, halogen, cyano, nitro, OH, ($C_1$-$C_{10}$)-alkyl, ($C_1$-$C_{10}$)-haloalkyl, ($C_1$-$C_{10}$)-alkoxy, ($C_1$-$C_{10}$)-haloalkoxy, ($C_1$-$C_{10}$)-alkylthio, ($C_1$-$C_{10}$)-haloalkylthio, ($C_1$-$C_{10}$)-alkylsulphonyl, ($C_1$-$C_{10}$)-haloalkylsulphonyl, ($C_1$-$C_{10}$)-alkylsulphanyl, ($C_1$-$C_{10}$)-haloalkylsulphanyl or (3- to 14-membered cyclic group)-O—;

$M^4$ represents hydrogen, halogen, cyano, nitro, OH, ($C_1$-$C_{10}$)-alkyl, ($C_1$-$C_{10}$)-haloalkyl, ($C_1$-$C_{10}$)-alkoxy, ($C_1$-$C_{10}$)-haloalkoxy, ($C_1$-$C_{10}$)-alkylthio, ($C_1$-$C_{10}$)-haloalkylthio, ($C_1$-$C_{10}$)-alkylsulphonyl, ($C_1$-$C_{10}$)-haloalkylsulphonyl, ($C_1$-$C_{10}$)-alkylsulphanyl, ($C_1$-$C_{10}$)-haloalkylsulphanyl or (3- to 14-membered cyclic group)-O—;

k represents 1, 2 or 3;

$R^{21}$, $R^{22}$ each independently of one another represent hydrogen, halogen or optionally mono- or poly-$M^2$-substituted ($C_1$-$C_{10}$)-alkyl, ($C_2$-$C_{10}$)-alkenyl, ($C_2$-$C_{10}$)-alkynyl, ($C_1$-$C_{10}$)-haloalkyl, ($C_2$-$C_{10}$)-haloalkenyl, ($C_2$-$C_{10}$)-haloalkynyl, ($C_1$-$C_{10}$)-alkoxy, ($C_1$-$C_{10}$)-haloalkoxy, ($C_2$-$C_{10}$)-alkenyloxy, ($C_3$-$C_{10}$)-alkynyloxy, ($C_3$-$C_{14}$)-cycloalkyl-($C_1$-$C_{10}$)-alkyl or represent an optionally mono- or poly-$M^2$-substituted 3- to 14-membered cyclic group;

$R^{21}$, $R^{22}$ together represent an optionally mono- or poly-$M^2$-substituted spiro-attached 3- to 14-membered carbo- or 3- to 10-membered heterocyclic group;

$R^{31}$, $R^{32}$ each independently of one another represent hydrogen, halogen or optionally mono- or poly-$M^2$-substituted ($C_1$-$C_{10}$)-alkyl, ($C_2$-$C_{10}$)-alkenyl, ($C_2$-$C_{10}$)-alkynyl, ($C_1$-$C_{10}$)-haloalkyl, ($C_2$-$C_{10}$)-haloalkenyl, ($C_2$-$C_{10}$)-haloalkynyl, ($C_3$-$C_{14}$)-cycloalkyl-($C_1$-$C_{10}$)-alkyl or represent an optionally mono- or poly-$M^2$-substituted 3- to 14-membered cyclic group;

$R^{31}$, $R^{32}$ together represent an optionally mono- or poly-$M^5$-substituted spiro-attached 3- to 14-membered carbo- or 3- to 10-membered heterocyclic group;

$M^5$ in each case independently of the others represents halogen, formyl, cyano, nitro, ($C_1$-$C_{10}$)-alkyl, ($C_1$-$C_{10}$)-haloalkyl, ($C_2$-$C_{10}$)-alkenyl, ($C_2$-$C_{10}$)-haloalkenyl, ($C_2$-$C_{10}$)-alkynyl, ($C_2$-$C_{10}$)-haloalkynyl, ($C_1$-$C_{10}$)-alkoxy, ($C_1$-$C_{10}$)-haloalkoxy, ($C_2$-$C_{10}$)-alkenyloxy, ($C_2$-$C_{10}$)-haloalkenyloxy, ($C_3$-$C_{10}$)-alkynyloxy, ($C_3$-$C_{10}$)-haloalkynyloxy, ($C_1$-$C_{10}$)-alkylthio, ($C_1$-$C_{10}$)-haloalkylthio, ($C_2$-$C_{10}$)-alkenylthio, ($C_2$-$C_{10}$)-haloalkenylthio, ($C_3$-$C_{10}$)-alkynylthio, ($C_3$-$C_{10}$)-haloalkynylthio, ($C_1$-$C_{10}$)-alkylsulphonyl, ($C_1$-$C_{10}$)-haloalkylsulphonyl, ($C_2$-$C_{10}$)-alkenylsulphonyl, ($C_2$-$C_{10}$)-haloalkenylsulphonyl, ($C_3$-$C_{10}$)-alkynylsulphonyl, ($C_3$-$C_{10}$)-haloalkynylsulphonyl, ($C_1$-$C_{10}$)-alkylsulphanyl, ($C_1$-$C_{10}$)-haloalkylsulphanyl, ($C_2$-$C_{10}$)-alkenylsulphanyl, ($C_2$-$C_{10}$-haloalkenylsulphanyl, ($C_3$-$C_{10}$)-alkynylsulphanyl, ($C_3$-$C_{10}$)-haloalkynylsulphanyl, ($C_1$-$C_{10}$)-alkylcarbonyl, ($C_1$-$C_{10}$)-haloalkylcarbonyl, ($C_2$-$C_{10}$)-alkenylcarbonyl, ($C_2$-$C_{10}$)-haloalkenylcarbonyl, ($C_2$-$C_{10}$)-alkynylcarbonyl, ($C_2$-$C_{10}$)-haloalkynylcarbonyl, ($C_1$-$C_{10}$)-alkoxycarbonyl, ($C_1$-$C_{10}$)-haloalkoxycarbonyl, ($C_2$-$C_{10}$)-alkenyloxycarbonyl, ($C_2$-$C_{10}$)-haloalkenyloxycarbonyl, ($C_3$-$C_{10}$)-alkynyloxycarbonyl, ($C_3$-$C_{10}$)-haloalkynyloxycarbonyl, ($C_1$-$C_{10}$)-alkylcarbonyloxy, ($C_1$-$C_{10}$)-haloalkylcazarbonyloxy, ($C_2$-$C_{10}$)-alkenylcarbonyloxy, ($C_2$-$C_{10}$)-haloalkenylcarbonyloxy, ($C_2$-$C_{10}$)-alkynylcarbonyloxy, ($C_2$-$C_{10}$)-haloalkynylcarbonyloxy, a 3- to 14-membered cyclic group;

and salts, N-oxides and tautomeric forms of the compounds of the formula (I), except for the compounds
N-[2-(pyridin-2-yloxy)ethyl]-4-(trifluoromethyl)nicotinamide:

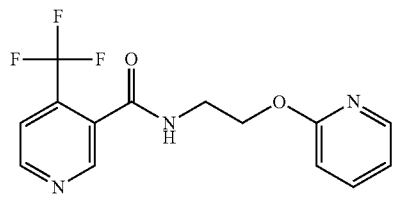

and
4-(trifluoromethyl)-N-(2-{[5-(trifluoromethyl)pyridin-2-yl]oxy}ethyl)nicotinamide:

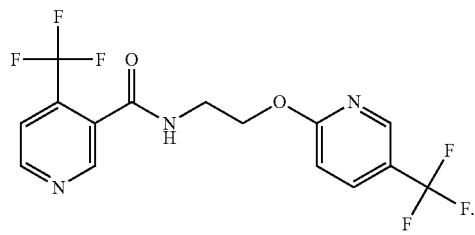 [SMILES: O=C(NCCOc1ccc(C(F)(F)F)cn1)c1cnccc1C(F)(F)F]

DETAILED DESCRIPTION OF A PREFERRED EMBODIMENT

A further embodiment provides novel compounds of the formula (I)

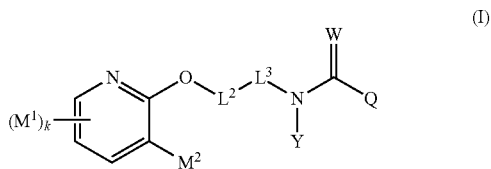

in which
Q represents the structural elements below, where n for each Q is in each case as defined below:

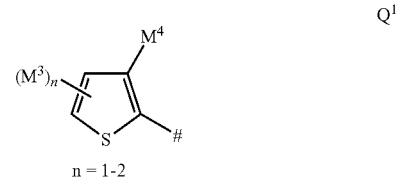

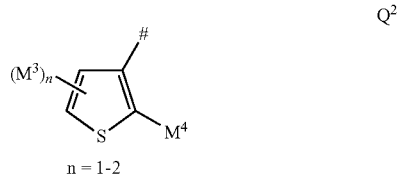

-continued
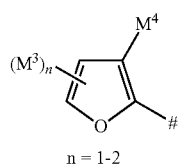
n = 1-2
Q³
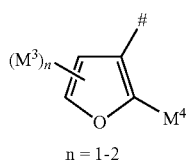
n = 1-2
Q⁴
Q⁵
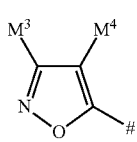
Q⁶
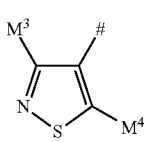
Q⁷
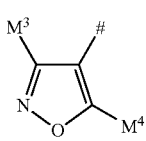
Q⁸
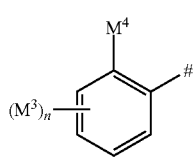
n = 1-4
Q⁹
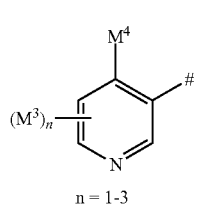
n = 1-3
Q¹⁰
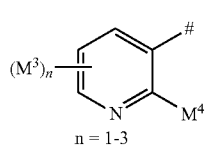
n = 1-3
Q¹¹
-continued
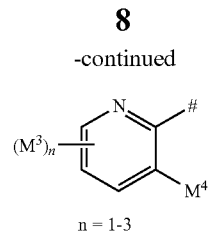
n = 1-3
Q¹²
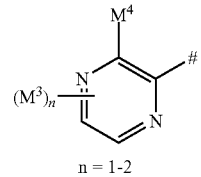
n = 1-2
Q¹³
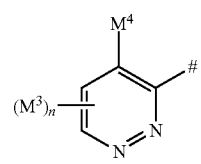
n = 1-2
Q¹⁴
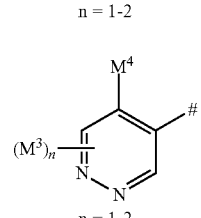
n = 1-2
Q¹⁵
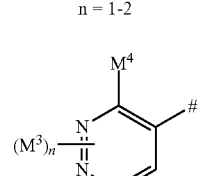
n = 1-2
Q¹⁶
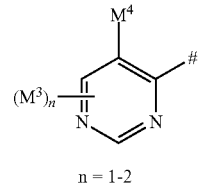
n = 1-2
Q¹⁷
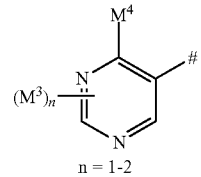
n = 1-2
Q¹⁸
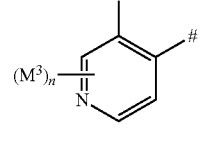
n = 1-3
Q¹⁹
Y represents hydrogen or represents optionally mono- or poly-M²-substituted ($C_1$-$C_{10}$)-alkyl, ($C_2$-$C_{10}$)-alkenyl, ($C_2$-$C_{10}$)-alkynyl, ($C_1$-$C_{10}$)-haloalkyl, ($C_2$-$C_{10}$)-haloalkenyl, ($C_2$-$C_{10}$)-haloalkynyl, ($C_1$-$C_{10}$)-alkoxy, ($C_2$-$C_{10}$)-alkenyloxy, ($C_3$-$C_{10}$)-alkynyloxy, ($C_3$-$C_{14}$)-cycloalkyl-($C_1$-$C_{10}$)-alkyl or represents an optionally mono- or poly-$M^2$-substituted 3- to 14-membered cyclic group;

W represents oxygen or sulphur;

$L^2$ represents —C($R^{21}$, $R^{22}$)—;

$L^3$ represents —C($R^{31}$, $R^{32}$)—;

$M^1$, $M^2$ and $M^3$ each independently of one another represent hydrogen, halogen, cyano, nitro, OH, ($C_1$-$C_{10}$)-alkyl, ($C_1$-$C_{10}$)-haloalkyl, ($C_1$-$C_{10}$)-alkoxy, ($C_1$-$C_{10}$)-haloalkoxy, ($C_1$-$C_{10}$)-alkylthio, ($C_1$-$C_{10}$)-haloalkylthio, ($C_1$-$C_{10}$)-alkylsulphonyl, ($C_1$-$C_{10}$)-haloalkylsulphonyl, ($C_1$-$C_{10}$)-alkylsulphanyl, ($C_1$-$C_{10}$)-haloalkylsulphanyl or (3- to 14-membered cyclic group)-O—;

$M^4$ represents hydrogen, halogen, cyano, nitro, OH, ($C_1$-$C_{10}$)-alkyl, ($C_1$-$C_{10}$)-haloalkyl, ($C_1$-$C_{10}$)-alkoxy, ($C_1$-$C_{10}$)-haloalkoxy, ($C_1$-$C_{10}$)-alkylthio, ($C_1$-$C_{10}$)-haloalkylthio, ($C_1$-$C_{10}$)-alkylsulphonyl, ($C_1$-$C_{10}$)-haloalkylsulphonyl, ($C_1$-$C_{10}$)-alkylsulphanyl, ($C_1$-$C_{10}$)-haloalkylsulphanyl or (3- to 14-membered cyclic group)-O—;

k represents 1, 2 or 3;

$R^{21}$, $R^{22}$ each independently of one another represent hydrogen, halogen or optionally mono- or poly-$M^2$-substituted ($C_1$-$C_{10}$)-alkyl, ($C_2$-$C_{10}$)-alkenyl, ($C_2$-$C_{10}$)-alkynyl, ($C_1$-$C_{10}$)-haloalkyl, ($C_2$-$C_{10}$)-haloalkenyl, ($C_2$-$C_{10}$)-haloalkynyl, ($C_1$-$C_{10}$)-alkoxy, ($C_1$-$C_{10}$)-haloalkoxy, ($C_2$-$C_{10}$)-alkenyloxy, ($C_3$-$C_{10}$)-alkynyloxy, ($C_3$-$C_{14}$)-cycloalkyl-($C_1$-$C_{10}$)-alkyl or represent an optionally mono- or poly-$M^2$-substituted 3- to 14-membered cyclic group;

$R^{21}$, $R^{22}$ together represent an optionally mono- or poly-$M^2$-substituted spiro-attached 3- to 14-membered carbo- or 3- to 10-membered heterocyclic group;

$R^{31}$, $R^{32}$ each independently of one another represent hydrogen, halogen or optionally mono- or poly-$M^2$-substituted ($C_1$-$C_{10}$)-alkyl, ($C_2$-$C_{10}$)-alkenyl, ($C_2$-$C_{10}$)-alkynyl, ($C_1$-$C_{10}$)-haloalkyl, ($C_2$-$C_{10}$)-haloalkenyl, ($C_2$-$C_{10}$)-haloalkynyl, ($C_3$-$C_{14}$)-cycloalkyl-($C_1$-$C_{10}$)-alkyl or represent an optionally mono- or poly-$M^2$-substituted 3- to 14-membered cyclic group;

$R^{31}$, $R^{32}$ together represent an optionally mono- or poly-$M^5$-substituted spiro-attached 3- to 14-membered carbo- or 3- to 10-membered heterocyclic group;

$M^5$ in each case independently of the others represents halogen, formyl, cyano, nitro, ($C_1$-$C_{10}$)-alkyl, ($C_1$-$C_{10}$)-haloalkyl, ($C_2$-$C_{10}$)-alkenyl, ($C_2$-$C_{10}$)-haloalkenyl, ($C_2$-$C_{10}$)-alkynyl, ($C_2$-$C_{10}$)-haloalkynyl, ($C_1$-$C_{10}$)-alkoxy, ($C_1$-$C_{10}$)-haloalkoxy, ($C_2$-$C_{10}$)-alkenyloxy, ($C_2$-$C_{10}$)-haloalkenyloxy, ($C_3$-$C_{10}$)-alkynyloxy, ($C_3$-$C_{10}$)-haloalkynyloxy, ($C_1$-$C_{10}$)-alkylthio, ($C_1$-$C_{10}$)-haloalkylthio, ($C_2$-$C_{10}$-alkenylthio, ($C_2$-$C_{10}$)-haloalkenylthio, ($C_3$-$C_{10}$)-alkynylthio, ($C_3$-$C_{10}$)-haloalkynylthio, ($C_1$-$C_{10}$)-alkylsulphonyl, ($C_1$-$C_{10}$)-haloalkylsulphonyl, ($C_2$-$C_{10}$)-alkenylsulphonyl, ($C_2$-$C_{10}$)-haloalkenylsulphonyl, ($C_3$-$C_{10}$)-alkynylsulphonyl, ($C_3$-$C_{10}$)-haloalkynylsulphonyl, ($C_1$-$C_{10}$)-alkylsulphanyl, ($C_1$-$C_{10}$)-haloalkylsulphanyl, ($C_2$-$C_{10}$)-alkenylsulphanyl, ($C_2$-$C_{10}$)-haloalkenylsulphanyl, ($C_3$-$C_{10}$)-alkynylsulphanyl, ($C_3$-$C_{10}$)-haloalkynylsulphanyl, ($C_1$-$C_{10}$)-alkylcarbonyl, ($C_1$-$C_{10}$)-haloalkylcarbonyl, ($C_2$-$C_{10}$)-alkenylcarbonyl, ($C_2$-$C_{10}$-haloalkenylcarbonyl, ($C_2$-$C_{10}$)-alkynylcarbonyl, ($C_2$-$C_{10}$)-haloalkynylcarbonyl, ($C_1$-$C_{10}$)-alkoxycarbonyl, ($C_1$-$C_{10}$)-haloalkoxycarbonyl, ($C_2$-$C_{10}$)-alkenyloxycarbonyl, ($C_2$-$C_{10}$)-haloalkenyloxycarbonyl, ($C_3$-$C_{10}$)-alkynyloxycarbonyl, ($C_3$-$C_{10}$)-haloalkynyloxycarbonyl, ($C_1$-$C_{10}$)-alkylcarbonyloxy, ($C_1$-$C_{10}$)-haloalkylcarbonyloxy, ($C_2$-$C_{10}$)-alkenylcarbonyloxy, ($C_2$-$C_{10}$)-haloalkenylcarbonyloxy, ($C_2$-$C_{10}$)-alkynylcarbonyloxy, ($C_2$-$C_{10}$)-haloalkynylcarbonyloxy, a 3- to 14-membered cyclic group;

and salts, N-oxides and tautomeric forms of the compounds of the formula (I).

The novel compounds according to formula (I) have endoparasiticidal action in animals and humans and can be used as medicaments in animals or humans, in particular against endoparasites.

The novel compounds according to formula (I) have nematicidal action against phytopathogenic nematodes and can be used for controlling these nematodes in agriculture and forestry.

The compounds of the formula (I) may, where appropriate, depending on the nature of the substituents, be in the form of geometric and/or optically active isomers or corresponding isomer mixtures of varying composition. The invention relates both to the pure isomers and to the isomer mixtures.

The compounds according to the invention can also be present as metal complexes.

DEFINITIONS

A nematicide in crop protection, as described herein, means that the active compound is capable of controlling nematodes.

"Controlling nematodes" for the purpose of use of the present invention means killing the nematodes or preventing their development or growth. Here, in a comparison the efficacy of the compounds with respect to mortalities, gall formation, cyst formation, nematode density per volume of soil, nematode density per root, number of nematode eggs per soil volume, mobility of the nematodes between a plant or plant part treated with the compound according to the invention or the treated soil and an untreated plant or plant part or the untreated soil (100%). Here, the reduction achieved is preferably 25-50% in comparison to an untreated plant, plant part or the untreated soil, particularly preferably 40-79% and very particularly preferably the complete kill or the complete prevention of development and growth of the nematodes by a reduction of 70 to 100%. The control of nematodes as described herein also comprises the control of proliferation of the nematodes (development of cysts and/or eggs). Active compounds as described herein can also be used to keep the organisms healthy, and they can be employed curatively, preventatively or systemically for the control of nematodes.

The person skilled in the art knows methods for determining mortalities, gall formation, cyst formation, nematode density per volume of soil, nematode density per root, number of nematode eggs per volume of soil, mobility of the nematodes.

The "organism" described above can be a plant. The use of an active compound as described herein may keep the plant healthy and also comprises a reduction of the damage caused by nematodes and an increase of the harvest yield.

The term animals does not include humans.

The term "mono- or poly-" means preferably mono- to hexa-, particularly preferably mono- to tetra-, very particularly preferably mono- to tri- and especially preferably mono- or di-.

The person skilled in the art is aware that the expressions "a" or "an" as used in the present application may, depending on the situation, mean "one (1)", "one (1) or more" or "at least one (1)".

For all ring systems hitherto described, adjacent atoms must not be —O—O— or —O—S—.

For the sake of simplicity, structures having a variable number of possible carbon atoms (C atoms) are referred to as $C_1$-$C_{10}$-structures ($C_1$-$C_{10}$) in the present application. Example: an alkyl group of 1 to 10 carbon atoms corresponds to ($C_1$-$C_{10}$)-alkyl. Ring structures of carbon atoms and heteroatoms are referred to as "3- to 14-membered" structures.

If a collective term for a substituent, for example ($C_1$-$C_{10}$)-alkyl, is at the end of a composite substituent such as, for example, ($C_3$-$C_{14}$)-cycloalkyl-($C_1$-$C_{10}$)-alkyl, the component at the end of the composite substituent, for example the ($C_1$-$C_{10}$)-alkyl, may be mono- or polysubstituted by identical or different substituents and independently of the substituent at the beginning, for example ($C_3$-$C_{14}$)-cycloalkyl.

Unless defined differently, the definition for collective terms also applies to these collective terms in composite substituents. Example: The definition of ($C_1$-$C_{10}$)-alkyl also applies to ($C_1$-$C_{10}$)-alkyl as component of a composite substituent such as, for example, ($C_3$-$C_{14}$)-cycloalkyl-($C_1$-$C_{10}$)-alkyl.

It is obvious to the person skilled in the art that the examples given in the present application are not to be considered as limiting, but rather describe some embodiments in more detail.

In the definitions of the symbols given in the formulae above, collective terms were used which are generally representative of the following substituents:

Collective Terms

Halogen, unless defined otherwise: elements of the 7th main group; preference is given to fluorine, chlorine, bromine and iodine.

($C_1$-$C_{10}$)-Alkyl, unless defined differently elsewhere: saturated straight-chain or branched hydrocarbon radicals having preferably ($C_1$-$C_6$)-, particularly preferably ($C_1$-$C_4$)- carbon atoms. Examples: methyl, ethyl, isopropyl, n-propyl, 1-methylethyl, butyl, tert-butyl, etc.

($C_2$-$C_{10}$)-Alkenyl, unless defined differently elsewhere: unsaturated straight-chain or branched hydrocarbon radicals having a double bond. Preference is given to ($C_2$-$C_6$)- or ($C_2$-$C_4$)-alkenyl. Examples: ethenyl, 1-propenyl, 3-butenyl, etc.

($C_2$-$C_{10}$)-Alkynyl, unless defined differently elsewhere: unsaturated straight-chain or branched hydrocarbon radicals having a triple bond. Preference is given to ($C_2$-$C_6$)- or ($C_2$-$C_4$)-alkynyl. Examples: ethynyl, 1-propynyl, etc.

($C_1$-$C_{10}$)-Alkoxy (alkyl radical-O—), unless defined differently elsewhere: an alkyl radical which is attached to the skeleton via an oxygen atom (—O—). Preference is given to ($C_1$-$C_6$)- or ($C_1$-$C_4$)-alkoxy. Examples: methoxy, ethoxy, propoxy, 1-methylethoxy, etc.

Analogously, ($C_2$-$C_{10}$)-alkenyloxy and ($C_3$-$C_{10}$)-alkynyloxy, unless defined differently elsewhere, are alkenyl radicals and alkynyl radicals, respectively, which are attached to the skeleton via —O—. Preference is given to ($C_2$-$C_6$)- or ($C_2$-$C_4$)-alkenyloxy. Preference is given to ($C_3$-$C_6$)- or ($C_3$-$C_4$)-alkynyloxy.

($C_1$-$C_{10}$)-Alkylcarbonyl (alkyl radical-C(=O)—), unless defined differently elsewhere: preference is given to ($C_1$-$C_6$)- or ($C_1$-$C_4$)-alkylcarbonyl. Here, the number of the carbon atoms refers to the alkyl radical in the alkylcarbonyl group.

Analogously, ($C_2$-$C_{10}$)-alkenylcarbonyl and ($C_3$-$C_{10}$)-alkynylcarbonyl, unless defined differently elsewhere, are: alkenyl radicals and alkynyl radicals, respectively, which are attached to the skeleton via —C(=O)—. Preference is given to ($C_2$-$C_6$)- or ($C_2$-$C_4$)-alkenylcarbonyl. Preference is given to ($C_2$-$C_6$)- or ($C_2$-$C_4$)-alkynylcarbonyl.

($C_1$-$C_{10}$)-Alkoxycarbonyl (alkyl radical-O—C(=O)—), unless defined differently elsewhere: preference is given to ($C_1$-$C_6$)- or ($C_1$-$C_4$)-alkoxycarbonyl. Here, the number of the carbon atoms refers to the alkyl radical in the alkoxycarbonyl group.

Analogously, ($C_2$-$C_{10}$)-alkenyloxycarbonyl and ($C_3$-$C_{10}$)-alkynyloxycarbonyl, unless defined differently elsewhere, are: alkenyl radicals and alkynyl radicals, respectively, which are attached to the skeleton via —O—C(=O)—. Preference is given to ($C_2$-$C_6$)- or ($C_2$-$C_4$)-alkenyloxycarbonyl. Preference is given to ($C_3$-$C_6$)- or ($C_3$-$C_4$)-alkynyloxycarbonyl.

($C_1$-$C_{10}$)-Alkylcarbonyloxy (alkyl radical-C(=O)—O—), unless defined differently elsewhere: an alkyl radical which is attached to the skeleton via a carbonyloxy group (—C(=O)—O—) with the oxygen. Preference is given to ($C_1$-$C_6$)- or ($C_1$-$C_4$)-alkylcarbonyloxy.

Analogously, ($C_2$-$C_{10}$)-alkenylcarbonyloxy and ($C_2$-$C_{10}$)-alkynylcarbonyloxy, unless defined differently elsewhere, are: alkenyl radicals and alkynyl radicals, respectively, which are attached to the skeleton via (—C(=O)—O—). Preference is given to ($C_2$-$C_6$)- or ($C_2$-$C_4$)-alkenylcarbonyloxy. Preference is given to ($C_2$-$C_6$)- or ($C_2$-$C_4$)-alkynylcarbonyloxy.

($C_1$-$C_{10}$)-Alkylthio, unless defined differently elsewhere: an alkyl radical which is attached to the skeleton via —S—. Preference is given to ($C_1$-$C_6$)- or ($C_1$-$C_4$)-alkylthio.

Analogously, ($C_2$-$C_{10}$)-alkenylthio and ($C_3$-$C_{10}$)-alkynylthio, unless defined differently elsewhere, are: alkenyl radicals and alkynyl radicals, respectively, which are attached to the skeleton via —S—. Preference is given to ($C_2$-$C_6$)- or ($C_2$-$C_4$)-alkenylthio. Preference is given to ($C_3$-$C_6$)- or ($C_3$-$C_4$)-alkynylthio.

($C_1$-$C_{10}$)-Alkylsulphinyl, unless defined differently elsewhere: an alkyl radical which is attached to the skeleton via —S(=O)—. Preference is given to ($C_1$-$C_6$)- or ($C_1$-$C_4$)-alkylsulphinyl.

Analogously, ($C_2$-$C_{10}$)-alkenylsulphinyl and ($C_3$-$C_{10}$)-alkynylsulphinyl, unless defined differently elsewhere, are: alkenyl radicals and alkynyl radicals, respectively, which are attached to the skeleton via —S(=O)—. Preference is given to ($C_2$-$C_6$)- or ($C_2$-$C_4$)-alkenylsulphinyl. Preference is given to ($C_3$-$C_6$)- or ($C_3$-$C_4$)-alkynylsulphinyl.

($C_1$-$C_{10}$)-Alkylsulphonyl, unless defined differently elsewhere: an alkyl radical which is attached to the skeleton via —S(=O)$_2$—. Preference is given to ($C_1$-$C_6$)- or ($C_1$-$C_4$)-alkylsulphonyl.

Analogously, ($C_2$-$C_{10}$)-alkenylsulphonyl and ($C_3$-$C_{10}$)-alkynylsulphonyl, unless defined differently elsewhere, are: alkenyl radicals and alkynyl radicals, respectively, which are attached to the skeleton via —S(=O)$_2$—. Preference is given to ($C_2$-$C_6$)- or ($C_2$-$C_4$)-alkenylsulphonyl. Preference is given to ($C_3$-$C_6$)- or ($C_3$-$C_4$)-alkynylsulphonyl.

($C_1$-$C_{10}$)-Haloalkyl, ($C_2$-$C_{10}$)-haloalkenyl, ($C_2$-$C_{10}$)-haloalkynyl, ($C_1$-$C_{10}$)-haloalkoxy, ($C_2$-$C_{10}$)-haloalkenyloxy, ($C_3$-$C_{10}$)-haloalkynyloxy, ($C_1$-$C_{10}$)-haloalkylcarbonyl, ($C_2$-$C_{10}$)-haloalkenylcarbonyl, ($C_2$-$C_{10}$)-haloalkynylcarbonyl, ($C_1$-$C_{10}$)-haloalkoxycarbonyl, ($C_2$-$C_{10}$)-haloalkenyloxycarbonyl, ($C_3$-$C_{10}$)-haloalkynyloxycarbonyl, ($C_2$-$C_{10}$)-haloalkylcarbonyloxy, ($C_2$-$C_{10}$)-haloalkenylcarbonyloxy, ($C_2$-$C_{10}$)-haloalkynylcarbonyloxy, ($C_1$-$C_{10}$)-haloalkylthio, ($C_2$-

$C_{10}$)-haloalkenylthio, ($C_3$-$C_{10}$)-haloalkynylthio, ($C_1$-$C_{10}$)-haloalkylsulphinyl, ($C_2$-$C_{10}$)-haloalkenylsulphinyl, ($C_3$-$C_{10}$)-haloalkynylsulphinyl, ($C_1$-$C_{10}$-haloalkylsulphonyl, ($C_2$-$C_{10}$)-haloalkenylsulphonyl, ($C_3$-$C_{10}$)-haloalkynylsulphonyl are, unless defined differently, defined analogously to ($C_1$-$C_{10}$)-alkyl, ($C_2$-$C_{10}$)-alkenyl, ($C_2$-$C_{10}$)-alkynyl, ($C_1$-$C_{10}$)-alkoxy, ($C_2$-$C_{10}$)-alkenyloxy, ($C_3$-$C_{10}$)-alkynyloxy, ($C_1$-$C_{10}$)-alkylcarbonyl, ($C_2$-$C_{10}$)-alkenylcarbonyl, ($C_2$-$C_{10}$-alkynylcarbonyl, ($C_1$-$C_{10}$)-alkoxycarbonyl, ($C_2$-$C_{10}$)-alkenyloxycarbonyl, ($C_3$-$C_{10}$)-alkynyloxycarbonyl, ($C_1$-$C_{10}$)-alkylcarbonyloxy, ($C_2$-$C_{10}$)-alkenylcarbonyloxy, ($C_2$-$C_{10}$)-alkynylcarbonyloxy, ($C_1$-$C_{10}$)-alkylthio, ($C_2$-$C_{10}$)-alkenylthio, ($C_3$-$C_{10}$)-alkynylthio, ($C_1$-$C_{10}$)-alkylsulphinyl, ($C_2$-$C_{10}$)-alkenylsulphinyl, ($C_3$-$C_{10}$)-alkynylsulphinyl, ($C_1$-$C_{10}$)-alkylsulphonyl, ($C_3$-$C_{10}$)-alkenylsulphonyl, ($C_3$-$C_{10}$)-alkynylsulphonyl, where at least one hydrogen atom is replaced by a halogen atom as defined above. In one embodiment, all hydrogen atoms are replaced by halogen. Examples of halogenated structures are, for example, chloromethyl, trichloromethyl, fluoromethyl, chlorodifluoromethyl, dichlorofluoromethyl, trifluoromethyl, 2,2-difluoroethyl, difluoromethyl, difluoromethoxy, trifluoromethoxy, difluoromethylthio, trifluoromethylthio.

Cyclic Groups 3- to 14-membered cyclic group, unless defined differently elsewhere: ($C_3$-$C_{14}$)-carbocyclic group, 3- to 10-membered heterocyclic group, halogenated ($C_3$-$C_{14}$)-carbocyclic group, halogenated 3- to 10-membered heterocyclic group.

($C_3$-$C_{14}$)-Carbocyclic group, unless defined differently elsewhere: ($C_3$-$C_{14}$)-cycloalkyl, ($C_3$-$C_{14}$)-cycloalkenyl, ($C_6$-$C_{14}$)-aryl, cycloalkenyl, halogenated ($C_3$-$C_{14}$)-cycloalkyl, halogenated ($C_3$-$C_{14}$)-halogenated ($C_6$-$C_{14}$)-aryl.

($C_3$-$C_{14}$)-Cycloalkyl, unless defined differently elsewhere: mono-, bi- or tricyclic saturated hydrocarbon groups preferably having ($C_3$-$C_{14}$)-, ($C_3$-$C_8$)- or ($C_3$-$C_6$)-ring atoms. Cycloalkyl may also be a spirocyclic group. Examples: cyclopropyl, -butyl, -pentyl, -hexyl, -heptyl, bicyclo[2.2.1]heptyl or adamantyl. "Cycloalkyl" preferably represents monocyclic groups of 3, 4, 5, 6 or 7 ring atoms.

Analogously, ($C_3$-$C_{14}$)-cycloalkenyl, unless defined differently elsewhere, is: a mono-, bi- or tricyclic, but partially unsaturated hydrocarbon group having at least one double bond, preferably having ($C_3$-$C_8$)— or ($C_3$-$C_6$)-ring atoms. Examples: cyclopropenyl, cyclobutenyl, cyclopentenyl and cyclohexenyl.

($C_6$-$C_{14}$)-Aryl, unless defined differently elsewhere: mono-, bi- or tricyclic ring system group where at least one cycle is aromatic, preferably having ($C_6$-$C_8$)- or ($C_6$)-ring atoms. Preferably, aryl is an aromatic $C_6$-monocyclic ring system group; a bicyclic ($C_8$-$C_{14}$)-ring system group; or a tricyclic ($C_{10}$-$C_{14}$)-ring system group. Examples: phenyl, naphthyl, anthryl, phenanthryl, tetrahydronaphthyl, indenyl, indanyl, fluorenyl.

Halogenated ($C_3$-$C_{14}$)-carbocyclic group, halogenated ($C_3$-$C_{14}$)-cycloalkyl, halogenated ($C_3$-$C_{14}$)-cycloalkenyl, halogenated ($C_6$-$C_{14}$)-aryl are in each case, unless defined differently, defined analogously to ($C_3$-$C_{14}$)-carbocyclic group, ($C_3$-$C_{14}$)-aryl, where at least -cycloalkyl, ($C_3$-$C_{14}$)-cycloalkenyl, ($C_6$-$C_{14}$) one hydrogen atom is replaced by a halogen atom as mentioned above. In one embodiment, all hydrogen atoms are replaced by halogen. Examples of halogenated structures are 3-chlorophenyl, 2-bromocyclopentyl.

Heteroatom: for example N, O, S, P, B, Si.

3- to 10-membered heterocyclic group, unless defined differently elsewhere: 3- to 9-membered heterocyclyl group or 5- to 10-membered heteroaryl group, halogenated 3- to 9-membered heterocyclyl group or halogenated 5- to 10-membered heteroaryl group.

3- to 9-membered heterocyclyl, unless defined differently elsewhere: 3- to 9-membered saturated or partially unsaturated mono-, bi- or tricyclic ring system group of carbon atoms and at least one heteroatom preferably selected from the group consisting of N, O and S. The ring system is preferably a 3- to 6-membered ring system. Preferably, the ring system contains 1, 2, 3 or 4 heteroatoms, particularly preferably 1 or 2 heteroatoms. Preference is also given to a monocyclic ring system. In a further preferred embodiment, a monocyclic ring system is a partially unsaturated monocyclic ring system having a double bond. Heterocyclyl may be a spirocyclic system. Examples: piperazinyl, dihydropyridyl, morpholinyl, etc. This definition also applies to heterocyclyl as component of a composite substituent such as, for example, 3- to 9-membered heterocyclyl-($C_1$-$C_{10}$)-alkyl, unless defined differently elsewhere.

5- to 10-membered heteroaryl, unless defined differently elsewhere: mono-, bi- or tricyclic 5- to 10-membered heterocyclic group of carbon atoms and at least one heteroatom, preferably selected from the group consisting of N, O and S, where at least one cycle is aromatic. The ring system is preferably a 5- to 6-membered ring system. In one embodiment, heteroaryl is an aromatic monocyclic ring system of 5 or 6 ring atoms. Preferably, heteroaryl is an aromatic monocyclic ring system containing 1 to 4 heteroatoms from the group consisting of O, N and S. Furthermore, heteroaryl may be a bicyclic ring system consisting of 8 to 14 ring atoms or a tricyclic ring system consisting of 13 or 14 ring atoms. Examples: furyl, thienyl, pyrazolyl, imidazolyl, triazolyl, thiazolyl, indolyl, benzimidazolyl, indazolyl, benzofuranyl, benzothiophenyl, benzothiazolyl, benzoxazolyl, quinolinyl, isoquinolinyl. This definition also applies to heteroaryl as component of a composite substituent such as, for example, 5- to 10-membered heteroaryl-($C_5$-$C_{10}$)-alkyl, unless defined differently elsewhere. 5- and 6-membered heteroaryl groups are described in more detail below:

5-membered heteroaryl, unless defined differently elsewhere: heteroaryl group containing one to three or one to four nitrogen, oxygen and/or sulphur atom(s) as ring atoms. Examples: furanyl, thienyl, oxazolyl, thiazolyl. In one embodiment, a 5-membered heteroaryl group contains, in addition to carbon atoms, one to four nitrogen atoms or one to three nitrogen atoms as ring members. Examples: pyrrolyl, pyrazolyl, triazolyl, imidazolyl. In a further embodiment, a 5-membered heteroaryl contains one to three nitrogen atoms or one nitrogen atom and one oxygen or sulphur atom. Examples: thiazolyl, oxazolyl, oxadiazolyl.

6-membered heteroaryl, unless defined differently elsewhere: heteroaryl group containing one to three or one to four nitrogen atom(s) as ring atoms. In one embodiment, a 6-membered heteroaryl group contains one to three nitrogen atoms. Examples: pyridyl, pyridazinyl, pyrimidinyl, pyrazinyl, triazinyl, tetrazinyl.

Halogenated 3- to 9-membered heterocyclyl group or halogenated 5- to 10-membered heteroaryl group, in each case unless defined differently, are defined analogously to 3- to 9-membered heterocyclyl group or 5- to 10-membered heteroaryl group, where at least one hydrogen atom is replaced by a halogen atom as mentioned above. In one embodiment, all hydrogen atoms are replaced by halogen. Example of halogenated heterocyclic structures: 3-chlorotetrahydrothiopyran-2-yl, 4-chloropyridin-2-yl.

Not included are combinations which are against natural laws and which the person skilled in the art would therefore exclude based on his/her expert knowledge. Ring structures having three or more adjacent oxygen atoms, for example, are excluded.

EMBODIMENTS OF THE COMPOUNDS ACCORDING TO THE INVENTION

It is obvious to the person skilled in the art that all embodiments can be present on their own or in combination. In particular, the various radical definitions for the compounds according to formula (I) may be combined with one another.

The compounds of the formula (I) may, where appropriate, depending on the nature of the substituents, be in the form of salts, tautomers, geometric and/or optically active isomers or corresponding isomer mixtures in different compositions.

If appropriate, the compounds according to the invention may be present in various polymorphic forms or as mixtures of different polymorphic forms. Both the pure polymorphs and the polymorph mixtures are provided by the invention and can be used in accordance with the invention.

Embodiments of the compounds of the formula (I) are described in more detail below:

Q preferably represents the structural elements below, where n for each Q is in each case as defined below:

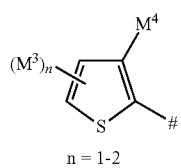
$Q^1$
n = 1-2

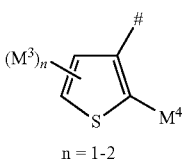
$Q^2$
n = 1-2

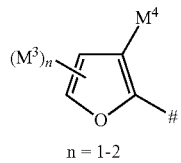
$Q^3$
n = 1-2

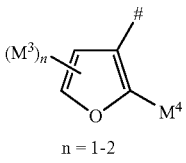
$Q^4$
n = 1-2

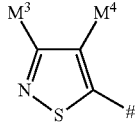
$Q^5$

-continued

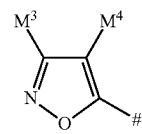
$Q^6$

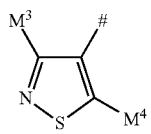
$Q^7$

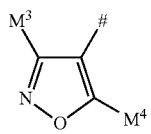
$Q^8$

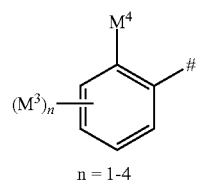
$Q^9$
n = 1-4

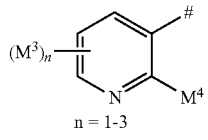
$Q^{11}$
n = 1-3

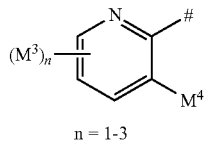
$Q^{12}$
n = 1-3

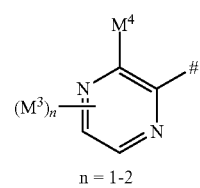
$Q^{13}$
n = 1-2

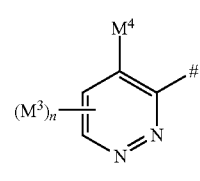
$Q^{14}$
n = 1-2

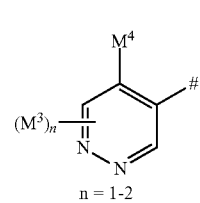
$Q^{15}$
n = 1-2

-continued
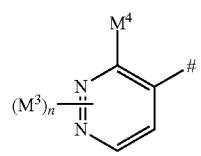
Q16
n = 1-2
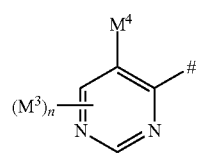
Q17
n = 1-2
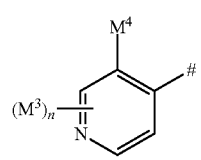
Q19
n = 1-3
Q particularly preferably represents the structural elements below, where n for each Q is in each case as defined below:
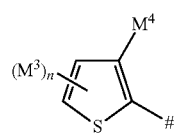
Q1
n = 1-2
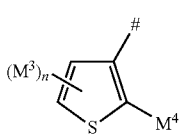
Q2
n = 1-2
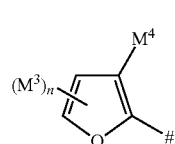
Q3
n = 1-2
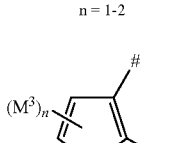
Q4
n = 1-2
-continued
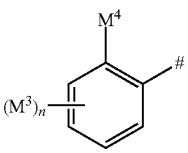
Q9
n = 1-4
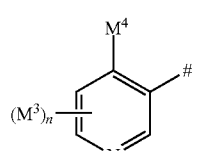
Q10
n = 1-3
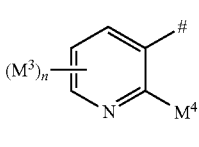
Q11
n = 1-3
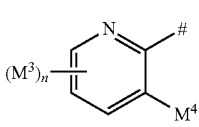
Q12
n = 1-3
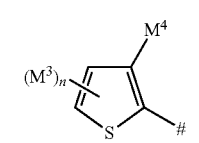
Q13
n = 1-2
Q particularly preferably represents the structural elements below, where n for each Q is in each case as defined below:
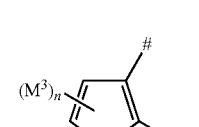
Q1
n = 1-2
Q2
n = 1-2

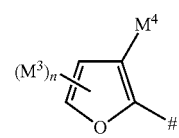 Q³
n = 1-2
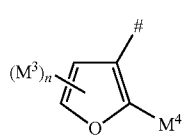 Q⁴
n = 1-2
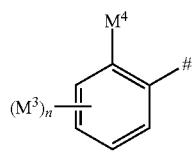 Q⁹
n = 1-4
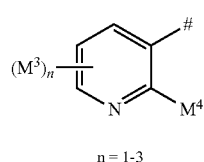 Q¹¹
n = 1-3
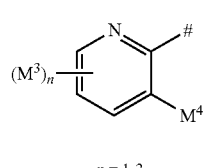 Q¹²
n = 1-3
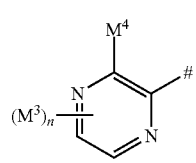 Q¹³
n = 1-2
Q very particularly preferably represents the structural elements below, where n for each Q is in each case as defined below:
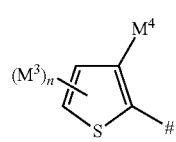 Q¹
n = 1
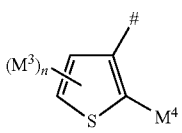 Q²
n = 1
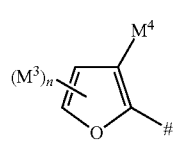 Q³
n = 1
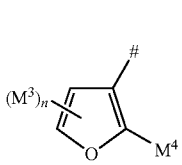 Q⁴
n = 0-1
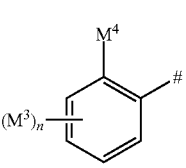 Q⁹
n = 1-3
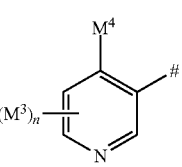 Q¹⁰
n = 1-2
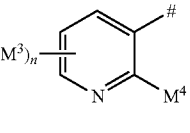 Q¹¹
n = 1-2
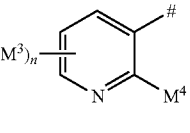 Q¹²
n = 1-2

-continued
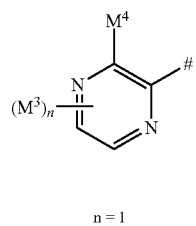
Q¹³
n = 1
Q very particularly preferably represents the structural elements below, where n for each Q is in each case as defined below:
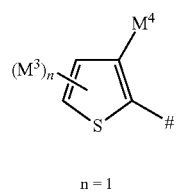
Q¹
n = 1
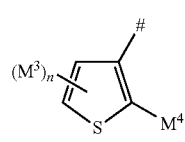
Q²
n = 1
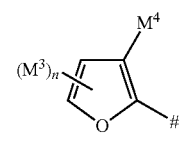
Q³
n = 1
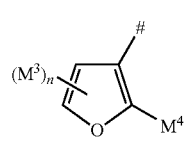
Q⁴
n = 0-1
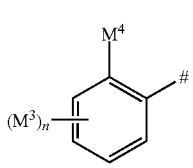
Q⁹
n = 1-3
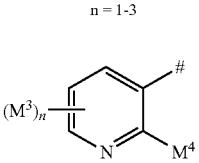
Q¹¹
n = 1-2
-continued
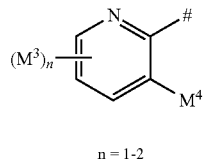
Q¹²
n = 1-2
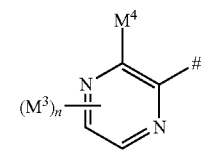
Q¹³
n = 1
Q very particularly preferably represents the structural elements below, where n for each Q is in each case as defined below:
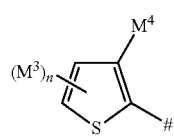
Q¹
n = 1
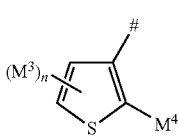
Q²
n = 1
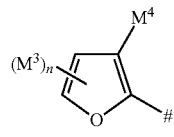
Q³
n = 1
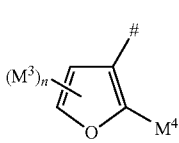
Q⁴
n = 0-1
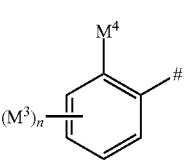
Q⁹
n = 1-3

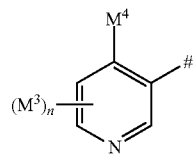

Q¹⁰ n = 1-2

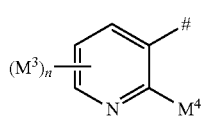

Q¹¹ n = 1-2

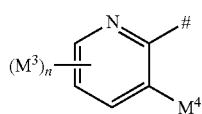

Q¹² n = 1-2

Q very particularly preferably represents the structural elements below, where n for each Q is in each case as defined below:

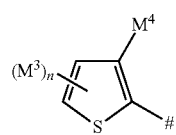

Q¹ n = 1

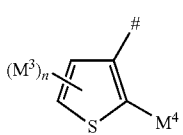

Q² n = 1

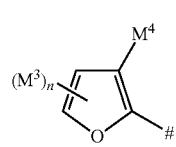

Q³ n = 1

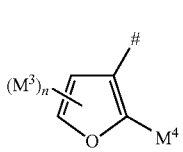

Q⁴ n = 0-1

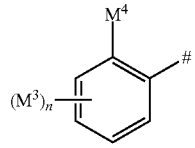

Q⁹ n = 1-3

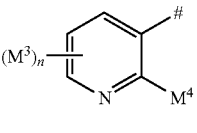

Q¹¹ n = 1-2

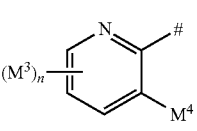

Q¹² n = 1-2

Q in particular very particularly preferably represents 2-thienyl, 3-fluoro-2-thienyl, 3-chloro-2-thienyl, 3,4-dichloro-2-thienyl, 2,5-dichloro-3-thienyl, 3,4,5-trichloro-2-thienyl, 3-bromo-2-thienyl, 3-iodo-2-thienyl, 3-cyano-2-thienyl, 3-methyl-2-thienyl, 3-(trifluoromethyl)-2-thienyl, 3-methoxy-2-thienyl, 3-ethoxy-2-thienyl, 3-thienyl, 2-fluoro-3-thienyl, 2-chloro-3-thienyl, 2-bromo-3-thienyl, 2-iodo-3-thienyl, 2-cyano-3-thienyl, 2-methyl-3-thienyl, 2-(trifluoromethyl)-3-thienyl, 2-methoxy-3-thienyl, 2-ethoxy-3-thienyl, 2-furanyl, 3-fluoro-2-furanyl, 3-chloro-2-furanyl, 3-bromo-2-furanyl, 3-iodo-2-furanyl, 3-cyano-2-furanyl, 3-methyl-2-furanyl, 3-(trifluoromethyl)-2-furanyl, 3-methoxy-2-furanyl, 3-ethoxy-2-furanyl, 3-furanyl, 2-chloro-3-furanyl, 2-bromo-3-furanyl, 2-iodo-3-furanyl, 2-cyano-3-furanyl, 2-methyl-3-furanyl, 2-(trifluoromethyl)-3-furanyl, 2-methoxy-3-furanyl, 2-ethoxy-3-furanyl, 2-methylphenyl, 2-fluorophenyl, 2,6-difluorophenyl, 2-chlorophenyl, 2,6-dichlorophenyl, 2-bromophenyl, 2-iodophenyl, 2-(difluoromethyl)phenyl, 2-(trifluoromethyl)phenyl, 2-(methylsulphanyl)phenyl, 2-(methylsulphonyl)phenyl, 2-(trifluoromethoxy)phenyl, 2-(trifluoromethylsulphanyl)phenyl, 2-(trifluoromethylsulphonyl)-phenyl, 2-nitrophenyl, 2-chloro-3-pyridyl, 3-chloro-2-pyridyl, 2-(difluoromethyl)-3-pyridyl, 2-(trifluoromethyl)-3-pyridyl, 2-(methylsulphanyl)-3-pyridyl, 2-(methylsulphonyl)-3-pyridyl, 2-(trifluoromethoxy)-3-pyridyl, 2-(trifluoromethylsulphanyl)-3-pyridyl or 2-(trifluoromethylsulphonyl)-3-pyridyl;

Q in particular very particularly preferably represents 2-thienyl, 3-fluoro-2-thienyl, 3-chloro-2-thienyl, 3,4-dichloro-2-thienyl, 3,4,5-trichloro-2-thienyl, 3-bromo-2-thienyl, 3-iodo-2-thienyl, 3-cyano-2-thienyl, 3-methyl-2-thienyl, 3-(trifluoromethyl)-2-thienyl, 3-methoxy-2-thienyl, 3-ethoxy-2-thienyl, 3-thienyl, 2-fluoro-3-thienyl, 2-chloro-3-thienyl, 2-bromo-3-thienyl, 2-iodo-3-thienyl, 2-cyano-3-thienyl, 2-methyl-3-thienyl, 2-(trifluoromethyl)-3-thienyl, 2-methoxy-3-thienyl, 2-ethoxy-3-thienyl, 2-furanyl, 3-fluoro-2-furanyl, 3-chloro-2-furanyl, 3-bromo-2-furanyl, 3-iodo-2-furanyl, 3-cyano-2-furanyl, 3-methyl-2-furanyl, 3-(trifluoromethyl)-2-furanyl, 3-methoxy-2-furanyl, 3-ethoxy-2-furanyl, 3-furanyl, 2-chloro-3-furanyl, 2-bromo-3-furanyl, 2-iodo-3-furanyl, 2-cyano-3-furanyl, 2-methyl-3-furanyl, 2-(trifluoromethyl)-3-furanyl, 2-methoxy-3-furanyl, 2-ethoxy-3-furanyl, 2-methylphenyl, 2-fluorophenyl, 2,6-difluorophenyl, 2-chlorophenyl, 2,6-dichlorophenyl, 2-bromophenyl, 2-iodophenyl, 2-(difluoromethyl)phenyl, 2-(trifluoromethyl)phenyl, 2-nitrophenyl, 2-chloro-3-pyridyl, 3-chloro-2-pyridyl, 2-(difluoromethyl)-3-pyridyl, 2-(trifluoromethyl)-3-pyridyl;

Y preferably represents hydrogen or represents optionally mono- or poly-$M^2$-substituted $(C_1-C_6)$-alkyl, $(C_2-C_6)$-alkenyl, $(C_2-C_6)$-alkynyl, $(C_1-C_6)$-haloalkyl, $(C_2-C_6)$-haloalkenyl, $(C_2-C_6)$-haloalkynyl, $(C_1-C_6)$-alkoxy, $(C_2-C_6)$-alkenyloxy, $(C_3-C_6)$-alkynyloxy, $(C_3-C_{10})$-cycloalkyl-$(C_1-C_6)$-alkyl or represents an optionally mono- or poly-$M^2$-substituted 3- to 10-membered cyclic group;

Y preferably represents hydrogen or represents optionally mono- or poly-$M^2$-substituted $(C_1-C_4)$-alkyl, $(C_2-C_4)$-alkenyl, $(C_3-C_4)$-alkynyl, $(C_1-C_4)$-haloalkyl, $(C_2-C_4)$-haloalkenyl, $(C_3-C_4)$-haloalkynyl, $(C_1-C_4)$-alkoxy, $(C_2-C_4)$-alkenyloxy, $(C_3-C_4)$-alkynyloxy, $(C_3-C_6)$-cycloalkyl-$(C_1-C_4)$-alkyl or represents an optionally mono- or poly-$M^2$-substituted $C_3$- to $C_6$-membered carbocyclic Y particularly preferably represents hydrogen or represents optionally mono- or poly-$M^2$-substituted $(C_1-C_4)$-alkyl, $(C_2-C_4)$-alkenyl, $(C_3-C_4)$-alkynyl, $(C_1-C_4)$-haloalkyl, $(C_2-C_4)$-haloalkenyl, $(C_1-C_4)$-alkoxy, $(C_3-C_6)$-cycloalkyl, $(C_3-C_6)$-cycloalkyl-$(C_1-C_4)$-alkyl;

Y particularly preferably represents hydrogen, methyl, ethyl, n-propyl, isopropyl, n-butyl, sec-butyl, isobutyl, tert-butyl, cyanomethyl, 2,2-difluoroethyl, 2,2,2-trifluoroethyl, allyl, butenyl, propargyl, butynyl, 3,3-dichloroprop-2-enyl, methoxy, ethoxy, cyclopropylmethyl, cyclopropyl, cyclobutyl, cyclopentyl or cyclohexyl;

Y very particularly preferably represents hydrogen, methyl, ethyl, n-propyl, isopropyl, n-butyl, sec-butyl, isobutyl, tert-butyl, methoxy, ethoxy, cyclopropylmethyl, cyclopropyl, cyclobutyl;

Y very particularly preferably represents hydrogen, cyclopropyl;

Y very particularly preferably represents hydrogen;

W preferably represents oxygen;

W preferably represents sulphur;

$M^1$, $M^2$ and $M^3$ each independently of one another preferably represent hydrogen, halogen, cyano, nitro, OH, $(C_1-C_6)$-alkyl, $(C_1-C_6)$-haloalkyl, $(C_1-C_6)$-alkoxy, $(C_1-C_6)$-haloalkoxy, $(C_1-C_6)$-alkylthio, $(C_1-C_6)$-haloalkylthio, $(C_1-C_6)$-alkylsulphonyl, $(C_1-C_6)$-haloalkylsulphonyl, $(C_1-C_6)$-alkylsulphanyl, $(C_1-C_6)$-haloalkylsulphanyl, $(C_3-C_{14})$-cycloalkyl-O—, $(C_3-C_{14})$-cycloalkenyl-O—, $(C_6-C_{14})$-aryl-O—, halogenated $(C_3-C_{14})$-cycloalkyl-O—, halogenated $(C_3-C_{14})$-cycloalkenyl-O—, halogenated $(C_6-C_{14})$-aryl-O—;

$M^1$, $M^2$ and $M^3$ each independently of one another preferably represent hydrogen, halogen, cyano, nitro, OH, $(C_1-C_6)$-alkyl, $(C_1-C_6)$-haloalkyl, $(C_1-C_6)$-alkoxy, $(C_1-C_6)$-haloalkoxy, $(C_1-C_6)$-alkylthio, $(C_1-C_6)$-haloalkylthio, $(C_1-C_6)$-alkylsulphonyl, $(C_1-C_6)$-haloalkylsulphonyl, $(C_1-C_6)$-alkylsulphanyl, $(C_1-C_6)$-haloalkylsulphanyl, $(C_3-C_{14})$-cycloalkyl-O—, $(C_3-C_{14})$-cycloalkenyl-O—, $(C_6-C_{14})$-aryl-O—, halogenated $(C_3-C_{14})$-cycloalkyl-O—, halogenated $(C_3-C_{14})$-cycloalkenyl-O—, halogenated $(C_6-C_{14})$-aryl-O—, where, if Q corresponds to $Q^{11}$, $M^3$ is not $(C_1-C_4)$-haloalkyl in position 4 at the pyridyl;

$M^1$, $M^2$ and $M^3$ each independently of one another preferably represent hydrogen, halogen, cyano, nitro, OH, $(C_1-C_4)$-alkyl, $(C_1-C_4)$-haloalkyl, $(C_1-C_4)$-alkoxy, $(C_1-C_4)$-haloalkoxy, $(C_1-C_4)$-alkylthio, $(C_1-C_4)$-haloalkylthio, $(C_1-C_4)$-alkylsulphonyl, $(C_1-C_4)$-haloalkylsulphonyl, $(C_1-C_4)$-alkylsulphanyl, $(C_1-C_6)$-haloalkylsulphanyl, $(C_3-C_{14})$-cycloalkyl-O—, $(C_3-C_{14})$-cycloalkenyl-O—, $(C_6-C_{14})$-aryl-O—, halogenated $(C_3-C_{14})$-cycloalkyl-O—, halogenated $(C_3-C_{14})$-cycloalkenyl-O—, halogenated $(C_6-C_{14})$-aryl-O—, where, if Q corresponds to $Q^{11}$, $M^3$ is not $(C_1-C_4)$-haloalkyl in position 4 at the pyridyl;

$M^1$, $M^2$ and $M^3$ each independently of one another very particularly preferably represent hydrogen, halogen, cyano, nitro, OH, $(C_1-C_4)$-alkyl, $(C_1-C_4)$-haloalkyl, $(C_1-C_4)$-alkoxy, $(C_1-C_4)$-haloalkoxy, $(C_1-C_4)$-alkylthio, $(C_1-C_4)$-haloalkylthio, $(C_1-C_4)$-alkylsulphonyl, $(C_1-C_4)$-haloalkylsulphonyl, $(C_1-C_4)$-alkylsulphanyl, $(C_1-C_4)$-haloalkylsulphanyl, $(C_6-C_{14})$-aryl-O—, halogenated $(C_6-C_{14})$-aryl-O—;

$M^1$, $M^2$ and $M^3$ each independently of one another very particularly preferably represent hydrogen, halogen, cyano, nitro, OH, $(C_1-C_4)$-alkyl, $(C_1-C_4)$-haloalkyl, $(C_1-C_4)$-alkoxy, $(C_1-C_4)$-haloalkoxy, $(C_1-C_4)$-alkylthio, $(C_1-C_4)$-haloalkylthio, $(C_1-C_4)$-alkylsulphonyl, $(C_1-C_4)$-haloalkylsulphonyl, $(C_1-C_4)$-alkylsulphanyl, $(C_1-C_4)$-haloalkylsulphanyl, $(C_6-C_{14})$-aryl-O—, halogenated $(C_6-C_{14})$-aryl-O—, where, if Q corresponds to $Q^{11}$, $M^3$ is not $(C_1-C_4)$-haloalkyl in position 4 at the pyridyl;

$M^1$, $M^2$ and $M^3$ each independently of one another very particularly preferably represent hydrogen, halogen, cyano, nitro, OH, $(C_1-C_2)$-alkyl, $(C_1-C_2)$-haloalkyl, $(C_1-C_2)$-alkoxy, $(C_1-C_2)$-haloalkoxy, $(C_1-C_2)$-alkylthio, $(C_1-C_2)$-haloalkylthio, $(C_1-C_2)$-alkylsulphonyl, $(C_1-C_2)$-haloalkylsulphonyl, $(C_1-C_2)$-alkylsulphanyl, $(C_1-C_2)$-haloalkylsulphanyl, $(C_6)$-aryl-O—, halogenated $(C_6)$-aryl-O—;

$M^1$, $M^2$ and $M^3$ each independently of one another very particularly preferably represent hydrogen, halogen, cyano, nitro, OH, $(C_1-C_2)$-alkyl, $(C_1-C_2)$-haloalkyl, $(C_1-C_2)$-alkoxy, $(C_1-C_2)$-haloalkoxy, $(C_1-C_2)$-alkylthio, $(C_1-C_2)$-haloalkylthio, $(C_1-C_2)$-alkylsulphonyl, $(C_1-C_2)$-haloalkylsulphonyl, $(C_1-C_2)$-alkylsulphanyl, $(C_1-C_2)$-haloalkylsulphanyl, $(C_6)$-aryl-O—, halogenated $(C_6)$-aryl-O—, where, if Q corresponds to $Q^{11}$, $M^3$ is not $(C_1-C_2)$-haloalkyl in position 4 at the pyridyl;

$M^1$, $M^2$ and $M^3$ each independently of one another very particularly preferably represent hydrogen, fluorine, bromine, chlorine, iodine, cyano, nitro, OH, methyl, ethyl, n-propyl, isopropyl, n-butyl, isobutyl, sec-butyl, tert-butyl, trifluoromethyl, difluoromethyl, fluoromethyl, trichloromethyl, dichloromethyl, chloromethyl, methoxy, ethoxy, isopropoxy, trifluoromethoxy, difluoromethoxy, methylthio, trifluoromethylthio, difluoromethylthio, 2,2,2-trifluoroethylthio, methylsulphonyl, ethylsulphonyl, trifluoromethylsulphonyl, 2,2,2-trifluoroethylsulphonyl, methylsulphanyl, ethylsulphanyl, trifluoromethylsulphanyl, 2,2,2-trifluoroethylsulphanyl or phenoxy;

$M^1$, $M^2$ and $M^3$ each independently of one another very particularly preferably represent hydrogen, fluorine, bromine, chlorine, iodine, cyano, nitro, OH, methyl, ethyl, n-propyl, isopropyl, n-butyl, isobutyl, sec-butyl, tert-butyl, trifluoromethyl, difluoromethyl, fluoromethyl, trichloromethyl, dichloromethyl, chloromethyl, methoxy, ethoxy, isopropoxy, trifluoromethoxy, difluoromethoxy, methylthio, trifluoromethylthio, difluoromethylthio, 2,2,2-trifluoroethylthio, methylsulphonyl, ethylsulphonyl, trifluoromethylsulphonyl, 2,2,2-trifluoroethylsulphonyl, methylsulphanyl, ethylsulphanyl, trifluoromethylsulphanyl, 2,2,2-trifluoroethylsulphanyl or phenoxy, where, if Q corresponds to $Q^{11}$, $M^3$ is not trifluoromethyl in position 4 at the pyridyl;

$M^1$, $M^2$ and $M^3$ each independently of one another very particularly preferably represent hydrogen, fluorine, bromine, chlorine, iodine, cyano, nitro, OH, methyl, ethyl, isopropyl, tert-butyl, trifluoromethyl, difluoromethyl, methoxy, ethoxy, isopropoxy, trifluoromethoxy, difluoromethoxy, methylthio, trifluoromethylthio, difluoromethylthio, 2,2,2-trifluoroethylthio, methylsulphonyl, ethylsulphonyl, trifluoromethylsulphonyl, 2,2,2-trifluoroethylsulphonyl, methylsulphanyl, ethylsulphanyl, trifluoromethylsulphanyl, 2,2,2-trifluoroethylsulphanyl or phenoxy;

$M^1$, $M^2$ and $M^3$ each independently of one another very particularly preferably represent hydrogen, fluorine, bromine, chlorine, iodine, cyano, nitro, OH, methyl, ethyl, isopropyl, tert-butyl, trifluoromethyl, difluoromethyl, methoxy, ethoxy, isopropoxy, trifluoromethoxy, difluoromethoxy, methylthio, trifluoromethylthio, difluoromethylthio, 2,2,2-trifluoroethylthio, methylsulphonyl, ethylsulphonyl, trifluoromethylsulphonyl, 2,2,2-trifluoroethylsulphonyl, methylsulphanyl, ethylsulphanyl, trifluoromethylsulphanyl, 2,2,2-trifluoroethylsulphanyl or phenoxy, where, if Q corresponds to $Q^{11}$, $M^3$ is not trifluoromethyl in position 4 at the pyridyl;

$M^1$, $M^2$ and $M^3$ each independently of one another in particular very particularly preferably represent hydrogen, fluorine, bromine, chlorine, iodine, cyano, nitro, methyl, trifluoromethyl, difluoromethyl, methoxy, ethoxy, isopropoxy or phenoxy;

$M^1$, $M^2$ and $M^3$ each independently of one another in particular very particularly preferably represent hydrogen, fluorine, bromine, chlorine, iodine, cyano, nitro, methyl, trifluoromethyl, difluoromethyl, methoxy, ethoxy, isopropoxy or phenoxy, where, if Q corresponds to $Q^{11}$, $M^3$ is not trifluoromethyl in position 4 at the pyridyl;

$M^1$, $M^2$ and $M^3$ each independently of one another in particular very particularly preferably represent hydrogen, fluorine, bromine, chlorine, iodine, cyano, nitro, trifluoromethyl, difluoromethyl;

$M^1$, $M^2$ and $M^3$ each independently of one another in particular very particularly preferably represent hydrogen, fluorine, bromine, chlorine, iodine, cyano, nitro, trifluoromethyl, difluoromethyl, where, if Q corresponds to $Q^{11}$, $M^3$ is not trifluoromethyl in position 4 at the pyridyl;

$M^4$ preferably represent hydrogen, halogen, cyano, nitro, OH, $(C_1-C_6)$-alkyl, $(C_1-C_6)$-haloalkyl, $(C_1-C_6)$-alkoxy, $(C_1-C_6)$-haloalkoxy, $(C_1-C_6)$-alkylthio, $(C_1-C_6)$-haloalkylthio, $(C_1-C_6)$-alkylsulphonyl, $(C_1-C_6)$-haloalkylsulphonyl, $(C_1-C_6)$-alkylsulphanyl, $(C_1-C_6)$-haloalkylsulphanyl, $(C_3-C_{14})$-cycloalkyl-O—, $(C_3-C_{14})$-cycloalkenyl-O—, $(C_6-C_{14})$-aryl-O—, halogenated $(C_3-C_{14})$-cycloalkyl-O—, halogenated $(C_3-C_{14})$-cycloalkenyl-O—, halogenated $(C_6-C_{14})$-aryl-O—;

$M^4$ preferably represents hydrogen, halogen, cyano, nitro, OH, $(C_1-C_6)$-alkyl, $(C_1-C_6)$-haloalkyl, $(C_1-C_6)$-alkoxy, $(C_1-C_6)$-haloalkoxy, $(C_1-C_6)$-alkylthio, $(C_1-C_6)$-haloalkylthio, $(C_1-C_6)$-alkylsulphonyl, $(C_1-C_6)$-haloalkylsulphonyl, $(C_1-C_6)$-alkylsulphanyl, $(C_1-C_6)$-haloalkylsulphanyl, $(C_3-C_{14})$-cycloalkyl-O—, $(C_3-C_{14})$-cycloalkenyl-O—, $(C_6-C_{14})$-aryl-O—, halogenated $(C_3-C_{14})$-cycloalkyl-O—, halogenated $(C_3-C_{14})$-cycloalkenyl-O—, halogenated $(C_6-C_{14})$-aryl-O—, where, if Q corresponds to $Q^{10}$, $M^4$ is not $(C_1-C_4)$-haloalkyl;

$M^4$ preferably represents hydrogen, halogen, cyano, nitro, OH, $(C_1-C_4)$-alkyl, $(C_1-C_4)$-haloalkyl, $(C_1-C_4)$-alkoxy, $(C_1-C_4)$-haloalkoxy, $(C_1-C_4)$-alkylthio, $(C_1-C_4)$-haloalkylthio, $(C_1-C_4)$-alkylsulphonyl, $(C_1-C_4)$-haloalkylsulphonyl, $(C_1-C_4)$-alkylsulphanyl, $(C_1-C_6)$-haloalkylsulphanyl, $(C_3-C_{14})$-cycloalkyl-O—, $(C_3-C_{14})$-cycloalkenyl-O—, $(C_6-C_{14})$-aryl-O—, halogenated $(C_3-C_{14})$-cycloalkyl-O—, halogenated $(C_3-C_{14})$-cycloalkenyl-O—, halogenated $(C_6-C_{14})$-aryl-O—;

$M^4$ preferably represents hydrogen, halogen, cyano, nitro, OH, $(C_1-C_4)$-alkyl, $(C_1-C_4)$-haloalkyl, $(C_1-C_4)$-alkoxy, $(C_1-C_4)$-haloalkoxy, $(C_1-C_4)$-alkylthio, $(C_1-C_4)$-haloalkylthio, $(C_1-C_4)$-alkylsulphonyl, $(C_1-C_4)$-haloalkylsulphonyl, $(C_1-C_4)$-alkylsulphanyl, $(C_1-C_6)$-haloalkylsulphanyl, $(C_3-C_{14})$-cycloalkyl-O—, $(C_3-C_{14})$-cycloalkenyl-O—, $(C_6-C_{14})$-aryl-O—, halogenated $(C_3-C_{14})$-cycloalkyl-O—, halogenated $(C_3-C_{14})$-cycloalkenyl-O—, halogenated $(C_6-C_{14})$-aryl-O—, where, if Q corresponds to $Q^{10}$, $M^4$ is not $(C_1-C_4)$-haloalkyl;

$M^4$ very particularly preferably represents hydrogen, halogen, cyano, nitro, OH, $(C_1-C_4)$-alkyl, $(C_1-C_4)$-haloalkyl, $(C_1-C_4)$-alkoxy, $(C_1-C_4)$-haloalkoxy, $(C_1-C_4)$-alkylthio, $(C_1-C_4)$-haloalkylthio, $(C_1-C_4)$-alkylsulphonyl, $(C_1-C_4)$-haloalkylsulphonyl, $(C_1-C_4)$-alkylsulphanyl, $(C_1-C_4)$-haloalkylsulphanyl, $(C_6-C_{14})$-aryl-O—, halogenated $(C_6-C_{14})$-aryl)-O—;

$M^4$ very particularly preferably represents hydrogen, halogen, cyano, nitro, OH, $(C_1-C_4)$-alkyl, $(C_1-C_4)$-haloalkyl, $(C_1-C_4)$-alkoxy, $(C_1-C_4)$-haloalkoxy, $(C_1-C_4)$-alkylthio, $(C_1-C_4)$-haloalkylthio, $(C_1-C_4)$-alkylsulphonyl, $(C_1-C_4)$-haloalkylsulphonyl, $(C_1-C_4)$-alkylsulphanyl, $(C_1-C_4)$-haloalkylsulphanyl, $(C_6-C_{14})$-aryl-O—, halogenated $(C_6-C_{14})$-aryl-O—, where, if Q corresponds to $Q^{10}$, $M^4$ is not $(C_1-C_2)$-haloalkyl;

$M^4$ very particularly preferably represents hydrogen, halogen, cyano, nitro, OH, $(C_1-C_2)$-alkyl, $(C_1-C_2)$-haloalkyl, $(C_1-C_2)$-alkoxy, $(C_1-C_2)$-haloalkoxy, $(C_1-C_2)$-alkylthio, $(C_1-C_2)$-haloalkylthio, $(C_1-C_2)$-alkylsulphonyl, $(C_1-C_2)$-haloalkylsulphonyl, $(C_1-C_2)$-alkylsulphanyl, $(C_1-C_2)$-haloalkylsulphanyl, $(C_6)$-aryl-O—, halogenated $(C_6)$-aryl)-O—;

$M^4$ very particularly preferably represents hydrogen, halogen, cyano, nitro, OH, $(C_1-C_2)$-alkyl, $(C_1-C_2)$-haloalkyl, $(C_1-C_2)$-alkoxy, $(C_1-C_2)$-haloalkoxy, $(C_1-C_2)$-alkylthio, $(C_1-C_2)$-haloalkylthio, $(C_1-C_2)$-alkylsulphonyl, $(C_1-C_2)$-haloalkylsulphonyl, $(C_1-C_2)$-alkylsulphanyl, $(C_1-C_2)$-haloalkylsulphanyl, $(C_6)$-aryl-O—, halogenated $(C_6)$-aryl-O—, where, if Q corresponds to $Q^{10}$, $M^4$ is not $(C_1-C_2)$-haloalkyl;

$M^4$ very particularly preferably represents fluorine, bromine, chlorine, iodine, cyano, nitro, OH, methyl, ethyl, n-propyl, isopropyl, n-butyl, isobutyl, sec-butyl, tert-butyl, trifluoromethyl, difluoromethyl, fluoromethyl, trichloromethyl, dichloromethyl, chloromethyl, methoxy, ethoxy, isopropoxy, trifluoromethoxy, difluoromethoxy, methylthio, trifluoromethylthio, difluoromethylthio, 2,2,2-trifluoroethylthio, methylsulphonyl, ethylsulphonyl, trifluoromethylsulphonyl, 2,2,2-trifluoroethylsulphonyl, methylsulphanyl, ethylsulphanyl, trifluoromethylsulphanyl, 2,2,2-trifluoroethylsulphanyl or phenoxy;

$M^4$ very particularly preferably represents hydrogen, fluorine, bromine, chlorine, iodine, cyano, nitro, OH, methyl, ethyl, n-propyl, isopropyl, n-butyl, isobutyl, sec-butyl, tert-butyl, trifluoromethyl, difluoromethyl, fluoromethyl, trichloromethyl, dichloromethyl, chloromethyl, methoxy, ethoxy, isopropoxy, trifluoromethoxy, difluoromethoxy, methylthio, trifluoromethylthio, difluoromethylthio, 2,2,2-trifluoroethylthio, methylsulphonyl, ethylsulphonyl, trifluoromethylsulphonyl, 2,2,2-trifluoroethylsulphonyl, methylsulphanyl, ethylsulphanyl, trifluoromethylsulphanyl, 2,2,2-trifluoroethylsulphanyl or phenoxy, where, if Q corresponds to $Q^{10}$, $M^4$ is not trifluoromethyl;

$M^4$ very particularly preferably represents hydrogen, fluorine, bromine, chlorine, iodine, cyano, nitro, OH, methyl, ethyl, isopropyl, tert-butyl, trifluoromethyl, difluoromethyl, methoxy, ethoxy, isopropoxy, trifluoromethoxy, difluoromethoxy, methylthio, trifluoromethylthio, difluoromethylthio, 2,2,2-trifluoroethylthio, methylsulphonyl, ethylsulphonyl, trifluoromethylsulphonyl, 2,2,2-trifluoroethylsulphonyl, methylsulphanyl, ethylsulphanyl, trifluoromethylsulphanyl, 2,2,2-trifluoroethylsulphanyl or phenoxy;

$M^4$ very particularly preferably represents hydrogen, fluorine, bromine, chlorine, iodine, cyano, nitro, OH, methyl, ethyl, isopropyl, tert-butyl, trifluoromethyl, difluoromethyl, methoxy, ethoxy, isopropoxy, trifluoromethoxy, difluoromethoxy, methylthio, trifluoromethylthio, difluoromethylthio, 2,2,2-trifluoroethylthio, methylsulphonyl, ethylsulphonyl, trifluoromethylsulphonyl, 2,2,2-trifluoroethylsulphonyl, methylsulphanyl, ethylsulphanyl, trifluoromethylsulphanyl, 2,2,2-trifluoroethylsulphanyl or phenoxy, where, if Q corresponds to $Q^{10}$, $M^4$ is not trifluoromethyl;

$M^4$ in particular very particularly preferably represents fluorine, bromine, chlorine, iodine, cyano, nitro, methyl, trifluoromethyl, difluoromethyl, methoxy, trifluoromethylsulphanyl, trifluoromethoxy, difluoromethoxy, ethoxy, isopropoxy or phenoxy;

$M^4$ in particular very particularly preferably represents hydrogen, fluorine, bromine, chlorine, iodine, cyano, nitro, methyl, trifluoromethyl, difluoromethyl, methoxy, trifluoromethylsulphanyl, trifluoromethoxy, difluoromethoxy, ethoxy, isopropoxy or phenoxy, where, if Q corresponds to $Q^{10}$, $M^4$ is not trifluoromethyl;

$M^4$ in particular very particularly preferably represents fluorine, bromine, chlorine, iodine, cyano, nitro, trifluoromethyl, difluoromethyl, methoxy, trifluoromethylsulphanyl, trifluoromethoxy, difluoromethoxy;

$M^4$ in particular very particularly preferably represents hydrogen, fluorine, bromine, chlorine, iodine, cyano, nitro, trifluoromethyl, difluoromethyl, methoxy, trifluoromethylsulphanyl, trifluoromethoxy, difluoromethoxy, where, if Q corresponds to $Q^{10}$, $M^4$ is not trifluoromethyl;

$M^4$ in particular very particularly preferably represents fluorine, bromine, chlorine, iodine, cyano, nitro, methyl, trifluoromethyl, difluoromethyl, methoxy, ethoxy, isopropoxy or phenoxy;

$M^4$ in particular very particularly preferably represents hydrogen, fluorine, bromine, chlorine, iodine, cyano, nitro, methyl, trifluoromethyl, difluoromethyl, methoxy, ethoxy, isopropoxy or phenoxy, where, if Q corresponds to $Q^{10}$, $M^4$ is not trifluoromethyl;

k preferably represents 1 or 2;

k particularly preferably represents 1;

$R^{21}$, $R^{22}$ preferably each independently of one another represent hydrogen, fluorine or optionally mono- or poly-$M^2$-substituted $(C_1-C_6)$-alkyl, $(C_2-C_6)$-alkenyl, $(C_2-C_6)$-alkynyl, $(C_1-C_6)$-haloalkyl, $(C_2-C_6)$-haloalkenyl, $(C_2-C_6)$-haloalkynyl, $(C_1-C_6)$-alkoxy, $(C_1-C_6)$-haloalkoxy, $(C_2-C_6)$-alkenyloxy, $(C_3-C_6)$-alkynyloxy, $(C_3-C_6)$-cycloalkyl-$(C_1-C_6)$-alkyl or represent an optionally mono- or poly-$M^2$-substituted $(C_3-C_{14})$-carbocyclic group;

$R^{21}$, $R^{22}$ preferably each independently of one another represent hydrogen, fluorine or optionally mono- or poly-$M^2$-substituted $(C_1-C_4)$-alkyl, $(C_2-C_4)$-alkenyl, $(C_2-C_4)$-alkynyl, $(C_1-C_4)$-haloalkyl, $(C_2-C_4)$-haloalkenyl, $(C_2-C_4)$-haloalkynyl, $(C_1-C_6)$-alkoxy, $(C_1-C_4)$-haloalkoxy, $(C_2-C_4)$-alkenyloxy, $(C_3-C_4)$-alkynyloxy, $(C_3-C_4)$-cycloalkyl-$(C_1-C_4)$-alkyl, $(C_3-C_8)$-cycloalkyl or halogenated $(C_3-C_8)$-cycloalkyl;

$R^{21}$, $R^{22}$ preferably represent $C(R^{21}, R^{22})$ as spiro-$C(CH_2—CH_2)$;

$R^{21}$, $R^{22}$ particularly preferably each independently of one another represent hydrogen, fluorine or optionally mono- or poly-$M^2$-substituted $(C_1-C_4)$-alkyl, $(C_2-C_4)$-alkenyl, $(C_2-C_4)$-alkynyl, $(C_1-C_4)$-haloalkyl, $(C_1-C_6)$-alkoxy, $(C_2-C_4)$-alkenyloxy, $(C_3-C_4)$-alkynyloxy, $(C_3-C_4)$-cycloalkyl-$(C_1-C_4)$-alkyl, $(C_3-C_6)$-cycloalkyl;

$R^{21}$, $R^{22}$ preferably each independently of one another represent hydrogen, fluorine, methyl, ethyl, n-propyl, isopropyl, tert-butyl, butyl, allyl, propargyl, chloromethyl, trichloromethyl, fluoromethyl, chlorodifluoromethyl, dichlorofluoromethyl, trifluoromethyl, 2,2-difluoroethyl, difluoromethyl, methoxy, ethoxy, allyloxy, propargyloxy, cyclopropylmethyl, cyclopropyl;

$R^{21}$, $R^{22}$ preferably each independently of one another represent hydrogen, fluorine, methyl, ethyl, n-propyl, isopropyl, allyl, propargyl, methoxy, ethoxy, allyloxy, propargyloxy, cyclopropylmethyl, cyclopropyl;

$R^{21}$, $R^{22}$ very particularly preferably each independently of one another represent hydrogen, fluorine or $(C_1-C_4)$-alkyl, $(C_1-C_4)$-haloalkyl;

$R^{21}$, $R^{22}$ in particular very particularly preferably represent hydrogen, methyl or ethyl;

$R^{31}$, $R^{32}$ preferably each independently of one another represent hydrogen, fluorine or optionally mono- or poly-$M^2$-substituted $(C_1-C_6)$-alkyl, $(C_2-C_6)$-alkenyl, $(C_2-C_6)$-alkynyl, $(C_1-C_6)$-haloalkyl, $(C_2-C_6)$-haloalkenyl, $(C_2-C_6)$-haloalkynyl, $(C_1-C_6)$-alkoxy, $(C_1-C_6)$-haloalkoxy, $(C_2-C_6)$-alkenyloxy, $(C_3-C_6)$-alkynyloxy, $(C_3-C_6)$-cycloalkyl-$(C_1-C_6)$-alkyl or represent an optionally mono- or poly-$M^2$-substituted $(C_3-C_{14})$-carbocyclic group;

$R^{31}$, $R^{32}$ preferably each independently of one another represent hydrogen, fluorine or optionally mono- or poly-$M^2$-substituted $(C_1-C_4)$-alkyl, $(C_2-C_4)$-alkenyl, $(C_2-C_4)$-alkynyl, $(C_1-C_4)$-haloalkyl, $(C_2-C_4)$-haloalkenyl, $(C_2-C_4)$-haloalkynyl, $(C_1-C_6)$-alkoxy, $(C_1-C_4)$-haloalkoxy, $(C_2-C_4)$-alkenyloxy, $(C_3-C_4)$-alkynyloxy, $(C_3-C_4)$-cycloalkyl-$(C_1-C_4)$-alkyl or represent an optionally mono- or poly-$M^2$-substituted $(C_3-C_8)$-cycloalkyl or halogenated $(C_3-C_8)$-cycloalkyl;

$R^{31}$, $R^{32}$ preferably represents $C(R^{31}, R^{32})$ as spiro-$C(CH_2—CH_2)$;

$R^{31}$, $R^{32}$ particularly preferably represents $C(R^{31}, R^{32})$ as 1,1-cyclopropyl;

$R^{31}$, $R^{32}$ particularly preferably each independently of one another represent hydrogen, fluorine or optionally mono- or poly-$M^2$-substituted $(C_1-C_4)$-alkyl, $(C_1-C_4)$-haloalkyl, $(C_2-C_4)$-haloalkenyl, $(C_2-C_4)$-alkenyl, $(C_2-C_4)$-alkynyl, $(C_1-C_6)$-alkoxy, $(C_2-C_4)$-alkenyloxy, $(C_3-C_4)$-alkynyloxy, $(C_3-C_4)$-cycloalkyl-$(C_3-C_4)$-alkyl, $(C_3-C_6)$-cycloalkyl;

$R^{31}$, $R^{32}$ particularly preferably each independently of one another represent hydrogen, methyl, ethyl, n-propyl, isopropyl, tert-butyl, allyl, propargyl, methoxy, ethoxy, allyloxy, propargyloxy, cyclopropylmethyl, cyclopropyl;

$R^{31}$, $R^{32}$ very particularly preferably each independently of one another represent hydrogen, fluorine or $(C_1-C_4)$-alkyl;

$R^{31}$, $R^{32}$ in particular very particularly preferably each independently of one another represent hydrogen, methyl, ethyl, n-propyl, isopropyl or tert-butyl;

$M^5$ preferably in each case independently of the others represents halogen, formyl, cyano, nitro, $(C_1-C_6)$-alkyl, $(C_1-C_6)$-haloalkyl, $(C_2-C_6)$-alkenyl, $(C_2-C_6)$-haloalkenyl, $(C_2-C_6)$-alkynyl, $(C_2-C_6)$-haloalkynyl, $(C_1-C_6)$-alkoxy, $(C_1-C_6)$-haloalkoxy, $(C_2-C_6)$-alkenyloxy, $(C_2-C_6)$-haloalkenyloxy, $(C_3-C_6)$-alkynyloxy, $(C_3-C_6)$-haloalkynyloxy, $(C_1-C_6)$-alkylthio, $(C_1-C_6)$-haloalkylthio, $(C_2-C_6)$-alkenylthio, $(C_2-C_6)$-haloalkenylthio, $(C_3-C_6)$-alkynylthio, $(C_3-C_6)$-haloalkynylthio, alkylsulphonyl, $(C_1-C_6)$-haloalkylsulphonyl, $(C_2-C_6)$-alkenylsulphonyl, $(C_2-C_6)$-haloalkenylsulphonyl, $(C_3-C_6)$-alkynylsulphonyl, $(C_3-C_6)$-haloalkynylsulphonyl, alkylsulphanyl, $(C_1-C_6)$-haloalkylsulphanyl, $(C_2-C_6)$-alkenylsulphanyl, $(C_2-C_6)$-haloalkenylsulphanyl, $(C_3-C_6)$-alkynylsulphanyl, $(C_3-C_6)$-haloalkynylsulphanyl, formyl, alkylcarbonyl, $(C_1-C_6)$-haloalkylcarbonyl, $(C_2-C_6)$-alkenylcarbonyl, $(C_2-C_6)$-haloalkenylcarbonyl, $(C_2-C_6)$-alkynylcarbonyl, $(C_2-C_6)$-haloalkynylcarbonyl, $(C_1-C_6)$-alkoxycarbonyl, haloalkoxycarbonyl, $(C_2-C_6)$-alkenyloxycarbonyl, $(C_2-C_6)$-haloalkenyloxycarbonyl, $(C_3-C_6)$-alkynyloxycarbonyl, $(C_3-C_6)$-haloalkynyloxycarbonyl, $(C_1-C_6)$-alkylcarbonyloxy, $(C_1-C_6)$-haloalkylcarbonyloxy, $(C_2-C_6)$-alkenylcarbonyloxy, $(C_2-C_6)$-haloalkenylcarbonyloxy, $(C_2-C_6)$-alkynylcarbonyloxy, $(C_2-C_6)$-haloalkynylcarbonyloxy or $(C_3-C_{14})$-cycloalkyl.

$M^5$ particularly preferably in each case independently of the others represents halogen, formyl, cyano, nitro, $(C_1-C_4)$-alkyl, $(C_1-C_4)$-haloalkyl, $(C_2-C_4)$-alkenyl, $(C_2-C_4)$-haloalkenyl, $(C_2-C_4)$-alkynyl, $(C_2-C_4)$-haloalkynyl, $(C_1-C_4)$-alkoxy, $(C_1-C_4)$-haloalkoxy, $(C_2-C_4)$-alkenyloxy, $(C_2-C_4)$-haloalkenyloxy, $(C_3-C_4)$-alkynyloxy, $(C_3-C_4)$-haloalkynyloxy, $(C_1-C_4)$-alkylthio, $(C_1-C_4)$-haloalkylthio, $(C_2-C_4)$-alkenylthio, $(C_2-C_4)$-haloalkenylthio, $(C_3-C_4)$-alkynylthio, $(C_3-C_4)$-haloalkynylthio, $(C_1-C_4)$-alkylsulphonyl, $(C_1-C_4)$-haloalkylsulphonyl, $(C_2-C_4)$-alkenylsulphonyl, $(C_2-C_4)$-haloalkenylsulphonyl, $(C_3-C_4)$-alkynylsulphonyl, $(C_3-C_4)$-haloalkynylsulphonyl, $(C_1-C_4)$-alkylsulphanyl, $(C_1-C_4)$-haloalkylsulphanyl, $(C_2-C_4)$-alkenylsulphanyl, $(C_2-C_4)$-haloalkenylsulphanyl, $(C_3-C_4)$-alkynylsulphanyl, $(C_3-C_4)$-haloalkynylsulphanyl, $(C_1-C_4)$-alkylcarbonyl, $(C_1-C_4)$-haloalkylcarbonyl, $(C_2-C_4)$-alkenylcarbonyl, $(C_2-C_4)$-haloalkenylcarbonyl, $(C_2-C_4)$-alkynylcarbonyl, $(C_2-C_4)$-haloalkynylcarbonyl, $(C_1-C_4)$-alkoxycarbonyl, $(C_1-C_4)$-haloalkoxycarbonyl, $(C_2-C_4)$-alkenyloxycarbonyl, $(C_2-C_4)$-haloalkenyloxycarbonyl, $(C_3-C_4)$-alkynyloxycarbonyl, $(C_3-C_4)$-haloalkynyloxycarbonyl, $(C_1-C_4)$-alkylcarbonyloxy, $(C_1-C_4)$-haloalkylcarbonyloxy, $(C_2-C_4)$-alkenylcarbonyloxy, $(C_2-C_4)$-haloalkenylcarbonyloxy, $(C_2-C_4)$-alkynylcarbonyloxy, $(C_2-C_4)$-haloalkynylcarbonyloxy or $(C_3-C_6)$-cycloalkyl.

$M^5$ very particularly preferably in each case independently of the others represents chlorine, fluorine, formyl, cyano, nitro, $(C_1-C_4)$-alkyl, $(C_1-C_4)$-haloalkyl, $(C_1-C_4)$-alkoxy, $(C_1-C_4)$-haloalkoxy, $(C_1-C_4)$-alkylthio, $(C_1-C_4)$-haloalkylthio, $(C_1-C_4)$-alkylsulphonyl, $(C_1-C_4)$-haloalkylsulphonyl, $(C_1-C_4)$-alkylsulphanyl, $(C_1-C_4)$-haloalkylsulphanyl, $(C_1-C_4)$-alkylcarbonyl, $(C_1-C_4)$-haloalkylcarbonyl or $(C_3-C_6)$-cycloalkyl.

$M^5$ very particularly preferably in each case independently of the others represents fluorine, bromine, chlorine, iodine, cyano, nitro, methyl, ethyl, isopropyl, tert-butyl, trifluoromethyl, difluoromethyl, methoxy, ethoxy, isopropoxy, trifluoromethoxy, difluoromethoxy, methylthio, trifluoromethylthio, difluoromethylthio, 2,2,2-trifluoroethylthio, methylsulphonyl, ethylsulphonyl, trifluoromethylsulphonyl, 2,2,2-trifluoroethylsulphonyl, methylsulphanyl, ethylsulphanyl, trifluoromethylsulphanyl, 2,2,2-trifluoroethylsulphanyl, cyclopropyl, cyclobutyl or cyclopentyl.

However, the general or preferred radical definitions or explanations given above can also be combined with one another as desired, i.e. including combinations between the respective ranges and preferred ranges. They apply both to the end products and, correspondingly, to precursors and intermediates.

The definitions mentioned can be combined with one another as desired. Moreover, individual definitions may not apply.

Preference, particular preference and very particular preference is given to compounds of the formula (I) which carry the substituents mentioned under preferred, particularly preferred, very particularly preferred or in particular very particularly preferred in each case.

Preference is furthermore given to compounds of the formula (I)

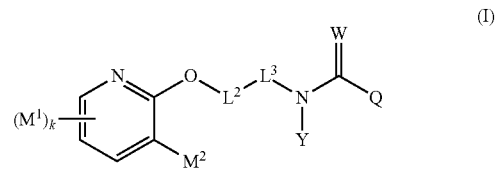

in which $M^1$, $M^2$, $M^3$, $M^4$, $M^5$, k, $L^2$, $L^3$, W and Y are as defined above and Q preferably represents the structural elements below, where n for each Q is in each case as defined below:

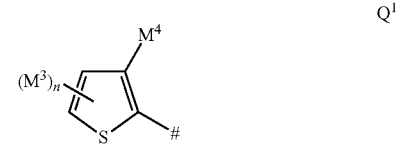

n = 1-2

n = 1-2

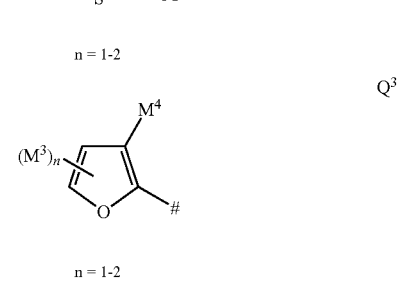

n = 1-2

-continued
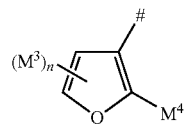
Q⁴
n = 1-2
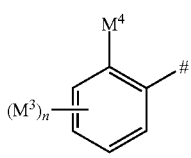
Q⁹
n = 1-4
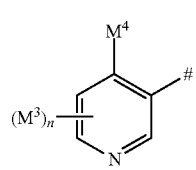
Q¹⁰
n = 1-3
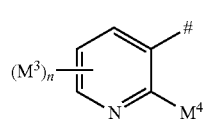
Q¹¹
n = 1-3
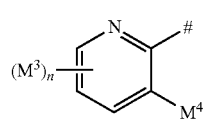
Q¹²
n - 1-3
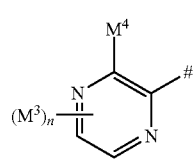
Q¹³
n = 1-2
Q preferably represents the structural elements below, where n for each Q is in each case as defined below:
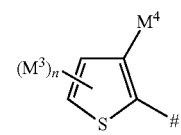
Q¹
n = 1-2
-continued
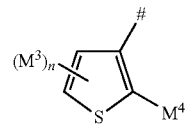
Q²
n = 1-2
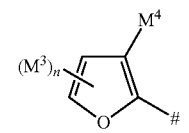
Q³
n = 1-2
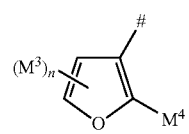
Q⁴
n = 1-2
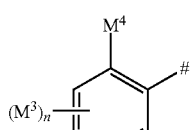
Q⁹
n = 1-4
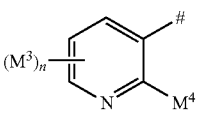
Q¹¹
n = 1-3
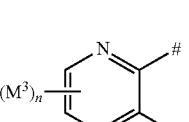
Q¹²
n = 1-3
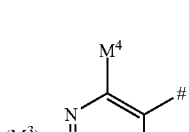
Q¹³
n = 1-2
Q preferably represents the structural elements below, where n for each Q is in each case as defined below:

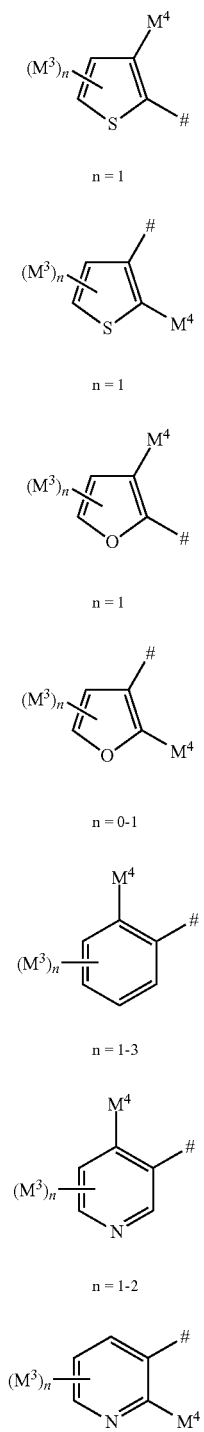
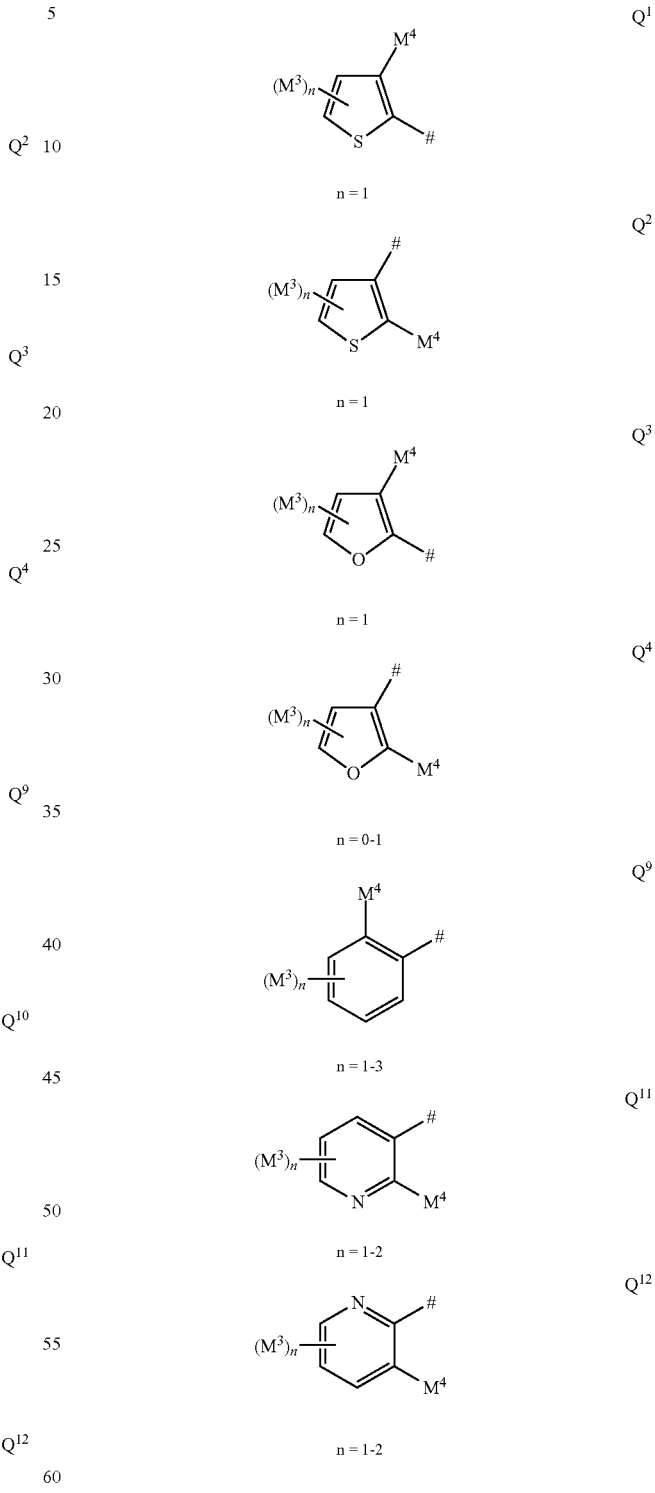

Q preferably represents the structural elements below, where n for each Q is in each case as defined below:

Q particularly preferably represents 2-thienyl, 3-fluoro-2-thienyl, 3-chloro-2-thienyl, 3,4-dichloro-2-thienyl, 2,5-dichloro-3-thienyl, 3,4,5-trichloro-2-thienyl, 3-bromo-2-thienyl, 3-iodo-2-thienyl, 3-cyano-2-thienyl, 3-methyl-2-thienyl, 3-(trifluoromethyl)-2-thienyl, 3-methoxy-2-thienyl, 3-ethoxy-2-thienyl, 3-thienyl, 2-fluoro-3-thienyl, 2-chloro-3-thienyl, 2-bromo-3-thienyl, 2-iodo-3-thienyl, 2-cyano-3-thienyl, 2-methyl-3-thienyl, 2-(trifluoromethyl)-3-thienyl, 2-methoxy-3-thienyl, 2-ethoxy-3-thienyl, 2-furanyl, 3-fluoro-2-furanyl, 3-chloro-2-furanyl, 3-bromo-2-furanyl, 3-iodo-2-furanyl, 3-cyano-2-furanyl, 3-methyl-2-furanyl, 3-(trifluoromethyl)-2-furanyl, 3-methoxy-2-furanyl, 3-ethoxy-2-furanyl, 3-furanyl, 2-chloro-3-furanyl, 2-bromo-3-furanyl, 2-iodo-3-furanyl, 2-cyano-3-furanyl, 2-methyl-3-furanyl, 2-(trifluoromethyl)-3-furanyl, 2-methoxy-3-furanyl, 2-ethoxy-3-furanyl, 2-methylphenyl, 2-fluorophenyl, 2,6-difluorophenyl, 2-chlorophenyl, 2,6-dichlorophenyl, 2-bromophenyl, 2-iodophenyl, 2-(difluoromethyl)phenyl, 2-(trifluoromethyl)phenyl, 2-(methylsulphanyl)phenyl, 2-(methylsulphonyl)phenyl, 2-(trifluoromethoxy)phenyl, 2-(trifluoromethylsulphanyl)phenyl, 2-(trifluoromethylsulphonyl)phenyl, 2-nitrophenyl, 2-chloro-3-pyridyl, 3-chloro-2-pyridyl, 2-(difluoromethyl)-3-pyridyl, 2-(trifluoromethyl)-3-pyridyl, 2-(methylsulphanyl)-3-pyridyl, 2-(methylsulphonyl)-3-pyridyl, 2-(trifluoromethoxy)-3-pyridyl, 2-(trifluoromethylsulphanyl)-3-pyridyl or 2-(trifluoromethylsulphonyl)-3-pyridyl;

Q particularly preferably represents 2-thienyl, 3-fluoro-2-thienyl, 3-chloro-2-thienyl, 3,4-dichloro-2-thienyl, 3,4,5-trichloro-2-thienyl, 3-bromo-2-thienyl, 3-iodo-2-thienyl, 3-cyano-2-thienyl, 3-methyl-2-thienyl, 3-(trifluoromethyl)-2-thienyl, 3-methoxy-2-thienyl, 3-ethoxy-2-thienyl, 3-thienyl, 2-fluoro-3-thienyl, 2-chloro-3-thienyl, 2-bromo-3-thienyl, 2-iodo-3-thienyl, 2-cyano-3-thienyl, 2-methyl-3-thienyl, 2-(trifluoromethyl)-3-thienyl, 2-methoxy-3-thienyl, 2-ethoxy-3-thienyl, 2-furanyl, 3-fluoro-2-furanyl, 3-chloro-2-furanyl, 3-bromo-2-furanyl, 3-iodo-2-furanyl, 3-cyano-2-furanyl, 3-methyl-2-furanyl, 3-(trifluoromethyl)-2-furanyl, 3-methoxy-2-furanyl, 3-ethoxy-2-furanyl, 3-furanyl, 2-chloro-3-furanyl, 2-bromo-3-furanyl, 2-iodo-3-furanyl, 2-cyano-3-furanyl, 2-methyl-3-furanyl, 2-(trifluoromethyl)-3-furanyl, 2-methoxy-3-furanyl, 2-ethoxy-3-furanyl, 2-methylphenyl, 2-fluorophenyl, 2,6-difluorophenyl, 2-chlorophenyl, 2,6-dichlorophenyl, 2-bromophenyl, 2-iodophenyl, 2-(difluoromethyl)phenyl, 2-(trifluoromethyl)phenyl, 2-nitrophenyl, 2-chloro-3-pyridyl, 3-chloro-2-pyridyl or 2-(trifluoromethyl)-3-pyridyl.

Preference is furthermore given to compounds of the formula (I)

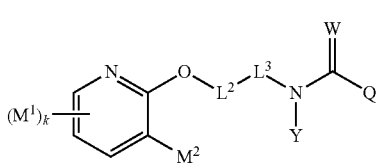

in which $M^1$, $M^2$, $M^3$, $M^4$, $M^5$, k, $L^2$, $L^3$, Q and W are as defined above and Y preferably represents hydrogen or represents optionally mono- or poly-$M^2$-substituted $(C_1-C_4)$-alkyl, $(C_2-C_4)$-alkenyl, $(C_3-C_4)$-alkynyl, $(C_1-C_4)$-haloalkyl, $(C_2-C_4)$-haloalkenyl, $(C_3-C_4)$-haloalkynyl, $(C_1-C_4)$-alkoxy, $(C_2-C_4)$-alkenyloxy, $(C_3-C_4)$-alkynyloxy, $(C_3-C_6)$-cycloalkyl-$(C_1-C_4)$-alkyl or represents an optionally substituted $C_3$- to $C_6$-membered carbocyclic group;

Y particularly preferably represents hydrogen, methyl, ethyl, n-propyl, isopropyl, n-butyl, sec-butyl, isobutyl, tert-butyl, cyanomethyl, 2,2-difluoroethyl, 2,2,2-trifluoroethyl, allyl, butenyl, propargyl, butynyl, 3,3-dichloroprop-2-enyl, methoxy, ethoxy, cyclopropylmethyl, cyclopropyl, cyclobutyl, cyclopentyl or cyclohexyl;

Y very particularly preferably represents hydrogen.

Preference is furthermore given to compounds of the formula (I)

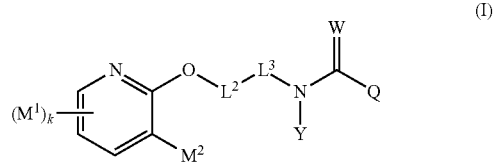

in which $M^1$, $M^2$, $M^3$, $M^4$, $M^5$, k, $L^2$, $L^3$, Q and Y are as defined above and W preferably represents oxygen.

Preference is furthermore given to compounds of the formula (I)

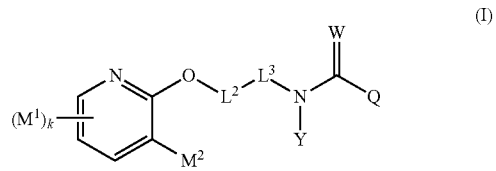

in which $M^1$, $M^2$, $M^3$, $M^4$, $M^5$, k, $L^3$, Q, W and Y are as defined above and $L^2$ preferably represents $C(R^{21}, R^{22})$, where $R^{21}$ and $R^{22}$ each independently of one another represent hydrogen, fluorine or optionally mono- or poly-$M^2$-substituted $(C_1-C_4)$-alkyl, $(C_3-C_4)$-alkenyl, $(C_3-C_4)$-alkynyl, $(C_1-C_4)$-haloalkyl, $(C_3-C_4)$-haloalkenyl, $(C_3-C_4)$-haloalkynyl, $(C_1-C_4)$-alkoxy, $(C_3-C_4)$-alkenyloxy, $(C_3-C_4)$-alkynyloxy, $(C_3-C_6)$-cycloalkyl-$(C_1-C_4)$-alkyl or represents an optionally substituted $C_3$- to $C_6$-membered carbocyclic group, or where $R^{21}$ and $R^{22}$ together represent an optionally substituted spiro-linked 3- to 6-membered cyclic group;

$L^2$ particularly preferably represents $C(R^{21}, R^{22})$ where $R^{21}$ and $R^{22}$ each independently of one another represent hydrogen, fluorine, methyl, ethyl, n-propyl, isopropyl, allyl, propargyl, methoxy, ethoxy, allyloxy, propargyloxy, cyclopropylmethyl, cyclopropyl, or where $C(R^{21}, R^{22})$ represents spiro-$C(CH_2—CH_2)$.

Preference is furthermore given to compounds of the formula (I)

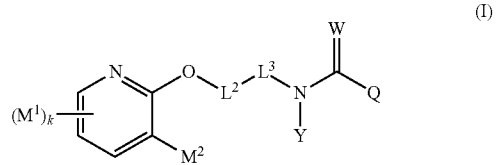

in which $M^1$, $M^2$, $M^3$, $M^4$, $M^5$, k, $L^2$, Q, W and Y are as defined above and $L^3$ preferably represents $C(R^{31}, R^{32})$, where $R^{31}$ and $R^{32}$ each independently of one another represent hydrogen, fluorine or optionally mono- or poly-$M^2$-substituted $(C_1-C_4)$-alkyl, $(C_3-C_4)$-alkenyl, $(C_3-C_4)$-alkynyl, $(C_1-C_4)$-haloalkyl, (C₃-C₄)-haloalkenyl, (C₃-C₄)-haloalkynyl, (C₁-C₄)-alkoxy, (C₃-C₄)-alkenyloxy, (C₃-C₄)-alkynyloxy, (C₃-C₆)-cycloalkyl-(C₁-C₄)-alkyl or represents an optionally substituted C₃- to C₆-membered carbocyclic group, or where R³¹ and R³² together represent an optionally substituted spiro-linked 3- to 6-membered cyclic group;

L³ particularly preferably represents C(R³¹, R³²) where R³¹ and R³² each independently of one another represent hydrogen, methyl, ethyl, n-propyl, isopropyl, allyl, propargyl, methoxy, ethoxy, allyloxy, propargyloxy, cyclopropylmethyl, cyclopropyl, or where C(R³¹, R³²) represents spiro-C(CH₂—CH₂);

and salts, N-oxides and tautomeric forms of the compounds of the formula (I).

Very particular preference is furthermore given to compounds of the formula (I)

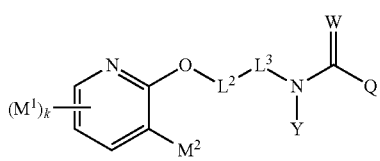

in which

Q represents 2-thienyl, 3-fluoro-2-thienyl, 3-chloro-2-thienyl, 3,4-dichloro-2-thienyl, 3,4,5-trichloro-2-thienyl, 3-bromo-2-thienyl, 3-iodo-2-thienyl, 3-cyano-2-thienyl, 3-methyl-2-thienyl, 3-(trifluoromethyl)-2-thienyl, 3-methoxy-2-thienyl, 3-ethoxy-2-thienyl, 3-thienyl, 2-fluoro-3-thienyl, 2-chloro-3-thienyl, 2-bromo-3-thienyl, 2-iodo-3-thienyl, 2-cyano-3-thienyl, 2-methyl-3-thienyl, 2-(trifluoromethyl)-3-thienyl, 2-methoxy-3-thienyl, 2-ethoxy-3-thienyl, 2-furanyl, 3-fluoro-2-furanyl, 3-chloro-2-furanyl, 3-bromo-2-furanyl, 3-iodo-2-furanyl, 3-cyano-2-furanyl, 3-methyl-2-furanyl, 3-(trifluoromethyl)-2-furanyl, 3-methoxy-2-furanyl, 3-ethoxy-2-furanyl, 3-furanyl, 2-chloro-3-furanyl, 2-bromo-3-furanyl, 2-iodo-3-furanyl, 2-cyano-3-furanyl, 2-methyl-3-furanyl, 2-(trifluoromethyl)-3-furanyl, 2-methoxy-3-furanyl, 2-ethoxy-3-furanyl, 2-methylphenyl, 2-fluorophenyl, 2,6-difluorophenyl, 2-chlorophenyl, 2,6-dichlorophenyl, 2-bromophenyl, 2-iodophenyl, 2-(difluoromethyl)phenyl, 2-(trifluoromethyl)phenyl, 2-nitrophenyl, 2-chloro-3-pyridyl, 3-chloro-2-pyridyl or 2-(trifluoromethyl)-3-pyridyl;

Y represents hydrogen, methyl, ethyl, n-propyl, isopropyl, n-butyl, sec-butyl, isobutyl, tert-butyl, cyanomethyl, 2,2-difluoroethyl, 2,2,2-trifluoroethyl, allyl, butenyl, propargyl, butynyl, 3,3-dichloroprop-2-enyl, methoxy, ethoxy, cyclopropylmethyl, cyclopropyl, cyclobutyl, cyclopentyl or cyclohexyl;

W represents oxygen;

L² represents C(R²¹, R²²) where R²¹ and R²² each independently of one another represent hydrogen, fluorine, methyl, ethyl, n-propyl, isopropyl, allyl, propargyl, methoxy, ethoxy, allyloxy, propargyloxy, cyclopropylmethyl, cyclopropyl, or where C(R²¹, R²²) represents spiro-C(CH₂—CH₂);

L³ represents C(R³¹, R³²) where R³¹ and R³² each independently of one another represent hydrogen, methyl, ethyl, n-propyl, isopropyl, allyl, propargyl, methoxy, ethoxy, allyloxy, propargyloxy, cyclopropylmethyl, cyclopropyl, or where C(R³¹, R³²) represents spiro-C(CH₂—CH₂);

k represents 1 and

M¹ and M² each independently of one another represent hydrogen, fluorine, bromine, chlorine, iodine, cyano, methyl, trifluoromethyl, difluoromethyl, methoxy, ethoxy, isopropoxy or phenoxy;

and salts, N-oxides and tautomeric forms of the compounds of the formula (I).

Very particular preference is furthermore given to compounds of the formula (I)

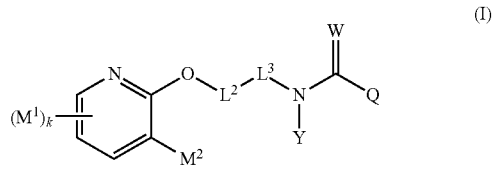

in which

Q represents the structural elements below, where n for each Q is in each case as defined below:

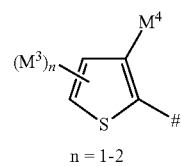

n = 1-2

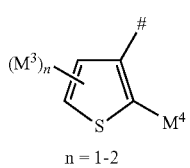

n = 1-2

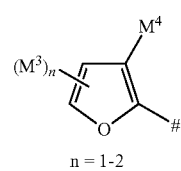

n = 1-2

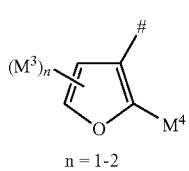

n = 1-2

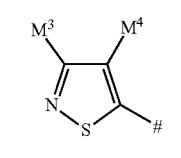

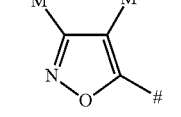

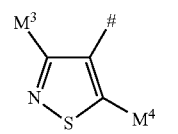

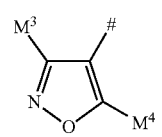

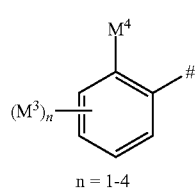
n = 1-4

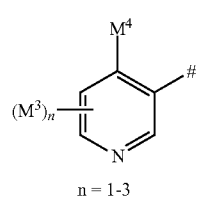
n = 1-3

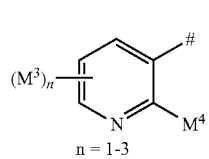
n = 1-3

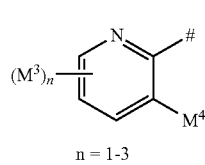
n = 1-3

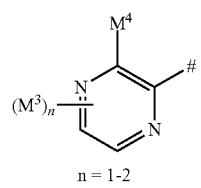
n = 1-2

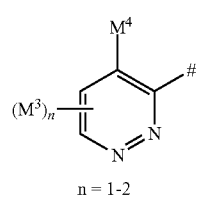
n = 1-2

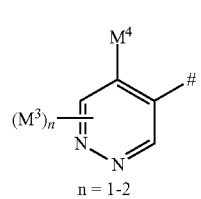
n = 1-2

Q⁷

Q⁸

Q⁹

Q¹⁰

Q¹¹

Q¹²

Q¹³

Q¹⁴

Q¹⁵

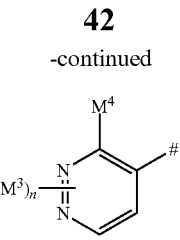
n = 1-2

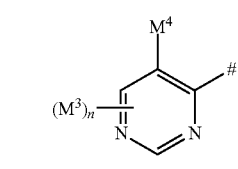
n = 1-2

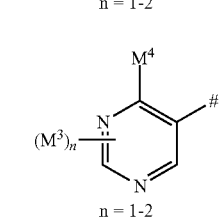
n = 1-2

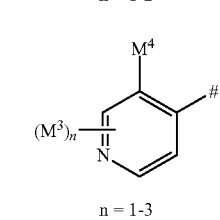
n = 1-3

Q¹⁶

Q¹⁷

Q¹⁸

Q¹⁹

Y represents hydrogen or represents optionally mono- or poly-$M^2$-substituted ($C_1$-$C_{10}$)-alkyl, ($C_2$-$C_{10}$)-alkenyl, ($C_2$-$C_{10}$)-alkynyl, ($C_1$-$C_{10}$)-haloalkyl, ($C_2$-$C_{10}$)-haloalkenyl, ($C_2$-$C_{10}$)-haloalkynyl, ($C_1$-$C_{10}$)-alkoxy, ($C_2$-$C_{10}$)-alkenyloxy, ($C_3$-$C_{10}$)-alkynyloxy, ($C_3$-$C_{14}$)-cycloalkyl-($C_1$-$C_{10}$)-alkyl or represents an optionally mono- or poly-$M^2$-substituted 3- to 14-membered cyclic group;

W represents oxygen or sulphur;

$L^2$ represents —C($R^{21}$, $R^{22}$)—;

$L^3$ represents —C($R^{31}$, $R^{32}$)—;

$M^1$, $M^2$ and $M^3$ each independently of one another represent hydrogen, halogen, cyano, nitro, OH, ($C_1$-$C_{10}$)-alkyl, ($C_1$-$C_{10}$)-haloalkyl, ($C_1$-$C_{10}$)-alkoxy, ($C_1$-$C_{10}$)-haloalkoxy, ($C_1$-$C_{10}$)-alkylthio, ($C_1$-$C_{10}$)-haloalkylthio, ($C_1$-$C_{10}$)-alkylsulphonyl, ($C_1$-$C_{10}$)-haloalkylsulphonyl, ($C_1$-$C_{10}$)-alkylsulphanyl, ($C_1$-$C_{10}$)-haloalkylsulphanyl or (3- to 14-membered cyclic group)-O—, where, if Q corresponds to $Q^{11}$, $M^3$ is not ($C_1$-$C_4$)-haloalkyl in position 4 at the pyridyl;

$M^4$ represents hydrogen, halogen, cyano, nitro, OH, ($C_1$-$C_{10}$)-alkyl, ($C_1$-$C_{10}$)-haloalkyl, ($C_1$-$C_{10}$)-alkoxy, ($C_1$-$C_{10}$)-haloalkoxy, ($C_1$-$C_{10}$)-alkylthio, ($C_1$-$C_{10}$)-haloalkylthio, ($C_1$-$C_{10}$)-alkylsulphonyl, ($C_1$-$C_{10}$)-haloalkylsulphonyl, ($C_1$-$C_{10}$)-alkylsulphanyl, ($C_1$-$C_{10}$)-haloalkylsulphanyl, or (3- to 14-membered cyclic group)-O—, where, if Q corresponds to $Q^{10}$, $M^4$ is not ($C_1$-$C_4$)-haloalkyl;

k represents 1, 2 or 3;

$R^{21}$, $R^{22}$ each independently of one another represent hydrogen, halogen or optionally mono- or poly-$M^2$-substituted ($C_1$-$C_{10}$)-alkyl, ($C_2$-$C_{10}$)-alkenyl, ($C_2$-$C_{10}$)-alkynyl, ($C_1$-$C_{10}$)-haloalkyl, ($C_2$-$C_{10}$)-haloalkenyl, ($C_2$-$C_{10}$)-haloalkynyl, ($C_1$-$C_{10}$)-alkoxy, ($C_1$-$C_{10}$)-haloalkoxy, ($C_2$-$C_{10}$)-alkenyloxy, ($C_3$-$C_{10}$)-alkynyloxy, ($C_3$-$C_{14}$)-cycloalkyl-($C_1$-$C_{10}$)-alkyl or represent an optionally mono- or poly-$M^2$-substituted 3- to 14-membered cyclic group;

$R^{21}$, $R^{22}$ together represent an optionally mono- or poly-$M^2$-substituted spiro-attached 3- to 14-membered carbo- or 3- to 10-membered heterocyclic group;

$R^{31}$, $R^{32}$ each independently of one another represent hydrogen, halogen or optionally mono- or poly-$M^2$-substituted ($C_1$-$C_{10}$)-alkyl, ($C_2$-$C_{10}$)-alkenyl, ($C_2$-$C_{10}$)-alkynyl, ($C_1$-$C_{10}$)-haloalkyl, ($C_2$-$C_{10}$)-haloalkenyl, ($C_2$-$C_{10}$)-haloalkynyl, ($C_3$-$C_{14}$)-cycloalkyl-($C_1$-$C_{10}$)-alkyl or represent an optionally mono- or poly-$M^2$-substituted 3- to 14-membered cyclic group;

$R^{31}$, $R^{32}$ together represent an optionally mono- or poly-$M^5$-substituted spiro-attached 3- to 14-membered carbo- or 3- to 10-membered heterocyclic group;

$M^5$ in each case independently of the others represents halogen, formyl, cyano, nitro, ($C_1$-$C_{10}$)-alkyl, ($C_1$-$C_{10}$)-haloalkyl, ($C_2$-$C_{10}$)-alkenyl, ($C_2$-$C_{10}$)-haloalkenyl, ($C_2$-$C_{10}$)-alkynyl, ($C_2$-$C_{10}$)-haloalkynyl, ($C_1$-$C_{10}$)-alkoxy, ($C_1$-$C_{10}$)-haloalkoxy, ($C_2$-$C_{10}$)-alkenyloxy, ($C_2$-$C_{10}$)-haloalkenyloxy, ($C_3$-$C_{10}$)-alkynyloxy, ($C_3$-$C_{10}$)-haloalkynyloxy, ($C_1$-$C_{10}$)-alkylthio, ($C_1$-$C_{10}$)-haloalkylthio, ($C_2$-$C_{10}$)-alkenylthio, ($C_2$-$C_{10}$)-haloalkenylthio, ($C_3$-$C_{10}$)-alkynylthio, ($C_3$-$C_{10}$)-haloalkynylthio, ($C_1$-$C_{10}$)-alkylsulphonyl, ($C_1$-$C_{10}$)-haloalkylsulphonyl, ($C_2$-$C_{10}$)-alkenylsulphonyl, ($C_2$-$C_{10}$)-haloalkenylsulphonyl, ($C_3$-$C_{10}$)-alkynylsulphonyl, ($C_3$-$C_{10}$)-haloalkynylsulphonyl, ($C_1$-$C_{10}$)-alkylsulphanyl, ($C_1$-$C_{10}$)-haloalkylsulphanyl, ($C_2$-$C_{10}$)-alkenylsulphanyl, ($C_2$-$C_{10}$)-haloalkenylsulphanyl, ($C_3$-$C_{10}$)-alkynylsulphanyl, ($C_3$-$C_{10}$)-haloalkynylsulphanyl, ($C_1$-$C_{10}$)-alkylcarbonyl, ($C_1$-$C_{10}$)-haloalkylcarbonyl, ($C_2$-$C_{10}$)-alkenylcarbonyl, ($C_2$-$C_{10}$)-haloalkenylcarbonyl, ($C_2$-$C_{10}$)-alkynylcarbonyl, ($C_2$-$C_{10}$)-haloalkynylcarbonyl, ($C_1$-$C_{10}$)-alkoxycarbonyl, ($C_1$-$C_{10}$)-haloalkoxycarbonyl, ($C_2$-$C_{10}$)-alkenyloxycarbonyl, ($C_2$-$C_{10}$)-haloalkenyloxycarbonyl, ($C_3$-$C_{10}$)-alkynyloxycarbonyl, ($C_3$-$C_{10}$)-haloalkynyloxycarbonyl, ($C_1$-$C_{10}$)-alkylcarbonyloxy, ($C_1$-$C_{10}$)-haloalkylcarbonyloxy, ($C_2$-$C_{10}$)-alkenylcarbonyloxy, ($C_2$-$C_{10}$)-haloalkenylcarbonyloxy, ($C_2$-$C_{10}$)-alkynylcarbonyloxy, ($C_2$-$C_{10}$)-haloalkynylcarbonyloxy, a 3- to 14-membered cyclic group;

and salts, N-oxides and tautomeric forms of the compounds of the formula (I).

Very particular preference is furthermore given to compounds of the formula (I)

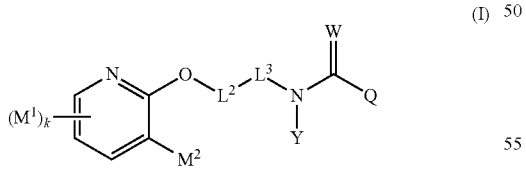

in which

Q represents 2-thienyl, 3-fluoro-2-thienyl, 3-chloro-2-thienyl, 3,4-dichloro-2-thienyl, 2,5-dichloro-3-thienyl, 3,4,5-trichloro-2-thienyl, 3-bromo-2-thienyl, 3-iodo-2-thienyl, 3-cyano-2-thienyl, 3-methyl-2-thienyl, 3-(trifluoromethyl)-2-thienyl, 3-methoxy-2-thienyl, 3-ethoxy-2-thienyl, 3-thienyl, 2-fluoro-3-thienyl, 2-chloro-3-thienyl, 2-bromo-3-thienyl, 2-iodo-3-thienyl, 2-cyano-3-thienyl, 2-methyl-3-thienyl, 2-(trifluoromethyl)-3-thienyl, 2-methoxy-3-thienyl, 2-ethoxy-3-thienyl, 2-furanyl, 3-fluoro-2-furanyl, 3-chloro-2-furanyl, 3-bromo-2-furanyl, 3-iodo-2-furanyl, 3-cyano-2-furanyl, 3-methyl-2-furanyl, 3-(trifluoromethyl)-2-furanyl, 3-methoxy-2-furanyl, 3-ethoxy-2-furanyl, 3-furanyl, 2-chloro-3-furanyl, 2-bromo-3-furanyl, 2-iodo-3-furanyl, 2-cyano-3-furanyl, 2-methyl-3-furanyl, 2-(trifluoromethyl)-3-furanyl, 2-methoxy-3-furanyl, 2-ethoxy-3-furanyl, 2-methylphenyl, 2-fluorophenyl, 2,6-difluorophenyl, 2-chlorophenyl, 2,6-dichlorophenyl, 2-bromophenyl, 2-iodophenyl, 2-(difluoromethyl)phenyl, 2-(trifluoromethyl)phenyl, 2-(methylsulphanyl)phenyl, 2-(methylsulphonyl)phenyl, 2-(trifluoromethoxy)phenyl, 2-(trifluoromethylsulphanyl)phenyl, 2-(trifluoromethylsulphonyl)phenyl, 2-nitrophenyl, 2-chloro-3-pyridyl, 3-chloro-2-pyridyl, 2-(difluoromethyl)-3-pyridyl, 2-(trifluoromethyl)-3-pyridyl, 2-(methylsulphanyl)-3-pyridyl, 2-(methylsulphonyl)-3-pyridyl, 2-(trifluoromethoxy)-3-pyridyl, 2-(trifluoromethylsulphanyl)-3-pyridyl or 2-(trifluoromethylsulphonyl)-3-pyridyl;

Y represents hydrogen, methyl, ethyl, n-propyl, isopropyl, n-butyl, sec-butyl, isobutyl, tert-butyl, cyanomethyl, 2,2-difluoroethyl, 2,2,2-trifluoroethyl, allyl, butenyl, propargyl, butynyl, 3,3-dichloroprop-2-enyl, methoxy, ethoxy, cyclopropylmethyl, cyclopropyl, cyclobutyl, cyclopentyl or cyclohexyl;

W represents oxygen;

$L^2$ represents $C(R^{21}, R^{22})$ where $R^{21}$ and $R^{22}$ each independently of one another represent hydrogen, fluorine, methyl, ethyl, n-propyl, isopropyl, allyl, propargyl, methoxy, ethoxy, allyloxy, propargyloxy, cyclopropylmethyl, cyclopropyl, or where $C(R^{21}, R^{22})$ represents spiro-$C(CH_2—CH_2)$;

$L^3$ represents $C(R^{31}, R^{32})$ where $R^{31}$ and $R^{32}$ each independently of one another represent hydrogen, methyl, ethyl, n-propyl, isopropyl, allyl, propargyl, methoxy, ethoxy, allyloxy, propargyloxy, cyclopropylmethyl, cyclopropyl, or where $C(R^{31}, R^{32})$ represents spiro-$C(CH_2—CH_2)$;

k represents 1 and $M^1$ and $M^2$ each independently of one another represent hydrogen, fluorine, bromine, chlorine, iodine, cyano, methyl, trifluoromethyl, difluoromethyl, methoxy, ethoxy, isopropoxy or phenoxy;

and salts, N-oxides and tautomeric forms of the compounds of the formula (I).

Very particular preference is furthermore given to compounds of the formula (I)

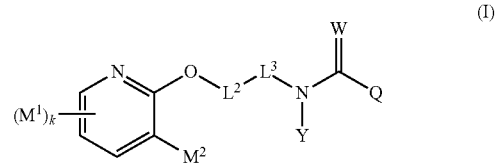

in which

Q represents 2-thienyl, 3-fluoro-2-thienyl, 3-chloro-2-thienyl, 3,4-dichloro-2-thienyl, 2,5-dichloro-3-thienyl, 3,4,5-trichloro-2-thienyl, 3-bromo-2-thienyl, 3-iodo-2-thienyl, 3-cyano-2-thienyl, 3-methyl-2-thienyl, 3-(trifluoromethyl)-2-thienyl, 3-methoxy-2-thienyl, 3-ethoxy-2-thienyl, 3-thienyl, 2-fluoro-3-thienyl, 2-chloro-3-thienyl, 2-bromo-3-thienyl, 2-iodo-3-thienyl, 2-cyano-3-thienyl, 2-methyl-3-thienyl, 2-(trifluoromethyl)-3-thienyl, 2-methoxy-3-thienyl, 2-ethoxy-3-thienyl, 2-furanyl, 3-fluoro-2-furanyl, 3-chloro-2-furanyl, 3-bromo-2-furanyl, 3-iodo-2-furanyl, 3-cyano-2-furanyl, 3-methyl-2-furanyl, 3-(trifluoromethyl)-2-furanyl, 3-methoxy-2-furanyl, 3-ethoxy-2-furanyl, 3-furanyl, 2-chloro-3-furanyl, 2-bromo-3-furanyl, 2-iodo-3-furanyl, 2-cyano-3-furanyl, 2-methyl-3-furanyl, 2-(trifluoromethyl)-3-furanyl, 2-methoxy-3-furanyl, 2-ethoxy-3-furanyl, 2-methylphenyl, 2-fluorophenyl, 2,6-difluorophenyl, 2-chlorophenyl, 2,6-dichlorophenyl, 2-bromophenyl, 2-iodophenyl, 2-(difluoromethyl)phenyl, 2-(trifluoromethyl)phenyl, 2-(methylsulphanyl)phenyl, 2-(methylsulphonyl)phenyl, 2-(trifluoromethoxy)phenyl, 2-(trifluoromethylsulphanyl)phenyl, 2-(trifluoromethylsulphonyl)phenyl, 2-nitrophenyl, 2-chloro-3-pyridyl, 3-chloro-2-pyridyl, 2-(difluoromethyl)-3-pyridyl, 2-(trifluoromethyl)-3-pyridyl, 2-(methylsulphanyl)-3-pyridyl, 2-(methylsulphonyl)-3-pyridyl, 2-(trifluoromethoxy)-3-pyridyl, 2-(trifluoromethylsulphanyl)-3-pyridyl or 2-(trifluoromethylsulphonyl)-3-pyridyl;

Y represents hydrogen;

W represents oxygen;

$L^2$ represents $C(R^{21}, R^{22})$, where $R^{21}$ and $R^{22}$ each independently of one another represent hydrogen, methyl, cyclopropyl;

$L^3$ represents $C(R^{31}, R^{32})$, where $R^{31}$ and $R^{32}$ each independently of one another represent hydrogen, methyl, ethyl, n-propyl, isopropyl, or where $C(R^{31}, R^{32})$ represents 1,1-cyclopropyl;

k represents 1 and $M^1$ and $M^2$ each independently of one another represent hydrogen, fluorine, bromine, chlorine, cyano, trifluoromethyl, difluoromethyl or nitro;

and salts, N-oxides and tautomeric forms of the compounds of the formula (I).

Very particular preference is given to compounds of the formula (I)

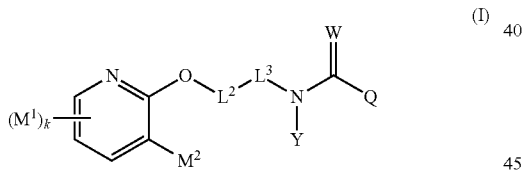

(I)

where

Q represents the structural elements below, where n for each Q is in each case as defined below:

$Q^1$

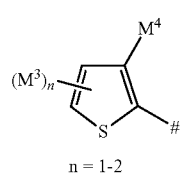

n = 1-2

$Q^2$

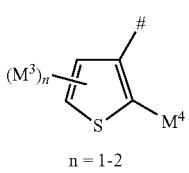

n = 1-2

$Q^3$

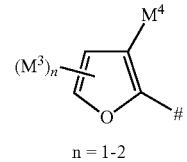

n = 1-2

$Q^4$

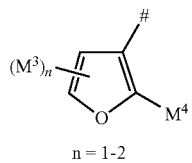

n = 1-2

$Q^9$

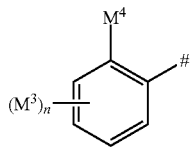

n = 1-4

$Q^{10}$

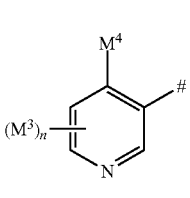

n = 1-3

$Q^{11}$

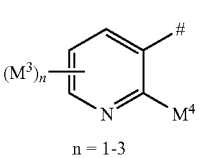

n = 1-3

$Q^{12}$

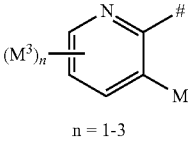

n = 1-3

$Q^{13}$

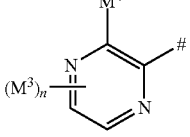

n = 1-2

Y represents hydrogen or represents optionally mono- or poly-$M^2$-substituted $(C_1-C_6)$-alkyl, $(C_2-C_6)$-alkenyl, $(C_2-C_6)$-alkynyl, $(C_1-C_6)$-haloalkyl, $(C_2-C_6)$-haloalkenyl, $(C_2-C_6)$-haloalkynyl, $(C_1-C_6)$-alkoxy, $(C_2-C_6)$-alkenyloxy, $(C_3-C_6)$-alkynyloxy, $(C_3-C_{10})$-cycloalkyl-$(C_1-C_6)$-alkyl or represents an optionally mono- or poly-$M^2$-substituted 3- to 10-membered cyclic group;

W represents oxygen;

$M^1$, $M^2$ and $M^3$ each independently of one another preferably represent hydrogen, halogen, cyano, nitro, OH, $(C_1-C_6)$-alkyl, $(C_1-C_6)$-haloalkyl, $(C_1-C_6)$-alkoxy, $(C_1-C_6)$-haloalkoxy, $(C_1-C_6)$-alkylthio, $(C_1-C_6)$-haloalkylthio, $(C_1-C_6)$-alkylsulphonyl, $(C_1-C_6)$-haloalkylsulphonyl, ($C_1$-$C_6$)-alkylsulphanyl, ($C_1$-$C_6$)-haloalkylsulphanyl, ($C_3$-$C_{14}$)-cycloalkyl-O—, ($C_3$-$C_{14}$)-cycloalkenyl-O—, ($C_6$-$C_{14}$)-aryl-O—, halogenated ($C_3$-$C_{14}$)-cycloalkyl-O—, halogenated ($C_3$-$C_{14}$)-cycloalkenyl-O—, halogenated ($C_6$-$C_{14}$)-aryl-O—, where, if Q corresponds to $Q^{11}$, $M^3$ is not ($C_1$-$C_4$)-haloalkyl in position 4 at the pyridyl;

$M^4$ represents hydrogen, halogen, cyano, nitro, OH, ($C_1$-$C_6$)-alkyl, ($C_1$-$C_6$)-haloalkyl, ($C_1$-$C_6$)-alkoxy, ($C_1$-$C_6$)-haloalkoxy, ($C_1$-$C_6$)-alkylthio, ($C_1$-$C_6$)-haloalkylthio, ($C_1$-$C_6$)-alkylsulphonyl, ($C_1$-$C_6$)-haloalkylsulphonyl, ($C_1$-$C_6$)-alkylsulphanyl, ($C_1$-$C_6$)-haloalkylsulphanyl, ($C_3$-$C_{14}$)-cycloalkyl-O—, ($C_3$-$C_{14}$)-cycloalkenyl-O—, ($C_6$-$C_{14}$)-aryl-O—, halogenated ($C_3$-$C_{14}$)-cycloalkyl-O—, halogenated ($C_3$-$C_{14}$)-cycloalkenyl-O—, halogenated ($C_6$-$C_{14}$)-aryl-O—, where, if Q corresponds to $Q^{10}$, $M^4$ is not ($C_1$-$C_4$)-haloalkyl;

$M^5$ in each case independently of the others represents halogen, formyl, cyano, nitro, ($C_1$-$C_6$)-alkyl, ($C_1$-$C_6$)-haloalkyl, ($C_2$-$C_6$)-alkenyl, ($C_2$-$C_6$)-haloalkenyl, ($C_2$-$C_6$)-alkynyl, ($C_2$-$C_6$)-haloalkynyl, ($C_1$-$C_6$)-alkoxy, ($C_1$-$C_6$)-haloalkoxy, ($C_2$-$C_4$)-alkenyloxy, ($C_2$-$C_6$)-haloalkenyloxy, ($C_3$-$C_6$)-alkynyloxy, ($C_3$-$C_6$)-haloalkynyloxy, ($C_1$-$C_6$)-alkylthio, ($C_1$-$C_6$)-haloalkylthio, ($C_2$-$C_6$)-alkenylthio, ($C_2$-$C_6$)-haloalkenylthio, ($C_3$-$C_6$)-alkynylthio, ($C_3$-$C_6$)-haloalkynylthio, ($C_1$-$C_6$)-alkylsulphonyl, ($C_1$-$C_6$)-haloalkylsulphonyl, ($C_2$-$C_6$)-alkenylsulphonyl, ($C_2$-$C_6$)-haloalkenylsulphonyl, ($C_3$-$C_6$)-alkynylsulphonyl, ($C_3$-$C_6$)-haloalkynylsulphonyl, ($C_1$-$C_6$)-alkylsulphanyl, ($C_1$-$C_6$)-haloalkylsulphanyl, ($C_2$-$C_6$)-alkenylsulphanyl, ($C_2$-$C_6$)-haloalkenylsulphanyl, ($C_3$-$C_6$)-alkynylsulphanyl, ($C_3$-$C_6$)-haloalkynylsulphanyl, ($C_1$-$C_6$)-alkylcarbonyl, ($C_1$-$C_6$)-haloalkylcarbonyl, ($C_2$-$C_6$)-alkenylcarbonyl, ($C_2$-$C_6$)-haloalkenylcarbonyl, ($C_2$-$C_6$)-alkynylcarbonyl, ($C_2$-$C_6$)-haloalkynylcarbonyl, ($C_1$-$C_6$)-alkoxycarbonyl, ($C_1$-$C_6$)-haloalkoxycarbonyl, ($C_2$-$C_6$)-alkenyloxycarbonyl, ($C_2$-$C_6$)-haloalkenyloxycarbonyl, ($C_3$-$C_6$)-alkynyloxycarbonyl, ($C_3$-$C_6$)-haloalkynyloxycarbonyl, ($C_1$-$C_6$)-alkylcarbonyloxy, ($C_1$-$C_6$)-haloalkylcarbonyloxy, ($C_2$-$C_6$)-alkenylcarbonyloxy, ($C_2$-$C_6$)-haloalkenylcarbonyloxy, ($C_2$-$C_6$)-alkynylcarbonyloxy, ($C_2$-$C_6$)-haloalkynylcarbonyloxy or ($C_3$-$C_{14}$)-cycloalkyl.

k represents 1 or 2;

$R^{21}$, $R^{22}$ each independently of one another represent hydrogen, fluorine or optionally mono- or poly-$M^2$-substituted ($C_1$-$C_6$)-alkyl, ($C_2$-$C_6$)-alkenyl, ($C_2$-$C_6$)-alkynyl, ($C_1$-$C_6$)-haloalkyl, ($C_2$-$C_6$)-haloalkenyl, ($C_2$-$C_6$)-haloalkynyl, ($C_1$-$C_6$)-alkoxy, ($C_1$-$C_6$)-haloalkoxy, ($C_2$-$C_6$)-alkenyloxy, ($C_3$-$C_6$)-alkynyloxy, ($C_3$-$C_6$)-cycloalkyl-($C_1$-$C_6$)-alkyl or represent an optionally mono- or poly-$M^2$-substituted ($C_3$-$C_{14}$)-carbocyclic group; or $R^{21}$, $R^{22}$ represents $C(R^{21}, R^{22})$ as spiro-$C(CH_2$—$CH_2)$;

$R^{31}$, $R^{32}$ each independently of one another represent hydrogen, fluorine or optionally mono- or poly-$M^2$-substituted ($C_1$-$C_6$)-alkyl, ($C_2$-$C_6$)-alkenyl, ($C_2$-$C_6$)-alkynyl, ($C_1$-$C_6$)-haloalkyl, ($C_2$-$C_6$)-haloalkenyl, ($C_2$-$C_6$)-haloalkynyl, ($C_1$-$C_6$)-alkoxy, ($C_1$-$C_6$)-haloalkoxy, ($C_2$-$C_6$)-alkenyloxy, ($C_3$-$C_6$)-alkynyloxy, ($C_3$-$C_6$)-cycloalkyl-($C_1$-$C_6$)-alkyl or represent an optionally mono- or poly-$M^2$-substituted ($C_3$-$C_{14}$)-carbocyclic group; or $R^{31}$, $R^{32}$ represents $C(R^{31}, R^{32})$ as spiro-$C(CH_2$—$CH_2)$;

$M^5$ in each case independently of the others represents halogen, formyl, cyano, nitro, ($C_1$-$C_6$)-alkyl, ($C_1$-$C_6$)-haloalkyl, ($C_2$-$C_6$)-alkenyl, ($C_2$-$C_6$)-haloalkenyl, ($C_2$-$C_6$)-alkynyl, ($C_2$-$C_6$)-haloalkynyl, ($C_1$-$C_6$)-alkoxy, ($C_1$-$C_6$)-haloalkoxy, ($C_2$-$C_4$)-alkenyloxy, ($C_2$-$C_6$)-haloalkenyloxy, ($C_3$-$C_6$)-alkynyloxy, ($C_3$-$C_6$)-haloalkynyloxy, ($C_1$-$C_6$)-alkylthio, ($C_1$-$C_6$)-haloalkylthio, ($C_2$-$C_6$)-alkenylthio, ($C_2$-$C_6$)-haloalkenylthio, ($C_3$-$C_6$)-alkynylthio, ($C_3$-$C_6$)-haloalkynylthio, ($C_1$-$C_6$)-alkylsulphonyl, ($C_1$-$C_6$)-haloalkylsulphonyl, ($C_2$-$C_6$)-alkenylsulphonyl, ($C_2$-$C_6$)-haloalkenylsulphonyl, ($C_3$-$C_6$)-alkynylsulphonyl, ($C_3$-$C_6$)-haloalkynylsulphonyl, ($C_1$-$C_6$)-alkylsulphanyl, ($C_1$-$C_6$)-haloalkylsulphanyl, ($C_2$-$C_6$)-alkenylsulphanyl, ($C_2$-$C_6$)-haloalkenylsulphanyl, ($C_3$-$C_6$)-alkynylsulphanyl, ($C_3$-$C_6$)-haloalkynylsulphanyl, ($C_1$-$C_6$)-alkylcarbonyl, ($C_1$-$C_6$)-haloalkylcarbonyl, ($C_2$-$C_6$)-alkenylcarbonyl, ($C_2$-$C_6$)-haloalkenylcarbonyl, ($C_2$-$C_6$)-alkynylcarbonyl, ($C_2$-$C_6$)-haloalkynylcarbonyl, ($C_1$-$C_6$)-alkoxycarbonyl, ($C_1$-$C_6$)-haloalkoxycarbonyl, ($C_2$-$C_6$)-alkenyloxycarbonyl, ($C_2$-$C_6$)-haloalkenyloxycarbonyl, ($C_3$-$C_6$)-alkynyloxycarbonyl, ($C_3$-$C_6$)-haloalkynyloxycarbonyl, ($C_1$-$C_6$)-alkylcarbonyloxy, ($C_1$-$C_6$)-haloalkylcarbonyloxy, ($C_2$-$C_6$)-alkenylcarbonyloxy, ($C_2$-$C_6$)-haloalkenylcarbonyloxy, ($C_2$-$C_6$)-alkynylcarbonyloxy, ($C_2$-$C_6$)-haloalkynylcarbonyloxy or ($C_3$-$C_{14}$)-cycloalkyl.

Very particular preference is furthermore given to compounds of the formula (I)

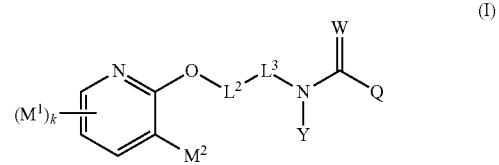

(I)

where
Q represents the structural elements below, where n for each Q is in each case as defined below:

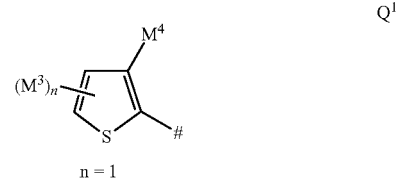

$Q^1$ n = 1

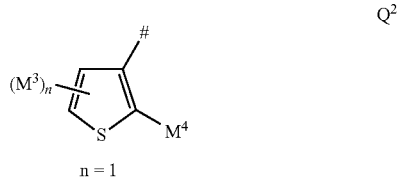

$Q^2$ n = 1

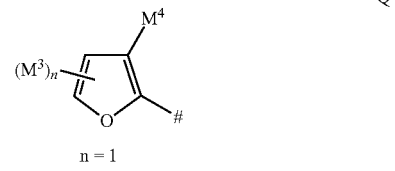

$Q^3$ n = 1

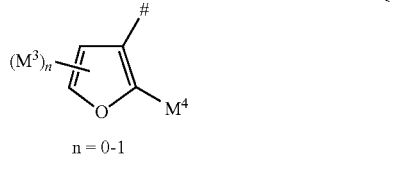

$Q^4$ n = 0-1

Q⁹
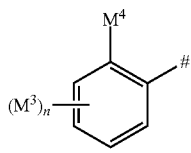
n = 1-3

Q¹⁰
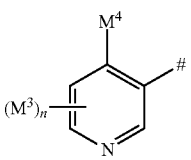
n = 1-2

Q¹¹
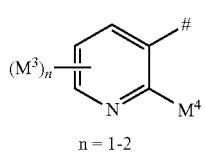
n = 1-2

Q¹²
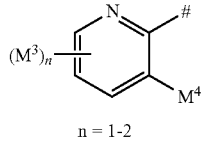
n = 1-2

Q¹³
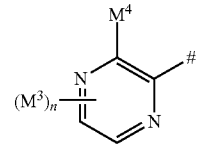
n = 1

Y represents hydrogen or represents optionally mono- or poly-$M^2$-substituted ($C_1$-$C_4$)-alkyl, ($C_2$-$C_4$)-alkenyl, ($C_3$-$C_4$)-alkynyl, ($C_1$-$C_4$)-haloalkyl, ($C_2$-$C_4$)-haloalkenyl, ($C_3$-$C_4$)-haloalkynyl, ($C_1$-$C_4$)-alkoxy, ($C_2$-$C_4$)-alkenyloxy, ($C_3$-$C_4$)-alkynyloxy, ($C_3$-$C_6$)-cycloalkyl-($C_1$-$C_4$)-alkyl or represents an optionally mono- or poly-$M^2$-substituted $C_3$- to $C_6$-membered carbocyclic group;

$M^1$, $M^2$ and $M^3$ represent hydrogen, halogen, cyano, nitro, OH, ($C_1$-$C_4$)-alkyl, ($C_1$-$C_4$)-haloalkyl, ($C_1$-$C_4$)-alkoxy, ($C_1$-$C_4$)-haloalkoxy, ($C_1$-$C_4$)-alkylthio, ($C_1$-$C_4$)-haloalkylthio, ($C_1$-$C_4$)-alkylsulphonyl, ($C_1$-$C_4$)-haloalkylsulphonyl, ($C_1$-$C_4$)-alkylsulphanyl, ($C_1$-$C_6$)-haloalkylsulphanyl, ($C_3$-$C_{14}$)-cycloalkyl-O—, ($C_3$-$C_{14}$)-cycloalkenyl-O—, ($C_6$-$C_{14}$)-aryl-O—, halogenated ($C_3$-$C_{14}$)-cycloalkyl-O—, halogenated ($C_3$-$C_{14}$)-cycloalkenyl-O—, halogenated ($C_6$-$C_{14}$)-aryl-O—, where, if Q corresponds to $Q^{11}$, $M^3$ is not ($C_1$-$C_4$)-haloalkyl in position 4 at the pyridyl;

$M^4$ represents hydrogen, halogen, cyano, nitro, OH, ($C_1$-$C_4$)-alkyl, ($C_1$-$C_4$)-haloalkyl, ($C_1$-$C_4$)-alkoxy, ($C_1$-$C_4$)-haloalkoxy, ($C_1$-$C_4$)-alkylthio, ($C_1$-$C_4$)-haloalkylthio, ($C_1$-$C_4$)-alkylsulphonyl, ($C_1$-$C_4$)-haloalkylsulphonyl, ($C_1$-$C_4$)-alkylsulphanyl, ($C_1$-$C_6$)-haloalkylsulphanyl, ($C_3$-$C_{14}$)-cycloalkyl-O—, ($C_3$-$C_{14}$)-cycloalkenyl-O—, ($C_6$-$C_{14}$)-aryl-O—, halogenated ($C_3$-$C_{14}$)-cycloalkyl-O—, halogenated ($C_3$-$C_{14}$)-cycloalkenyl-O—, halogenated ($C_6$-$C_{14}$)-aryl-O—, where, if Q corresponds to $Q^{10}$, $M^4$ is not ($C_1$-$C_4$)-haloalkyl;

k represents 1;

$R^{21}$, $R^{22}$ each independently of one another represent hydrogen, fluorine or optionally mono- or poly-$M^2$-substituted ($C_1$-$C_4$)-alkyl, ($C_2$-$C_4$)-alkenyl, ($C_2$-$C_4$)-alkynyl, ($C_1$-$C_4$)-haloalkyl, ($C_2$-$C_4$)-haloalkenyl, ($C_2$-$C_4$)-haloalkynyl, ($C_1$-$C_6$)-alkoxy, ($C_1$-$C_4$)-haloalkoxy, ($C_2$-$C_4$)-alkenyloxy, ($C_3$-$C_4$)-alkynyloxy, ($C_3$-$C_4$)-cycloalkyl-($C_1$-$C_4$)-alkyl, ($C_3$-$C_8$)-cycloalkyl or halogenated ($C_3$-$C_8$)-cycloalkyl;

$R^{31}$, $R^{32}$ preferably each independently of one another represent hydrogen, fluorine or optionally mono- or poly-$M^2$-substituted ($C_1$-$C_4$)-alkyl, ($C_2$-$C_4$)-alkenyl, ($C_2$-$C_4$)-alkynyl, ($C_1$-$C_4$)-haloalkyl, ($C_2$-$C_4$)-haloalkenyl, ($C_2$-$C_4$)-haloalkynyl, ($C_1$-$C_6$)-alkoxy, ($C_1$-$C_4$)-haloalkoxy, ($C_2$-$C_4$)-alkenyloxy, ($C_3$-$C_4$)-alkynyloxy, ($C_3$-$C_4$)-cycloalkyl-($C_1$-$C_4$)-alkyl or represent an optionally mono- or poly-$M^2$-substituted ($C_3$-$C_8$)-cycloalkyl or halogenated ($C_3$-$C_8$)-cycloalkyl;

$M^5$ represents in each case independently of the others halogen, formyl, cyano, nitro, ($C_1$-$C_4$)-alkyl, ($C_1$-$C_4$)-haloalkyl, ($C_2$-$C_4$)-alkenyl, ($C_2$-$C_4$)-haloalkenyl, ($C_2$-$C_4$)-alkynyl, ($C_2$-$C_4$)-haloalkynyl, ($C_1$-$C_4$)-alkoxy, ($C_1$-$C_4$)-haloalkoxy, ($C_2$-$C_4$)-alkenyloxy, ($C_2$-$C_4$)-haloalkenyloxy, ($C_3$-$C_4$)-alkynyloxy, ($C_3$-$C_4$)-haloalkynyloxy, ($C_1$-$C_4$)-alkylthio, ($C_1$-$C_4$)-haloalkylthio, ($C_2$-$C_4$)-alkenylthio, ($C_2$-$C_4$)-haloalkenylthio, ($C_3$-$C_4$)-alkynylthio, ($C_3$-$C_4$)-haloalkynylthio, ($C_1$-$C_4$)-alkylsulphonyl, ($C_1$-$C_4$)-haloalkylsulphonyl, ($C_2$-$C_4$)-alkenylsulphonyl, ($C_2$-$C_4$)-haloalkenylsulphonyl, ($C_3$-$C_4$)-alkynylsulphonyl, ($C_3$-$C_4$)-haloalkynylsulphonyl, ($C_1$-$C_4$)-alkylsulphanyl, ($C_1$-$C_4$)-haloalkylsulphanyl, ($C_2$-$C_4$)-alkenylsulphanyl, ($C_2$-$C_4$)-haloalkenylsulphanyl, ($C_3$-$C_4$)-alkynylsulphanyl, ($C_3$-$C_4$)-haloalkynylsulphanyl, ($C_1$-$C_4$)-alkylcarbonyl, ($C_1$-$C_4$)-haloalkylcarbonyl, ($C_2$-$C_4$)-alkenylcarbonyl, ($C_2$-$C_4$)-haloalkenylcarbonyl, ($C_2$-$C_4$)-alkynylcarbonyl, ($C_2$-$C_4$)-haloalkynylcarbonyl, ($C_1$-$C_4$)-alkoxycarbonyl, ($C_1$-$C_4$)-haloalkoxycarbonyl, ($C_2$-$C_4$)-alkenyloxycarbonyl, ($C_2$-$C_4$)-haloalkenyloxycarbonyl, ($C_3$-$C_4$)-alkynyloxycarbonyl, ($C_3$-$C_4$)-haloalkynyloxycarbonyl, ($C_1$-$C_4$)-alkylcarbonyloxy, ($C_1$-$C_4$)-haloalkylcarbonyloxy, ($C_2$-$C_4$)-alkenylcarbonyloxy, ($C_2$-$C_4$)-haloalkenylcarbonyloxy, ($C_2$-$C_4$)-alkynylcarbonyloxy, ($C_2$-$C_4$)-haloalkynylcarbonyloxy or ($C_3$-$C_6$)-cycloalkyl.

Preparation Process A

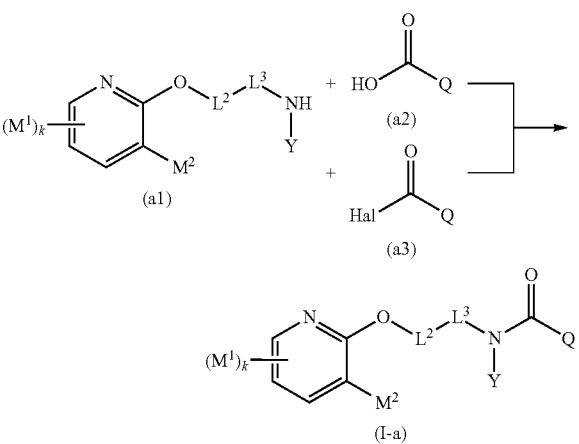

The radicals $M^1$, $M^2$, $L^2$, $L^3$, Q and Y and k have the meanings described above. W in this case represents oxygen.

Compounds of the general formula (I-a) according to the invention can be prepared proceeding from amines of the formula (a1) and carboxylic acids of the formula (a2) or halides thereof of the formula (a3) by generally known processes as described, for example, in WO-A 2009/012998. The amines of the formula (a1) and carboxylic acids of the formula (a2) and their halides of the formula (a3) are commercially available. Alternatively, the halides of the formula (a3) can be prepared by generally known methods from carboxylic acids of the formula (a2) using appropriate halogenating agents, for example phosphoryl chloride, phosphoryl bromide, thionyl chloride, oxalyl chloride or phosgene.

When using carbonyl halides of the general structure (a3), the compounds of the general formula (I-a) according to the invention are preferably prepared in the presence of a reaction auxiliary. Suitable reaction auxiliaries are all customary inorganic or organic bases. These include, for example, alkaline earth metal or alkali metal hydrides, hydroxides, amides, alcoholates, acetates, carbonates or hydrogencarbonates, such as, for example, sodium hydride, sodium amide, sodium methoxide, sodium ethoxide, potassium tert-butoxide, sodium hydroxide, potassium hydroxide, ammonium hydroxide, sodium acetate, potassium acetate, calcium acetate, ammonium acetate, sodium carbonate, potassium carbonate, potassium hydrogencarbonate or ammonium carbonate, and also tertiary amines, such as, for example, trimethylamine, triethylamine, diisopropylethylamine, tributylamine, N,N-dimethylaniline, pyridine, N-methylpiperidine, 4-(N,N-dimethylamino)pyridine, diazabicyclooctane (DABCO), diazabicyclononene (DBN) or diazabicycloundecene (DBU), in particular triethylamine.

When using carboxylic acids of the general structure (a2), the compounds of the general formula (I-a) according to the invention are prepared in the presence of a condensing agent. The carboxylic acids are commercially available. Suitable condensing agents are especially dehydrating chemicals. These preferably include acid anhydrides and acid halides, such as, for example, acetic anhydride, propionic anhydride, phosphorus(V) oxide, phosphoryl chloride, phosphoryl bromide, phosphorus trichloride, phosphorus tribromide, thionyl chloride, oxalyl chloride, phosgene, diphosgene, methyl formate, ethyl formate, and also carbodiimides such as, for example, N,N'-dicyclohexylcarbodiimide (DCC) or 1-ethyl-3-(3-dimethylaminopropyl)carbodiimide hydrochloride (EDC-HCl). Other known condensing agents are triphenylphosphine/carbon tetrachloride, 4-(4,6-dimethoxy[1.3.5]triazin-2-yl)-4-methylmorpholinium chloride hydrate or hydroxybenzotriazole (HOBt). Particular mention may be made here of the combination of 1-ethyl-3-(3-dimethylaminopropyl)carbodiimide hydrochloride (EDC-HCl) and hydroxybenzotriazole (HOBt).

The compounds of the general formula (I-a) according to the invention are optionally prepared using one or more diluents. Suitable diluents are especially inert organic solvents. These include in particular aliphatic, alicyclic or aromatic, optionally halogenated hydrocarbons such as, for example, benzine, benzene, toluene, xylene, chlorobenzene, dichlorobenzene, petroleum ether, hexane, cyclohexane, dichloromethane, chloroform, carbon tetrachloride, tetrahydrofuran, dioxane, acetonitrile or dimethylformamide.

When carrying out process A-1, the reaction temperatures can be varied within a relatively wide range. In general, the process is carried out at temperatures between 0° C. and 150° C., preferably between 10° C. and 120° C.

Process A is generally carried out under atmospheric pressure. However, it is also possible to carry out process A under elevated or reduced pressure—generally between 0.1 bar and 10 bar.

Preparation Process B

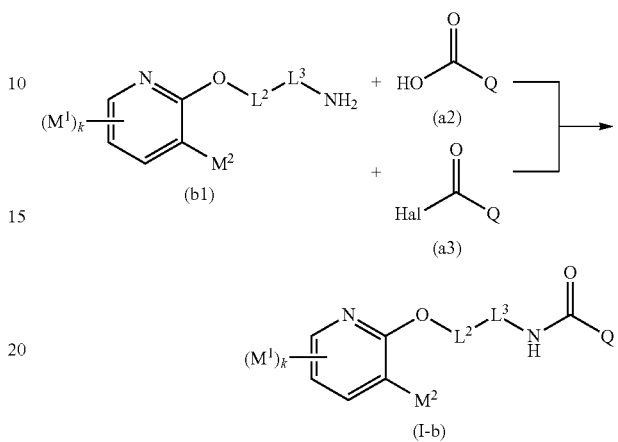

The radicals $M^1$, $M^2$, $L^2$, $L^3$ and Q and k have the meanings described above. W in this case represents oxygen.

Compounds of the general formula (I-a) according to the invention can be prepared from amines of the formula (b1) and carboxylic acids of the formula (a2) or halides thereof of the formula (a3) by generally known processes as described, for example, in WO-A 2009/012998. The amines of the formula (b1) and carboxylic acids of the formula (a2) and their halides of the formula (a3) are commercially available. Alternatively, the halides of the formula (a3) can be prepared by generally known methods from carboxylic acids of the formula (a2) using appropriate halogenating agents, for example phosphoryl chloride, phosphoryl bromide, thionyl chloride, oxalyl chloride or phosgene.

Preparation Process C

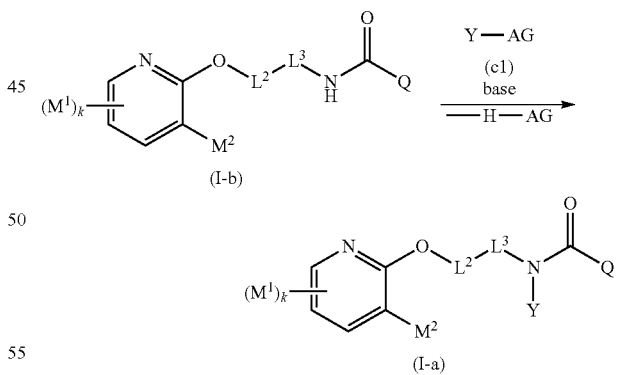

The radicals $M^1$, $M^2$, $L^2$, $L^3$, Q and Y and k have the meanings described above. In this case, W represents oxygen and AG represents a leaving group, for example halogens or alkyl- or arylsulphonates such as, for example, tolylsulphonates or benzenesulphonates.

Compounds of the general formula (I) according to the invention and their embodiment (I-a) can be prepared from amides of the formula (I-b) and alkylating agents of the formula (c1) by generally known processes as described, for example, in EP2007060166.

Preparation Process D

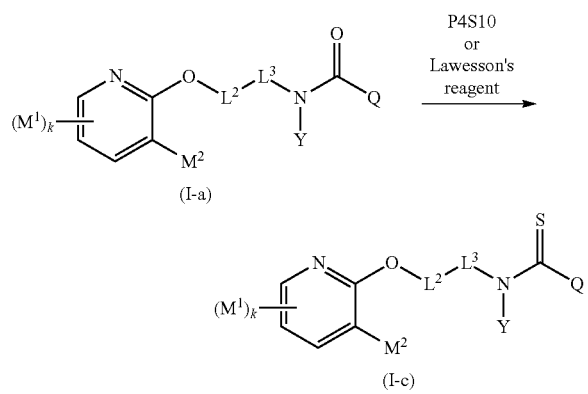

The radicals $M^1$, $M^2$, $L^2$, $L^3$, Q and Y and k have the meanings described above. W=oxygen is transformed directly into W=sulphur.

Compounds of the general formula (I) according to the invention and their embodiment (I-c) can be prepared from compounds of the formula (I-a) and appropriate sulphurizing agents, for example tetraphosphorus decasulphide ("phosphorus pentasulphide") or 2,4-bis[4-methoxyphenyl]-2,4-dithiono-1,2,3,4-dithiadiphosphetane ("Lawesson's reagent"), by generally known processes. Process examples are known inter alia from Houben-Weyl, Methoden der Organischen Chemie [Methods of Organic Chemistry], E5, 1255 (Thieme Verlag, Stuttgart, 1985).

A further aspect of the present invention is a method for controlling endoparasitic pests or nematodes, which method is characterized in that a compound of the formula (I) or (I-a)-(I-c) according to the invention or a salt, N-oxide or tautomeric form thereof is allowed to act on the pests and/or their habitat.

Field of Anthelmintic Use

The compositions according to the invention are suitable for controlling pathogenic endoparasites which occur in humans and in animal keeping and animal breeding in the case of agricultural animals, breeding animals, zoo animals, laboratory animals, experimental animals and pets. They may be employed against all or individual stages of development of the pests and against resistant and normally sensitive endoparasite isolates. By controlling the pathogenic endoparasites, it is intended to reduce disease, mortality and decreasing performance (for example in the production of meat, milk, wool, hides, eggs, honey, etc.), so that more economical, simpler and healthier animal husbandry is possible by using the active compounds. The pathogenic endoparasites include helminths such as Platyhelmintha (in particular Monogenea, cestodes and trematodes), nematodes, Pentastoma and Acanthocephala. Examples which may be mentioned are:

Monogenea: for example: *Gyrodactylus* spp., *Dactylogyrus* spp., *Polystoma* spp.

Cestodes: From the order of the Pseudophyllidea, for example: *Diphyllobothrium* spp., *Spirometra* spp., *Schistocephalus* spp., *Ligula* spp., *Bothridium* spp., *Diphlogonoporus* spp.

From the order of the Cyclophyllidea, for example: *Mesocestoides* spp., *Anoplocephala* spp., *Paranoplocephala* spp., *Moniezia* spp., *Thysanosoma* spp., *Thysaniezia* spp., *Avitellina* spp., *Stilesia* spp., *Cittotaenia* spp., *Andyra* spp., *Bertiella* spp., *Taenia* spp., *Echinococcus* spp., *Hydatigera* spp., *Davainea* spp., *Raillietina* spp., *Hymenolepis* spp., *Echinolepis* spp., *Echinocotyle* spp., *Diochis* spp., *Dipylidium* spp., *Joyeuxiella* spp., *Diplopylidium* spp.

Trematodes: From the class of the Digenea, for example: *Diplostomum* spp., *Posthodiplostomum* spp., *Schistosoma* spp., *Trichobilharzia* spp., *Ornithobilharzia* spp., *Austrobilharzia* spp., *Gigantobilharzia* spp., *Leucochloridium* spp., *Brachylaima* spp., *Echinostoma* spp., *Echinoparyphium* spp., *Echinochasmus* spp., *Hypoderaeum* spp., *Fasciola* spp., *Fasciolides* spp., *Fasciolopsis* spp., *Cyclocoelum* spp., *Typhlocoelum* spp., *Paramphistomum* spp., *Calicophoron* spp., *Cotylophoron* spp., *Gigantocotyle* spp., *Fischoederius* spp., *Gastrothylacus* spp., *Notocotylus* spp., *Catatropis* spp., *Plagiorchis* spp., *Prosthogonimus* spp., *Dicrocoelium* spp., *Eurytrema* spp., *Troglotrema* spp., *Paragonimus* spp., *Collyriclum* spp., *Nanophyetus* spp., *Opisthorchis* spp., *Clonorchis* spp. *Metorchis* spp., *Heterophyes* spp., *Metagonimus* spp.

Acanthocephala: from the order of the Oligacanthorhynchida, for example: *Macracanthorhynchus* spp., *Prosthenorchis* spp.; from the order of the Polymorphida, for example: *Filicollis* spp.; from the order of the Moniliformida, for example: *Moniliformis* spp., from the order of the Echinorhynchida, for example, *Acanthocephalus* spp., *Echinorhynchus* spp., *Leptorhynchoides* spp.

Pentastoma: from the order of the Porocephalida, for example, *Linguatula* spp.

Nematodes: From the order of the Trichinellida, for example: *Trichuris* spp., *Capillaria* spp., *Trichomosoides* spp., *Trichinella* spp.

From the order of the Tylenchida, for example: *Micronema* spp., *Strongyloides* spp.

From the order of the Rhabditina, for example: *Strongylus* spp., *Triodontophorus* spp., *Oesophagodontus* spp., *Trichonema* spp., *Gyalocephalus* spp., *Cylindropharynx* spp., *Poteriostomum* spp., *Cyclococercus* spp., *Cylicostephanus* spp., *Oesophagostomum* spp., *Chabertia* spp., *Stephanurus* spp., *Ancylostoma* spp., *Uncinaria* spp., *Bunostomum* spp., *Globocephalus* spp., *Syngamus* spp., *Cyathostoma* spp., *Metastrongylus* spp., *Dictyocaulus* spp., *Muellerius* spp., *Protostrongylus* spp., *Neostrongylus* spp., *Cystocaulus* spp., *Pneumostrongylus* spp., *Spicocaulus* spp., *Elaphostrongylus* spp. *Parelaphostrongylus* spp., *Crenosoma* spp., *Paracrenosoma* spp., *Angiostrongylus* spp., *Aelurostrongylus* spp., *Filaroides* spp., *Parafilaroides* spp., *Trichostrongylus* spp., *Haemonchus* spp., *Ostertagia* spp., *Marshallagia* spp., *Cooperia* spp., *Nematodirus* spp., *Hyostrongylus* spp., *Obeliscoides* spp., *Amidostomum* spp., *Ollulanus* spp.

From the order of the Spirurida, for example: *Oxyuris* spp., *Enterobius* spp., *Passalurus* spp., *Syphacia* spp., *Aspiculuris* spp., *Heterakis* spp.; *Ascaris* spp., *Toxascaris* spp., *Toxocara* spp., *Baylisascaris* spp., *Parascaris* spp., *Anisakis* spp., *Ascaridia* spp.; *Gnathostoma* spp., *Physaloptera* spp., *Thelazia* spp., *Gongylonema* spp., *Habronema* spp., *Parabronema* spp., *Draschia* spp., *Dracunculus* spp.; *Stephanofilaria* spp., *Parafilaria* spp., *Setaria* spp., *Loa* spp., *Dirofilaria* spp., *Litomosoides* spp., *Brugia* spp., *Wuchereria* spp., *Onchocerca* spp.

Acantocephala: From the order of the Oligacanthorhynchida, for example: *Macracanthorhynchus* spp., *Prosthenorchis* spp.; from the order of the Polymorphida, for example: *Filicollis* spp.; from the order of the Moniliformida, for example: *Moniliformis* spp., from the order of the Echinorhynchida, for example, *Acanthocephalus* spp., *Echinorhynchus* spp., *Leptorhynchoides* spp.

Pentastoma: From the order of the Porocephalida, for example, *Linguatula* spp.

According to a preferred embodiment, the compounds of the formula (I) are used for controlling nematodes. The following nematodes may be mentioned with particular preference: Trichinellida, Tylenchida, Rhabditina or the following from the order of the Spirurida: *Gnathostoma* spp., *Physaloptera* spp., *Thelazia* spp., *Gongylonema* spp., *Habronema* spp., *Parabronema* spp., *Draschia* spp., *Dracunculus* spp.

A further particularly preferred embodiment provides the use for controlling Strongylida, in particular *Haemonchus* spp. (e.g. *Haemonchus contortus*), *Trichostrongylus* spp. (e.g. *Trichostrongylus colubriformis*), *Cooperia* spp., and *Ostertagia* spp. or *Teladorsagia* spp.

A further particularly preferred embodiment provides the use for controlling Ascaridida such as, for example, *Parascaris* spp.

Animals can be fish, reptiles, birds or in particular mammals.

The agricultural and breeding livestock include mammals such as, for example, cattle, horses, sheep, pigs, goats, camels, water buffalo, donkeys, rabbits, fallow deer, reindeer, fur-bearing animals such as, for example, mink, chinchilla, racoon, birds such as, for example, chicken, geese, turkeys, ducks, ostriches, fish such as trout, salmon, carp, perches, pikes, eels.

Laboratory and experimental animals include mice, rats, guinea pigs, golden hamsters, dogs and cats.

Pets include dogs and cats.

According to the invention, the use for animals is preferred; however, in principle, the use for humans is also possible. In humans, *Ascaris* spp., *Ancylostoma* spp, *Necator* spp., *Trichuris* spp., *Strongyloides* spp. and *Enterobius* spp. are controlled with preference.

According to one embodiment, from among the mammals, herbivores, that is animals living mainly off plants, are preferred for the use according to the invention. Particular preference is given to the treatment of ruminants (such as, for example, sheep, goats, cattle).

A preferred example of a non-ruminating mammalian herbivore are horses. Here, the abovementioned combinations can preferably be employed, for example, for controlling Strongylida or in particular Ascaridida such as *Parascaris equorum*.

In the case of the ruminants, preference is given to controlling Strongylida, in particular *Haemonchus* spp., *Trichostrongylus* spp., *Cooperia* spp. and *Ostertagia* spp.

According to the invention, particular preference is given to treating sheep.

According to the invention, particular preference is likewise given to treating cattle.

The active compounds according to the invention are employed in the veterinary sector and in animal husbandry in a manner known per se directly or in the form of suitable preparations. Administration can be effected prophylactically as well as therapeutically.

The compounds of the formula (I) as defined above can be used as medicaments for controlling endoparasites in animals or humans.

The compounds of the formula (I) as defined above can be used for preparing a medicament for controlling endoparasites in animals or humans.

The compounds of the formula (I) as defined above can be used in the control of endoparasites in animals by administering the compounds and their salts, N-oxides and tautomeric forms prophylactically or therapeutically to animals or humans.

What is claimed are endoparasiticidal compositions comprising the compounds of the formula (I) as defined above.

What is described are endoparasiticidal compositions comprising one or more compounds of the formula (I) as defined above and one or more pharmaceutically acceptable auxiliaries.

What is described is a method for treating endoparasites in humans and animals by administering a compound of the formula (I) as described above or a pharmaceutical composition comprising these compounds.

What is described is a method for treating endoparasites in animals by administering a compound of the formula (I) as described above or a pharmaceutical composition comprising these compounds.

What is described is a method for treating endoparasites in cattle and sheep by administering a compound of the formula (I) as described above or a pharmaceutical composition comprising these compounds.

Field of Nematicidal Use:

In the present context, the term "nematicides" comprises substances suitable for controlling nematodes living in the soil or in plants or plant parts and damaging these.

In the present context, the term "nematodes" comprises all species of the order Nematoda and in particular species causing health problems for plants or for fungi (for example species of the order Aphelenchida, Meloidogyne, Tylenchida and other) or for humans and animals (for example species of the orders Trichinellida, Tylenchida, Rhabditina and Spirurida), and also other parasitic helminths.

In the present context, the term "phytopathogenic nematodes" refers to plant nematodes, which are understood to mean phytoparasitic nematodes which damage plants. Plant nematodes comprise phytoparasitic nematodes and soil-borne nematodes. The phytoparasitic nematodes include, without limitation, ectoparasites such as *Xiphinema* spp., *Longidorus* spp. and *Trichodorus* spp.; semiparasites such as *Tylenchulus* spp.; migratory endoparasites such as *Pratylenchus* spp., *Radopholus* spp. and *Scutellonema* spp.; non-migratory parasites such as *Heterodera* spp., *Globoderal* spp. and *Meloidogyne* spp., and also stem and leaf endoparasites such as *Ditylenchus* spp., *Aphelenchoides* spp. and *Hirshmaniella* spp. Particularly damaging root-parasitic soil nematodes are, for example, cyst-forming nematodes of the genera *Heterodera* or *Globodera*, and/or root gall nematodes of the genus *Meloidogyne*. Damaging species of these genera are, for example, *Meloidogyne incognita*, *Heterodera glycines* (soya bean cyst nematode), *Globodera pallida* and *Globodera rostochiensis* (yellow potato cyst nematode), these species being controlled effectively by the compounds described in the present text. However, the use of the compounds described in the present text is by no means restricted to these genera or species, but also extends in the same manner to other nematodes.

The phytogenic nematodes include, without this being exclusive, for example *Aglenchus agricola*, *Anguina tritici*, *Aphelenchoides arachidis*, *Aphelenchoides fragaria* and the stem and leaf endoparasites *Aphelenchoides* spp. in general, *Belonolaimus gracilis*, *Belonolaimus longicaudatus*, *Belonolaimus nortoni*, *Bursaphelenchus eremus*, *Bursaphelenchus xylophilus* and *Bursaphelenchus* spp. in general, *Cacopaurus pestis*, *Criconemella curvata*, *Criconemella onoensis*, *Criconemella ornata*, *Criconemella rusium*, *Criconemella xenoplax* (=*Mesocriconema xenoplax*) and *Criconemella* spp. in general, *Criconemoides femiae*, *Cri-*

*conemoides onoense, Criconemoides ornatum* and *Criconemoides* spp. in general, *Ditylenchus destructor, Ditylenchus dipsaci, Ditylenchus myceliophagus* and also the stem and leaf endoparasites *Ditylenchus* spp. in general, *Dolichodorus heterocephalus, Globodera pallida* (=*Heterodera pallida*), *Globodera rostochiensis* (yellow potato cyst nematode), *Globodera solanacearum, Globodera tabacum, Globodera virginia* and the non-migratory cyst-forming parasites *Globodera* spp. in general, *Helicotylenchus digonicus, Helicotylenchus dihystera, Helicotylenchus erythrine, Helicotylenchus multicinctus, Helicotylenchus nannus, Helicotylenchus pseudorobustus* and *Helicotylenchus* spp., in general, *Hemicriconemoides, Hemicycliophora arenaria, Hemicycliophora nudata, Hemicycliophora parvana, Heterodera avenae, Heterodera cruciferae, Heterodera glycines* (soya bean cyst nematode), *Heterodera oryzae, Heterodera schachtii, Heterodera zeae* and the non-migratory cyst-forming parasites *Heterodera* spp. in general, *Hirschmaniella gracilis, Hirschmaniella oryzae, Hirschmaniella spinicaudata* and the stem and leaf endoparasites *Hirschmaniella* spp. in general, *Hoplolaimus aegyptii, Hoplolaimus californicus, Hoplolaimus columbus, Hoplolaimus galeatus, Hoplolaimus indicus, Hoplolaimus magnistylus, Hoplolaimus pararobustus, Longidorus africanus, Longidorus breviannulatus, Longidorus elongatus, Longidorus laevicapitatus, Longidorus vineacola* and the ectoparasites *Longidorus* spp. in general, *Meloidogyne acronea, Meloidogyne africana, Meloidogyne arenaria, Meloidogyne arenaria thamesi, Meloidogyne artiella, Meloidogyne chitwoodi, Meloidogyne coffeicola, Meloidogyne ethiopica, Meloidogyne exigua, Meloidogyne graminicola, Meloidogyne graminis, Meloidogyne hapla, Meloidogyne incognita, Meloidogyne incognita acrita, Meloidogyne javanica, Meloidogyne kikuyensis, Meloidogyne naasi, Meloidogyne paranaensis, Meloidogyne thamesi* and the non-migratory parasites *Meloidogyne* spp. in general, *Meloinema* spp., *Nacobbus aberrans, Neotylenchus vigissi, Paraphelenchus pseudoparietinus, Paratrichodorus allius, Paratrichodorus lobatus, Paratrichodorus minor, Paratrichodorus nanus, Paratrichodorus porosus, Paratrichodorus teres* and *Paratrichodorus* spp. in general, *Paratylenchus hamatus, Paratylenchus minutus, Paratylenchus projectus* and *Paratylenchus* spp. in general, *Pratylenchus agilis, Pratylenchus alleni, Pratylenchus andinus, Pratylenchus brachyurus, Pratylenchus cerealis, Pratylenchus coffeae, Pratylenchus crenatus, Pratylenchus delattrei, Pratylenchus giibbicaudatus, Pratylenchus goodeyi, Pratylenchus hamatus, Pratylenchus hexincisus, Pratylenchus loosi, Pratylenchus neglectus, Pratylenchus penetrans, Pratylenchus pratensis, Pratylenchus scribneri, Pratylenchus teres, Pratylenchus thornei, Pratylenchus vulnus, Pratylenchus zeae* and the migratory endoparasites *Pratylenchus* spp. in general, *Pseudohalenchus minutus, Psilenchus magnidens, Psilenchus tumidus, Punctodera chalcoensis, Quinisulcius acutus, Radopholus citrophilus, Radopholus similis*, the migratory endoparasites *Radopholus* spp. in general, *Rotylenchulus borealis, Rotylenchulus parvus, Rotylenchulus reniformis* and *Rotylenchulus* spp. in general, *Rotylenchus laurentinus, Rotylenchus macrodoratus, Rotylenchus robustus, Rotylenchus uniformis* and *Rotylenchus* spp. in general, *Scutellonema brachyurum, Scutellonema bradys, Scutellonema clathricaudatum* and the migratory endoparasites *Scutellonema* spp. in general, *Subanguina radiciola, Tetylenchus nicotianae, Trichodorus cylindricus, Trichodorus minor, Trichodorus primitivus, Trichodorus proximus, Trichodorus similis, Trichodorus sparsus* and the ectoparasites *Trichodorus* spp. in general, *Tylenchorhynchus agri, Tylenchorhynchus brassicae, Tylenchorhynchus clarus, Tylenchorhynchus claytoni, Tylenchorhynchus digitatus, Tylenchorhynchus ebriensis, Tylenchorhynchus maximus, Tylenchorhynchus nudus, Tylenchorhynchus vulgaris* and *Tylenchorhynchus* spp. in general, *Tylenchulus semipenetrans* and the semiparasites *Tylenchulus* spp. in general, *Xiphinema americanum, Xiphinema brevicolle, Xiphinema dimorphicaudatum, Xiphinema index* and the ectoparasites *Xiphinema* spp. in general.

Exemplary nematodes for which a nematicide according to the invention may be used include, but not exclusively, nematodes of the genus *Meloidogyne* such as the Southern root-knot nematode (*Meloidogyne incognita*), the Javanese root-knot nematode (*Meloidogyne javanica*), the Northern root-knot nematode (*Meloidogyne hapla*) and the peanut root-knot nematode (*Meloidogyne arenaria*); nematodes of the genus *Ditylenchus* such as the potato rot nematode (*Ditylenchus destructor*) and stem and bulb eelworm (*Ditylenchus dipsaci*); nematodes of the genus *Pratylenchus* such as the cob root-lesion nematode (*Pratylenchus penetrans*), the chrysanthemum root-lesion nematode (*Pratylenchus fallax*), the coffee root nematode (*Pratylenchus coffeae*), the tea root nematode (*Pratylenchus loosi*) and the walnut root-lesion nematode (*Pratylenchus vulnus*); nematodes of the genus *Globodera* such as the yellow potato cyst nematode (*Globodera rostochiensis*) and the white potato cyst nematode (*Globodera pallida*); nematodes of the genus *Heterodera* such as the soya bean cyst nematode (*Heterodera glycines*) and beet cyst eelworm (*Heterodera schachtii*); nematodes of the genus *Aphelenchoides* such as the rice white-tip nematode (*Aphelenchoides besseyi*), the chrysanthemum nematode (*Aphelenchoides ritzemabosi*) and the strawberry nematode (*Aphelenchoides fragariae*); nematodes of the genus *Aphelenchus* such as the fungivorous nematode (*Aphelenchus avenae*); nematodes of the genus *Radopholus*, such as the burrowing nematode (*Radopholus similis*); nematodes of the genus *Tylenchulus* such as the citrus root nematode (*Tylenchulus semipenetrans*); nematodes of the genus *Rotylenchulus* such as the reniform nematode (*Rotylenchulus reniformis*); tree-dwelling nematodes such as the pine wood nematode (*Bursaphelenchus xylophilus*) and the like.

Plants which can be used for a nematicide according to the invention are not particularly restricted; thus, for example, mention may be made of plants such as cereals (for example rice, barley, wheat, rye, oats, maize, kaoliang 5 and the like), beans (soya bean, aduki bean, bean, broadbean, peas, peanuts and the like), fruit trees/fruits (apples, citrus species, pears, grapevines, peaches, Japanese apricots, cherries, walnuts, almonds, bananas, strawberries and the like), vegetable species (cabbage, tomato, spinach, broccoli, lettuce, onions, spring onion, pepper and the like), root crops (carrot, potato, sweet potato, radish, lotus root, turnip and the like), plant raw materials (cotton, hemp, paper mulberry, mitsumata, rape, beet, hops, sugar cane, sugar beet, olive, rubber, coffee, tobacco, tea and the like), cucurbits (pumpkin, cucumber, water melon, melon and the like), meadow plants (cocksfoot, sorghum, timothy-grass, clover, alfalfa and the like), lawn grasses (mascarene grass, bentgrass and the like), spice plants etc. (lavender, rosemary, thyme, parsley, pepper, ginger and the like) and flowers (chrysanthemums, rose, orchid and the like).

The compound(s) and the composition(s) comprising the compound(s) according to the invention is/are suitable in particular for controlling coffee nematodes belonging to at least one species from the group of the phytoparasitic nematodes consisting of *Pratylenchus brachyurus, Praty-*

*lenchus coffeae, Meloidogyne exigua, Meloidogyne incognita, Meloidogyne coffeicola, Helicotylenchus* spp. and of *Meloidogyne paranaensis, Rotylenchus* spp., *Xiphinema* spp., *Tylenchorhynchus* spp., *Scutellonema* spp.

The compound(s) and the composition(s) comprising the compound(s) according to the invention is/are suitable in particular for controlling potato nematodes belonging to at least one species from the group of the phytoparasitic nematodes consisting of *Pratylenchus brachyurus, ratylenchus pratensis, Pratylenchus scribneri, Pratylenchus penetrans, Pratylenchus coffeae, Ditylenchus dipsaci* and of *Pratylenchus alleni, Pratylenchus andinus, Pratylenchus cerealis, Pratylenchus crenatus, Pratylenchus hexincisus, Pratylenchus loosi, Pratylenchus neglectus, Pratylenchus teres, Pratylenchus thornei, Pratylenchus vulnus, Belonolaimus longicaudatus, Trichodorus cylindricus, Trichodorus primitivus, Trichodorus proximus, Trichodorus similis, Trichodorus sparsus, Paratrichodorus minor, Paratrichodorus allius, Paratrichodorus nanus, Paratrichodorus teres, Meloidogyne arenaria, Meloidogyne hapla, Meloidogyne thamesi, Meloidogyne incognita, Meloidogyne chitwoodi, Meloidogyne javanica, Nacobbus aberrans, Globodera rostochiensis, Globodera pallida, Ditylenchus destructor, Radopholus similis, Rotylenchulus reniformis, Neotylenchus vigissi, Paraphelenchus pseudoparietinus, Aphelenchoides fragariae, Meloinema* spp.

The compound(s) and the composition(s) comprising the compound(s) according to the invention is/are suitable in particular for controlling tomato nematodes belonging to at least one species from the group of the phytoparasitic nematodes consisting of *Meloidogyne arenaria, Meloidogyne hapla, Meloidogyne javanica, Meloidogyne incognita, Pratylenchus penetrans* and of *Pratylenchus brachyurus, Pratylenchus coffeae, Pratylenchus scribneri, Pratylenchus vulnus, Paratrichodorus minor, Meloidogyne exigua, Nacobbus aberrans, Globodera solanacearum, Dolichodorus heterocephalus, Rotylenchulus reniformis.*

The compound(s) and the composition(s) comprising the compound(s) according to the invention is/are suitable in particular for controlling *Cucumis* nematodes belonging to at least one species from the group of the phytoparasitic nematodes consisting of *Meloidogyne arenaria, Meloidogyne hapla, Meloidogyne javanica, Meloidogyne incognita, Rotylenchulus reniformis* and *Pratylenchus thornei.*

The compound(s) and the composition(s) comprising the compound(s) according to the invention is/are suitable in particular for controlling cotton nematodes belonging to at least one species from the group of the phytoparasitic nematodes consisting of *Belonolaimus longicaudatus, Meloidogyne incognita, Hoplolaimus columbus, Hoplolaimus galeatus, Rotylenchulus reniformis.*

The compound(s) and the composition(s) comprising the compound(s) according to the invention is/are suitable in particular for controlling maize nematodes belonging to at least one species from the group of the phytoparasitic nematodes consisting in particular of *Belonolaimus longicaudatus, Paratrichodorus minor* and of *Pratylenchus brachyurus, Pratylenchus delattrei, Pratylenchus hexincisus, Pratylenchus penetrans, Pratylenchus zeae,* (*Belonolaimus gracilis*), *Belonolaimus nortoni, Longidorus breviannulatus, Meloidogyne arenaria, Meloidogyne arenaria thamesi, Meloidogyne graminis, Meloidogyne incognita, Meloidogyne incognita acrita, Meloidogyne javanica, Meloidogyne naasi, Heterodera avenae, Heterodera oryzae, Heterodera zeae, Punctodera chalcoensis, Ditylenchus dipsaci, Hoplolaimus aegyptii, Hoplolaimus magnistylus, Hoplolaimus galeatus, Hoplolaimus indicus, Helicotylenchus digonicus, Helicotylenchus dihystera, Helicotylenchus pseudorobustus, Xiphinema americanum, Dolichodorus heterocephalus, Criconemella ornata, Criconemella onoensis, Radopholus similis, Rotylenchus borealis, Rotylenchulus parvus, Tylenchorhynchus agri, Tylenchorhynchus clarus, Tylenchorhynchus claytoni, Tylenchorhynchus maximus, Tylenchorhynchus nudus, Tylenchorhynchus vulgaris, Quinisulcius acutus, Paratylenchus minutus, Hemicycliophora parvana, Aglenchus agricola, Anguina tritici, Aphelenchoides arachidis, Scutellonema brachyurum, Subanguina radiciola.*

The compound(s) and the composition(s) comprising the compound(s) according to the invention is/are suitable in particular for controlling soya bean nematodes belonging to at least one species from the group of the phytoparasitic nematodes consisting in particular of *Pratylenchus brachyurus, Pratylenchus pratensis, Pratylenchus penetrans, Pratylenchus scribneri, Belonolaimus longicaudatus, Heterodera glycines, Hoplolaimus columbus* and of *Pratylenchus coffeae, Pratylenchus hexincisus, Pratylenchus neglectus, Pratylenchus crenatus, Pratylenchus alleni, Pratylenchus agilis, Pratylenchus zeae, Pratylenchus vulnus,* (*Belonolaimus gracilis*), *Meloidogyne arenaria, Meloidogyne incognita, Meloidogyne javanica, Meloidogyne hapla, Hoplolaimus columbus, Hoplolaimus galeatus, Rotylenchulus reniformis.*

The compound(s) and the composition(s) comprising the compound(s) according to the invention is/are suitable in particular for controlling soya bean nematodes belonging to at least one species from the group of the phytoparasitic nematodes consisting in particular of *Pratylenchus brachyurus, Pratylenchus pratensis, Pratylenchus penetrans, Pratylenchus scribneri, Belonolaimus longicaudatus, Hoplolaimus columbus* and of *Pratylenchus coffeae, Pratylenchus hexincisus, Pratylenchus neglectus, Pratylenchus crenatus, Pratylenchus alleni, Pratylenchus agilis, Pratylenchus zeae, Pratylenchus vulnus,* (*Belonolaimus gracilis*), *Meloidogyne arenaria, Meloidogyne incognita, Meloidogyne javanica, Meloidogyne hapla, Hoplolaimus columbus, Hoplolaimus galeatus, Rotylenchulus reniformis.*

The compound(s) and the composition(s) comprising the compound(s) according to the invention is/are suitable in particular for controlling tobacco nematodes belonging to at least one species from the group of the phytoparasitic nematodes consisting of *Meloidogyne incognita, Meloidogyne javanica* and of *Pratylenchus brachyurus, Pratylenchus pratensis, Pratylenchus hexincisus, Pratylenchus penetrans, Pratylenchus neglectus, Pratylenchus crenatus, Pratylenchus thornei, Pratylenchus vulnus, Pratylenchus zeae, Longidorus elongatu, Paratrichodorus lobatus, Trichodorus* spp., *Meloidogyne arenaria, Meloidogyne hapla, Globodera tabacum, Globodera solanacearum, Globodera virginiae, Ditylenchus dipsaci, Rotylenchus* spp., *Helicotylenchus* spp., *Xiphinema americanum, Criconemella* spp., *Rotylenchulus reniformis, Tylenchorhynchus claytoni, Paratylenchus* spp., *Tetylenchus nicotianae.*

The compound(s) and the composition(s) comprising the compound(s) according to the invention is/are suitable in particular for controlling citrus nematodes belonging to at least one species from the group of the phytoparasitic nematodes consisting in particular of *Pratylenchus coffeae* and of *Pratylenchus brachyurus, Pratylenchus vulnus, Belonolaimus longicaudatus, Paratrichodorus minor, Paratrichodorus porosus, Trichodorus, Meloidogyne incognita, Meloidogyne incognita acrita, Meloidogyne javanica, Rotylenchus macrodoratus, Xiphinema americanum, Xiphinema brevicolle, Xiphinema index, Criconemella* spp., Hemicriconemoides, (Radopholus similis), Radopholus citrophilus, Hemicycliophora arenaria, Hemicycliophora nudata, Tylenchulus semipenetrans.

The compound(s) and the composition(s) comprising the compound(s) according to the invention is/are suitable in particular for controlling banana nematodes belonging to at least one species from the group of the phytoparasitic nematodes consisting in particular of *Pratylenchus coffeae, Radopholus similis* and of *Pratylenchus giibbicaudatus, Pratylenchus loosi, Meloidogyne* spp., *Helicotylenchus multicinctus, Helicotylenchus dihystera, Rotylenchulus* spp.

The compound(s) and the composition(s) comprising the compound(s) according to the invention is/are suitable in particular for controlling pineapple nematodes belonging to at least one species from the group of the phytoparasitic nematodes consisting in particular of *Pratylenchus zeae, Pratylenchus pratensis, Pratylenchus brachyurus, Pratylenchus goodeyi., Meloidogyne* spp., *Rotylenchulus reniformis* and of *Longidorus elongatus, Longidorus laevicapitatus, Trichodorus primitivus, Trichodorus minor, Heterodera* spp., *Ditylenchus myceliophagus, Hoplolaimus californicus, Hoplolaimus pararobustus, Hoplolaimus indicus, Helicotylenchus dihystera, Helicotylenchus nannus, Helicotylenchus multicinctus, Helicotylenchus erythrine, Xiphinema dimorphicaudatum, Radopholus similis, Tylenchorhynchus digitatus, Tylenchorhynchus ebriensis, Paratylenchus minutus, Scutellonema clathricaudatum, Scutellonema bradys, Psilenchus tumidus, Psilenchus magnidens, Pseudohalenchus minutus, Criconemoides ferniae, Criconemoides onoense, Criconemoides ornatum.*

The compound(s) and the composition(s) comprising the compound(s) according to the invention is/are suitable in particular for controlling grapevine nematodes belonging to at least one species from the group of the phytoparasitic nematodes consisting in particular of *Pratylenchus vulnus, Meloidogyne arenaria, Meloidogyne incognita, Meloidogyne javanica, Xiphinema americanum, Xiphinema index* and of *Pratylenchus pratensis, Pratylenchus scribneri, Pratylenchus neglectus, Pratylenchus brachyurus, Pratylenchus thornei, Tylenchulus semipenetrans.*

The compound(s) and the composition(s) comprising the compound(s) according to the invention is/are suitable in particular for controlling tree crop-pome fruit nematodes belonging to at least one species from the group of the phytoparasitic nematodes consisting in particular of *Pratylenchus penetrans* and of *Pratylenchus vulnus, Longidorus elongatus, Meloidogyne incognita, Meloidogyne hapla.*

The compound(s) and the composition(s) comprising the compound(s) according to the invention is/are suitable in particular for controlling tree crop-stone fruit nematodes belonging to at least one species from the group of the phytoparasitic nematodes consisting in particular of *Pratylenchus penetrans, Pratylenchus vulnus, Meloidogyne arenaria, Meloidogyne hapla, Meloidogyne javanica, Meloidogyne incognita, Criconemella xenoplax* and of *Pratylenchus brachyurus, Pratylenchus coffeae, Pratylenchus scribneri, Pratylenchus zeae, Belonolaimus longicaudatus, Helicotylenchus dihystera, Xiphinema americanum, Criconemella curvata, Tylenchorhynchus claytoni, Paratylenchus hamatus, Paratylenchus projectus, Scutellonema brachyurum, Hoplolaimus galeatus.*

The compound(s) and the composition(s) comprising the compound(s) according to the invention is/are suitable in particular for controlling tree crop-nuts nematodes belonging to at least one species from the group of the phytoparasitic nematodes consisting in particular of *Trichodorus* spp., *Criconemella rusium* and of *Pratylenchus vulnus, Paratrichodorus* spp., *Meloidogyne incognita, Helicotylenchus* spp., *Tylenchorhynchus* spp., *Cacopaurus pestis.*

The present invention further relates to formulations and use forms prepared therefrom as crop protection compositions and/or pesticides, for example drench, drip and spray liquors, comprising at least one of the active compounds according to the invention. In some cases, the use forms comprise further crop protection agents and/or pesticides and/or adjuvants which improve action, such as penetrants, e.g. vegetable oils, for example rapeseed oil, sunflower oil, mineral oils, for example paraffin oils, alkyl esters of vegetable fatty acids, for example rapeseed oil methyl ester or soya bean oil methyl ester, or alkanol alkoxylates, and/or spreaders, for example alkylsiloxanes, and/or salts, for example organic or inorganic ammonium or phosphonium salts, for example ammonium sulphate or diammonium hydrogenphosphate, and/or retention promoters, for example dioctyl sulphosuccinate or hydroxypropyl guar polymers, and/or humectants, for example glycerol, and/or fertilizers, for example ammonium-, potassium- or phosphorus-containing fertilizers.

Customary formulations are, for example, water-soluble liquids (SL), emulsion concentrates (EC), emulsions in water (EW), suspension concentrates (SC, SE, FS, OD), water-dispersible granules (WG), granules (GR) and capsule concentrates (CS); these and further possible formulation types are described, for example, by Crop Life International and in Pesticide Specifications, Manual on development and use of FAO and WHO specifications for pesticides, FAO Plant Production and Protection Papers—173, prepared by the FAO/WHO Joint Meeting on Pesticide Specifications, 2004, ISBN: 9251048576. The formulations, in addition to one or more active compounds according to the invention, optionally comprise further agrochemically active compounds.

These are preferably formulations or use forms which comprise auxiliaries, for example extenders, solvents, spontaneity promoters, carriers, emulsifiers, dispersants, antifreezes, biocides, thickeners and/or further auxiliaries, for example adjuvants. An adjuvant in this context is a component which enhances the biological effect of the formulation, without the component itself having a biological effect. Examples of adjuvants are agents which promote retention, spreading, attachment to the leaf surface or penetration.

These formulations are prepared in a known way, for example by mixing the active compounds with auxiliaries such as, for example, extenders, solvents and/or solid carriers and/or other auxiliaries such as, for example, surfactants. The formulations are prepared either in suitable installations or else before or during application.

Auxiliaries used may be substances capable of giving the formulation of the active compound, or the application forms prepared from these formulations (such as ready-to-use crop protection compositions, for example, such as spray liquors or seed dressings) particular properties, such as certain physical, technical and/or biological properties.

Suitable extenders are, for example, water, polar and nonpolar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulphones and sulphoxides (such as dimethyl sulphoxide).

If the extender used is water, it is also possible to employ, for example, organic solvents as auxiliary solvents. Useful liquid solvents are essentially: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, and also water.

In principle it is possible to use all suitable solvents. Examples of suitable solvents are aromatic hydrocarbons, such as xylene, toluene or alkylnaphthalenes, chlorinated aromatic or chlorinated aliphatic hydrocarbons, such as chlorobenzene, chloroethylene or methylene chloride, aliphatic hydrocarbons, such as cyclohexane, paraffins, petroleum fractions, mineral and vegetable oils, alcohols, such as methanol, ethanol, isopropanol, butanol or glycol and their ethers and esters, ketones such as acetone, methyl ethyl ketone, methyl isobutyl ketone or cyclohexanone, strongly polar solvents, such as dimethyl sulphoxide, and also water.

In principle it is possible to use all suitable carriers. Useful carriers include in particular: for example ammonium salts and ground natural minerals such as kaolins, clays, talc, chalk, quartz, attapulgite, montmorillonite or diatomaceous earth, and ground synthetic materials such as finely divided silica, alumina and natural or synthetic silicates, resins, waxes and/or solid fertilizers. Mixtures of such carriers can likewise be used. Useful carriers for granules include: for example crushed and fractionated natural rocks such as calcite, marble, pumice, sepiolite, dolomite, and synthetic granules of inorganic and organic meals, and also granules of organic material such as sawdust, paper, coconut shells, maize cobs and tobacco stalks.

Liquefied gaseous extenders or solvents can also be used. Particularly suitable extenders or carriers are those which are gaseous at ambient temperature and under atmospheric pressure, for example aerosol propellant gases, such as halogenated hydrocarbons, and also butane, propane, nitrogen and carbon dioxide.

Examples of emulsifiers and/or foam-formers, dispersants or wetting agents with ionic or nonionic properties, or mixtures of these surfactants, are salts of polyacrylic acid, salts of lignosulphonic acid, salts of phenolsulphonic acid or naphthalenesulphonic acid, polycondensates of ethylene oxide with fatty alcohols or with fatty acids or with fatty amines, with substituted phenols (preferably alkylphenols or arylphenols), salts of sulphosuccinic esters, taurine derivatives (preferably alkyl taurates), phosphoric esters of polyethoxylated alcohols or phenols, fatty esters of polyols, and derivatives of the compounds containing sulphates, sulphonates and phosphates, for example alkylaryl polyglycol ethers, alkylsulphonates, alkyl sulphates, arylsulphonates, protein hydrolysates, lignosulphite waste liquors and methylcellulose. The presence of a surfactant is advantageous if one of the active compounds and/or one of the inert carriers is insoluble in water and when the application takes place in water.

Further auxiliaries which may be present in the formulations and the use forms derived therefrom include dyes such as inorganic pigments, for example iron oxide, titanium oxide and Prussian Blue, and organic dyes such as alizarin dyes, azo dyes and metal phthalocyanine dyes, and nutrients and trace nutrients such as salts of iron, manganese, boron, copper, cobalt, molybdenum and zinc.

Additional components may be stabilizers, such as cold stabilizers, preservatives, antioxidants, light stabilizers, or other agents which improve chemical and/or physical stability. Foam-formers or antifoams may also be present.

Tackifiers such as carboxymethylcellulose and natural and synthetic polymers in the form of powders, granules or lattices, such as gum arabic, polyvinyl alcohol and polyvinyl acetate, or else natural phospholipids such as cephalins and lecithins and synthetic phospholipids may also be present as additional auxiliaries in the formulations and the use forms derived therefrom. Further possible auxiliaries are mineral and vegetable oils.

If appropriate, the formulations and the use forms derived therefrom may also comprise further auxiliaries. Examples of such additives include fragrances, protective colloids, binders, adhesives, thickeners, thixotropic agents, penetrants, retention promoters, stabilizers, sequestrants, complexing agents, humectants, spreaders. Generally speaking, the active compounds may be combined with any solid or liquid adjuvant commonly used for purposes of formulation.

Useful retention promoters include all those substances which reduce the dynamic surface tension, for example dioctyl sulphosuccinate, or increase the viscoelasticity, for example hydroxypropylguar polymers.

Penetrants contemplated in the present context include all those substances which are commonly used to promote the penetration of agrochemically active compounds into plants. Penetrants are defined in this context by their ability to penetrate from the (generally aqueous) spray liquor and/or from the spray coating into the cuticle of the plant and thereby increase the mobility of active compounds in the cuticle. The method described in the literature (Baur et al., 1997, Pesticide Science 51, 131-152) may be used for the purpose of determining this quality. Examples include alcohol alkoxylates such as coconut fatty ethoxylate (10) or isotridecyl ethoxylate (12), fatty acid esters, for example rapeseed oil methyl ester or soya oil methyl ester, fatty amine alkoxylates, for example tallowamine ethoxylate (15), or ammonium and/or phosphonium salts, for example ammonium sulphate or diammonium hydrogenphosphate.

The formulations preferably comprise between 0.001% and 98% by weight of active compound or, with particular preference, between 0.01% and 95% by weight of active compound, more preferably between 0.5% and 90% by weight of active compound, based on the weight of the formulation.

The treatment of the plants and plant parts with the compounds and compositions according to the invention is carried out directly or by action on their surroundings, habitat or storage space using customary treatment methods, for example by dipping, spraying, atomizing, irrigating, evaporating, dusting, fogging, broadcasting, foaming, painting, spreading-on, injecting, watering (drenching), drip irrigating and, in the case of propagation material, in particular in the case of seed, furthermore as a powder for dry seed treatment, a solution for seed treatment, a water-soluble powder for slurry treatment, by incrusting, by coating with one or more coats, etc. It is furthermore possible to apply the active compounds by the ultra-low volume method or to inject the active compound preparation or the active compound itself into the soil.

A preferred direct treatment of the plants is foliar application, i.e. compounds or compositions according to the invention are applied to the foliage, where the treatment frequency and the application rate can be adapted to the level of infestation with the phytopathogenic nematodes in question.

In the case of systemically active compounds, the compounds or compositions according to the invention access the plants via the root system. The plants are then treated by the action of the compounds or compositions according to the invention on the habitat of the plant. This may be done, for example, by drenching, or by mixing into the soil or the nutrient solution, i.e. the locus of the plant (e.g. soil or hydroponic systems) is impregnated with a liquid form of the active compounds or active compound combinations or compositions according to the invention, or by soil application, i.e. the active compounds or active compound combinations or compositions according to the invention are introduced in solid form (e.g. in the form of granules) into the locus of the plants. In the case of paddy rice crops, this can also be done by metering the invention in a solid application form (for example as granules) into a flooded paddy field.

The invention can be used to treat all plants and parts of plants. Plants in this context are understood to include all plants and plant populations, such as desired and unwanted wild plants or crop plants (including naturally occurring crop plants). Crop plants can be plants which can be obtained by conventional breeding and optimization methods or by biotechnological and genetic engineering methods or combinations of these methods, including the transgenic plants and including the plant varieties which can or cannot be protected by varietal property rights. Plant parts should be understood to mean all parts and organs of the plants above and below ground, such as shoot, leaf, flower and root, examples given being leaves, needles, stems, flowers, fruit bodies, fruits and seeds, and also tubers, roots and rhizomes. Parts of plants also include harvested plants and vegetative and generative propagation material, for example seedlings, tubers, rhizomes, cuttings and seeds.

As already mentioned above, it is possible to treat all plants and their parts according to the invention. In a preferred embodiment, wild plant species and plant cultivars, or those obtained by conventional biological breeding methods, such as crossing or protoplast fusion, and also parts thereof, are treated. In a further preferred embodiment, transgenic plants and plant cultivars obtained by genetic engineering, if appropriate in combination with conventional methods (Genetically Modified Organisms), and parts thereof are treated. The term "parts" or "parts of plants" or "plant parts" has been explained above. The invention is used with particular preference to treat plants of the respective commercially customary cultivars or those that are in use. Plant cultivars are to be understood as meaning plants having new properties ("traits") and which have been obtained by conventional breeding, by mutagenesis or by recombinant DNA techniques. They can be cultivars, varieties, bio- or genotypes.

Preferred plants are those from the group of the useful plants, ornamentals, turfs, generally used trees which are employed as ornamentals in the public and domestic sectors, and forestry trees. Forestry trees comprise trees for the production of timber, cellulose, paper and products made from parts of the trees.

The term useful plants as used in the present context refers to crop plants which are employed as plants for obtaining foodstuffs, feedstuffs, fuels or for industrial purposes.

The useful plants which can be improved by the process according to the invention include, for example, the following plant species: turf, vines, cereals, for example wheat, barley, rye, oats, rice, maize and millet/sorghum; beet, for example sugar beet and fodder beet; fruits, for example pome fruit, stone fruit and soft fruit, for example apples, pears, plums, peaches, almonds, cherries and berries, for example strawberries, raspberries, blackberries; legumes, for example beans, lentils, peas and soya beans; oil crops, for example oilseed rape, mustard, poppies, olives, sunflowers, coconuts, castor oil plants, cacao beans and peanuts; cucurbits, for example pumpkin/squash, cucumbers and melons; fibre plants, for example cotton, flax, hemp and jute; citrus fruit, for example oranges, lemons, grapefruit and tangerines; vegetables, for example spinach, lettuce, asparagus, cabbage species, carrots, onions, tomatoes, potatoes and bell peppers; Lauraceae, for example avocado, Cinnamomum, camphor, or also plants such as tobacco, nuts, coffee, aubergine, sugar cane, tea, pepper, grapevines, hops, bananas, latex plants and ornamentals, for example flowers, shrubs, deciduous trees and coniferous trees. This enumeration does not constitute a limitation.

The following plants are considered to be particularly suitable target crops for applying the method according to the invention: cotton, aubergine, turf, pome fruit, stone fruit, soft fruit, maize, wheat, barley, cucumber, tobacco, vines, rice, cereals, pear, beans, soya beans, oilseed rape, tomato, bell pepper, melons, cabbage, potatoes and apples.

Examples of trees which can be improved in accordance with the method according to the invention are: *Abies* sp., *Eucalyptus* sp., *Picea* sp., *Pinus* sp., *Aesculus* sp., *Platanus* sp., *Tilia* sp., *Acer* sp., *Tsuga* sp., *Fraxinus* sp., *Sorbus* sp., *Betula* sp., *Crataegus* sp., *Ulmus* sp., *Quercus* sp., *Fagus* sp., *Salix* sp., *Populus* sp.

Preferred trees which can be improved by the method according to the invention include: from the tree species *Aesculus: A. hippocastanum, A. pariflora, A. carnea*; from the tree species *Platanus: P. aceriflora, P. occidentalis, P. racemosa*; from the tree species *Picea: P. abies*; from the tree species *Pinus: P. radiate, P. ponderosa, P. contorta, P. sylvestre, P. elliottii, P. montecola, P. albicaulis, P. resinosa, P. palustris, P. taeda, P. flexilis, P. jeffregi, P. baksiana, P. strobes*; from the tree species *Eucalyptus: E. grandis, E. globulus, E. camadentis, E. nitens, E. obliqua, E. regnans, E. pilularus*.

Particularly preferred trees which can be improved by the method according to the invention include: from the tree species *Pinus: P. radiate, P. ponderosa, P. contorta, P. sylvestre, P. strobes*; from the tree species *Eucalyptus: E. grandis, E. globulus, E. camadentis*.

Very particularly preferred trees which can be improved by the method according to the invention are: horse chestnut, Platanaceae, linden tree, maple tree.

The present invention can also be applied to any turf grasses, including cool-season turf grasses and warm-season turf grasses. Examples of cool-season turf grasses are bluegrasses (*Poa* spp.), such as Kentucky bluegrass (*Poa pratensis* L.), rough bluegrass (*Poa trivialis* L.), Canada bluegrass (*Poa compressa* L.), annual bluegrass (*Poa annua* L.), upland bluegrass (*Poa glaucantha* Gaudin), wood bluegrass (*Poa nemoralis* L.) and bulbous bluegrass (*Poa bulbosa* L.); bentgrasses (*Agrostis* spp.) such as creeping bentgrass (*Agrostis palustris* Huds.), colonial bentgrass (*Agrostis tenuis* Sibth.), velvet bentgrass (*Agrostis canina* L.), South German Mixed Bentgrass (*Agrostis* spp. including *Agrostis tenius* Sibth., *Agrostis canina* L., and *Agrostis palustris* Huds.), and redtop (*Agrostis alba* L.);

fescues (*Festuca* spp.), such as red fescue (*Festuca rubra* L. spp. *rubra*), creeping fescue (*Festuca rubra* L.), chewings fescue (*Festuca rubra commutata* Gaud.), sheep fescue (*Festuca ovina* L.), hard fescue (*Festuca longifolia* Thuill.), hair fescue (*Festucu capillata* Lam.), tall fescue (*Festuca arundinacea* Schreb.) and meadow fescue (*Festuca elanor* L.);

ryegrasses (*Lolium* spp.), such as annual ryegrass (*Lolium multiflorum* Lam.), perennial ryegrass (*Lolium perenne* L.) and italian ryegrass (*Lolium multiflorum* Lam.);

and wheatgrasses (*Agropyron* spp.), such as fairway wheatgrass (*Agropyron cristatum* (L.) Gaertn.), crested wheatgrass (*Agropyron desertorum* (Fisch.) Schult.) and western wheatgrass (*Agropyron smithii* Rydb.).

Examples of further cool-season turfgrasses are beachgrass (*Ammophila breviligulata* Fern.), smooth bromegrass (*Bromus inermis* Leyss.), cattails such as Timothy (*Phleum pratense* L.), sand cattail (*Phleum subulatum* L.), orchard grass (*Dactylis glomerata* L.), weeping alkaligrass (*Puccinellia distans* (L.) Parl.) and crested dog's-tail (*Cynosurus cristatus* L.).

Examples of warm-season turfgrasses are Bermuda grass (*Cynodon* spp. L. C. Rich), zoysia grass (*Zoysia* spp. Willd.), St. Augustine grass (*Stenotaphrum secundatum* Walt Kuntze), centipede grass (Eremochloa ophiuroides Munro Hack.), carpet grass (*Axonopus affinis* Chase), Bahia grass (*Paspalum notatum* Flugge), Kikuyu grass (*Pennisetum clandestinum* Hochst. ex Chiov.), buffalo grass (*Buchloe dactyloids* (Nutt.) Engelm.), Blue gramma (*Bouteloua gracilis* (H.B.K.) Lag. ex Griffiths), seashore *paspalum* (*Paspalum vaginatum* Swartz) and sideoats grama (*Bouteloua curtipendula* (Michx. Torr.). Cool-season turfgrasses are generally preferred for the use in accordance with the invention. Particular preference is given to bluegrass, bentgrass and redtop, fescues and ryegrasses. Bentgrass is especially preferred.

The examples below illustrate the invention without limiting it.

PREPARATION EXAMPLES

Example 1-20

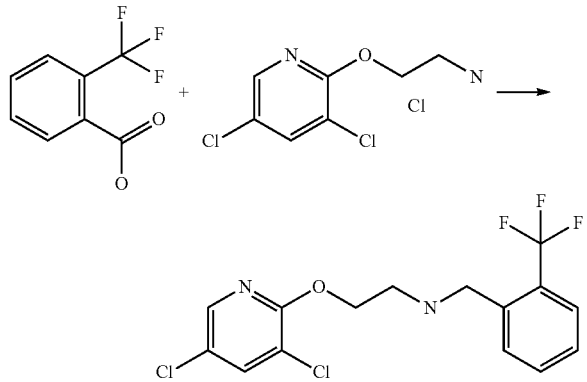

76 mg (0.4 mmol) of 2-(trifluoromethyl)benzoic acid, 107.2 mg (0.44 mmol) of 2-[(3,5-dichloropyridin-2-yl)oxy] ethanamine (hydrochloride), 30.6 mg (0.2 mmol) of 1-hydroxybenzotriazole (HOBt), 24.4 mg (0.02 mmol) of DMAP, 76.7 mg (0.4 mmol) of EDC hydrochloride and 51.7 mg (0.4 mmol) of diisopropylethylamine are dissolved in 10 ml of dichloromethane, and the solution is stirred at room temperature for 16 h. After the reaction has ended, 10 ml of water are added, the organic phase is separated off and the aqueous phase is re-extracted with 5 ml of dichloromethane. The dichloromethane phases are filtered through sodium sulphate/silica gel cartridges, the solvent is evaporated and the residue is separated by preparative HPLC.

Yield: 107 mg (70.6% of theory), colourless solid.

$^1$H-NMR (d6-DMSO): δ [ppm], 8.70 (t, NH), 8.22 (s, 1H), 8.18 (d, 1H), 7.78-7.49 (m, 4H), 4.46 (t, 2H), 3.65-3.61 (q, 2H).

The examples listed in the table below can be prepared in the same manner.

TABLE 1

(I-1)

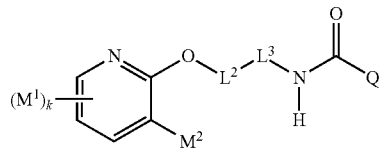

| Number | Q | $M^1$ | $M^2$ | $L^2$ | $L^3$ |
|---|---|---|---|---|---|
| 1-1 | 2-(trifluoromethyl)phenyl | 5-CF3 | Cl | CH2 | CH2 |
| 1-2 | 2-(difluoromethyl)phenyl | 5-CF3 | Cl | CH2 | CH2 |
| 1-3 | 3-chloro-2-pyridyl | 5-CF3 | Cl | CH2 | CH2 |
| 1-4 | 2-(trifluoromethyl)phenyl | 5-CF3 | Cl | CH2 | CH(CH3) |
| 1-5 | 2-fluorophenyl | H | Cl | CH2 | CH2 |
| 1-6 | 2-chlorophenyl | H | Cl | CH2 | CH2 |
| 1-7 | 2-bromophenyl | H | Cl | CH2 | CH2 |
| 1-8 | 2-iodophenyl | H | Cl | CH2 | CH2 |
| 1-9 | 2,6-difluorophenyl | H | Cl | CH2 | CH2 |
| 1-10 | 2-(trifluoromethyl)phenyl | H | Cl | CH2 | CH2 |
| 1-11 | 2-chloro-3-pyridyl | H | Cl | CH2 | CH2 |
| 1-12 | 3-iodothien-2-yl | H | Cl | CH2 | CH2 |
| 1-13 | 3-chlorothien-2-yl | H | Cl | CH2 | CH2 |
| 1-14 | 3-bromofuran-2-yl | H | Cl | CH2 | CH2 |
| 1-15 | 2-fluorophenyl | 5-Cl | Cl | CH2 | CH2 |

TABLE 1-continued (I-1)

| Number | Q | M¹ | M² | L² | L³ |
|---|---|---|---|---|---|
| 1-16 | 2-chlorophenyl | 5-Cl | Cl | CH2 | CH2 |
| 1-17 | 2-bromophenyl | 5-Cl | Cl | CH2 | CH2 |
| 1-18 | 2-iodophenyl | 5-Cl | Cl | CH2 | CH2 |
| 1-19 | 2,6-difluorophenyl | 5-Cl | Cl | CH2 | CH2 |
| 1-20 | 2-(trifluoromethyl)phenyl | 5-Cl | Cl | CH2 | CH2 |
| 1-21 | 2-chloro-3-pyridyl | 5-Cl | Cl | CH2 | CH2 |
| 1-22 | 3-iodothien-2-yl | 5-Cl | Cl | CH2 | CH2 |
| 1-23 | 3-chlorothien-2-yl | 5-Cl | Cl | CH2 | CH2 |
| 1-24 | 3-bromofuran-2-yl | 5-Cl | Cl | CH2 | CH2 |
| 1-25 | 2-(trifluoromethyl)phenyl | 5-CF3 | Cl | CH(CH3) | CH2 |
| 1-26 | 2-chlorophenyl | 5-CF3 | Cl | CH2 | CH2 |
| 1-27 | 2-bromophenyl | 5-CF3 | Cl | CH2 | CH2 |
| 1-28 | 2-iodophenyl | 5-CF3 | Cl | CH2 | CH2 |
| 1-29 | 2-methylphenyl | 5-CF3 | Cl | CH2 | CH2 |
| 1-30 | 2-(trifluoromethyl)phenyl | 5-CF3 | Cl | CH(cPr) | CH2 |
| 1-31 | 2-fluorophenyl | 5-Cl | H | CH2 | CH2 |
| 1-32 | 2-chlorophenyl | 5-Cl | H | CH2 | CH2 |
| 1-33 | 2-bromophenyl | 5-Cl | H | CH2 | CH2 |
| 1-34 | 2-iodophenyl | 5-Cl | H | CH2 | CH2 |
| 1-35 | 2,6-difluorophenyl | 5-Cl | H | CH2 | CH2 |
| 1-36 | 2-(trifluoromethyl)phenyl | 5-Cl | H | CH2 | CH2 |
| 1-37 | 2-chloro-3-pyridyl | 5-Cl | H | CH2 | CH2 |
| 1-38 | 3-iodothien-2-yl | 5-Cl | H | CH2 | CH2 |
| 1-39 | 3-chlorothien-2-yl | 5-Cl | H | CH2 | CH2 |
| 1-40 | 3-bromofuran-2-yl | 5-Cl | H | CH2 | CH2 |
| 1-41 | 2-fluorophenyl | 5-CF3 | H | CH2 | CH2 |
| 1-42 | 2-chlorophenyl | 5-CF3 | H | CH2 | CH2 |
| 1-43 | 2-bromophenyl | 5-CF3 | H | CH2 | CH2 |
| 1-44 | 2-iodophenyl | 5-CF3 | H | CH2 | CH2 |
| 1-45 | 2,6-difluorophenyl | 5-CF3 | H | CH2 | CH2 |
| 1-46 | 2-(trifluoromethyl)phenyl | 5-CF3 | H | CH2 | CH2 |
| 1-47 | 2-chloro-3-pyridyl | 5-CF3 | H | CH2 | CH2 |
| 1-48 | 3-iodothien-2-yl | 5-CF3 | H | CH2 | CH2 |
| 1-49 | 3-chlorothien-2-yl | 5-CF3 | H | CH2 | CH2 |
| 1-50 | 3-bromofuran-2-yl | 5-CF3 | H | CH2 | CH2 |
| 1-51 | 2-fluorophenyl | 5-CF3 | Cl | CH2 | CH2 |
| 1-52 | 2,6-difluorophenyl | 5-CF3 | Cl | CH2 | CH2 |
| 1-53 | 2-nitrophenyl | 5-CF3 | Cl | CH2 | CH2 |
| 1-54 | 2-chloro-3-pyridyl | H | Cl | CH2 | CH2 |
| 1-55 | 3-chloro-2-thienyl | H | Cl | CH2 | CH2 |
| 1-56 | 3-bromofuran-2-yl | 5-CF3 | Cl | CH2 | CH2 |
| 1-57 | 2-(trifluoromethyl)-3-pyridyl | 5-CF3 | H | CH2 | CH2 |
| 1-58 | 2-(trifluoromethyl)-3-pyridyl | H | H | CH2 | CH2 |
| 1-59 | 2-(trifluoromethyl)-5-chloro-3-pyridyl | 5-CF3 | Cl | CH2 | CH2 |
| 1-60 | 2-(trifluoromethyl)-5-chloro-3-pyridyl | 5-CF3 | H | CH2 | CH2 |
| 1-61 | 2-(trifluoromethyl)-5-chloro-3-pyridyl | H | Cl | CH2 | CH2 |
| 1-62 | 2-chloro-4-(trifluormethyl)-3-pyridyl | H | Cl | CH2 | CH2 |
| 1-63 | 2-(trifluoromethyl)-3-pyridyl | 5-CF3 | Cl | CH2 | CH2 |
| 1-64 | 2-chloro-4-(trifluormethyl)-3-pyridyl | 5-CF3 | H | CH2 | CH2 |
| 1-65 | 2-nitrophenyl | H | Cl | CH2 | C(CH3)(CH2CH3) |
| 1-66 | 2-nitrophenyl | H | CF3 | CH2 | CH2 |
| 1-67 | 2-nitrophenyl | H | F | CH2 | CH2 |
| 1-68 | 2-nitrophenyl | H | CF3 | CH2 | C(CH3)2 |
| 1-69 | 2-nitrophenyl | Cl | Cl | CH2 | C(CH3)2 |
| 1-70 | 2-(trifluoromethyl)-3-pyridyl | H | F | CH2 | CH2 |
| 1-71 | 2-(trifluoromethyl)-3-pyridyl | 5-CF3 | H | CH2 | C(CH3)2 |
| 1-72 | 2-nitrophenyl | H | Br | CH2 | C(CH3)2 |
| 1-73 | 2-(trifluoromethyl)-3-pyridyl | H | Cl | CH2 | C(CH3)(CH2CH3) |
| 1-74 | 2-(trifluoromethyl)-3-pyridyl | H | CF3 | CH2 | CH2 |
| 1-75 | 2-(trifluoromethyl)-3-pyridyl | H | Br | CH2 | C(CH3)2 |
| 1-76 | 2-(trifluoromethyl)-3-pyridyl | H | CF3 | CH2 | C(CH3)2 |
| 1-77 | 2-(trifluoromethyl)-3-pyridyl | Cl | Cl | CH2 | C(CH3)2 |
| 1-78 | 2-(trifluoromethyl)phenyl | 5-CF3 | H | CH2 | C(CH3)2 |
| 1-79 | 2-(trifluoromethyl)phenyl | H | F | CH2 | CH2 |
| 1-80 | 2-(trifluoromethyl)phenyl | H | Cl | CH2 | C(CH3)(CH2CH3) |
| 1-81 | 2-(trifluoromethyl)phenyl | H | CF3 | CH2 | CH2 |
| 1-82 | 2-(trifluoromethyl)phenyl | Cl | Cl | CH2 | C(CH3)2 |
| 1-83 | 2-(trifluoromethyl)phenyl | H | Br | CH2 | C(CH3)2 |
| 1-84 | 2,6-difluorophenyl | 5-CF3 | H | CH2 | C(CH3)2 |

TABLE 1-continued (I-1)

| Number | Q | M¹ | M² | L² | L³ |
|---|---|---|---|---|---|
| 1-85 | 2,6-difluorophenyl | H | F | CH2 | CH2 |
| 1-86 | 2,6-difluorophenyl | H | CF3 | CH2 | CH2 |
| 1-87 | 2,6-difluorophenyl | H | Cl | CH2 | C(CH3)(CH2CH3) |
| 1-88 | 2,6-difluorophenyl | Cl | Cl | CH2 | C(CH3)2 |
| 1-89 | 2,6-difluorophenyl | H | Br | CH2 | C(CH3)2 |
| 1-90 | 2-nitrophenyl | 5-CF3 | H | CH2 | C(CH3)2 |
| 1-91 | 2-(trifluoromethylsulphanyl)phenyl | 5-CF3 | Cl | CH2 | CH2 |
| 1-92 | 2-(trifluoromethylsulphanyl)phenyl | 5-CF3 | H | CH2 | CH2 |
| 1-93 | 2-(trifluoromethylsulphanyl)phenyl | H | CF3 | CH2 | CH2 |
| 1-94 | 2-(trifluoromethylsulphanyl)phenyl | 5-CF3 | H | CH2 | C(CH3)2 |
| 1-95 | 2-(trifluoromethylsulphanyl)phenyl | H | Cl | CH2 | CH2 |
| 1-96 | 2-(trifluoromethylsulphanyl)-3-pyridyl | 5-CF3 | Cl | CH2 | CH2 |
| 1-97 | 2-(trifluoromethylsulphonyl)phenyl | 5-CF3 | Cl | CH2 | CH2 |
| 1-98 | 2-(trifluoromethylsulphonyl)phenyl | H | Cl | CH2 | CH2 |
| 1-99 | 2-(trifluoromethylsulphonyl)phenyl | H | CF3 | CH2 | CH2 |
| 1-100 | 2-(trifluoromethylsulphonyl)-3-pyridyl | 5-CF3 | Cl | CH2 | CH2 |
| 1-101 | 2-(trifluoromethoxy)-3-pyridyl | H | CF3 | CH2 | CH2 |
| 1-102 | 2-(trifluoromethoxy)-3-pyridyl | 5-CF3 | H | CH2 | C(CH3)2 |
| 1-103 | 2-(trifluoromethoxy)-3-pyridyl | H | Cl | CH2 | CH2 |
| 1-104 | 2-(trifluoromethoxy)-3-pyridyl | 5-CF3 | H | CH2 | CH2 |
| 1-105 | 2-(trifluoromethoxy)-3-pyridyl | 5-CF3 | Cl | CH2 | CH2 |
| 1-106 | 2-(difluoromethoxy)-3-pyridyl | 5-CF3 | Cl | CH2 | CH2 |
| 1-107 | 2-fluorophenyl | 4-CN | H | CH2 | CH2 |
| 1-108 | 2-chlorophenyl | 4-CN | H | CH2 | CH2 |
| 1-109 | 2-bromophenyl | 4-CN | H | CH2 | CH2 |
| 1-110 | 2-iodophenyl | 4-CN | H | CH2 | CH2 |
| 1-111 | 2,6-difluorophenyl | 4-CN | H | CH2 | CH2 |
| 1-112 | 2-(trifluoromethyl)phenyl | 4-CN | H | CH2 | CH2 |
| 1-113 | 2-chloro-3-pyridyl | 4-CN | H | CH2 | CH2 |
| 1-114 | 2-(trifluoromethyl)-3-pyridyl | 4-CN | H | CH2 | CH2 |
| 1-115 | 2-(trifluoromethoxy)-3-pyridyl | 4-CN | H | CH2 | CH2 |
| 1-116 | 2-(trifluoromethyl)phenyl | 4-Cl | H | CH2 | CH2 |
| 1-117 | 2-(trifluoromethyl)-3-pyridyl | 4-Cl | H | CH2 | CH2 |
| 1-118 | 2,6-difluorophenyl | 4-Cl | H | CH2 | CH2 |
| 1-119 | 2-iodophenyl | 4-Cl | H | CH2 | CH2 |
| 1-120 | 2-fluorophenyl | 4-CF3 | H | CH2 | CH2 |
| 1-121 | 2-chlorophenyl | 4-CF3 | H | CH2 | CH2 |
| 1-122 | 2-bromophenyl | 4-CF3 | H | CH2 | CH2 |
| 1-123 | 2-iodophenyl | 4-CF3 | H | CH2 | CH2 |
| 1-124 | 2,6-difluorophenyl | 4-CF3 | H | CH2 | CH2 |
| 1-125 | 2-(trifluoromethyl)phenyl | 4-CF3 | H | CH2 | CH2 |
| 1-126 | 2-chloro-3-pyridyl | 4-CF3 | H | CH2 | CH2 |
| 1-127 | 2-(trifluoromethyl)-3-pyridyl | 4-CF3 | H | CH2 | CH2 |
| 1-128 | 2-(trifluoromethoxy)-3-pyridyl | 4-CF3 | H | CH2 | CH2 |
| 1-129 | 2-(trifluoromethylsulphanyl)-3-pyridyl | 4-CF3 | H | CH2 | CH2 |
| 1-130 | 2-(trifluoromethylsulphanyl)phenyl | 4-CF3 | H | CH2 | CH2 |
| 1-131 | 2-fluorophenyl | 5-F | F | CH2 | CH2 |
| 1-132 | 2-bromophenyl | 5-F | F | CH2 | CH2 |
| 1-133 | 2,6-difluorophenyl | 5-F | F | CH2 | CH2 |
| 1-134 | 2-(trifluoromethyl)phenyl | 5-F | F | CH2 | CH2 |
| 1-135 | 2-chloro-3-pyridyl | 5-F | F | CH2 | CH2 |
| 1-136 | 2-(trifluoromethyl)-3-pyridyl | 5-F | F | CH2 | CH2 |
| 1-137 | 2-(trifluoromethoxy)-3-pyridyl | 5-F | F | CH2 | CH2 |
| 1-138 | 2-(trifluoromethylsulphanyl)-3-pyridyl | 5-F | F | CH2 | CH2 |
| 1-139 | 2-(trifluoromethylsulphanyl)phenyl | 5-F | F | CH2 | CH2 |
| 1-140 | 2,6-bis(trifluoromethyl)phenyl | 5-F | F | CH2 | CH2 |
| 1-141 | 2-iodophenyl | 5-F | F | CH2 | CH2 |
| 1-142 | 2,6-difluorophenyl | 6-CF3 | H | CH2 | CH2 |
| 1-143 | 2-(trifluoromethylsulphanyl)phenyl | 6-CF3 | H | CH2 | CH2 |
| 1-144 | 2-bromo-3-pyridyl | 6-CF3 | H | CH2 | CH2 |
| 1-145 | 2-(trifluoromethyl)phenyl | 6-CF3 | H | CH2 | CH2 |
| 1-146 | 2-(trifluoromethylsulphanyl)-3-pyridyl | 6-CF3 | H | CH2 | CH2 |
| 1-147 | 2-(trifluoromethyl)-3-pyridyl | 6-CF3 | H | CH2 | CH2 |
| 1-148 | 2-bromo-3-pyridyl | H | NO2 | CH2 | CH2 |
| 1-149 | 2-(trifluoromethyl)phenyl | H | NO2 | CH2 | CH2 |
| 1-150 | 2,6-difluorophenyl | H | NO2 | CH2 | CH2 |
| 1-151 | 2-(trifluoromethylsulphanyl)phenyl | H | NO2 | CH2 | CH2 |
| 1-152 | 2-(trifluoromethylsulphanyl)-3-pyridyl | H | NO2 | CH2 | CH2 |
| 1-153 | 2,5-dichloro-3-thienyl | 5-CF3 | H | CH2 | CH2 |

TABLE 1-continued (I-1)

| Number | Q | M¹ | M² | L² | L³ |
|---|---|---|---|---|---|
| 1-154 | 2,5-dichloro-3-thienyl | 5-CF3 | Cl | CH2 | CH2 |
| 1-155 | 2-methoxy-3-pyridyl | 5-CF3 | Cl | CH2 | CH2 |
| 1-156 | 2-chlorophenyl | 5-CF3 | Cl | CH(CH3) | CH2 |
| 1-157 | 2-(difluoromethyl)phenyl | 5-CF3 | Cl | CH2 | CH(CH3) |
| 1-158 | 2-(difluoromethyl)phenyl | 5-CF3 | Cl | CH2 | C(CH3)2 |
| 1-159 | 2-(difluoromethyl)phenyl | 5-CF3 | Cl | CH(CH3) | CH2 |
| 1-160 | 2-nitrophenyl | 5-CF3 | Cl | CH2 | CH(CH3) |
| 1-161 | 2-nitrophenyl | 5-CF3 | Cl | CH2 | C(CH3)2 |
| 1-162 | 2-nitrophenyl | 5-CF3 | Cl | CH(CH3) | CH2 |
| 1-163 | 2-fluorophenyl | 5-CF3 | Cl | CH2 | CH(CH3) |
| 1-164 | 2-(trifluoromethyl)phenyl | 5-CN | F | CH2 | CH2 |
| 1-165 | 2-bromophenyl | 5-CF3 | Cl | CH2 | 1,1-cPr |
| 1-166 | 2-(trifluoromethoxy)-3-pyridyl | 5-CF3 | Cl | CH2 | 1,1-cPr |
| 1-167 | 2,6-difluorophenyl | 5-CF3 | Cl | CH2 | 1,1-cPr |
| 1-168 | 2,6-difluorophenyl | 5-CF3 | H | CH2 | 1,1-cPr |
| 1-169 | 2-(trifluoromethyl)phenyl | 5-CF3 | Cl | CH2 | 1,1-cPr |
| 1-170 | 2-iodophenyl | 5-CF3 | Cl | CH2 | 1,1-cPr |
| 1-171 | 2-bromo-3-pyridyl | 5-CF3 | Cl | CH2 | 1,1-cPr |
| 1-172 | 2-chloro-3-pyridyl | 5-CF3 | Cl | CH2 | 1,1-cPr |
| 1-173 | 2-(trifluoromethyl)phenyl | 5-CF3 | H | CH2 | 1,1-cPr |
| 1-174 | 2-iodophenyl | 5-CF3 | H | CH2 | 1,1-cPr |
| 1-175 | 2-bromo-3-pyridyl | 5-CF3 | H | CH2 | 1,1-cPr |
| 1-176 | 2-bromophenyl | 5-CF3 | H | CH2 | 1,1-cPr |
| 1-177 | 2-chloro-3-pyridyl | 5-CF3 | H | CH2 | 1,1-cPr |
| 1-178 | 2-(trifluoromethyl)-2-pyridyl | 5-CF3 | H | CH2 | 1,1-cPr |
| 1-179 | 2-(trifluoromethyl)-2-pyridyl | 5-CF3 | Cl | CH2 | 1,1-cPr |
| 1-180 | 2-(trifluoromethoxy)-3-pyridyl | 5-CF3 | H | CH2 | 1,1-cPr |
| 1-181 | 2-nitrophenyl | 5-CN | H | CH2 | CH2 |
| 1-182 | 2-(trifluoromethyl)-2-pyridyl | 5-CN | F | CH2 | CH2 |
| 1-183 | 2-nitrophenyl | 5-CN | F | CH2 | CH2 |
| 1-184 | 2-chloro-3-pyridyl | 5-CN | F | CH2 | CH2 |
| 1-185 | 2-iodophenyl | 5-CN | H | CH2 | CH2 |
| 1-186 | 2-bromo-3-pyridyl | 5-CN | F | CH2 | CH2 |
| 1-187 | 2-iodophenyl | 5-CN | F | CH2 | CH2 |
| 1-188 | 2,6-difluorophenyl | 5-CN | H | CH2 | CH2 |
| 1-189 | 2,6-difluorophenyl | 5-CN | F | CH2 | CH2 |
| 1-190 | 2-(trifluoromethoxy)-3-pyridyl | 5-CN | H | CH2 | CH2 |
| 1-191 | 2-bromophenyl | 5-CN | H | CH2 | CH2 |
| 1-192 | 2-bromophenyl | 5-CN | F | CH2 | CH2 |
| 1-193 | 2-fluorophenyl | 5-CN | H | CH2 | CH2 |
| 1-194 | 2-fluorophenyl | 5-CN | F | CH2 | CH2 |
| 1-195 | 2-nitrophenyl | 5-CF3 | Cl | CH2 | 1,1-cPr |
| 1-196 | 2-nitrophenyl | 5-CF3 | H | CH2 | 1,1-cPr |
| 1-197 | 2-iodophenyl | 5-CF3 | Cl | CH(CH3) | CH2 |
| 1-198 | 2-(trifluoromethyl)-3-pyridyl | 5-CF3 | Cl | CH2 | CH(CH3) |
| 1-199 | 2-(trifluoromethyl)-3-pyridyl | 5-CF3 | Cl | CH2 | C(CH3)2 |
| 1-200 | 2-(trifluoromethyl)-3-pyridyl | 5-CF3 | Cl | CH(CH3) | CH2 |
| 1-201 | 2-bromophenyl | 5-CF3 | Cl | CH2 | CH(CH3) |
| 1-202 | 2-bromophenyl | 5-CF3 | Cl | CH(CH3) | CH2 |
| 1-203 | 2-chlorophenyl | 5-CF3 | Cl | CH2 | CH(CH3) |
| 1-204 | 2,6-difluorophenyl | 5-CF3 | Cl | CH(CH3) | CH2 |
| 1-205 | 2-chloro-3-pyridyl | 5-CF3 | Cl | CH2 | C(CH3)2 |
| 1-206 | 2-chloro-3-pyridyl | 5-CF3 | Cl | CH(CH3) | CH2 |
| 1-207 | 2-chloro-3-pyridyl | 5-CF3 | Cl | CH2 | CH(CH3) |
| 1-208 | 3-chloro-2-pyridyl | 5-CF3 | Cl | CH2 | CH(CH3) |
| 1-209 | 3-chloro-2-pyridyl | 5-CF3 | Cl | CH(CH3) | CH2 |
| 1-210 | 2-(trifluoromethylsulphanyl)-3-pyridyl | 5-CF3 | Cl | CH(CH3) | CH2 |
| 1-211 | 2-iodophenyl | 5-CF3 | Cl | CH2 | CH(CH3) |
| 1-212 | 2-iodophenyl | 5-CF3 | Cl | CH2 | C(CH3)2 |

¹H NMR Data

The ¹H NMR data were determined with a Bruker Avance 400 equipped with a flow probe head (volume 60 μl), with tetramethylsilane as a reference (0.0) and the solvents $CD_3CN$, $CDCl_3$ or $D_6$-DMSO.

The NMR data for selected examples are listed either in conventional form (δ values, multiplet splitting, number of hydrogen atoms) or as NMR peak lists.

NMR Peak List Method

The ¹H NMR data of selected examples are stated in the form of ¹H NMR peak lists. For each signal peak, first the δ value in ppm and then the signal intensity in round brackets are listed. The δ value—signal intensity number pairs for different signal peaks are listed with separation from one another by semicolons.

The peak list for one example therefore takes the form of:

$\delta_1$ (intensity$_1$); $\delta_2$ (intensity$_2$); . . . ; $\delta_i$ (intensity$_i$); . . . ; $\delta_n$ (intensity$_n$)

The intensity of sharp signals correlates with the height of the signals in a printed example of an NMR spectrum in cm and shows the true ratios of the signal intensities. In the case of broad signals, several peaks or the middle of the signal and their relative intensities may be shown in comparison to the most intense signal in the spectrum.

For calibration of the chemical shift of the $^1$H NMR spectra we use tetramethylsilane and/or the chemical shift of the solvent, particularly in the case of spectra measured in DMSO. Therefore, the tetramethylsilane peak may but need not occur in the NMR peak lists.

The lists of the $^1$H NMR peaks are similar to the conventional $^1$H NMR printouts and thus usually contain all peaks listed in conventional NMR interpretations.

In addition, like conventional $^1$H NMR printouts, they may show solvent signals, signals of stereoisomers of the target compounds, which likewise form part of the subject matter of the invention, and/or peaks of impurities.

In the reporting of compound signals in the delta range of solvents and/or water, our lists of $^1$H NMR peaks show the usual solvent peaks, for example peaks of DMSO in DMSO-$d_6$ and the peak of water, which usually have a high intensity on average.

The peaks of stereoisomers of the target compounds and/or peaks of impurities usually have a lower intensity on average than the peaks of the target compounds (for example with a purity of >90%).

Such stereoisomers and/or impurities may be typical of the particular preparation process. Their peaks can thus help to identify reproduction of our preparation process with reference to "by-product fingerprints".

An expert calculating the peaks of the target compounds by known methods (MestreC, ACD simulation, but also with empirically evaluated expected values) can, if required, isolate the peaks of the target compounds, optionally using additional intensity filters. This isolation would be similar to the relevant peak picking in conventional $^1$H NMR interpretation.

Further details of 1H NMR peak lists can be found in Research Disclosure Database Number 564025.

TABLE 2

Compound No. 1-1, solvent: [CD$_3$CN], spectrometer: 399.95 MHz 8.4284 (6.38); 8.4257 (6.49); 8.0664 (7.14); 8.0618 (6.79); 7.7463 (4.17); 7.7269 (5.38); 7.6702 (1.71); 7.6528 (4.6); 7.6515 (4.61); 7.6345 (3.86); 7.6125 (3.65); 7.5936 (4.22); 7.5758 (1.45); 7.5747 (1.44); 7.4977 (5.11); 7.4792 (4.09); 7.0749 (1.4); 4.6125 (9); 4.5988 (16); 4.5851 (9.66); 3.7802 (4.97); 3.7659 (12.33); 3.7521 (11.66); 3.7381 (4.63); 2.1732 (9.66); 2.1635 (17.44); 1.9645 (0.67); 1.9583 (0.92); 1.9526 (8.01); 1.9465 (15.25); 1.9403 (21.55); 1.9341 (14.99); 1.9279 (7.75); 1.1711 (0.37); 1.0063 (0.37); 0.008 (0.36); −0.0002 (10.83); −0.0085 (0.43)

Compound No. 1-2, solvent: [CD$_3$CN], spectrometer: 399.95 MHz 8.4217 (4.67); 8.4193 (5.86); 8.4166 (5.83); 8.4142 (4.68); 8.0677 (6.82); 8.0622 (6.3); 7.7497 (3.69); 7.731 (4.89); 7.6271 (1.55); 7.6207 (2.22); 7.6093 (2.32); 7.6048 (3.32); 7.5924 (1.73); 7.5854 (3.35); 7.5792 (1.49); 7.5622 (5.53); 7.5606 (5.55); 7.5519 (6.26); 7.5473 (8.57); 7.545 (9.21); 7.5332 (1.06); 7.5263 (0.43); 7.3905 (4.12); 7.2516 (8.53); 7.2134 (1.33); 7.1127 (4.22); 4.6435 (9.63); 4.63 (16); 4.6164 (10.18); 3.7901 (5.4); 3.7758 (12.66); 3.7622 (11.61); 3.7482 (4.97); 2.1411 (18.4); 2.1134 (0.34); 2.1072 (0.42); 1.964 (3.92); 1.9579 (6.31); 1.952 (26.19); 1.9458 (45.34); 1.9397 (58.55); 1.9335 (40.04); 1.9273 (20.35); 1.9144 (0.33); 1.7682 (0.34); 1.3405 (1.98); 1.285 (2.34); 1.2691 (0.66); −0.0002 (2.57)

Compound No. 1-3, solvent: [CD3CN], spectrometer: 399.95 MHz 8.4897 (5.13); 8.4865 (4.96); 8.4783 (5.26); 8.4751 (4.92); 8.4115 (5.97); 8.4089 (5.88); 8.0542 (6.81); 8.0489 (6.42); 7.9599 (1.2); 7.8971 (5.31); 7.8939 (5.01); 7.8766 (5.82); 7.8734 (5.39); 7.4658 (5.54); 7.4543 (5.42); 7.4453 (5.07); 7.4338 (4.86); 4.6485 (9.38); 4.635 (16); 4.6214 (9.95); 3.8205 (5.16); 3.8062 (11.71); 3.7925 (11.16); 3.7783 (4.78); 2.1357 (15.92); 1.965 (2.63); 1.9588 (4.06); 1.9529 (17.77); 1.9468 (31.07); 1.9407 (40.7); 1.9345 (28.17); 1.9283 (14.43); 1.3408 (1.08); 1.2849 (1.27); 1.2691 (0.45); 1.2574 (0.75); 1.2423 (0.73); −0.0002 (1.76)

Compound No. 1-4, solvent: [CD3CN], spectrometer: 399.95 MHz 8.4 (0.65); 8.3973 (0.67); 8.3819 (0.4); 8.0603 (0.75); 8.0549 (0.72); 7.4706 (0.54); 7.4573 (0.44); 7.4502 (1.05); 7.2413 (0.6); 7.2352 (0.64); 7.2201 (0.41); 7.2138 (0.39); 6.9853 (0.69); 5.7284 (1.61); 5.2623 (0.38); 4.8564 (5.11); 4.6238 (0.39); 4.6127 (0.4); 4.6012 (0.49); 4.1401 (0.39); 4.1287 (0.39); 4.1173 (0.36); 4.0177 (0.48); 2.1329 (19.61); 1.9638 (1.92); 1.9578 (3.13); 1.9519 (13.39); 1.9457 (23.31); 1.9396 (30.3); 1.9334 (20.84); 1.9272 (10.7); 1.3864 (0.7); 1.3714 (12.25); 1.3631 (0.66); 1.3571 (0.62); 1.3404 (13.77); 1.2851 (16); 1.2765 (6.8); −0.0002 (1.15)

Compound No. 1-5, solvent: [DMSO], spectrometer: 399.95 MHz 8.4706 (2.94); 8.3172 (0.85); 8.1327 (6.06); 8.1287 (6.13); 8.1205 (6.34); 8.1165 (6.03); 7.9076 (6); 7.9036 (5.72); 7.8884 (6.41); 7.8844 (5.75); 7.6334 (2.5); 7.6292 (2.7); 7.615 (4.86); 7.6106 (5.38); 7.5955 (2.92); 7.5914 (2.69); 7.5526 (1.31); 7.5481 (1.28); 7.5392 (1.64); 7.5343 (3.16); 7.5315 (2.68); 7.5199 (2.75); 7.5137 (3.22); 7.5089 (1.79); 7.5001 (1.8); 7.4957 (1.49); 7.3031 (4.1); 7.2923 (4.87); 7.2813 (4.41); 7.2741 (9.97); 7.2547 (7.39); 7.0504 (6.17); 7.0381 (6.12); 7.0312 (5.98); 7.0189 (5.71); 4.5057 (7.56); 4.491 (16); 4.4765 (7.9); 3.685 (3.83); 3.6706 (10.58); 3.6563 (10.29); 3.6418 (3.5); 3.3281 (50.62); 3.3049 (0.37); 2.6723 (0.4); 2.5075 (47.63); 2.5032 (59.17); 2.4989 (43.36); 2.3299 (0.38); 1.3372 (1.1); 1.2499 (1.27); 1.2351 (0.56); −0.0002 (1.95)

TABLE 2-continued

Compound No. 1-6, solvent: [DMSO], spectrometer: 399.95 MHz 8.6342 (1.87); 8.621 (3.44); 8.6076 (1.88); 8.1404 (6.62); 8.1363 (7.05); 8.1282 (6.96); 8.124 (7.03); 7.9088 (6.78); 7.9047 (6.8); 7.8896 (7.35); 7.8855 (6.86); 7.4934 (3.36); 7.4917 (3.43); 7.4738 (8.03); 7.4724 (7.59); 7.4541 (3.52); 7.4477 (4.06); 7.4383 (4.54); 7.4319 (6.37); 7.4284 (1.86); 7.4189 (2.93); 7.4126 (7.37); 7.4005 (10.48); 7.3951 (12.85); 7.3919 (9.09); 7.3793 (4.26); 7.3761 (4.62); 7.3729 (1.76); 7.3603 (1.31); 7.357 (1.29); 7.0511 (7.39); 7.0389 (7.21); 7.0319 (7.12); 7.0197 (6.96); 5.7569 (1.91); 4.5022 (7.34); 4.4877 (16); 4.4731 (7.74); 3.6597 (3.85); 3.6454 (10.93); 3.631 (10.59); 3.6166 (3.53); 3.3257 (36.46); 2.6712 (0.36); 2.5243 (1.33); 2.511 (22.59); 2.5066 (44.58); 2.502 (58.55); 2.4975 (42.71); 2.493 (20.81); 2.3288 (0.39); 1.3367 (0.76); 1.2496 (0.95); −0.0002 (2.47)

Compound No. 1-7, solvent: [DMSO], spectrometer: 399.95 MHz 8.6304 (1.96); 8.6172 (3.66); 8.6035 (1.98); 8.1417 (6.77); 8.1376 (7.18); 8.1295 (7.18); 8.1254 (7.11); 7.9087 (7.11); 7.9045 (6.98); 7.8895 (7.63); 7.8853 (7.02); 7.6479 (6.53); 7.6299 (6.22); 7.6278 (6.86); 7.4449 (2.04); 7.4421 (2.13); 7.4244 (5.77); 7.4082 (6.48); 7.4053 (5.91); 7.3924 (0.37); 7.381 (5.01); 7.377 (9.95); 7.3683 (6.62); 7.3629 (6.37); 7.3575 (4.06); 7.3507 (4.86); 7.3491 (5.4); 7.3457 (3.92); 7.3441 (3.84); 7.3312 (2.95); 7.3262 (2.31); 7.0511 (7.51); 7.0389 (7.38); 7.0319 (7.26); 7.0197 (7.1); 5.7567 (0.94); 4.5031 (7.3); 4.4884 (16); 4.4738 (7.71); 3.6539 (3.83); 3.6395 (10.87); 3.6251 (10.56); 3.6106 (3.51); 3.325 (36.04); 2.6711 (0.39); 2.5242 (1.47); 2.5109 (23.79); 2.5065 (46.61); 2.5019 (60.68); 2.4974 (44.11); 2.493 (21.44); 2.3286 (0.41); 1.9892 (0.9); 1.3366 (0.75); 1.2496 (0.91); 1.175 (0.49); −0.0002 (2.49)

Compound No. 1-8, solvent: [DMSO], spectrometer: 399.95 MHz 8.5946 (1.92); 8.581 (3.66); 8.5673 (1.93); 8.1423 (6.72); 8.1382 (7.16); 8.1301 (7.07); 8.126 (7.09); 7.9081 (6.71); 7.904 (6.68); 7.8982 (0.58); 7.8889 (7.4); 7.8848 (7.24); 7.8803 (6.62); 7.878 (6.78); 7.8605 (6.79); 7.8582 (6.69); 7.4538 (2.91); 7.4512 (3.01); 7.4351 (6.91); 7.4324 (6.93); 7.4164 (4.56); 7.4137 (4.42); 7.3186 (6.45); 7.3145 (7.13); 7.2997 (5.2); 7.2955 (5.05); 7.1814 (3.87); 7.1772 (3.77); 7.1622 (5.67); 7.158 (5.41); 7.1432 (3.3); 7.1389 (3.06); 7.0512 (7.48); 7.039 (7.28); 7.032 (7.15); 7.0198 (7.05); 5.7563 (1.36); 4.5058 (7.03); 4.4909 (16); 4.476 (7.48); 3.6449 (3.68); 3.6303 (10.55); 3.6159 (10.24); 3.6011 (3.36); 3.3232 (54.71); 2.6752 (0.49); 2.6708 (0.64); 2.6661 (0.46); 2.524 (2.03); 2.5107 (37.32); 2.5062 (73.77); 2.5016 (96.79); 2.4971 (70.12); 2.4926 (33.56); 2.3328 (0.46); 2.3284 (0.63); 2.3237 (0.45); 1.9889 (0.55); 1.336 (0.75); 1.2496 (0.97); −0.0002 (3.84)

Compound No. 1-9, solvent: [DMSO], spectrometer: 399.95 MHz 8.9333 (1.93); 8.9203 (3.44); 8.9072 (1.89); 8.1368 (6.83); 8.1326 (7.3); 8.1246 (7.18); 8.1204 (7.15); 7.9073 (7.02); 7.9032 (6.96); 7.8881 (7.52); 7.884 (7.03); 7.5403 (1.3); 7.5237 (2.86); 7.5191 (2.58); 7.507 (1.96); 7.5026 (5.47); 7.4981 (2.04); 7.4858 (2.68); 7.4815 (3.23); 7.4649 (1.49); 7.1826 (1.24); 7.1795 (1.66); 7.172 (8.97); 7.1527 (11.37); 7.132 (7.6); 7.1243 (1.35); 7.0531 (7.63); 7.0408 (7.39); 7.0339 (7.26); 7.0216 (7.09); 4.4754 (7.5); 4.461 (16); 4.4466 (7.91); 3.6791 (3.98); 3.6649 (11.09); 3.6506 (10.74); 3.6364 (3.61); 3.3242 (62.43); 3.31 (0.38); 2.6756 (0.45); 2.6709 (0.6); 2.6665 (0.43); 2.5241 (2.2); 2.5109 (34.82); 2.5065 (67.05); 2.502 (86.82); 2.4974 (62.84); 2.4929 (30.3); 2.3331 (0.41); 2.3287 (0.55); 2.3241 (0.41); 1.3363 (1.11); 1.2497 (1.37); −0.0002 (3.16)

Compound No. 1-10, solvent: [DMSO], spectrometer: 399.95 MHz 8.7155 (1.98); 8.702 (3.69); 8.6889 (1.96); 8.144 (6.72); 8.1399 (7.07); 8.1318 (7.05); 8.1277 (7); 7.9115 (6.74); 7.9075 (6.53); 7.8924 (7.17); 7.8882 (6.63); 7.7801 (4.83); 7.7606 (6.4); 7.7362 (2.1); 7.7176 (5.47); 7.699 (4); 7.6573 (3.85); 7.6381 (4.89); 7.6192 (1.81); 7.5103 (5.82); 7.4915 (4.87); 7.0541 (7.36); 7.0419 (7.18); 7.0349 (7.05); 7.0227 (6.95); 5.757 (2.59); 4.4825 (7.25); 4.4679 (16); 4.4533 (7.67); 3.6571 (3.83); 3.6427 (10.84); 3.6283 (10.5); 3.6139 (3.46); 3.3247 (50.54); 2.6756 (0.39); 2.671 (0.52); 2.6665 (0.38); 2.5243 (1.76); 2.5109 (31.68); 2.5065 (61.85); 2.502 (80.34); 2.4974 (58.04); 2.493 (27.81); 2.3332 (0.4); 2.3288 (0.51); 2.3243 (0.38); 1.9891 (0.46); 1.3366 (0.72); 1.2497 (0.91); −0.0002 (2.89)

Compound No. 1-11, solvent: [DMSO], spectrometer: 399.95 MHz 8.823 (1.96); 8.8094 (3.58); 8.7962 (1.92); 8.4847 (0.37); 8.4708 (6.39); 8.4659 (6.69); 8.4587 (6.71); 8.4539 (6.51); 8.316 (0.5); 8.1423 (6.67); 8.1382 (7.3); 8.1301 (6.99); 8.126 (6.95); 8.1157 (0.58); 7.922 (0.37); 7.9126 (6.78); 7.9085 (6.69); 7.8934 (7.57); 7.8893 (6.78); 7.8795 (0.6); 7.8687 (6.56); 7.8638 (6.62); 7.8499 (7.54); 7.845 (7.37); 7.8247 (0.47); 7.6927 (0.37); 7.6743 (0.36); 7.521 (0.57); 7.5049 (7.6); 7.4929 (7.28); 7.4861 (6.75); 7.4741 (6.55); 7.055 (7.39); 7.0427 (7.2); 7.0358 (7.06); 7.0236 (6.87); 6.5738 (2.9); 4.5027 (7.4); 4.4929 (16); 4.4786 (7.88); 3.7336 (0.74); 3.7185 (0.47); 3.6769 (3.96); 3.6627 (11.19); 3.6485 (10.86); 3.6343 (3.62); 3.5788 (0.6); 3.5642 (0.49); 3.3225 (134.17); 2.6752 (1.15); 2.6707 (1.55); 2.6662 (1.11); 2.6616 (0.53); 2.5238 (5.54); 2.5105 (89.08); 2.5061 (173.3); 2.5016 (226.16); 2.4971 (163.99); 2.4926 (79.08); 2.3373 (0.57); 2.3329 (1.12); 2.3284 (1.49); 2.3239 (1.06); 2.3194 (0.5); 1.9888 (0.55); 1.3358 (0.52); 1.2983 (0.35); 1.2586 (0.56); 1.2493 (0.81); 1.235 (1.49); 1.1748 (0.34); −0.0002 (6.57)

Compound No. 1-12, solvent: [DMSO], spectrometer: 399.95 MHz 8.3525 (2.3); 8.3394 (4.18); 8.3261 (2.25); 8.3159 (1.27); 8.1334 (6.69); 8.1293 (6.81); 8.1211 (7.01); 8.1171 (6.65); 7.9049 (7.12); 7.9008 (6.74); 7.8857 (7.62); 7.8816 (6.83); 7.7097 (12.31); 7.697 (12.92); 7.3366 (0.66); 7.3324 (0.66); 7.2183 (13.38); 7.2055 (12.71); 7.1815 (1.17); 7.1762 (0.71); 7.0501 (7.33); 7.0379 (7.26); 7.0309 (7.11); 7.0187 (6.86); 5.7564 (0.42); 4.5015 (7.42); 4.4868 (16); 4.4723 (7.78); 3.6655 (3.98); 3.6511 (10.96); 3.6368 (10.66); 3.6224 (3.59); 3.3221 (169.56); 2.6754 (1.52); 2.671 (2); 2.6665 (1.45); 2.5103 (126.03); 2.5064 (232.83); 2.5019 (294.1); 2.4974 (214.49); 2.3331 (1.53); 2.3286 (2); 2.3241 (1.46); 1.351 (0.78); 1.3359 (11.56); 1.2986 (1.04); 1.2587 (1.99); 1.2497 (13.56); 1.2352 (2.69); 1.1875 (0.76); 1.1478 (0.38); 0.8541 (0.41); 0.0079 (0.4); −0.0001 (8.45); −0.0084 (0.35)

TABLE 2-continued

Compound No. 1-13, solvent: [DMSO], spectrometer: 399.95 MHz 8.3163 (0.6); 8.2175 (0.79); 8.204 (1.37); 8.1919 (0.76); 8.137 (0.45); 8.1268 (2.53); 8.1229 (2.55); 8.1147 (2.76); 8.1106 (2.44); 7.9085 (2.51); 7.9044 (2.34); 7.8893 (2.65); 7.8853 (2.37); 7.8425 (4.48); 7.8293 (4.62); 7.3365 (0.79); 7.333 (0.72); 7.182 (1.34); 7.1767 (0.78); 7.1477 (4.72); 7.1345 (4.52); 7.0507 (2.71); 7.0385 (2.67); 7.0315 (2.6); 7.0193 (2.49); 6.574 (2.18); 4.5135 (3.03); 4.499 (6.48); 4.4847 (3.17); 3.6937 (1.62); 3.6793 (4.63); 3.6651 (4.48); 3.6507 (1.48); 3.3228 (240.25); 2.6757 (1.66); 2.6713 (2.19); 2.6666 (1.54); 2.6624 (0.7); 2.5242 (8.37); 2.5109 (136.82); 2.5067 (256.87); 2.5022 (327.09); 2.4977 (233.46); 2.4934 (110.5); 2.3335 (1.67); 2.329 (2.19); 2.3244 (1.54); 1.3516 (0.87); 1.3362 (13.59); 1.2988 (1.08); 1.2591 (1.99); 1.2501 (16); 1.236 (2.12); 1.1878 (0.94); 1.1484 (0.41); 0.8544 (0.35); 0.0083 (0.35); 0.0003 (8.84)

Compound No. 1-14, solvent: [DMSO], spectrometer: 399.95 MHz 8.5191 (1.8); 8.5052 (3.44); 8.4914 (1.79); 8.126 (6.24); 8.1218 (6.68); 8.1138 (6.56); 8.1096 (6.6); 7.9049 (13.44); 7.9003 (16); 7.8975 (7.67); 7.8823 (7); 7.8782 (6.46); 7.0472 (7.07); 7.035 (6.85); 7.028 (6.74); 7.0158 (6.61); 6.8501 (13.56); 6.8453 (13.35); 4.4823 (6.66); 4.4675 (15.09); 4.4527 (7.07); 3.6325 (3.5); 3.6179 (10.22); 3.6034 (9.96); 3.5887 (3.22); 3.3234 (94.86); 2.6803 (0.32); 2.6759 (0.68); 2.6714 (0.95); 2.6668 (0.69); 2.5246 (3.17); 2.5113 (54.87); 2.5069 (108.29); 2.5023 (142.67); 2.4977 (103.38); 2.4932 (49.73); 2.3382 (0.35); 2.3336 (0.71); 2.329 (0.95); 2.3244 (0.68); 2.3199 (0.33); 1.336 (2.65); 1.2585 (0.49); 1.2496 (3.32); 1.2342 (0.71); −0.0002 (4.46)

Compound No. 1-15, solvent: [DMSO], spectrometer: 399.95 MHz 8.4628 (2.84); 8.3169 (0.37); 8.207 (11.18); 8.2011 (15.18); 8.171 (14.45); 8.1651 (10.66); 7.6256 (2.56); 7.6211 (2.97); 7.6072 (4.99); 7.6025 (5.95); 7.5925 (0.74); 7.5876 (3.14); 7.5832 (3.12); 7.5523 (1.47); 7.5477 (1.4); 7.5391 (1.65); 7.5342 (3.27); 7.5312 (2.51); 7.5294 (2.4); 7.5271 (2.07); 7.5202 (2.63); 7.5185 (2.53); 7.5161 (2.52); 7.5133 (3.53); 7.5085 (1.94); 7.4999 (1.99); 7.4953 (1.72); 7.3788 (0.82); 7.3017 (4.26); 7.2916 (4.81); 7.2892 (4.64); 7.2806 (4.16); 7.2732 (10.06); 7.2537 (8.53); 4.4986 (7.3); 4.4841 (16); 4.4697 (7.79); 3.6787 (3.6); 3.6645 (10.28); 3.6502 (10.04); 3.6359 (3.36); 3.3253 (39.68); 2.6766 (0.37); 2.6721 (0.49); 2.6674 (0.36); 2.5254 (1.53); 2.512 (28.48); 2.5076 (56.26); 2.503 (73.42); 2.4984 (53.33); 2.494 (25.81); 2.3342 (0.34); 2.3298 (0.48); 2.3253 (0.35); 2.0612 (0.52); 2.0418 (0.5); 1.3368 (1.84); 1.3181 (0.36); 1.2729 (0.36); 1.2498 (2.21); 1.1881 (0.46); −0.0002 (2.5)

Compound No. 1-16, solvent: [DMSO], spectrometer: 399.95 MHz 8.6294 (2.12); 8.616 (4.03); 8.6027 (2.13); 8.2196 (10.99); 8.2137 (14.01); 8.1748 (12.77); 8.169 (9.97); 7.493 (3.9); 7.4736 (8.74); 7.4722 (8.38); 7.455 (3.58); 7.4481 (4.25); 7.4397 (4.64); 7.4328 (6.58); 7.4289 (1.88); 7.4198 (2.42); 7.4129 (5.92); 7.398 (12.53); 7.3955 (11.71); 7.3923 (14.07); 7.3801 (4.62); 7.3768 (4.61); 7.3611 (1.17); 7.3579 (1.12); 5.7567 (0.94); 4.4947 (7.41); 4.4804 (16); 4.4661 (7.79); 3.6557 (3.91); 3.6415 (11.01); 3.6273 (10.66); 3.613 (3.54); 3.3238 (41.2); 2.6756 (0.44); 2.6711 (0.6); 2.6668 (0.43); 2.5243 (1.93); 2.511 (34.39); 2.5066 (67.44); 2.5021 (88); 2.4976 (64.27); 2.4932 (31.35); 2.3333 (0.4); 2.3288 (0.54); 2.3245 (0.39); 1.3364 (1.72); 1.2496 (2.1); 1.2345 (0.39); −0.0002 (2.65)

Compound No. 1-18, solvent: [DMSO], spectrometer: 399.95 MHz 8.5901 (2.13); 8.5763 (4.19); 8.5625 (2.12); 8.2209 (12.78); 8.215 (16); 8.1723 (15.92); 8.1664 (12.64); 7.879 (6.65); 7.8767 (7.02); 7.8592 (7.27); 7.8569 (7.19); 7.4547 (3.16); 7.452 (3.27); 7.4359 (7.42); 7.4332 (7.5); 7.4172 (4.91); 7.4145 (4.78); 7.3149 (6.87); 7.3108 (7.62); 7.296 (5.6); 7.2918 (5.45); 7.1817 (4.36); 7.1775 (4.14); 7.1625 (6.05); 7.1583 (5.77); 7.1434 (3.64); 7.1392 (3.33); 5.7564 (0.34); 4.4968 (6.84); 4.4822 (15.38); 4.4677 (7.23); 3.6411 (3.61); 3.6268 (10.3); 3.6124 (9.99); 3.5979 (3.27); 3.3225 (68.56); 2.6753 (0.58); 2.6708 (0.81); 2.6662 (0.58); 2.5241 (2.63); 2.5193 (4.22); 2.5108 (45.29); 2.5063 (89.94); 2.5017 (118.6); 2.4971 (85.59); 2.4926 (40.71); 2.333 (0.57); 2.3284 (0.77); 2.3239 (0.56); 1.989 (0.48); 1.3359 (1.94); 1.2586 (0.36); 1.2495 (2.5); 1.2345 (0.4); −0.0002 (4.14)

Compound No. 1-19, solvent: [DMSO], spectrometer: 399.95 MHz 8.9233 (1.87); 8.9098 (3.5); 8.8965 (1.86); 8.2136 (11.78); 8.2078 (15.55); 8.174 (16); 8.1681 (12.07); 7.5404 (1.33); 7.5238 (2.85); 7.5191 (2.52); 7.5071 (1.84); 7.5026 (5.49); 7.4981 (1.94); 7.4859 (2.65); 7.4815 (3.22); 7.4649 (1.51); 7.1824 (1.11); 7.1792 (1.5); 7.1717 (9.2); 7.1524 (11.24); 7.1425 (1.44); 7.1317 (7.77); 7.124 (1.31); 5.7564 (1.55); 4.4717 (6.79); 4.4575 (14.5); 4.4433 (7.24); 3.6753 (3.55); 3.6612 (9.98); 3.6471 (9.68); 3.633 (3.27); 3.3233 (75.21); 2.6756 (0.5); 2.671 (0.72); 2.6662 (0.52); 2.5243 (2.38); 2.5193 (3.74); 2.5109 (41.31); 2.5064 (82.92); 2.5019 (109.87); 2.4973 (79.77); 2.4927 (38.45); 2.3333 (0.55); 2.3286 (0.75); 2.324 (0.54); 1.3358 (0.83); 1.2495 (0.9); 0.008 (1.65); −0.0002 (47.98); −0.0085 (1.59)

Compound No. 1-20, solvent: [DMSO], spectrometer: 399.95 MHz 8.7112 (1.85); 8.6977 (3.57); 8.6839 (1.84); 8.3161 (2.56); 8.2246 (12.63); 8.2187 (16); 8.1782 (15); 8.1723 (11.66); 7.7793 (4.55); 7.7599 (6.05); 7.7369 (1.97); 7.7195 (5.22); 7.7008 (3.79); 7.6586 (3.61); 7.6394 (4.62); 7.6204 (1.73); 7.5078 (5.53); 7.489 (4.66); 5.7564 (0.71); 4.4739 (6.53); 4.4595 (14.43); 4.4452 (6.92); 3.6534 (3.33); 3.6392 (9.44); 3.625 (9.18); 3.6107 (3.06); 3.3241 (92.23); 3.3003 (0.91); 2.6755 (0.54); 2.6711 (0.75); 2.6665 (0.55); 2.5244 (2.62); 2.5197 (4.12); 2.5111 (43.72); 2.5066 (87.05); 2.502 (114.72); 2.4974 (82.67); 2.4928 (39.27); 2.3334 (0.59); 2.3288 (0.78); 2.3242 (0.57); 1.3361 (1); 1.2496 (1.28); 0.008 (1.97); −0.0002 (55.4); −0.0086 (1.75)

Compound No. 1-21, solvent: [DMSO], spectrometer: 399.95 MHz 8.8179 (2.16); 8.8042 (4.07); 8.7906 (2.12); 8.472 (7.01); 8.4672 (7.48); 8.46 (7.48); 8.4551 (7.33); 8.3156 (2.8); 8.2234 (12.42); 8.2175 (15.92); 8.1801 (16); 8.1742 (12.38); 7.8707 (7.31); 7.8658 (7.43); 7.8519 (8.38); 7.847 (7.92); 7.5064 (8.23); 7.4943 (8.01); 7.4875 (7.51);

TABLE 2-continued 7.4755 (7.32); 5.7562 (0.42); 4.4992 (7.32); 4.4851 (15.51); 4.471 (7.79); 3.6736 (3.81); 3.6596 (10.75); 3.6454 (10.46); 3.6313 (3.55); 3.3229 (204.99); 3.2992 (1.58); 2.6796 (0.5); 2.6753 (1.08); 2.6707 (1.52); 2.6663 (1.08); 2.6617 (0.52); 2.524 (4.78); 2.5107 (87.35); 2.5062 (173.27); 2.5017 (227.98); 2.4971 (166.85); 2.4927 (81.56); 2.3373 (0.57); 2.333 (1.15); 2.3285 (1.56); 2.3239 (1.14); 2.3195 (0.56); 1.3357 (0.39); 1.2586 (0.34); 1.2494 (0.51); 1.234 (0.33); 0.1459 (0.36); 0.0079 (3.21); −0.0002 (90.25); −0.0085 (3.42); −0.1497 (0.4)
Compound No. 1-22, solvent: [DMSO], spectrometer: 399.95 MHz 8.3452 (2.08); 8.3315 (3.94); 8.3172 (2.07); 8.2057 (11.24); 8.1998 (14.92); 8.1932 (1.04); 8.166 (16); 8.1601 (11.87); 7.8415 (0.35); 7.8283 (0.35); 7.7404 (0.51); 7.7306 (0.35); 7.7099 (14); 7.6972 (14.54); 7.2166 (14.91); 7.2039 (14.09); 7.1463 (0.34); 5.7569 (0.6); 4.497 (6.57); 4.4827 (14.1); 4.4684 (6.79); 3.6621 (3.5); 3.6479 (9.66); 3.6336 (9.43); 3.6193 (3.28); 3.3246 (50.2); 2.6767 (0.39); 2.6721 (0.53); 2.6674 (0.37); 2.5254 (1.83); 2.5205 (2.99); 2.512 (31.02); 2.5076 (61.25); 2.503 (80.27); 2.4984 (57.89); 2.4939 (27.62); 2.3342 (0.39); 2.3297 (0.52); 2.3251 (0.37); 2.1006 (0.5); 2.0384 (0.43); 1.3365 (1.61); 1.2991 (0.52); 1.2588 (0.78); 1.2496 (1.93); 1.1878 (0.76); 0.008 (1.41); −0.0002 (38.07); −0.0085 (1.26)
Compound No. 1-23, solvent: [DMSO], spectrometer: 399.95 MHz 8.3161 (0.9); 8.2164 (1.85); 8.1999 (12.19); 8.194 (16); 8.1717 (15.01); 8.1658 (10.05); 7.8413 (12.95); 7.8281 (13.44); 7.1462 (13.84); 7.133 (13.38); 4.5076 (6.56); 4.4933 (14.2); 4.4791 (6.96); 3.6864 (3.48); 3.6723 (9.92); 3.658 (9.64); 3.6438 (3.2); 3.324 (113.44); 3.3005 (0.34); 2.6761 (0.61); 2.6716 (0.85); 2.667 (0.64); 2.5249 (2.67); 2.5201 (3.95); 2.5115 (46.64); 2.507 (94.88); 2.5024 (126.43); 2.4979 (92.04); 2.4933 (44.39); 2.3338 (0.59); 2.3292 (0.83); 2.3246 (0.59); 1.3359 (1.85); 1.2985 (0.55); 1.2586 (0.83); 1.2495 (2.17); 1.1874 (0.8); 0.0079 (1.77); −0.0003 (54.36); −0.0086 (1.77)
Compound No. 1-24, solvent: [DMSO], spectrometer: 399.95 MHz 8.5144 (1.98); 8.5005 (3.89); 8.4865 (1.99); 8.1974 (11.54); 8.1915 (16); 8.1641 (14.77); 8.1582 (10.52); 7.9049 (14.26); 7.9001 (14.22); 6.8501 (15.25); 6.8453 (15); 5.7572 (0.48); 4.4757 (6.7); 4.4611 (15.08); 4.4466 (7.08); 3.6273 (3.52); 3.6129 (10.25); 3.5984 (9.98); 3.5839 (3.23); 3.3252 (75.56); 2.6768 (0.48); 2.6721 (0.64); 2.6678 (0.46); 2.5256 (1.94); 2.5207 (3.12); 2.5123 (37.61); 2.5078 (75.19); 2.5032 (99.08); 2.4986 (71.38); 2.4941 (33.88); 2.3344 (0.47); 2.3299 (0.65); 2.3255 (0.48); 2.1031 (0.56); 2.038 (0.5); 1.3365 (1.43); 1.2991 (0.47); 1.2589 (0.7); 1.2498 (1.7); 0.008 (0.9); −0.0002 (26.9); −0.0085 (0.82)
Compound No. 1-25: $^1$H-NMR (400.0 MHz, DMSO): δ = 8.724 (1.3); 8.710 (2.6); 8.695 (1.3);

8.585 (0.6); 8.583 (0.7); 8.580 (0.6); 8.578 (0.6); 8.568 (4.0); 8.565 (4.9); 8.562 (4.8); 8.560 (4.0); 8.408 (0.5); 8.402 (0.4); 8.371 (5.5); 8.366 (5.2); 8.324 (0.7); 8.321 (0.7); 8.318 (1.2); 7.970 (0.8); 7.965 (0.8); 7.760 (3.1); 7.742 (3.9); 7.710 (1.3); 7.693 (3.3); 7.674 (2.5); 7.644 (2.5); 7.625 (3.0); 7.606 (1.1); 7.434 (3.5); 7.415 (3.1); 5.508 (1.2); 5.496 (1.5); 5.491 (2.1); 5.480 (2.0); 5.476 (1.6); 5.464 (1.2); 4.813 (0.8); 4.801 (0.9); 3.656 (0.9); 3.644 (1.2); 3.641 (1.2); 3.629 (1.1); 3.621 (1.7); 3.609 (2.0); 3.607 (2.0); 3.595 (1.5); 3.533 (1.5); 3.518 (2.2); 3.502 (1.8); 3.483 (1.3); 3.468 (0.9); 3.399 (0.4); 3.325 (22.2); 2.526 (0.9); 2.521 (1.4); 2.512 (16.1); 2.508 (32.1); 2.503 (42.6); 2.499 (30.9); 2.494 (14.7); 1.380 (16.0); 1.364 (15.8); 1.337 (1.3); 1.300 (0.6); 1.259 (0.9); 1.250 (2.0); 1.232 (1.2); 1.073 (2.8); 1.058 (2.8); 0.008 (0.8); 0.000 (20.8); −0.009 (0.7)
Compound No. 1-26:

$^1$H-NMR (400.0 MHz, CD3CN): δ = 8.426 (4.6); 8.423 (5.8); 8.420 (5.9); 8.418 (4.7); 8.064 (6.6); 8.058 (6.3); 7.477 (0.4); 7.472 (0.7); 7.467 (0.4); 7.459 (0.8); 74493.0000 (4.4); 74485.0000 (4.3); 7.447 (5.4); 7.445 (4.8); 7.437 (1.2); 7.431 (5.9); 7.427 (13.3); 7.423 (9.8); 7.421 (6.9); 7.416 (4.5); 7.403 (7.3); 7.399 (4.8); 7.389 (1.2); 7.383 (3.0); 7.379 (2.2); 7.371 (1.0); 7.366 (5.8); 7.361 (4.8); 7.348 (5.4); 7.344 (5.0); 7.331 (1.9); 7.326 (1.9); 7.043 (1.2); 4.635 (9.9); 4.622 (16.0); 4.608 (10.5); 3.791 (5.6); 3.777 (12.7); 3.764 (11.4); 3.749 (5.1); 3.741 (0.5); 3.737 (0.5); 3.727 (0.6); 3.722 (1.6); 3.710 (1.2); 3.708 (1.3); 3.681 (0.7); 3.679 (0.7); 3.667 (1.4); 3.661 (0.4); 3.652 (1.0); 3.648 (0.6); 2.136 (20.2); 2.107 (0.4); 1.964 (3.8); 1.958 (5.7); 1.952 (25.1); 1.946 (43.8); 1.940 (57.9); 1.933 (40.0); 1.927 (20.5); 1.915 (0.3); 1.768 (0.3); 1.436 (2.6); 1.372 (1.4); 1.340 (0.6); 1.285 (1.0); 1.276 (2.0); 1.269 (2.3); 1.200 (0.4); 1.014 (0.4); 0.000 (1.1)
Compound No. 1-27:

$^1$H-NMR (400.0 MHz, CD3CN): δ = 8.427 (4.6); 8.425 (5.8); 8.422 (5.9); 8.419 (4.7); 8.064 (6.4); 8.063 (6.3); 8.058 (6.4); 8.057 (6.0); 7.619 (4.0); 7.618 (5.1); 7.617 (5.2); 7.616 (4.2); 7.599 (4.5); 7.598 (7.7); 7.596 (4.6); 7.415 (0.7); 7.413 (0.6); 7.407 (5.9); 7.394 (6.0); 7.391 (6.8); 7.390 (7.0); 7.382 (15.8); 7.380 (16.0); 7.372 (1.5); 7.371 (1.3); 7.346 (0.7); 7.336 (4.9); 7.326 (3.4); 7.322 (3.1); 7.316 (4.2); 7.313 (2.8); 7.306 (2.8); 7.302 (3.0); 7.293 (2.3); 6.997 (1.2); 4.635 (10.0); 4.622 (15.9); 4.608 (10.7); 3.785 (5.6); 3.770 (12.2); 3.757 (11.3); 3.747 (0.8); 3.743 (5.2); 2.134 (13.5); 2.107 (0.3); 1.964 (3.4); 1.958 (4.9); 1.952 (22.8); 1.946 (40.4); 1.940 (53.6); 1.934 (37.2); 1.927 (19.2); 1.921 (0.6); 1.768 (0.3); 1.436 (1.7); 1.372 (0.6); 1.276 (0.7); 0.000 (1.1)
Compound No. 1-28:

$^1$H-NMR (400.0 MHz, CD3CN): δ = 8.429 (4.6); 8.426 (5.7); 8.424 (5.7); 8.421 (4.4); 8.063 (6.7); 8.057 (6.4); 7.888 (5.2); 7.885 (5.2); 7.868 (5.5); 7.865 (5.4); 7.436 (2.6); 7.433 (2.5); 7.417 (6.2); 7.415 (5.9); 7.398 (4.2); 7.396 (4.0); 7.330 (5.8); 7.326 (6.3); 7.311 (4.1); 7.307 (4.0); 7.160 (3.4); 7.155 (3.2); 7.141 (4.8); 7.136 (4.5); 7.121 (2.9); 7.117 (2.6); 6.958 (1.3); 4.640 (9.4); 4.627 (16.0); 4.613 (10.0); 3.779 (5.3); 3.764 (12.1); 3.751 (11.5); 3.737 (4.9); 2.135 (54.6); 2.120 (0.7); 2.113 (0.9); 2.107 (1.2); 2.101 (0.9); 2.095 (0.4); 1.971 (1.0); 1.964 (10.7); 1.958 (16.3); 1.952 (71.6); 1.946 (125.5); 1.940 (164.4); 1.933 (113.4); 1.927 (58.1); 1.914 (0.8); 1.780 (0.4); 1.774 (0.7); 1.768 (1.0); 1.762 (0.7); 1.756 (0.3); 1.437 (1.8); 1.372 (0.9); 1.285 (0.4); 1.277 (1.1); 1.271 (0.4); 1.222 (0.4); 0.000 (3.2)

TABLE 2-continued

Compound No. 1-29:

$^1$H-NMR (400.0 MHz, CD3CN): δ = 8.424 (1.9); 8.421 (2.3); 8.419 (2.3); 8.416 (1.8); 8.064 (2.6); 8.063 (2.5); 8.058 (2.5); 8.057 (2.4); 7.334 (0.6); 7.330 (1.3); 7.321 (1.3); 7.316 (2.4); 7.312 (1.8); 7.302 (2.0); 7.298 (2.9); 7.295 (2.5); 7.238 (1.8); 7.236 (2.3); 7.235 (1.9); 7.229 (0.4); 7.228 (0.3); 7.217 (2.2); 7.216 (2.2); 7.199 (1.6); 7.197 (1.6); 7.181 (0.6); 7.179 (0.7); 7.178 (0.6); 6.889 (0.4); 4.636 (4.1); 4.631 (0.6); 4.622 (6.4); 4.609 (4.3); 3.773 (2.3); 3.769 (0.4); 3.759 (5.1); 3.746 (4.6); 3.731 (2.1); 2.552 (1.8); 2.359 (16.0); 2.197 (0.4); 2.159 (3.2); 2.120 (0.5); 2.113 (0.4); 2.107 (0.4); 1.964 (2.0); 1.958 (2.9); 1.952 (13.1); 1.946 (23.0); 1.940 (30.0); 1.934 (20.6); 1.927 (10.6); 1.372 (0.7); 1.285 (0.4); 1.276 (0.9); 0.000 (0.6)

Compound No. 1-30:

$^1$H-NMR (400.0 MHz, DMSO): δ = 8.720 (4.2); 8.705 (8.1); 8.691 (4.2); 8.511 (14.0); 8.509 (14.0); 8.363 (16.0); 8.358 (15.1); 7.741 (8.5); 7.723 (11.6); 7.681 (3.5); 7.663 (9.7); 7.645 (8.0); 7.627 (7.9); 7.608 (8.7); 7.590 (3.0); 7.343 (10.4); 7.324 (9.2); 5.031 (3.2); 5.021 (3.8); 5.013 (4.9); 5.010 (4.7); 5.003 (4.8); 5.000 (4.9); 4.992 (4.1); 4.982 (3.3); 3.839 (2.9); 3.829 (3.4); 3.824 (3.3); 3.814 (3.3); 3.804 (4.1); 3.794 (4.2); 3.789 (4.3); 3.779 (3.5); 3.558 (3.5); 3.543 (4.9); 3.525 (5.0); 3.508 (3.9); 3.506 (3.9); 3.492 (2.8); 3.324 (49.6); 2.676 (0.5); 2.672 (0.6); 2.667 (0.5); 2.525 (1.9); 2.507 (73.3); 2.503 (95.9); 2.498 (71.5); 2.334 (0.5); 2.330 (0.7); 2.325 (0.5); 1.337 (4.0); 1.300 (2.9); 1.282 (1.9); 1.273 (2.7); 1.260 (7.2); 1.250 (8.1); 1.241 (5.4); 1.229 (3.2); 1.220 (2.1); 1.208 (1.0); 1.189 (0.4); 0.644 (1.0); 0.630 (1.7); 0.622 (4.1); 0.613 (4.1); 0.609 (4.7); 0.600 (5.4); 0.592 (2.8); 0.587 (3.2); 0.579 (2.5); 0.570 (2.3); 0.560 (3.5); 0.558 (3.4); 0.548 (4.6); 0.538 (4.8); 0.527 (4.3); 0.515 (2.0); 0.506 (3.0); 0.494 (3.3); 0.484 (4.8); 0.472 (6.4); 0.460 (5.0); 0.448 (2.2); 0.438 (2.8); 0.427 (5.2); 0.415 (6.0); 0.403 (4.8); 0.393 (2.7); 0.381 (1.1); 0.000 (1.7)

Compound No. 1-31:

$^1$H-NMR (400.0 MHz, DMSO): δ = 8.489 (2.3); 8.316 (0.4); 8.209 (7.6); 8.203 (7.6); 7.823 (7.0); 7.816 (6.7); 7.801 (7.2); 7.794 (7.0); 7.615 (2.4); 7.611 (2.8); 7.597 (4.6); 7.592 (5.5); 7.583 (0.5); 7.577 (3.0); 7.573 (3.0); 7.549 (1.4); 7.544 (1.3); 7.535 (1.5); 7.531 (3.2); 7.528 (2.1); 7.526 (2.0); 7.523 (1.8); 7.517 (2.3); 7.513 (2.1); 7.510 (3.2); 7.505 (1.7); 7.496 (1.8); 7.492 (1.6); 7.296 (3.9); 7.285 (4.3); 7.283 (4.4); 7.277 (3.1); 7.275 (3.6); 7.271 (3.8); 7.266 (8.1); 7.250 (2.8); 7.247 (7.5); 6.887 (9.3); 6.865 (8.9); 4.395 (7.2); 4.380 (16.0); 4.365 (7.7); 3.648 (3.5); 3.633 (9.9); 3.619 (9.7); 3.605 (3.2); 3.324 (141.6); 2.680 (0.4); 2.675 (0.9); 2.671 (1.3); 2.666 (0.9); 2.662 (0.4); 2.524 (3.7); 2.519 (5.8); 2.511 (70.8); 2.506 (143.1); 2.502 (189.7); 2.497 (136.7); 2.493 (64.8); 2.338 (0.4); 2.333 (0.9); 2.329 (1.3); 2.324 (0.9); 2.320 (0.4); 1.336 (1.3); 1.298 (0.4); 1.259 (0.5); 1.250 (1.6); 1.235 (0.5); 0.008 (0.7); 0.000 (22.5); −0.009 (0.7)

Compound No. 1-32:

$^1$H-NMR (400.0 MHz, DMSO): δ = 8.642 (1.4); 8.629 (2.7); 8.616 (1.5); 8.316 (1.8); 8.218 (6.8); 8.217 (7.1); 8.212 (7.2); 8.210 (6.9); 7.825 (6.7); 7.818 (6.4); 7.803 (6.9); 7.796 (6.8); 7.490 (3.4); 7.488 (2.6); 7.472 (5.6); 7.471 (6.9); 7.469 (6.5); 7.452 (3.4); 7.444 (4.0); 7.437 (4.1); 7.429 (5.7); 7.425 (1.7); 7.417 (2.3); 7.410 (3.9); 7.405 (0.6); 7.399 (2.7); 7.398 (2.3); 7.386 (16.0); 7.383 (8.7); 7.380 (6.5); 7.371 (4.5); 7.368 (4.0); 7.364 (0.9); 7.352 (0.9); 7.349 (0.9); 6.882 (8.7); 6.881 (8.6); 6.860 (8.4); 6.859 (8.2); 4.387 (6.4); 4.373 (14.4); 4.358 (6.9); 3.622 (3.3); 3.608 (9.3); 3.594 (9.0); 3.579 (3.0); 3.323 (100.9); 3.299 (0.6); 2.680 (0.4); 2.675 (0.7); 2.671 (1.0); 2.666 (0.7); 2.662 (0.3); 2.524 (3.2); 2.519 (4.9); 2.511 (56.4); 2.506 (113.3); 2.502 (149.6); 2.497 (106.9); 2.493 (50.2); 2.338 (0.3); 2.333 (0.7); 2.328 (1.0); 2.324 (0.7); 2.319 (0.3); 1.336 (0.7); 1.298 (0.7); 1.259 (1.1); 1.250 (0.9); 0.008 (1.4); 0.000 (43.2); −0.009 (1.2)

Compound No. 1-33:

$^1$H-NMR (400.0 MHz, DMSO): δ = 8.635 (1.8); 8.621 (3.3); 8.608 (1.7); 8.219 (7.8); 8.218 (8.0); 8.212 (8.5); 8.211 (7.9); 7.823 (7.8); 7.816 (7.4); 7.801 (8.1); 7.794 (7.8); 7.650 (1.7); 7.647 (3.7); 7.644 (7.1); 7.631 (2.5); 7.626 (5.1); 7.624 (8.0); 7.437 (2.2); 7.434 (2.4); 7.421 (2.8); 7.416 (7.7); 7.400 (6.7); 7.397 (6.2); 7.364 (14.5); 7.361 (8.0); 7.346 (11.0); 7.343 (6.3); 7.341 (6.3); 7.328 (3.3); 7.323 (2.4); 7.181 (0.8); 7.176 (0.5); 6.888 (10.7); 6.887 (10.5); 6.875 (0.4); 6.866 (9.5); 6.865 (9.3); 6.706 (0.5); 4.388 (7.1); 4.374 (16.0); 4.359 (7.6); 3.992 (0.4); 3.617 (3.7); 3.603 (10.6); 3.588 (10.3); 3.574 (3.4); 3.324 (78.3); 2.676 (0.6); 2.671 (0.8); 2.666 (0.6); 2.547 (0.5); 2.541 (0.5); 2.524 (2.5); 2.520 (3.8); 2.511 (41.6); 2.506 (83.3); 2.502 (109.9); 2.497 (78.7); 2.493 (36.9); 2.333 (0.5); 2.329 (0.7); 2.324 (0.5); 1.354 (0.8); 1.336 (15.6); 1.299 (2.0); 1.259 (3.1); 1.250 (11.9); 1.235 (1.1); 1.225 (0.4); 0.008 (1.1); 0.000 (31.1); −0.009 (0.9)

Compound No. 1-34:

$^1$H-NMR (400.0 MHz, DMSO): δ = 8.592 (1.9); 8.578 (3.7); 8.565 (1.9); 8.218 (8.1); 8.217 (8.4); 8.212 (8.6); 8.211 (8.1); 7.875 (6.5); 7.873 (6.7); 7.856 (7.0); 7.853 (6.9); 7.820 (7.9); 7.813 (7.5); 7.798 (8.2); 7.791 (7.9); 7.445 (3.1); 7.442 (3.2); 7.426 (7.3); 7.423 (7.3); 7.414 (0.4); 7.407 (4.8); 7.405 (4.6); 7.300 (6.6); 7.296 (7.4); 7.281 (5.4); 7.277 (5.3); 7.223 (0.3); 7.201 (0.3); 7.177 (4.2); 7.173 (4.0); 7.158 (6.0); 7.154 (5.6); 7.139 (3.6); 7.135 (3.3); 6.900 (10.0); 6.899 (10.0); 6.887 (0.4); 6.878 (9.5); 6.877 (9.5); 5.756 (1.9); 4.394 (7.1); 4.380 (16.0); 4.365 (7.6); 3.610 (3.7); 3.596 (10.6); 3.581 (10.2); 3.567 (3.4); 3.323 (98.2); 2.675 (0.6); 2.671 (0.8); 2.666 (0.6); 2.524 (2.8); 2.519 (4.4); 2.511 (46.5); 2.506 (92.7); 2.502 (122.4); 2.497 (88.1); 2.493 (41.7); 2.446 (0.3); 2.333 (0.6); 2.328 (0.8); 2.324 (0.6); 2.111 (0.6); 1.336 (0.8); 1.298 (0.4); 1.259 (0.5); 1.250 (1.1); 0.008 (1.1); 0.000 (32.7); −0.009 (1.0)

Compound No. 1-35:

$^1$H-NMR (400.0 MHz, DMSO): δ = 8.939 (1.8); 8.925 (3.2); 8.913 (1.7); 8.316 (1.4); 8.217 (8.7); 8.211 (8.3); 8.210 (8.5); 7.828 (8.0); 7.822 (7.6); 7.806 (8.3); 7.800 (8.0); 7.540 (1.5); 7.523 (3.1); 7.518 (2.7); 7.506 (1.9); 7.502 (5.9); 7.497 (2.0); 7.485 (2.7); 7.481 (3.4); 7.464 (1.6); 7.181 (1.2); 7.177 (1.6); 7.170 (9.8); 7.159 (1.5); 7.156 (1.9); 7.151 (11.7); 7.144 (2.0); 7.141 (1.4); 7.130 (8.1); 7.122 (1.3); 6.871 (10.3); 6.849 (9.9); 4.364 (7.4); 4.350 (16.0); 4.336 (8.1); 3.642 (3.9); 3.628 (10.9); 3.614 (10.5); 3.600 (3.6); 3.323 (331.6); 3.300 (0.8); 2.680 (0.6); 2.675 (1.4);

TABLE 2-continued 2.671 (1.9); 2.666 (1.4); 2.662 (0.6); 2.524 (5.6); 2.519 (8.6); 2.511 (104.4); 2.506 (212.2);
2.502 (282.3); 2.497 (203.7); 2.492 (96.7); 2.448 (0.6); 2.338 (0.7); 2.333 (1.4); 2.328 (1.9);
2.324 (1.4); 2.319 (0.6); 1.336 (1.5); 1.298 (1.1); 1.259 (1.6); 1.249 (1.7); 1.234 (0.5); 0.008 (2.2);
0.000 (67.9); −0.009 (2.1)
Compound No. 1-36:

$^1$H-NMR (400.0 MHz, DMSO): δ = 8.717 (1.9); 8.703 (3.5); 8.689 (1.8); 8.316 (1.3); 8.223 (8.0);
8.221 (8.8); 8.216 (8.5); 8.215 (8.6); 7.830 (8.0); 7.823 (7.6); 7.808 (8.2); 7.801 (8.1); 7.777 (4.7);
7.757 (6.2); 7.726 (2.0); 7.709 (5.3); 7.690 (4.0); 7.654 (3.8); 7.635 (4.8); 7.616 (1.8); 7.494 (5.7);
7.475 (4.8); 6.868 (9.8); 6.867 (10.3); 6.846 (9.5); 6.845 (9.9); 5.757 (0.6); 4.364 (7.2); 4.350 (16.0);
4.335 (7.8); 3.622 (3.7); 3.608 (10.5); 3.594 (10.2); 3.579 (3.4); 3.323 (105.8); 3.299 (0.4);
2.680 (0.3); 2.675 (0.7); 2.671 (1.0); 2.666 (0.7); 2.662 (0.3); 2.524 (3.3); 2.519 (5.1); 2.511 (55.6);
2.506 (111.9); 2.502 (148.2); 2.497 (107.5); 2.493 (51.5); 2.447 (0.4); 2.338 (0.4); 2.333 (0.7);
2.328 (1.0); 2.324 (0.7); 2.320 (0.4); 1.989 (0.5); 1.336 (1.0); 1.249 (1.3); 1.235 (0.5); 1.175 (0.3);
0.008 (1.2); 0.000 (35.3); −0.009 (1.1)
Compound No. 1-37:

$^1$H-NMR (400.0 MHz, DMSO): δ = 8.830 (1.8); 8.817 (3.4); 8.803 (1.8); 8.468 (7.3); 8.463 (7.8);
8.456 (7.9); 8.451 (7.7); 8.316 (0.4); 8.222 (8.1); 8.221 (8.9); 8.216 (8.7); 8.214 (8.8); 7.873 (7.7);
7.868 (7.9); 7.855 (8.8); 7.850 (8.3); 7.830 (8.4); 7.823 (8.0); 7.808 (8.7); 7.801 (8.5); 7.496 (8.7);
7.484 (8.4); 7.477 (8.0); 7.465 (7.8); 6.886 (10.2); 6.885 (10.8); 6.875 (0.3); 6.864 (9.8);
6.863 (10.3); 4.394 (7.4); 4.379 (16.0); 4.365 (8.0); 3.641 (3.9); 3.627 (11.0); 3.613 (10.6);
3.599 (3.6); 3.324 (172.2); 2.680 (0.5); 2.675 (1.0); 2.671 (1.4); 2.666 (1.0); 2.662 (0.4); 2.524 (4.2);
2.520 (6.5); 2.511 (74.3); 2.506 (150.5); 2.502 (199.5); 2.497 (143.7); 2.493 (68.0); 2.447 (0.5);
2.338 (0.5); 2.333 (1.0); 2.329 (1.3); 2.324 (0.9); 2.319 (0.4); 1.234 (0.4); 0.008 (1.6);
0.000 (48.7); −0.009 (1.5)
Compound No. 1-38:

$^1$H-NMR (400.0 MHz, DMSO): δ = 8.366 (1.9); 8.353 (3.5); 8.339 (1.9); 8.316 (0.7); 8.212 (8.4);
8.206 (8.4); 8.205 (8.2); 7.821 (8.1); 7.814 (7.8); 7.799 (8.4); 7.792 (8.1); 7.709 (15.0); 7.696 (15.8);
7.223 (0.4); 7.215 (16.0); 7.202 (15.2); 6.907 (10.1); 6.906 (10.3); 6.885 (9.6); 6.883 (9.8);
4.397 (6.9); 4.382 (15.3); 4.368 (7.4); 3.629 (3.6); 3.615 (10.2); 3.600 (9.9); 3.586 (3.3);
3.323 (178.2); 2.680 (0.6); 2.675 (1.3); 2.671 (1.9); 2.666 (1.3); 2.662 (0.6); 2.524 (5.3); 2.519 (8.1);
2.511 (101.6); 2.506 (207.1); 2.502 (275.5); 2.497 (199.2); 2.493 (95.0); 2.338 (0.6); 2.333 (1.3);
2.329 (1.8); 2.324 (1.3); 2.319 (0.6); 1.336 (1.7); 1.259 (0.4); 1.249 (2.1); 1.235 (0.5); 0.008 (2.0);
0.000 (64.2); −0.009 (2.0)
Compound No. 1-39:

$^1$H-NMR (400.0 MHz, DMSO): δ = 8.316 (0.4); 8.244 (1.7); 8.231 (3.1); 8.217 (1.8); 8.204 (8.2);
8.203 (8.2); 8.197 (8.6); 8.196 (7.9); 7.838 (15.2); 7.825 (16.0); 7.821 (8.7); 7.814 (8.0); 7.799 (8.6);
7.792 (8.3); 7.145 (16.0); 7.132 (15.5); 6.891 (10.1); 6.890 (9.7); 6.869 (9.7); 6.868 (9.2);
4.408 (7.2); 4.393 (15.9); 4.379 (7.7); 3.656 (3.8); 3.642 (11.0); 3.627 (10.7); 3.613 (3.5);
3.324 (71.3); 2.676 (0.5); 2.672 (0.7); 2.667 (0.5); 2.525 (2.0); 2.520 (3.1); 2.512 (38.6);
2.507 (77.9); 2.503 (103.1); 2.498 (73.9); 2.494 (34.7); 2.334 (0.5); 2.330 (0.7); 2.325 (0.5);
1.336 (2.1); 1.259 (0.5); 1.250 (2.7); 0.008 (0.8); 0.000 (25.2); −0.009 (0.7)
Compound No. 1-40:

$^1$H-NMR (400.0 MHz, DMSO): δ = 8.538 (1.7); 8.524 (3.3); 8.510 (1.7); 8.316 (0.5); 8.203 (7.4);
8.202 (7.7); 8.197 (8.0); 8.195 (7.5); 7.898 (15.0); 7.894 (15.2); 7.814 (7.6); 7.808 (7.3); 7.792 (7.8);
7.786 (7.7); 6.886 (9.3); 6.885 (9.1); 6.864 (8.9); 6.863 (9.0); 6.847 (16.0); 6.842 (15.8); 4.377 (6.4);
4.363 (14.3); 4.348 (6.8); 3.600 (3.3); 3.585 (9.7); 3.571 (9.5); 3.556 (3.1); 3.324 (109.0);
2.676 (0.7); 2.672 (0.9); 2.667 (0.7); 2.525 (2.7); 2.520 (4.2); 2.512 (51.4); 2.507 (104.5);
2.502 (138.9); 2.498 (100.6); 2.493 (48.1); 2.339 (0.3); 2.334 (0.7); 2.329 (0.9); 2.325 (0.7);
1.336 (1.5); 1.250 (1.9); 0.008 (1.1); 0.000 (33.2); −0.009 (1.1)
Compound No. 1-41:

$^1$H-NMR (400.0 MHz, DMSO): δ = 8.586 (5.6); 8.584 (5.7); 8.582 (5.7); 8.580 (5.6); 8.509 (2.5);
8.317 (1.2); 8.086 (4.1); 8.080 (4.0); 8.064 (4.3); 8.058 (4.2); 7.611 (2.5); 7.606 (2.9); 7.592 (4.8);
7.588 (5.7); 7.579 (0.6); 7.573 (3.2); 7.569 (3.2); 7.549 (1.5); 7.545 (1.4); 7.536 (1.6); 7.531 (3.2);
7.528 (2.3); 7.527 (2.2); 7.524 (1.9); 7.517 (2.5); 7.516 (2.3); 7.513 (2.3); 7.510 (3.4); 7.505 (1.8);
7.497 (2.0); 7.492 (1.6); 7.294 (4.0); 7.283 (4.5); 7.281 (4.7); 7.275 (3.4); 7.273 (3.8); 7.270 (4.1);
7.267 (5.5); 7.264 (8.4); 7.249 (3.1); 7.246 (7.2); 7.027 (7.0); 7.006 (6.7); 4.506 (7.4); 4.492 (16.0);
4.477 (7.8); 3.682 (3.5); 3.667 (10.1); 3.653 (9.8); 3.639 (3.3); 3.325 (90.3); 3.301 (0.4); 2.676 (0.6);
2.672 (0.8); 2.667 (0.6); 2.525 (2.7); 2.520 (4.3); 2.512 (47.1); 2.507 (93.9); 2.502 (123.7);
2.498 (89.5); 2.493 (42.7); 2.334 (0.6); 2.329 (0.8); 2.325 (0.6); 2.061 (0.4); 2.041 (0.3); 1.336 (2.0);
1.259 (0.4); 1.250 (2.5); 1.235 (0.7); 0.008 (0.5); 0.000 (15.3); −0.009 (0.5)
Compound No. 1-42:

$^1$H-NMR (400.0 MHz, DMSO): δ = 8.662 (1.5); 8.649 (2.9); 8.635 (1.5); 8.598 (5.1); 8.596 (5.1);
8.595 (5.1); 8.592 (5.1); 8.316 (3.5); 8.090 (3.7); 8.084 (3.7); 8.068 (3.9); 8.062 (3.8); 7.490 (3.9);
7.488 (2.7); 7.471 (7.3); 7.470 (6.9); 7.452 (3.4); 7.444 (4.0); 7.438 (4.1); 7.430 (5.6); 7.425 (1.6);
7.418 (2.5); 7.410 (3.5); 7.401 (0.4); 7.393 (2.1); 7.383 (16.0); 7.380 (9.3); 7.376 (6.7); 7.368 (4.7);
7.365 (4.1); 7.349 (0.8); 7.346 (0.8); 7.022 (6.3); 7.000 (6.1); 4.498 (6.4); 4.484 (13.8); 4.470 (6.8);
3.657 (3.2); 3.643 (9.1); 3.629 (8.9); 3.615 (3.0); 3.324 (101.5); 3.300 (1.2); 2.676 (0.6); 2.671 (0.8);
2.666 (0.6); 2.524 (2.7); 2.520 (4.2); 2.511 (45.8); 2.507 (91.6); 2.502 (120.9); 2.497 (87.1);
2.493 (41.3); 2.333 (0.6); 2.329 (0.8); 2.324 (0.6); 1.336 (1.3); 1.250 (1.6); 0.008 (0.5);
0.000 (14.7); −0.009 (0.4)

TABLE 2-continued

Compound No. 1-43:

$^1$H-NMR (400.0 MHz, DMSO): δ = 8.655 (2.0); 8.641 (3.7); 8.628 (1.9); 8.599 (6.1); 8.597 (6.2); 8.596 (6.2); 8.593 (6.1); 8.316 (0.6); 8.088 (4.4); 8.082 (4.3); 8.066 (4.6); 8.060 (4.5); 7.649 (4.6); 7.645 (6.1); 7.641 (1.7); 7.635 (1.5); 7.625 (8.5); 7.434 (2.2); 7.432 (2.4); 7.424 (0.6); 7.417 (3.2); 7.414 (6.4); 7.412 (4.7); 7.398 (6.9); 7.395 (6.2); 7.369 (2.0); 7.364 (10.0); 7.360 (9.9); 7.356 (8.0); 7.347 (7.1); 7.342 (7.9); 7.337 (4.5); 7.329 (3.5); 7.324 (2.3); 7.028 (7.4); 7.007 (7.2); 4.499 (7.4); 4.485 (16.0); 4.470 (7.8); 3.652 (3.9); 3.637 (10.9); 3.623 (10.5); 3.609 (3.5); 3.324 (96.0); 2.680 (0.3); 2.676 (0.7); 2.671 (0.9); 2.667 (0.6); 2.524 (3.0); 2.520 (4.8); 2.511 (50.5); 2.507 (99.8); 2.502 (130.7); 2.497 (94.0); 2.493 (44.5); 2.333 (0.6); 2.329 (0.9); 2.324 (0.6); 1.336 (1.6); 1.259 (0.4); 1.250 (2.0); 1.235 (0.4); 0.008 (0.6); 0.000 (16.8); −0.009 (0.5)

Compound No. 1-44:

$^1$H-NMR (400.0 MHz, DMSO): δ = 8.614 (2.3); 8.599 (10.1); 8.593 (7.9); 8.084 (4.5); 8.077 (4.5); 8.062 (4.7); 8.055 (4.6); 7.877 (6.9); 7.875 (7.2); 7.857 (7.6); 7.855 (7.4); 7.443 (3.3); 7.440 (3.4); 7.424 (7.7); 7.421 (7.7); 7.405 (5.1); 7.403 (4.9); 7.296 (7.0); 7.292 (7.9); 7.277 (5.8); 7.273 (5.7); 7.179 (4.4); 7.175 (4.2); 7.160 (6.2); 7.156 (5.9); 7.141 (3.7); 7.137 (3.4); 7.041 (7.6); 7.019 (7.3); 5.757 (1.7); 4.504 (7.3); 4.489 (16.0); 4.475 (7.8); 3.645 (3.9); 3.631 (10.9); 3.617 (10.5); 3.603 (3.5); 3.325 (64.0); 2.676 (0.4); 2.671 (0.6); 2.667 (0.4); 2.525 (2.0); 2.511 (34.9); 2.507 (69.7); 2.502 (91.9); 2.498 (67.0); 2.493 (32.3); 2.334 (0.4); 2.329 (0.6); 2.324 (0.4); 1.989 (0.8); 1.336 (1.2); 1.259 (0.4); 1.250 (1.5); 1.234 (0.4); 1.175 (0.5); 0.008 (0.4); 0.000 (12.7); −0.009 (0.4)

Compound No. 1-45:

$^1$H-NMR (400.0 MHz, DMSO): δ = 8.957 (1.9); 8.944 (3.6); 8.930 (1.9); 8.597 (6.3); 8.595 (6.3); 8.593 (6.4); 8.591 (6.3); 8.317 (0.6); 8.094 (4.6); 8.087 (4.6); 8.072 (4.8); 8.065 (4.7); 7.542 (1.5); 7.525 (3.3); 7.521 (2.8); 7.508 (2.1); 7.504 (6.2); 7.499 (2.2); 7.487 (2.8); 7.483 (3.6); 7.466 (1.7); 7.181 (1.3); 7.178 (1.7); 7.171 (10.3); 7.160 (1.6); 7.157 (2.2); 7.151 (12.5); 7.145 (2.2); 7.141 (1.5); 7.131 (8.6); 7.123 (1.5); 7.012 (7.8); 6.990 (7.5); 4.476 (7.8); 4.462 (16.0); 4.448 (8.3); 3.679 (4.1); 3.665 (11.1); 3.651 (10.8); 3.637 (3.7); 3.328 (115.6); 3.305 (0.3); 2.676 (0.5); 2.672 (0.6); 2.667 (0.5); 2.525 (2.0); 2.520 (3.2); 2.512 (35.3); 2.507 (70.5); 2.503 (92.8); 2.498 (66.8); 2.494 (31.7); 2.334 (0.4); 2.330 (0.6); 2.325 (0.4); 1.337 (1.9); 1.259 (0.4); 1.250 (2.4); 1.235 (0.4); 0.008 (0.4); 0.000 (12.7); −0.009 (0.4)

Compound No. 1-46:

$^1$H-NMR (400.0 MHz, DMSO): δ = 8.736 (2.0); 8.722 (3.8); 8.708 (2.0); 8.603 (6.2); 8.601 (6.2); 8.599 (6.2); 8.597 (6.2); 8.316 (0.6); 8.096 (4.6); 8.089 (4.5); 8.074 (4.7); 8.067 (4.7); 7.777 (4.9); 7.758 (6.5); 7.725 (2.0); 7.707 (5.5); 7.688 (4.2); 7.655 (4.0); 7.636 (5.0); 7.617 (1.8); 7.491 (5.9); 7.472 (5.0); 7.007 (7.6); 6.985 (7.3); 4.474 (7.5); 4.460 (16.0); 4.446 (7.9); 3.657 (3.9); 3.643 (10.9); 3.629 (10.5); 3.615 (3.5); 3.324 (150.7); 2.680 (0.5); 2.676 (1.0); 2.671 (1.3); 2.666 (0.9); 2.662 (0.4); 2.524 (4.2); 2.520 (6.7); 2.511 (73.3); 2.507 (145.7); 2.502 (191.4); 2.497 (137.2); 2.493 (64.5); 2.338 (0.4); 2.333 (0.9); 2.329 (1.3); 2.324 (0.9); 2.320 (0.4); 1.336 (1.2); 1.259 (0.3); 1.250 (1.5); 1.234 (0.4); 0.008 (0.8); 0.000 (23.6); −0.009 (0.7)

Compound No. 1-47:

$^1$H-NMR (400.0 MHz, DMSO): δ = 8.849 (2.0); 8.836 (3.8); 8.822 (2.1); 8.602 (6.4); 8.600 (6.6); 8.598 (6.6); 8.596 (6.4); 8.470 (7.1); 8.465 (7.5); 8.458 (7.7); 8.453 (7.4); 8.317 (3.3); 8.094 (4.6); 8.088 (4.5); 8.072 (4.8); 8.066 (4.6); 7.875 (7.5); 7.870 (7.5); 7.856 (8.5); 7.851 (8.0); 7.495 (8.3); 7.483 (8.1); 7.477 (7.7); 7.465 (7.4); 7.027 (7.9); 7.005 (7.5); 5.757 (0.6); 4.504 (7.8); 4.490 (16.0); 4.476 (8.2); 3.677 (4.0); 3.663 (11.0); 3.649 (10.7); 3.635 (3.7); 3.326 (74.6); 3.302 (1.4); 2.676 (0.5); 2.672 (0.7); 2.667 (0.5); 2.525 (2.5); 2.512 (41.5); 2.507 (81.4); 2.503 (106.1); 2.498 (76.9); 2.494 (37.0); 2.334 (0.5); 2.329 (0.7); 2.325 (0.5); 1.989 (0.8); 1.235 (0.4); 1.175 (0.5); 0.008 (0.5); 0.000 (13.7); −0.009 (0.5)

Compound No. 1-48:

1H-NMR (400.0 MHz, DMSO): δ = 8.589 (6.0); 8.587 (6.0); 8.586 (6.0); 8.583 (5.9); 8.391 (2.0); 8.377 (3.7); 8.363 (1.9); 8.317 (0.8); 8.084 (4.5); 8.077 (4.4); 8.062 (4.6); 8.055 (4.5); 7.709 (15.0); 7.697 (15.6); 7.216 (16.0); 7.203 (15.1); 7.047 (7.4); 7.025 (7.1); 4.507 (6.9); 4.492 (14.7); 4.478 (7.2); 3.663 (3.6); 3.649 (10.0); 3.635 (9.7); 3.620 (3.2); 3.325 (93.7); 2.676 (0.6); 2.672 (0.8); 2.667 (0.6); 2.525 (2.6); 2.520 (4.2); 2.512 (45.6); 2.507 (90.4); 2.503 (118.5); 2.498 (85.0); 2.494 (40.0); 2.334 (0.6); 2.329 (0.8); 2.325 (0.6); 1.336 (1.2); 1.259 (0.3); 1.250 (1.5); 0.008 (0.6); 0.000 (15.6); −0.009 (0.4)

Compound No. 1-49:

1H-NMR (400.0 MHz, DMSO): δ = 8.578 (6.2); 8.576 (6.4); 8.574 (6.4); 8.572 (6.3); 8.317 (1.3); 8.269 (2.0); 8.256 (3.6); 8.242 (1.9); 8.084 (4.5); 8.078 (4.6); 8.062 (4.8); 8.056 (4.6); 7.839 (14.0); 7.826 (14.5); 7.144 (15.0); 7.131 (14.5); 7.031 (7.6); 7.009 (7.3); 4.520 (7.5); 4.506 (16.0); 4.491 (8.0); 3.690 (4.0); 3.675 (11.2); 3.661 (10.9); 3.647 (3.7); 3.327 (56.7); 3.304 (0.3); 2.677 (0.4); 2.673 (0.5); 2.668 (0.4); 2.526 (1.7); 2.513 (29.5); 2.508 (58.8); 2.504 (77.8); 2.499 (57.2); 2.495 (28.0); 2.335 (0.4); 2.330 (0.5); 2.326 (0.4); 1.337 (1.1); 1.250 (1.3); 0.008 (0.4); 0.000 (10.0); −0.008 (0.3)

Compound No. 1-50:

1H-NMR (400.0 MHz, DMSO): δ = 8.577 (5.9); 8.575 (5.9); 8.573 (6.0); 8.571 (6.1); 8.548 (3.6); 8.534 (1.8); 8.317 (3.2); 8.077 (4.2); 8.071 (4.1); 8.055 (4.4); 8.049 (4.2); 7.897 (15.8); 7.893 (15.7); 7.027 (7.0); 7.005 (6.7); 6.849 (16.0); 6.844 (15.8); 4.487 (6.7); 4.472 (14.5); 4.458 (7.0); 3.633 (3.4); 3.619 (9.8); 3.605 (9.6); 3.590 (3.2); 3.326 (124.5); 3.302 (1.1); 2.677 (0.6); 2.672 (0.8); 2.668 (0.6); 2.525 (2.4); 2.521 (3.8); 2.512 (45.3); 2.508 (91.1); 2.503 (120.2); 2.498 (86.5); 2.494 (40.9); 2.334 (0.6); 2.330 (0.8); 2.325 (0.6); 1.336 (1.0); 1.250 (1.3); 1.235 (0.3); 0.008 (0.5); 0.000 (14.6); −0.009 (0.4)

TABLE 2-continued

Compound No. 1-51:

1H-NMR (400.0 MHz, DMSO): δ = 8.559 (8.2); 8.557 (8.2); 8.482 (3.2); 8.393 (9.2); 8.388 (8.8); 7.621 (2.7); 7.617 (3.1); 7.603 (5.2); 7.598 (6.2); 7.583 (3.2); 7.579 (3.2); 7.552 (1.5); 7.548 (1.4); 7.539 (1.7); 7.534 (3.4); 7.531 (2.7); 7.520 (2.8); 7.513 (3.6); 7.509 (2.0); 7.500 (2.1); 7.495 (1.7); 7.299 (4.6); 7.289 (5.1); 7.287 (4.8); 7.278 (4.5); 7.271 (11.6); 7.251 (8.8); 4.607 (7.5); 4.593 (16.0); 4.578 (8.0); 3.711 (3.8); 3.697 (10.7); 3.683 (10.5); 3.669 (3.6); 3.324 (34.2); 2.677 (0.4); 2.672 (0.6); 2.668 (0.4); 2.525 (1.6); 2.512 (32.6); 2.508 (63.9); 2.503 (84.1); 2.499 (61.9); 2.494 (30.5); 2.334 (0.4); 2.330 (0.6); 2.325 (0.4); 1.337 (1.0); 1.250 (1.2); 1.235 (0.4); 1.188 (0.3); 0.000 (0.8)

Compound No. 1-52:

1H-NMR (400.0 MHz, DMSO): δ = 8.936 (2.3); 8.923 (4.3); 8.909 (2.3); 8.572 (7.0); 8.569 (8.7); 8.567 (8.7); 8.564 (7.0); 8.397 (9.7); 8.391 (9.1); 7.541 (1.5); 7.525 (3.3); 7.520 (2.9); 7.508 (2.3); 7.504 (6.2); 7.499 (2.3); 7.487 (3.1); 7.483 (3.7); 7.466 (1.7); 7.181 (1.3); 7.178 (1.8); 7.171 (10.4); 7.151 (13.4); 7.131 (8.7); 7.123 (1.5); 4.582 (7.8); 4.568 (16.0); 4.554 (8.2); 3.711 (4.1); 3.697 (11.2); 3.683 (10.9); 3.669 (3.8); 3.323 (39.0); 2.676 (0.4); 2.672 (0.6); 2.667 (0.4); 2.525 (1.8); 2.512 (33.8); 2.507 (66.3); 2.503 (87.0); 2.498 (63.3); 2.494 (30.3); 2.334 (0.4); 2.329 (0.6); 2.325 (0.4); 1.990 (0.5); 1.337 (0.5); 1.250 (0.6); 0.000 (0.9)

Compound No. 1-53:

1H-NMR (400.0 MHz, DMSO): δ = 8.920 (2.4); 8.906 (4.6); 8.893 (2.4); 8.588 (6.8); 8.586 (8.5); 8.583 (8.5); 8.580 (6.9); 8.403 (9.6); 8.397 (9.1); 8.316 (0.7); 8.043 (6.8); 8.041 (7.0); 8.023 (7.9); 8.021 (7.7); 7.806 (3.2); 7.803 (3.3); 7.787 (8.2); 7.785 (8.0); 7.769 (5.7); 7.766 (5.3); 7.711 (5.0); 7.707 (5.6); 7.691 (6.1); 7.687 (6.5); 7.672 (3.3); 7.668 (3.2); 7.586 (7.7); 7.582 (7.6); 7.567 (6.7); 7.563 (6.2); 4.591 (7.4); 4.577 (16.0); 4.562 (7.8); 3.687 (3.9); 3.673 (11.0); 3.659 (10.7); 3.645 (3.6); 3.322 (159.6); 2.680 (0.7); 2.675 (1.5); 2.671 (2.0); 2.666 (1.5); 2.662 (0.7); 2.524 (6.0); 2.519 (9.6); 2.511 (113.4); 2.506 (225.8); 2.502 (299.5); 2.497 (219.4); 2.493 (106.4); 2.337 (0.7); 2.333 (1.5); 2.328 (2.0); 2.324 (1.5); 2.320 (0.7); 1.336 (0.9); 1.298 (0.6); 1.259 (1.1); 1.250 (1.4); 1.236 (0.6); 0.000 (2.2)

Compound No. 1-54:

1H-NMR (400.0 MHz, DMSO): δ = 8.824 (2.4); 8.811 (4.3); 8.798 (2.4); 8.490 (0.3); 8.485 (0.4); 8.471 (5.8); 8.467 (6.3); 8.459 (6.2); 8.455 (6.1); 8.143 (6.2); 8.139 (6.8); 8.130 (6.5); 8.127 (6.6); 7.913 (6.0); 7.909 (6.1); 7.894 (6.7); 7.890 (6.3); 7.881 (0.8); 7.869 (5.9); 7.865 (6.1); 7.851 (6.6); 7.846 (6.5); 7.506 (6.3); 7.493 (6.3); 7.487 (6.0); 7.475 (5.4); 7.055 (6.1); 7.043 (6.2); 7.036 (6.1); 7.024 (5.7); 5.757 (0.6); 4.508 (7.7); 4.494 (16.0); 4.479 (8.2); 3.735 (0.6); 3.720 (0.4); 3.678 (4.2); 3.664 (11.5); 3.649 (11.3); 3.635 (4.0); 3.580 (0.5); 3.565 (0.4); 3.324 (52.5); 2.671 (0.9); 2.667 (0.7); 2.506 (98.3); 2.502 (126.9); 2.498 (100.6); 2.333 (0.6); 2.329 (0.9); 2.325 (0.7); 1.235 (0.5); 0.000 (7.9)

Compound No. 1-55:

1H-NMR (400.0 MHz, DMSO): δ = 8.220 (1.8); 8.207 (3.2); 8.194 (1.8); 8.128 (6.9); 8.124 (7.2); 8.116 (7.3); 8.112 (7.1); 7.909 (7.4); 7.905 (7.3); 7.890 (8.0); 7.886 (7.3); 7.845 (13.3); 7.832 (13.7); 7.812 (0.4); 7.799 (0.4); 7.181 (0.4); 7.168 (0.4); 7.150 (14.3); 7.137 (13.8); 7.052 (8.1); 7.039 (7.8); 7.032 (7.7); 7.020 (7.6); 5.760 (7.2); 4.517 (7.5); 4.502 (16.0); 4.488 (7.9); 3.698 (4.0); 3.683 (11.3); 3.669 (11.0); 3.655 (3.7); 3.329 (30.0); 2.527 (0.9); 2.514 (17.0); 2.509 (33.6); 2.505 (43.8); 2.500 (31.3); 2.495 (14.7); 1.991 (1.2); 1.338 (1.1); 1.250 (1.3); 1.194 (0.4); 1.176 (0.7); 1.158 (0.3); 0.000 (4.0)

Compound No. 1-56:

1H-NMR (400.0 MHz, DMSO): δ = 8.550 (6.9); 8.547 (8.7); 8.545 (9.0); 8.542 (8.1); 8.525 (4.5); 8.510 (2.3); 8.387 (9.4); 8.382 (8.7); 7.905 (15.3); 7.900 (15.2); 7.338 (0.4); 7.333 (0.3); 7.183 (0.5); 7.177 (0.4); 6.852 (16.0); 6.847 (15.6); 5.759 (7.4); 4.583 (7.3); 4.569 (15.7); 4.555 (7.4); 4.057 (0.4); 4.039 (1.1); 4.021 (1.1); 4.004 (0.4); 3.661 (3.9); 3.647 (11.0); 3.633 (10.6); 3.618 (3.4); 3.327 (50.9); 2.678 (0.4); 2.673 (0.5); 2.669 (0.4); 2.527 (2.0); 2.513 (31.6); 2.509 (61.7); 2.504 (79.5); 2.500 (56.3); 2.495 (26.1); 2.336 (0.4); 2.331 (0.5); 2.326 (0.4); 1.991 (4.9); 1.353 (0.3); 1.337 (6.7); 1.300 (0.7); 1.259 (1.2); 1.250 (8.2); 1.235 (1.3); 1.194 (1.5); 1.188 (0.8); 1.176 (2.7); 1.158 (1.3); 0.854 (0.4); 0.008 (0.4); 0.000 (12.1); −0.009 (0.3)

Compound No. 1-57:

1H-NMR (400.0 MHz, DMSO): δ = 8.915 (2.2); 8.901 (4.3); 8.888 (2.2); 8.795 (5.6); 8.786 (5.4); 8.783 (5.5); 8.608 (6.6); 8.606 (6.8); 8.605 (6.8); 8.602 (6.6); 8.102 (4.8); 8.095 (4.7); 8.080 (5.0); 8.073 (4.9); 7.995 (4.9); 7.992 (5.1); 7.975 (6.0); 7.973 (5.9); 7.785 (5.5); 7.773 (5.5); 7.765 (4.8); 7.754 (4.5); 7.012 (8.0); 6.990 (7.7); 5.759 (0.3); 4.481 (7.8); 4.467 (16.0); 4.453 (8.2); 3.684 (4.1); 3.670 (11.2); 3.656 (10.8); 3.642 (3.7); 3.325 (44.6); 2.676 (0.5); 2.672 (0.6); 2.667 (0.5); 2.525 (1.9); 2.512 (36.4); 2.507 (72.1); 2.503 (94.0); 2.498 (67.4); 2.494 (32.0); 2.334 (0.4); 2.330 (0.6); 2.325 (0.4); 1.337 (0.5); 1.250 (0.6); 0.008 (1.8); 0.000 (49.0); −0.009 (1.6)

Compound No. 1-58:

1H-NMR (400.0 MHz, DMSO): δ = 8.897 (2.1); 8.884 (3.9); 8.870 (2.0); 8.814 (0.3); 8.799 (5.0); 8.797 (5.1); 8.788 (5.1); 8.785 (5.0); 8.147 (7.1); 8.143 (7.4); 8.135 (7.4); 8.131 (7.3); 7.985 (4.6); 7.983 (4.7); 7.966 (5.6); 7.963 (5.5); 7.915 (7.2); 7.911 (7.1); 7.896 (7.8); 7.892 (7.2); 7.796 (5.1); 7.784 (5.1); 7.777 (4.3); 7.765 (4.1); 7.059 (7.8); 7.046 (7.6); 7.039 (7.4); 7.027 (7.4); 4.490 (7.5); 4.475 (16.0); 4.461 (7.9); 3.722 (0.7); 3.707 (0.5); 3.683 (4.0); 3.669 (11.1); 3.655 (10.7); 3.640 (3.6); 3.584 (0.5); 3.569 (0.4); 3.326 (45.8); 2.676 (0.3); 2.672 (0.5); 2.667 (0.3); 2.525 (1.6); 2.511 (28.1); 2.507 (54.4); 2.503 (70.3); 2.498 (50.2); 2.493 (23.8); 2.334 (0.3); 2.329 (0.5); 2.325 (0.3); 1.337 (0.4); 1.250 (0.6); 0.008 (1.5); 0.000 (38.0); −0.009 (1.2)

TABLE 2-continued

Compound No. 1-59:

1H-NMR (400.0 MHz, DMSO): δ = 8.989 (2.6); 8.975 (5.2); 8.961 (2.6); 8.898 (9.5); 8.893 (9.6); 8.591 (7.6); 8.588 (9.5); 8.585 (9.5); 8.583 (7.8); 8.418 (10.5); 8.412 (9.9); 8.216 (10.3); 8.211 (10.1); 7.183 (0.4); 5.758 (3.6); 4.593 (7.8); 4.579 (16.0); 4.565 (8.2); 3.717 (4.1); 3.703 (11.2); 3.689 (10.8); 3.675 (3.8); 3.323 (70.1); 2.680 (0.4); 2.676 (0.8); 2.672 (1.0); 2.667 (0.7); 2.663 (0.4); 2.525 (3.0); 2.520 (4.7); 2.512 (56.7); 2.507 (114.4); 2.503 (150.8); 2.498 (108.2); 2.494 (51.2); 2.339 (0.4); 2.334 (0.7); 2.329 (1.0); 2.325 (0.7); 2.320 (0.3); 1.990 (0.9); 1.336 (4.6); 1.299 (0.4); 1.259 (0.7); 1.250 (5.7); 1.235 (0.7); 1.193 (0.3); 1.188 (0.4); 1.175 (0.6); 1.149 (0.4); 0.146 (0.3); 0.008 (3.0); 0.000 (89.8); −0.009 (2.8); −0.150 (0.4)

Compound No. 1-60:

1H-NMR (400.0 MHz, DMSO): δ = 8.993 (2.5); 8.980 (4.8); 8.966 (2.4); 8.892 (9.2); 8.886 (9.2); 8.608 (7.1); 8.606 (7.3); 8.604 (7.3); 8.602 (7.0); 8.556 (0.4); 8.554 (0.4); 8.387 (0.4); 8.382 (0.4); 8.240 (9.8); 8.235 (9.5); 8.105 (5.1); 8.099 (5.0); 8.083 (5.3); 8.077 (5.1); 7.183 (0.4); 7.016 (8.6); 6.994 (8.2); 5.759 (2.5); 4.489 (8.0); 4.475 (16.0); 4.461 (8.3); 4.393 (0.4); 4.378 (0.7); 4.364 (0.3); 3.686 (4.3); 3.672 (11.3); 3.658 (10.8); 3.644 (3.8); 3.325 (36.4); 2.932 (0.4); 2.677 (0.5); 2.672 (0.7); 2.668 (0.5); 2.526 (2.4); 2.512 (38.3); 2.508 (75.4); 2.503 (97.8); 2.499 (69.8); 2.494 (32.7); 2.335 (0.5); 2.330 (0.6); 2.325 (0.5); 1.337 (5.3); 1.300 (0.5); 1.259 (0.8); 1.250 (6.4); 1.235 (0.7); 1.163 (0.3); 0.008 (2.1); 0.000 (57.2); −0.009 (1.7)

Compound No. 1-61:

1H-NMR (400.0 MHz, DMSO): δ = 8.977 (2.2); 8.963 (4.3); 8.950 (2.2); 8.896 (8.3); 8.890 (8.4); 8.210 (8.9); 8.205 (8.6); 8.148 (7.4); 8.143 (7.9); 8.135 (7.9); 8.131 (7.9); 7.922 (7.6); 7.918 (7.6); 7.903 (8.3); 7.899 (7.7); 7.064 (8.3); 7.052 (8.1); 7.045 (7.9); 7.033 (7.8); 4.495 (7.5); 4.481 (16.0); 4.467 (7.9); 3.687 (3.9); 3.673 (11.0); 3.659 (10.7); 3.645 (3.6); 3.324 (39.5); 2.676 (0.5); 2.672 (0.6); 2.667 (0.4); 2.525 (1.9); 2.512 (35.5); 2.507 (70.8); 2.503 (92.7); 2.498 (66.9); 2.494 (32.0); 2.334 (0.4); 2.329 (0.6); 2.325 (0.4); 1.337 (1.7); 1.259 (0.3); 1.250 (2.0); 1.234 (0.3); 0.008 (1.7); 0.000 (49.5); −0.009 (1.6)

Compound No. 1-62:

1H-NMR (400.0 MHz, DMSO): δ = 9.086 (2.0); 9.072 (3.8); 9.059 (2.0); 8.735 (7.0); 8.734 (7.1); 8.722 (7.2); 8.721 (7.1); 8.627 (0.3); 8.555 (0.4); 8.386 (0.5); 8.380 (0.4); 8.317 (0.5); 8.143 (7.5); 8.139 (8.0); 8.131 (7.9); 8.127 (7.9); 8.059 (0.4); 7.913 (7.5); 7.909 (7.5); 7.894 (8.1); 7.890 (7.6); 7.877 (10.2); 7.864 (9.8); 7.336 (0.7); 7.332 (0.7); 7.182 (1.3); 7.177 (0.8); 7.056 (8.4); 7.044 (8.1); 7.037 (7.9); 7.024 (7.8); 4.493 (6.5); 4.479 (12.8); 4.465 (6.8); 4.379 (0.7); 4.365 (1.4); 4.350 (0.8); 3.709 (3.9); 3.695 (10.5); 3.681 (10.2); 3.667 (3.6); 3.383 (0.4); 3.368 (0.5); 3.322 (430.7); 2.928 (0.5); 2.913 (0.9); 2.898 (0.5); 2.680 (1.8); 2.675 (3.6); 2.670 (4.8); 2.666 (3.5); 2.661 (1.7); 2.646 (0.4); 2.643 (0.4); 2.524 (15.1); 2.519 (23.4); 2.510 (262.3); 2.506 (521.1); 2.501 (679.5); 2.497 (483.6); 2.492 (225.6); 2.337 (1.4); 2.333 (3.2); 2.328 (4.4); 2.324 (3.1); 2.319 (1.3); 1.989 (1.0); 1.350 (0.6); 1.335 (12.8); 1.298 (1.4); 1.258 (2.4); 1.249 (16.0); 1.235 (1.9); 1.192 (0.5); 1.187 (0.8); 1.175 (0.7); 1.157 (0.4); 1.147 (0.6); 1.108 (0.5); 0.853 (0.5); 0.834 (0.3); 0.146 (1.5); 0.008 (12.8); 0.000 (360.7); −0.009 (11.0); −0.150 (1.4)

Compound No. 1-63:

1H-NMR (400.0 MHz, DMSO): δ = 8.905 (2.5); 8.891 (4.8); 8.877 (2.5); 8.798 (6.0); 8.789 (5.9); 8.787 (6.0); 8.589 (7.0); 8.586 (9.0); 8.584 (9.1); 8.581 (7.6); 8.406 (10.1); 8.401 (9.7); 8.316 (0.5); 7.989 (5.2); 7.987 (5.5); 7.970 (6.4); 7.967 (6.5); 7.796 (5.8); 7.784 (5.7); 7.777 (5.0); 7.765 (4.7); 5.756 (0.6); 4.586 (7.7); 4.572 (16.0); 4.558 (8.1); 3.713 (4.0); 3.699 (11.2); 3.685 (10.9); 3.671 (3.8); 3.322 (125.4); 2.676 (1.0); 2.671 (1.5); 2.667 (1.1); 2.662 (0.5); 2.524 (4.2); 2.511 (82.7); 2.507 (167.5); 2.502 (222.2); 2.498 (162.6); 2.493 (79.6); 2.338 (0.6); 2.333 (1.1); 2.329 (1.5); 2.324 (1.1); 1.235 (1.9); 1.183 (0.6); 1.166 (0.9); 1.149 (0.6); 0.146 (0.7); 0.008 (5.4); 0.000 (157.9); −0.008 (5.7); −0.150 (0.7)

Compound No. 1-64:

1H-NMR (400.0 MHz, DMSO): δ = 9.100 (2.0); 9.086 (3.9); 9.073 (2.1); 8.735 (6.9); 8.724 (7.1); 8.649 (0.3); 8.603 (6.4); 8.315 (1.7); 8.191 (2.8); 8.098 (4.3); 8.092 (4.4); 8.076 (4.5); 8.070 (4.6); 7.879 (9.9); 7.866 (9.6); 6.991 (7.2); 6.969 (7.0); 6.545 (0.4); 5.756 (1.4); 4.861 (0.4); 4.849 (0.4); 4.618 (0.3); 4.481 (6.4); 4.468 (12.9); 4.454 (7.1); 4.394 (0.4); 4.380 (0.7); 4.365 (0.4); 4.039 (2.8); 4.022 (2.9); 3.913 (0.5); 3.897 (0.4); 3.709 (3.1); 3.695 (8.4); 3.682 (8.3); 3.668 (3.1); 3.324 (1015.0); 2.891 (0.4); 2.675 (5.5); 2.671 (7.6); 2.666 (5.5); 2.524 (21.5); 2.519 (35.9); 2.511 (443.8); 2.506 (887.9); 2.502 (1165.7); 2.497 (842.3); 2.493 (406.4); 2.337 (3.3); 2.333 (6.2); 2.328 (8.3); 2.324 (6.1); 2.300 (1.2); 2.280 (1.8); 2.263 (1.3); 2.193 (1.3); 2.074 (5.0); 1.770 (0.8); 1.566 (1.1); 1.235 (16.0); 1.179 (5.5); 1.165 (8.6); 1.148 (5.1); 0.871 (0.7); 0.854 (1.8); 0.837 (0.9); 0.146 (3.4); 0.008 (30.6); 0.000 (812.4); −0.009 (26.1); −0.150 (3.4)

Compound No. 1-65:

1H-NMR (400.0 MHz, DMSO): δ = 8.350 (2.9); 8.127 (2.5); 8.123 (2.7); 8.115 (2.7); 8.111 (2.7); 8.037 (2.1); 8.034 (2.2); 8.016 (2.5); 8.014 (2.4); 7.912 (2.6); 7.908 (2.6); 7.893 (2.9); 7.889 (2.6); 7.791 (1.0); 7.788 (1.1); 7.772 (2.5); 7.769 (2.5); 7.753 (1.7); 7.750 (1.6); 7.678 (1.5); 7.674 (1.6); 7.658 (1.8); 7.654 (1.9); 7.639 (1.1); 7.635 (1.0); 7.522 (2.3); 7.519 (2.3); 7.504 (2.1); 7.500 (1.9); 7.042 (2.8); 7.030 (2.7); 7.023 (2.6); 7.011 (2.6); 4.644 (2.6); 4.618 (3.4); 4.469 (3.4); 4.443 (2.7); 3.326 (66.8); 2.671 (0.3); 2.541 (5.5); 2.524 (1.0); 2.520 (1.5); 2.511 (18.3); 2.506 (36.9); 2.502 (48.5); 2.497 (34.5); 2.493 (16.2); 2.065 (0.8); 2.046 (0.9); 2.031 (1.1); 2.012 (1.0); 1.745 (1.0); 1.726 (1.2); 1.711 (1.0); 1.692 (0.9); 1.389 (16.0); 0.960 (3.7); 0.941 (8.3); 0.922 (3.4); 0.000 (6.8)

Compound No. 1-66:

1H-NMR (400.0 MHz, DMSO): δ = 8.870 (2.0); 8.857 (3.8); 8.843 (2.0); 8.466 (4.2); 8.463 (4.3); 8.454 (4.3); 8.451 (4.2); 8.122 (4.2); 8.119 (4.2); 8.104 (4.5); 8.101 (4.2); 8.042 (6.0); 8.039 (6.3);

TABLE 2-continued 8.021 (7.0); 8.019 (6.9); 7.811 (2.8); 7.808 (3.0); 7.792 (7.2); 7.789 (7.2); 7.773 (5.0); 7.770 (4.6); 7.710 (4.4); 7.706 (4.9); 7.690 (5.4); 7.686 (5.7); 7.671 (3.0); 7.667 (2.9); 7.553 (6.7); 7.549 (6.7); 7.534 (5.9); 7.530 (5.6); 7.212 (3.7); 7.199 (3.8); 7.194 (3.7); 7.181 (3.4); 4.555 (7.0); 4.540 (16.0); 4.525 (7.4); 3.649 (3.7); 3.634 (10.7); 3.620 (10.3); 3.605 (3.4); 3.327 (176.0); 3.306 (0.4); 2.676 (0.6); 2.671 (0.8); 2.667 (0.6); 2.542 (3.2); 2.525 (2.4); 2.520 (3.8); 2.511 (47.5); 2.507 (95.6); 2.502 (125.9); 2.498 (90.3); 2.493 (42.7); 2.333 (0.6); 2.329 (0.8); 2.324 (0.6); 0.008 (0.5); 0.000 (16.0); −0.009 (0.5)
Compound No. 1-67:

1H-NMR (400.0 MHz, DMSO): δ = 8.946 (1.7); 8.932 (3.3); 8.918 (1.7); 8.041 (5.8); 8.038 (5.9); 8.021 (6.8); 8.018 (6.5); 7.992 (5.4); 7.989 (5.5); 7.980 (5.6); 7.977 (5.5); 7.801 (2.8); 7.798 (2.9); 7.782 (7.3); 7.779 (7.2); 7.763 (5.1); 7.760 (4.8); 7.706 (7.5); 7.702 (7.9); 7.686 (9.0); 7.683 (9.1); 7.678 (3.9); 7.675 (3.8); 7.667 (3.2); 7.664 (3.1); 7.659 (3.9); 7.655 (3.6); 7.577 (6.7); 7.573 (6.5); 7.558 (5.8); 7.554 (5.3); 7.058 (3.7); 7.050 (4.0); 7.046 (3.7); 7.038 (6.0); 7.030 (3.5); 7.026 (3.5); 7.018 (3.3); 4.497 (7.3); 4.482 (16.0); 4.468 (7.7); 3.662 (3.8); 3.648 (10.8); 3.633 (10.5); 3.619 (3.4); 3.327 (150.7); 2.676 (0.5); 2.671 (0.7); 2.666 (0.5); 2.541 (3.7); 2.524 (2.2); 2.520 (3.5); 2.511 (43.2); 2.507 (86.8); 2.502 (114.0); 2.497 (81.4); 2.493 (38.3); 2.333 (0.5); 2.329 (0.7); 2.324 (0.5); 0.008 (0.5); 0.000 (13.8); −0.009 (0.4)
Compound No. 1-68:

1H-NMR (400.0 MHz, DMSO): δ = 8.461 (1.4); 8.450 (0.8); 8.447 (0.8); 8.437 (0.8); 8.434 (0.7); 8.123 (0.7); 8.120 (0.7); 8.104 (0.8); 8.101 (0.7); 8.058 (1.0); 8.056 (1.1); 8.038 (1.2); 8.035 (1.2); 7.795 (0.5); 7.792 (0.5); 7.776 (1.2); 7.774 (1.2); 7.758 (0.8); 7.755 (0.8); 7.679 (0.7); 7.676 (0.8); 7.659 (0.9); 7.656 (0.9); 7.640 (0.5); 7.637 (0.5); 7.478 (1.1); 7.474 (1.1); 7.459 (1.0); 7.455 (1.0); 7.199 (0.6); 7.186 (0.6); 7.181 (0.6); 7.168 (0.6); 4.588 (5.1); 3.326 (26.3); 2.542 (1.4); 2.525 (0.5); 2.520 (0.7); 2.511 (9.1); 2.507 (18.5); 2.502 (24.4); 2.498 (17.6); 2.493 (8.5); 1.431 (16.0); 0.000 (2.8)
Compound No. 1-69:

1H-NMR (400.0 MHz, DMSO): δ = 8.472 (1.5); 8.212 (2.0); 8.206 (2.9); 8.181 (2.8); 8.175 (2.0); 8.051 (1.1); 8.048 (1.1); 8.031 (1.2); 8.028 (1.2); 7.793 (0.5); 7.790 (0.5); 7.774 (1.3); 7.771 (1.2); 7.755 (0.8); 7.752 (0.8); 7.679 (0.7); 7.676 (0.8); 7.659 (0.9); 7.656 (0.9); 7.640 (0.5); 7.637 (0.5); 7.513 (1.2); 7.510 (1.2); 7.494 (1.0); 7.491 (1.0); 4.517 (5.2); 3.324 (19.4); 2.541 (4.0); 2.524 (0.5); 2.519 (0.7); 2.511 (8.9); 2.507 (17.9); 2.502 (23.5); 2.497 (16.9); 2.493 (8.0); 1.442 (16.0); 0.000 (3.6)
Compound No. 1-70:

1H-NMR (400.0 MHz, DMSO): δ = 8.925 (1.9); 8.912 (3.6); 8.898 (1.9); 8.794 (4.7); 8.792 (5.0); 8.783 (4.9); 8.780 (4.9); 7.990 (5.8); 7.987 (6.2); 7.978 (10.2); 7.974 (10.6); 7.957 (5.5); 7.955 (5.4); 7.787 (5.1); 7.775 (5.0); 7.767 (4.3); 7.756 (4.2); 7.707 (3.5); 7.703 (3.5); 7.687 (3.9); 7.683 (3.8); 7.679 (3.7); 7.675 (3.5); 7.659 (3.8); 7.656 (3.6); 7.058 (3.7); 7.050 (4.0); 7.046 (3.8); 7.038 (6.3); 7.030 (3.6); 7.026 (3.6); 7.018 (3.3); 4.490 (7.7); 4.476 (16.0); 4.462 (8.2); 3.686 (4.0); 3.672 (11.2); 3.658 (10.8); 3.644 (3.7); 3.326 (124.5); 2.676 (0.6); 2.671 (0.8); 2.667 (0.6); 2.541 (2.6); 2.524 (2.4); 2.520 (3.9); 2.511 (48.8); 2.507 (97.3); 2.502 (127.0); 2.498 (90.6); 2.493 (43.0); 2.333 (0.6); 2.329 (0.8); 2.324 (0.6); 0.008 (0.7); 0.000 (19.8); −0.009 (0.6)
Compound No. 1-71:

1H-NMR (400.0 MHz, DMSO): δ = 8.768 (0.8); 8.759 (0.8); 8.757 (0.8); 8.591 (1.0); 8.589 (1.0); 8.587 (1.0); 8.465 (1.4); 8.099 (0.7); 8.092 (0.7); 8.077 (0.7); 8.070 (0.7); 7.915 (0.7); 7.912 (0.7); 7.895 (0.9); 7.893 (0.9); 7.757 (0.8); 7.745 (0.8); 7.738 (0.7); 7.726 (0.6); 7.037 (1.2); 7.015 (1.1); 4.525 (5.1); 3.324 (31.1); 2.541 (0.6); 2.524 (0.8); 2.519 (1.3); 2.511 (15.9); 2.506 (32.0); 2.502 (42.0); 2.497 (30.2); 2.493 (14.4); 1.432 (16.0); 0.000 (7.6)
Compound No. 1-72:

1H-NMR (400.0 MHz, DMSO): δ = 8.470 (1.4); 8.163 (1.2); 8.159 (1.3); 8.151 (1.2); 8.146 (1.3); 8.056 (1.9); 8.052 (2.2); 8.037 (1.6); 8.033 (2.2); 7.794 (0.5); 7.791 (0.5); 7.775 (1.2); 7.772 (1.2); 7.756 (0.8); 7.753 (0.8); 7.680 (0.7); 7.676 (0.8); 7.660 (0.9); 7.657 (0.9); 7.641 (0.5); 7.637 (0.5); 7.541 (1.2); 7.538 (1.1); 7.522 (1.0); 7.519 (0.9); 6.973 (1.3); 6.961 (1.2); 6.954 (1.2); 6.942 (1.2); 4.504 (5.2); 3.325 (11.7); 2.541 (2.3); 2.524 (0.4); 2.511 (6.6); 2.507 (13.0); 2.502 (16.9); 2.497 (12.0); 2.493 (5.7); 1.455 (16.0); 0.000 (3.1)
Compound No. 1-73:

1H-NMR (400.0 MHz, DMSO): δ = 8.771 (1.8); 8.761 (1.7); 8.759 (1.7); 8.355 (2.9); 8.131 (2.4); 8.127 (2.6); 8.119 (2.6); 8.114 (2.6); 7.917 (2.6); 7.913 (2.6); 7.898 (4.2); 7.894 (3.3); 7.880 (2.0); 7.878 (2.0); 7.778 (1.8); 7.766 (1.8); 7.759 (1.4); 7.747 (1.3); 7.047 (2.7); 7.035 (2.6); 7.028 (2.5); 7.015 (2.5); 4.649 (2.6); 4.623 (3.3); 4.466 (3.4); 4.440 (2.7); 3.325 (54.4); 2.671 (0.3); 2.541 (5.1); 2.524 (1.0); 2.520 (1.7); 2.511 (20.2); 2.507 (40.3); 2.502 (52.9); 2.497 (38.3); 2.493 (18.6); 2.329 (0.3); 2.046 (0.8); 2.027 (1.0); 2.012 (1.1); 1.993 (1.0); 1.752 (1.0); 1.733 (1.2); 1.717 (1.0); 1.699 (0.9); 1.385 (16.0); 0.939 (3.7); 0.920 (8.2); 0.902 (3.4); 0.000 (7.9)
Compound No. 1-74:

1H-NMR (400.0 MHz, DMSO): δ = 8.841 (5.4); 8.828 (3.0); 8.800 (6.9); 8.798 (6.8); 8.788 (6.5); 8.464 (6.4); 8.451 (6.2); 8.123 (6.3); 8.105 (6.3); 7.941 (5.9); 7.921 (7.3); 7.801 (5.8); 7.789 (6.3); 7.782 (4.5); 7.770 (3.9); 7.212 (4.7); 7.199 (5.8); 7.181 (3.8); 4.553 (8.8); 4.539 (16.0); 4.525 (7.8); 3.671 (5.3); 3.657 (12.1); 3.643 (11.2); 3.629 (3.7); 3.332 (71.8); 3.326 (160.7); 2.676 (1.0); 2.671 (1.1); 2.541 (7.2); 2.540 (7.3); 2.507 (156.5); 2.502 (171.5); 2.498 (118.5); 2.333 (1.0); 2.329 (1.1); 1.236 (0.4); 0.005 (5.5); 0.000 (14.7); −0.002 (13.0); −0.008 (0.7)

TABLE 2-continued

Compound No. 1-75:

1H-NMR (400.0 MHz, DMSO): δ = 8.773 (0.8); 8.771 (0.9); 8.762 (0.9); 8.759 (0.9); 8.501 (1.5); 8.164 (1.3); 8.160 (1.5); 8.152 (1.4); 8.147 (1.4); 8.061 (1.4); 8.057 (1.4); 8.042 (1.6); 8.038 (1.4); 7.923 (0.7); 7.920 (0.8); 7.904 (1.0); 7.901 (0.9); 7.774 (0.9); 7.762 (0.9); 7.754 (0.7); 7.743 (0.7); 6.977 (1.5); 6.964 (1.4); 6.957 (1.4); 6.945 (1.4); 4.503 (5.3); 3.326 (16.5); 2.542 (2.0); 2.525 (0.3); 2.520 (0.5); 2.512 (5.6); 2.507 (11.1); 2.502 (14.5); 2.498 (10.3); 2.493 (4.8); 1.450 (16.0); 0.000 (2.5)

Compound No. 1-76:

1H-NMR (400.0 MHz, DMSO): δ = 8.772 (0.8); 8.770 (0.8); 8.761 (0.8); 8.758 (0.8); 8.496 (1.4); 8.449 (0.7); 8.447 (0.7); 8.437 (0.7); 8.434 (0.7); 8.126 (0.7); 8.123 (0.7); 8.108 (0.8); 8.105 (0.7); 7.859 (0.6); 7.856 (0.7); 7.839 (1.0); 7.836 (1.0); 7.776 (0.9); 7.764 (0.9); 7.756 (0.6); 7.745 (0.6); 7.202 (0.6); 7.189 (0.6); 7.184 (0.6); 7.171 (0.6); 4.580 (5.1); 3.324 (20.8); 2.542 (1.5); 2.525 (0.4); 2.520 (0.7); 2.511 (8.9); 2.507 (18.1); 2.502 (23.9); 2.498 (17.0); 2.493 (8.0); 1.429 (16.0); 0.000 (4.8)

Compound No. 1-77:

1H-NMR (400.0 MHz, DMSO): δ = 8.773 (0.8); 8.771 (0.9); 8.761 (0.8); 8.759 (0.8); 8.501 (1.5); 8.216 (2.2); 8.210 (3.4); 8.189 (3.3); 8.183 (2.2); 7.904 (0.7); 7.902 (0.7); 7.885 (1.0); 7.882 (0.9); 7.773 (0.9); 7.762 (0.9); 7.754 (0.7); 7.742 (0.7); 4.514 (5.2); 3.326 (29.4); 2.542 (4.1); 2.525 (0.4); 2.520 (0.7); 2.511 (8.7); 2.507 (17.6); 2.502 (23.2); 2.498 (16.5); 2.493 (7.8); 1.437 (16.0); 0.000 (3.5)

Compound No. 1-78:

1H-NMR (400.0 MHz, DMSO): δ = 8.586 (1.0); 8.584 (1.0); 8.582 (1.0); 8.580 (1.0); 8.293 (1.4); 8.092 (0.7); 8.085 (0.7); 8.069 (0.7); 8.063 (0.7); 7.745 (0.8); 7.725 (1.0); 7.700 (0.3); 7.682 (0.9); 7.663 (0.7); 7.626 (0.6); 7.607 (0.8); 7.431 (0.9); 7.413 (0.8); 7.032 (1.2); 7.010 (1.2); 4.534 (5.1); 3.325 (15.9); 2.525 (0.4); 2.520 (0.7); 2.511 (7.9); 2.507 (15.9); 2.502 (20.8); 2.498 (14.8); 2.493 (6.9); 1.423 (16.0); 0.000 (4.0)

Compound No. 1-79:

1H-NMR (400.0 MHz, DMSO): δ = 8.745 (1.8); 8.732 (3.4); 8.718 (1.8); 7.987 (5.5); 7.983 (5.7); 7.974 (5.8); 7.971 (5.7); 7.776 (4.6); 7.756 (6.2); 7.729 (2.0); 7.711 (5.4); 7.702 (3.8); 7.698 (3.9); 7.693 (4.1); 7.682 (3.9); 7.678 (3.8); 7.674 (3.7); 7.670 (3.5); 7.655 (7.3); 7.651 (6.1); 7.635 (4.7); 7.616 (1.7); 7.490 (5.6); 7.471 (4.7); 7.053 (3.6); 7.045 (3.9); 7.041 (3.6); 7.033 (6.1); 7.025 (3.4); 7.021 (3.4); 7.013 (3.2); 4.483 (7.4); 4.469 (16.0); 4.454 (7.8); 3.659 (3.8); 3.645 (10.8); 3.631 (10.5); 3.617 (3.5); 3.325 (120.8); 2.675 (0.6); 2.671 (0.8); 2.667 (0.6); 2.541 (1.7); 2.524 (2.6); 2.511 (48.6); 2.506 (96.6); 2.502 (126.3); 2.497 (90.6); 2.493 (43.0); 2.469 (0.4); 2.333 (0.6); 2.328 (0.8); 2.324 (0.6); 1.235 (0.3); 0.008 (0.6); 0.000 (19.7); −0.009 (0.6)

Compound No. 1-80:

1H-NMR (400.0 MHz, DMSO): δ = 8.184 (2.8); 8.126 (2.6); 8.122 (2.8); 8.114 (2.8); 8.110 (2.8); 7.913 (2.7); 7.908 (2.7); 7.893 (3.0); 7.889 (2.7); 7.748 (1.6); 7.728 (2.2); 7.715 (0.7); 7.697 (1.9); 7.678 (1.3); 7.628 (1.3); 7.609 (1.7); 7.590 (0.6); 7.472 (2.0); 7.454 (1.6); 7.040 (2.9); 7.028 (2.8); 7.021 (2.8); 7.009 (2.8); 4.665 (2.6); 4.639 (3.3); 4.457 (3.4); 4.431 (2.8); 3.325 (36.5); 2.541 (0.5); 2.524 (0.7); 2.520 (1.2); 2.511 (15.1); 2.506 (30.5); 2.502 (40.1); 2.497 (28.5); 2.493 (13.4); 2.063 (0.8); 2.044 (1.0); 2.028 (1.1); 2.010 (1.0); 1.740 (1.0); 1.721 (1.2); 1.705 (1.0); 1.687 (0.9); 1.373 (16.0); 0.932 (3.7); 0.914 (8.3); 0.895 (3.4); 0.000 (7.0)

Compound No. 1-81:

1H-NMR (400.0 MHz, DMSO): δ = 8.671 (2.0); 8.658 (3.8); 8.644 (2.0); 8.462 (4.4); 8.459 (4.5); 8.449 (4.6); 8.447 (4.4); 8.121 (4.4); 8.118 (4.4); 8.102 (4.7); 8.099 (4.5); 7.780 (5.0); 7.761 (6.6); 7.738 (2.2); 7.720 (5.6); 7.701 (4.0); 7.658 (3.9); 7.639 (5.0); 7.620 (1.9); 7.477 (5.9); 7.458 (5.1); 7.208 (3.8); 7.196 (3.9); 7.191 (3.9); 7.178 (3.6); 4.547 (7.2); 4.533 (16.0); 4.518 (7.6); 3.648 (3.8); 3.634 (10.8); 3.620 (10.4); 3.605 (3.5); 3.326 (87.0); 3.308 (0.4); 2.676 (0.5); 2.671 (0.7); 2.667 (0.5); 2.542 (1.4); 2.525 (2.1); 2.511 (42.1); 2.507 (84.0); 2.502 (109.9); 2.498 (79.3); 2.493 (38.1); 2.333 (0.5); 2.329 (0.7); 2.324 (0.5); 1.235 (0.4); 0.008 (0.6); 0.000 (16.6); −0.009 (0.5)

Compound No. 1-82:

1H-NMR (400.0 MHz, DMSO): δ = 8.327 (1.4); 8.210 (2.1); 8.204 (3.2); 8.183 (3.0); 8.177 (2.0); 7.746 (0.8); 7.726 (1.1); 7.709 (0.4); 7.692 (0.9); 7.673 (0.7); 7.627 (0.6); 7.608 (0.8); 7.448 (1.0); 7.429 (0.8); 4.521 (5.3); 3.325 (16.6); 2.541 (0.3); 2.524 (0.4); 2.520 (0.6); 2.511 (7.6); 2.507 (15.3); 2.502 (20.1); 2.497 (14.3); 2.493 (6.7); 1.428 (16.0); 0.000 (3.8)

Compound No. 1-83:

1H-NMR (400.0 MHz, DMSO): δ = 8.320 (1.4); 8.159 (1.2); 8.155 (1.3); 8.147 (1.3); 8.143 (1.3); 8.057 (1.2); 8.053 (1.2); 8.038 (1.3); 8.034 (1.2); 7.748 (0.9); 7.728 (1.1); 7.710 (0.4); 7.692 (1.0); 7.673 (0.7); 7.627 (0.7); 7.608 (0.9); 7.482 (1.0); 7.464 (0.9); 6.971 (1.3); 6.958 (1.3); 6.951 (1.2); 6.939 (1.2); 4.508 (5.3); 3.326 (13.1); 2.511 (5.5); 2.507 (11.0); 2.502 (14.5); 2.497 (10.5); 2.493 (5.1); 1.441 (16.0); 0.000 (2.3)

Compound No. 1-84:

1H-NMR (400.0 MHz, DMSO): δ = 8.582 (1.0); 8.581 (1.0); 8.578 (0.9); 8.536 (1.2); 8.087 (0.7); 8.081 (0.7); 8.065 (0.7); 8.059 (0.7); 7.484 (0.4); 7.480 (0.4); 7.463 (0.8); 7.446 (0.4); 7.442 (0.5); 7.132 (1.4); 7.113 (1.6); 7.111 (1.5); 7.092 (1.2); 7.008 (1.1); 6.987 (1.1); 4.521 (4.9); 3.327 (219.1); 3.299 (0.5); 2.675 (0.5); 2.671 (0.7); 2.666 (0.5); 2.541 (0.6); 2.524 (2.2); 2.519 (3.5); 2.511 (42.7); 2.506 (85.4); 2.502 (112.0); 2.497 (80.2); 2.493 (37.9); 2.333 (0.5); 2.328 (0.7); 2.324 (0.5); 1.425 (16.0); 0.000 (8.3)

TABLE 2-continued

Compound No. 1-85:

1H-NMR (400.0 MHz, DMSO): δ = 8.965 (1.8); 8.953 (3.2); 8.940 (1.8); 7.982 (5.6); 7.978 (5.9); 7.970 (5.8); 7.966 (5.8); 7.702 (3.2); 7.698 (3.2); 7.682 (3.6); 7.678 (3.5); 7.674 (3.5); 7.670 (3.2); 7.654 (3.5); 7.651 (3.2); 7.539 (1.3); 7.523 (2.7); 7.518 (2.6); 7.506 (1.8); 7.501 (5.3); 7.497 (1.9); 7.485 (2.6); 7.480 (3.1); 7.464 (1.4); 7.180 (1.1); 7.177 (1.5); 7.169 (8.8); 7.150 (11.5); 7.129 (7.3); 7.122 (1.3); 7.054 (3.4); 7.046 (3.7); 7.042 (3.5); 7.034 (6.0); 7.026 (3.3); 7.022 (3.2); 7.014 (2.9); 4.480 (7.7); 4.466 (16.0); 4.451 (8.1); 3.681 (4.0); 3.667 (11.1); 3.653 (10.7); 3.639 (3.6); 3.329 (240.2); 3.304 (0.5); 2.676 (0.7); 2.671 (0.9); 2.667 (0.6); 2.541 (1.8); 2.524 (3.2); 2.511 (54.5); 2.507 (106.2); 2.502 (137.7); 2.498 (99.8); 2.493 (48.5); 2.338 (0.3); 2.333 (0.7); 2.329 (0.9); 2.325 (0.6); 0.000 (8.6)

Compound No. 1-86:

1H-NMR (400.0 MHz, DMSO): δ = 8.869 (2.7); 8.856 (3.9); 8.843 (2.0); 8.452 (5.2); 8.449 (5.3); 8.440 (4.7); 8.437 (4.2); 8.115 (4.8); 8.112 (4.6); 8.096 (4.8); 8.093 (4.2); 7.537 (1.5); 7.520 (3.3); 7.515 (2.9); 7.503 (2.7); 7.499 (5.8); 7.494 (2.3); 7.482 (2.9); 7.478 (3.3); 7.461 (1.5); 7.206 (4.3); 7.205 (4.4); 7.192 (4.9); 7.187 (4.7); 7.175 (6.2); 7.168 (9.8); 7.154 (4.4); 7.148 (11.8); 7.138 (2.3); 7.128 (7.7); 7.120 (1.3); 4.544 (8.5); 4.529 (16.0); 4.515 (7.6); 3.669 (5.0); 3.655 (11.7); 3.641 (10.6); 3.627 (3.5); 3.335 (68.8); 3.328 (394.1); 3.292 (0.5); 3.288 (0.4); 2.680 (0.7); 2.676 (1.0); 2.671 (1.3); 2.667 (0.9); 2.541 (5.2); 2.511 (109.3); 2.507 (171.1); 2.502 (200.6); 2.497 (137.2); 2.493 (62.8); 2.334 (1.1); 2.329 (1.3); 2.324 (0.9); 1.235 (0.4); 0.008 (1.3); 0.005 (1.4); 0.000 (12.1); −0.008 (0.4)

Compound No. 1-87:

1H-NMR (400.0 MHz, DMSO): δ = 8.402 (2.5); 8.124 (2.5); 8.119 (2.6); 8.111 (2.6); 8.107 (2.6); 7.903 (2.5); 7.899 (2.5); 7.884 (2.7); 7.880 (2.5); 7.499 (0.4); 7.482 (0.9); 7.478 (0.8); 7.466 (0.6); 7.461 (1.8); 7.457 (0.6); 7.445 (0.9); 7.440 (1.0); 7.424 (0.5); 7.145 (0.3); 7.142 (0.5); 7.134 (2.9); 7.115 (3.4); 7.113 (3.2); 7.095 (2.4); 7.086 (0.4); 7.040 (2.7); 7.028 (2.6); 7.021 (2.5); 7.009 (2.6); 4.648 (2.6); 4.622 (3.3); 4.438 (3.4); 4.412 (2.8); 3.328 (77.8); 2.525 (0.7); 2.524 (1.0); 2.520 (1.6); 2.511 (18.3); 2.507 (36.3); 2.502 (47.2); 2.497 (33.7); 2.493 (15.8); 2.081 (0.8); 2.063 (1.0); 2.047 (1.1); 2.028 (0.9); 1.737 (1.0); 1.718 (1.2); 1.702 (1.0); 1.684 (0.9); 1.368 (16.0); 0.932 (3.7); 0.914 (8.3); 0.895 (3.4); 0.000 (5.1)

Compound No. 1-88:

1H-NMR (400.0 MHz, DMSO): δ = 8.554 (1.5); 8.203 (1.8); 8.197 (2.6); 8.174 (2.4); 8.168 (1.7); 7.481 (0.5); 7.477 (0.4); 7.460 (0.9); 7.443 (0.4); 7.439 (0.5); 7.131 (1.4); 7.112 (1.9); 7.092 (1.2); 5.3); 4.514 (5.3); 3.325 (25.8); 2.541 (0.4); 2.524 (0.4); 2.507 (18.6); 2.502 (24.1); 2.498 (17.6); 1.433 (16.0); 0.000 (3.2)

Compound No. 1-89:

1H-NMR (400.0 MHz, DMSO): δ = 8.560 (1.2); 8.157 (1.1); 8.153 (1.3); 8.145 (1.2); 8.141 (1.3); 8.049 (1.2); 8.045 (1.2); 8.030 (1.3); 8.025 (1.2); 7.483 (0.5); 7.479 (0.4); 7.462 (0.9); 7.458 (0.3); 7.445 (0.4); 7.441 (0.5); 7.134 (1.4); 7.115 (1.7); 7.113 (1.6); 7.094 (1.2); 6.970 (1.3); 6.958 (1.2); 6.951 (1.2); 6.939 (1.2); 4.486 (5.3); 3.324 (14.2); 2.541 (0.3); 2.524 (0.3); 2.511 (6.2); 2.507 (12.3); 2.502 (16.2); 2.497 (11.7); 2.493 (5.6); 1.451 (16.0); 0.000 (2.8)

Compound No. 1-90:

1H-NMR (400.0 MHz, DMSO): δ = 8.590 (1.0); 8.588 (1.0); 8.586 (1.0); 8.584 (1.0); 8.441 (1.4); 8.091 (0.7); 8.085 (0.7); 8.069 (0.7); 8.062 (0.7); 8.047 (1.0); 8.044 (1.1); 8.026 (1.2); 8.024 (1.1); 7.779 (0.5); 7.776 (0.5); 7.761 (1.2); 7.758 (1.2); 7.742 (0.7); 7.739 (0.8); 7.678 (0.7); 7.674 (0.8); 7.658 (0.9); 7.654 (0.9); 7.639 (0.5); 7.635 (0.5); 7.514 (1.1); 7.510 (1.1); 7.495 (1.0); 7.491 (0.9); 7.055 (1.2); 7.033 (1.2); 4.526 (5.0); 3.326 (24.9); 2.541 (1.7); 2.524 (0.5); 2.520 (0.7); 2.511 (8.9); 2.507 (17.9); 2.502 (23.3); 2.497 (16.6); 2.493 (7.8); 1.437 (16.0); 0.000 (3.1)

Compound No. 1-91:

1H-NMR (400.0 MHz, DMSO): δ = 8.817 (1.2); 8.803 (2.3); 8.790 (1.2); 8.569 (3.4); 8.566 (4.3); 8.563 (4.3); 8.561 (3.5); 8.392 (4.8); 8.387 (4.5); 7.730 (1.6); 7.722 (1.9); 7.717 (1.5); 7.713 (1.7); 7.606 (2.0); 7.593 (6.0); 7.590 (10.3); 7.587 (8.2); 7.582 (16.0); 7.578 (3.1); 5.757 (0.6); 4.617 (3.6); 4.603 (7.2); 4.590 (3.8); 3.711 (1.9); 3.697 (5.1); 3.683 (4.9); 3.669 (1.8); 3.324 (10.6); 2.525 (0.8); 2.521 (1.3); 2.512 (16.6); 2.508 (33.5); 2.503 (44.1); 2.498 (31.6); 2.494 (15.0); 0.008 (1.1); 0.000 (32.2); −0.009 (1.0)

Compound No. 1-92:

1H-NMR (400.0 MHz, DMSO): δ = 8.820 (1.2); 8.807 (2.2); 8.793 (1.2); 8.589 (3.5); 8.587 (3.7); 8.585 (3.7); 8.583 (3.5); 8.317 (0.5); 8.088 (2.4); 8.082 (2.4); 8.066 (2.5); 8.060 (2.5); 7.733 (1.4); 7.730 (1.4); 7.725 (1.9); 7.713 (2.0); 7.605 (0.9); 7.600 (2.7); 7.590 (4.8); 7.584 (8.4); 7.577 (16.0); 7.569 (3.1); 7.000 (4.2); 6.979 (4.0); 4.512 (3.9); 4.498 (8.0); 4.484 (4.2); 3.678 (2.0); 3.664 (5.5); 3.650 (5.4); 3.636 (1.9); 3.322 (23.3); 2.676 (0.4); 2.671 (0.6); 2.666 (0.4); 2.525 (1.8); 2.511 (33.9); 2.507 (67.2); 2.502 (87.4); 2.498 (63.5); 2.493 (31.0); 2.333 (0.4); 2.329 (0.6); 2.324 (0.4); 0.008 (1.9); 0.000 (49.4); −0.009 (1.7)

Compound No. 1-93:

1H-NMR (400.0 MHz, DMSO): δ = 8.766 (1.8); 8.753 (3.6); 8.740 (1.9); 8.454 (3.9); 8.451 (4.0); 8.441 (4.1); 8.438 (3.9); 8.317 (0.5); 8.112 (3.9); 8.109 (3.9); 8.093 (4.2); 8.090 (3.9); 7.735 (2.4); 7.727 (2.8); 7.724 (3.0); 7.714 (3.2); 7.610 (1.3); 7.602 (3.8); 7.593 (8.2); 7.587 (9.5); 7.579 (16.0); 7.572 (9.7); 7.564 (3.2); 7.558 (2.5); 7.548 (1.2); 7.201 (3.4); 7.189 (3.6); 7.184 (3.5); 7.171 (3.2); 4.576 (6.3); 4.562 (13.4); 4.547 (6.6); 3.674 (3.3); 3.660 (9.3); 3.646 (9.1); 3.632 (3.0); 3.323 (91.2); 2.675 (1.1); 2.671 (1.4); 2.666 (1.0); 2.662 (0.5); 2.524 (4.7); 2.511 (85.1); 2.506 (166.1); 2.502 (214.9); 2.497 (153.7); 2.493 (72.8); 2.333 (1.0); 2.328 (1.4); 2.324 (1.0); 2.319 (0.5); 1.989 (0.4); 0.146 (0.4); 0.008 (3.3); 0.000 (82.1); −0.009 (2.5)

TABLE 2-continued

Compound No. 1-94:

1H-NMR (400.0 MHz, DMSO): δ = 8.574 (1.2); 8.570 (1.1); 8.303 (1.6); 8.075 (0.8); 8.069 (0.8); 8.053 (0.8); 8.047 (0.8); 7.710 (0.6); 7.689 (0.8); 7.576 (0.9); 7.570 (1.3); 7.561 (2.4); 7.554 (1.4); 7.546 (1.0); 7.533 (0.3); 7.515 (1.3); 7.508 (0.8); 7.502 (0.5); 7.498 (0.5); 7.492 (0.6); 7.006 (1.3); 6.984 (1.2); 4.561 (5.2); 3.324 (5.8); 2.511 (6.4); 2.507 (12.2); 2.502 (15.7); 2.498 (11.4); 2.494 (5.6); 1.450 (16.0); 1.398 (3.3); 0.000 (6.2)

Compound No. 1-95:

1H-NMR (400.0 MHz, DMSO): δ = 8.804 (1.2); 8.791 (2.3); 8.777 (1.2); 8.134 (4.5); 8.130 (4.7); 8.122 (4.7); 8.118 (4.6); 7.904 (4.5); 7.900 (4.4); 7.885 (4.8); 7.881 (4.4); 7.737 (1.4); 7.729 (1.8); 7.723 (1.9); 7.721 (2.0); 7.719 (1.8); 7.715 (1.7); 7.621 (0.6); 7.609 (0.8); 7.606 (0.8); 7.593 (16.0); 7.586 (13.2); 7.571 (1.1); 7.046 (4.9); 7.034 (4.8); 7.027 (4.6); 7.015 (4.6); 4.510 (4.4); 4.496 (9.4); 4.482 (4.6); 3.679 (2.3); 3.665 (6.5); 3.651 (6.3); 3.637 (2.1); 3.323 (40.4); 2.675 (0.5); 2.671 (0.6); 2.666 (0.4); 2.524 (2.4); 2.511 (38.4); 2.506 (74.4); 2.502 (95.6); 2.497 (67.7); 2.493 (31.6); 2.333 (0.5); 2.329 (0.6); 2.324 (0.4); 1.989 (0.7); 1.175 (0.4); 0.008 (1.6); 0.000 (39.7); −0.009 (1.2)

Compound No. 1-96:

1H-NMR (400.0 MHz, DMSO): δ = 8.538 (0.4); 8.535 (0.4); 8.371 (0.5); 8.366 (0.5); 5.751 (16.0); 4.635 (0.4); 4.621 (0.7); 4.607 (0.4); 3.724 (0.5); 3.710 (0.5); 3.335 (3.4); 2.513 (1.6); 2.509 (2.0); 2.505 (1.5); 0.000 (1.3)

Compound No. 1-97:

1H-NMR (400.0 MHz, DMSO): δ = 9.238 (0.4); 8.863 (2.6); 8.849 (5.2); 8.835 (2.6); 8.592 (7.2); 8.590 (8.9); 8.587 (8.8); 8.585 (7.2); 8.536 (0.8); 8.533 (0.7); 8.401 (10.2); 8.396 (9.5); 8.382 (0.9); 8.377 (0.8); 8.317 (0.4); 8.168 (0.6); 8.151 (7.0); 8.131 (7.3); 8.110 (0.6); 8.093 (0.6); 8.056 (3.6); 8.053 (3.6); 8.037 (8.3); 8.034 (8.0); 8.018 (5.1); 8.015 (4.7); 7.944 (0.3); 7.941 (0.3); 7.925 (0.6); 7.906 (0.4); 7.903 (0.4); 7.874 (4.9); 7.871 (5.1); 7.854 (6.9); 7.852 (7.0); 7.843 (0.8); 7.835 (3.7); 7.832 (3.7); 7.827 (0.8); 7.824 (0.7); 7.679 (7.7); 7.677 (7.8); 7.660 (7.3); 7.657 (6.7); 5.757 (10.6); 4.627 (0.6); 4.613 (1.3); 4.599 (0.8); 4.582 (7.3); 4.568 (16.0); 4.554 (7.6); 3.741 (0.7); 3.727 (0.7); 3.713 (0.4); 3.696 (3.9); 3.682 (10.9); 3.667 (10.6); 3.653 (3.5); 3.323 (68.5); 2.681 (0.4); 2.676 (0.9); 2.671 (1.2); 2.667 (0.8); 2.662 (0.4); 2.525 (4.0); 2.511 (71.2); 2.507 (138.1); 2.502 (177.3); 2.498 (125.9); 2.493 (59.1); 2.338 (0.5); 2.334 (0.9); 2.329 (1.2); 2.325 (0.9); 1.236 (1.3); 1.175 (0.6); 1.167 (0.6); 1.151 (0.4); 0.146 (0.5); 0.008 (5.4); 0.000 (130.5); −0.009 (4.2); −0.150 (0.5)

Compound No. 1-98:

1H-NMR (400.0 MHz, DMSO): δ = 8.846 (2.2); 8.832 (4.3); 8.818 (2.2); 8.316 (0.5); 8.150 (11.7); 8.145 (8.7); 8.137 (9.0); 8.133 (13.3); 8.055 (3.3); 8.052 (3.4); 8.036 (7.4); 8.033 (7.1); 8.017 (4.6); 8.014 (4.2); 7.988 (0.4); 7.914 (7.7); 7.909 (7.8); 7.904 (1.0); 7.894 (8.4); 7.890 (7.9); 7.871 (4.4); 7.868 (4.7); 7.852 (6.0); 7.849 (6.2); 7.832 (3.3); 7.829 (3.1); 7.692 (0.3); 7.677 (6.8); 7.674 (6.8); 7.658 (6.3); 7.655 (5.9); 7.548 (0.3); 7.057 (8.1); 7.045 (7.7); 7.038 (7.6); 7.026 (7.5); 4.485 (7.2); 4.470 (16.0); 4.455 (7.5); 3.664 (3.8); 3.650 (10.7); 3.635 (10.4); 3.620 (3.4); 3.324 (63.7); 2.680 (0.5); 2.676 (1.0); 2.671 (1.4); 2.666 (1.0); 2.662 (0.5); 2.620 (0.6); 2.524 (6.6); 2.519 (10.3); 2.511 (83.4); 2.507 (163.8); 2.502 (213.8); 2.497 (154.7); 2.493 (74.7); 2.338 (0.5); 2.333 (1.1); 2.329 (1.4); 2.324 (1.1); 1.754 (2.5); 1.448 (0.6); 1.236 (1.7); 1.182 (0.5); 1.166 (0.7); 1.150 (0.4); 0.008 (2.2); 0.000 (61.0); −0.009 (2.1)

Compound No. 1-99:

1H-NMR (400.0 MHz, DMSO): δ = 8.806 (2.6); 8.793 (5.0); 8.779 (2.5); 8.465 (5.3); 8.455 (5.2); 8.155 (6.4); 8.135 (7.5); 8.124 (5.3); 8.121 (5.2); 8.105 (5.3); 8.073 (0.3); 8.060 (3.3); 8.058 (3.4); 8.041 (7.4); 8.040 (7.2); 8.022 (4.4); 7.904 (0.4); 7.899 (0.5); 7.895 (0.4); 7.873 (4.4); 7.871 (4.5); 7.852 (7.0); 7.835 (3.2); 7.832 (3.1); 7.630 (7.2); 7.612 (6.7); 7.548 (0.3); 7.213 (4.3); 7.200 (4.4); 7.194 (4.5); 7.182 (4.0); 5.757 (3.6); 4.547 (7.3); 4.532 (16.0); 4.517 (7.6); 4.039 (0.6); 4.023 (0.6); 3.651 (4.0); 3.636 (11.0); 3.622 (10.7); 3.607 (3.6); 3.324 (28.5); 2.676 (0.8); 2.672 (1.0); 2.667 (0.8); 2.507 (118.7); 2.503 (153.3); 2.498 (114.7); 2.334 (0.7); 2.329 (1.0); 2.325 (0.8); 1.755 (0.6); 1.236 (3.0); 1.183 (1.1); 1.166 (1.7); 1.150 (0.9); 0.854 (0.3); 0.008 (0.3); 0.000 (7.2)

Compound No. 1-100:

1H-NMR (400.0 MHz, DMSO): δ = 9.119 (1.5); 9.105 (2.9); 9.092 (1.4); 8.953 (0.3); 8.938 (4.9); 8.934 (5.2); 8.927 (5.2); 8.923 (5.0); 8.590 (4.3); 8.587 (5.3); 8.582 (4.2); 8.400 (6.0); 8.394 (5.6); 8.316 (0.5); 8.231 (4.0); 8.227 (4.1); 8.211 (5.0); 8.207 (4.7); 8.031 (5.6); 8.019 (5.3); 8.011 (4.6); 7.999 (4.5); 5.756 (8.6); 4.609 (0.7); 4.599 (4.5); 4.584 (9.4); 4.570 (4.5); 3.830 (0.4); 3.751 (0.7); 3.730 (2.9); 3.716 (7.0); 3.702 (6.9); 3.688 (2.8); 3.654 (0.6); 3.640 (0.5); 2.680 (0.4); 2.676 (0.9); 2.671 (1.3); 2.666 (0.9); 2.662 (0.4); 2.524 (4.4); 2.520 (6.9); 2.511 (70.2); 2.507 (140.4); 2.502 (184.6); 2.497 (132.5); 2.493 (63.3); 2.338 (0.4); 2.333 (0.9); 2.329 (1.2); 2.324 (0.8); 2.320 (0.4); 1.754 (16.0); 0.000 (2.7)

Compound No. 1-101:

1H-NMR (400.0 MHz, DMSO): δ = 8.694 (2.2); 8.681 (4.2); 8.668 (2.2); 8.449 (4.9); 8.447 (5.1); 8.437 (5.3); 8.431 (8.8); 8.426 (7.3); 8.418 (7.1); 8.413 (7.0); 8.316 (0.6); 8.110 (4.9); 8.107 (4.9); 8.092 (5.1); 8.089 (4.9); 8.028 (7.0); 8.023 (7.1); 8.009 (7.8); 8.004 (7.3); 7.519 (7.6); 7.507 (7.4); 7.501 (7.2); 7.488 (6.9); 7.201 (4.1); 7.189 (4.3); 7.183 (4.2); 7.170 (3.8); 4.557 (7.7); 4.543 (16.0); 4.529 (8.1); 3.687 (4.2); 3.673 (11.6); 3.659 (11.3); 3.645 (3.8); 3.324 (243.0); 2.680 (0.6); 2.676 (1.2); 2.671 (1.7); 2.667 (1.2); 2.662 (0.6); 2.542 (51.7); 2.525 (5.7); 2.511 (100.0); 2.507 (200.6); 2.502 (262.8); 2.498 (188.1); 2.493 (89.3); 2.338 (0.6); 2.333 (1.2); 2.329 (1.6); 2.324 (1.2); 1.259 (0.4); 1.235 (0.8); 0.008 (0.5); 0.000 (14.2); −0.009 (0.4)

TABLE 2-continued

Compound No. 1-102:

1H-NMR (400.0 MHz, DMSO): δ = 8.577 (1.0); 8.576 (1.0); 8.573 (1.0); 8.402 (1.0); 8.397 (1.1);
8.389 (1.1); 8.385 (1.1); 8.357 (1.4); 8.093 (0.7); 8.087 (0.7); 8.071 (0.7); 8.065 (0.7); 7.989 (1.0);
7.985 (1.1); 7.971 (1.2); 7.966 (1.1); 7.480 (1.1); 7.468 (1.1); 7.461 (1.1); 7.449 (1.1); 7.004 (1.2);
6.982 (1.1); 4.529 (5.0); 3.324 (24.6); 2.542 (5.2); 2.524 (0.7); 2.511 (13.9); 2.507 (28.0);
2.502 (36.8); 2.497 (26.3); 2.493 (12.5); 1.438 (16.0); 0.000 (2.3)

Compound No. 1-103:

1H-NMR (400.0 MHz, DMSO): δ = 8.773 (1.9); 8.760 (3.5); 8.746 (1.8); 8.433 (6.3); 8.428 (6.7);
8.421 (6.7); 8.416 (6.6); 8.316 (0.4); 8.133 (7.4); 8.129 (7.9); 8.121 (7.8); 8.117 (7.8); 8.059 (6.9);
8.054 (7.0); 8.040 (7.8); 8.035 (7.2); 7.907 (7.4); 7.903 (7.4); 7.888 (8.1); 7.884 (7.4); 7.518 (7.2);
7.506 (7.1); 7.499 (6.8); 7.487 (6.7); 7.050 (8.2); 7.038 (8.0); 7.031 (7.8); 7.019 (7.8); 4.494 (7.5);
4.480 (16.0); 4.465 (8.0); 3.687 (4.0); 3.673 (11.2); 3.659 (10.8); 3.644 (3.6); 3.324 (129.8);
2.680 (0.4); 2.676 (0.9); 2.671 (1.3); 2.667 (0.9); 2.662 (0.4); 2.541 (46.6); 2.525 (3.8); 2.520 (6.1);
2.511 (74.8); 2.507 (149.0); 2.502 (193.7); 2.498 (136.5); 2.493 (63.3); 2.338 (0.4); 2.333 (0.9);
2.329 (1.2); 2.324 (0.9); 2.320 (0.4); 1.235 (0.5); 0.008 (0.5); 0.000 (14.0); −0.009 (0.4)

Compound No. 1-104:

1H-NMR (400.0 MHz, DMSO): δ = 8.809 (2.2); 8.796 (4.1); 8.782 (2.1); 8.592 (6.7); 8.590 (6.9);
8.588 (6.9); 8.586 (6.8); 8.432 (7.0); 8.427 (7.6); 8.420 (7.5); 8.415 (7.4); 8.316 (0.4); 8.096 (4.8);
8.090 (4.7); 8.074 (5.2); 8.067 (5.4); 8.063 (8.2); 8.058 (7.9); 8.044 (8.6); 8.040 (8.0); 7.509 (8.1);
7.497 (7.9); 7.491 (7.7); 7.478 (7.5); 7.002 (8.2); 6.980 (7.9); 4.498 (7.9); 4.484 (16.0); 4.470 (8.4);
3.683 (4.2); 3.669 (11.5); 3.655 (11.1); 3.642 (3.8); 3.325 (136.0); 2.681 (0.4); 2.676 (0.9);
2.671 (1.3); 2.667 (0.9); 2.662 (0.4); 2.542 (23.5); 2.525 (4.1); 2.520 (6.3); 2.511 (73.5);
2.507 (148.4); 2.502 (194.7); 2.498 (139.1); 2.493 (65.7); 2.338 (0.4); 2.334 (0.9); 2.329 (1.2);
2.325 (0.9); 2.320 (0.4); 1.235 (0.5); 0.008 (0.4); 0.000 (13.1); −0.009 (0.4)

Compound No. 1-105:

1H-NMR (400.0 MHz, DMSO): δ = 8.782 (2.5); 8.769 (4.9); 8.755 (2.5); 8.570 (7.3); 8.567 (9.1);
8.564 (9.1); 8.562 (7.6); 8.434 (7.2); 8.430 (7.7); 8.422 (7.7); 8.417 (7.6); 8.398 (11.0); 8.393 (10.3);
8.317 (0.4); 8.061 (7.6); 8.056 (7.7); 8.042 (8.4); 8.037 (7.9); 7.518 (8.1); 7.505 (7.9); 7.499 (7.7);
7.487 (7.4); 4.597 (7.9); 4.584 (16.0); 4.570 (8.3); 3.717 (4.2); 3.703 (11.5); 3.689 (11.1);
3.675 (3.9); 3.326 (202.6); 2.676 (0.8); 2.672 (1.1); 2.667 (0.8); 2.542 (27.8); 2.525 (3.5);
2.512 (67.5); 2.507 (133.9); 2.503 (174.5); 2.498 (124.5); 2.494 (59.0); 2.339 (0.4); 2.334 (0.8);
2.330 (1.1); 2.325 (0.8); 1.235 (0.5); 0.000 (8.4)

Compound No. 1-106:

1H-NMR (400.0 MHz, DMSO): δ = 8.971 (2.6); 8.957 (4.7); 8.943 (2.4); 8.784 (7.0); 8.780 (7.4);
8.772 (7.3); 8.768 (7.1); 8.576 (7.6); 8.574 (9.4); 8.571 (9.4); 8.568 (7.6); 8.414 (10.6); 8.408 (10.0);
8.317 (0.4); 7.984 (5.1); 7.982 (5.4); 7.965 (5.9); 7.963 (6.1); 7.674 (5.1); 7.662 (5.0); 7.654 (4.6);
7.643 (4.3); 7.296 (5.6); 7.161 (12.7); 7.025 (6.2); 6.574 (4.8); 5.757 (2.1); 4.621 (8.0); 4.607 (16.0);
4.594 (8.2); 3.728 (4.2); 3.714 (11.3); 3.700 (10.9); 3.686 (3.8); 3.324 (109.5); 2.891 (3.6);
2.731 (2.9); 2.680 (0.4); 2.676 (0.8); 2.671 (1.2); 2.667 (0.8); 2.662 (0.4); 2.542 (0.8); 2.525 (3.7);
2.511 (67.8); 2.507 (134.9); 2.502 (175.9); 2.498 (124.2); 2.493 (57.6); 2.338 (0.4); 2.334 (0.8);
2.329 (1.1); 2.325 (0.8); 2.320 (0.4); 1.754 (2.5); 1.336 (0.3); 1.235 (0.3); 0.146 (0.5); 0.008 (5.2);
0.000 (129.8); −0.009 (3.9); −0.150 (0.5)

Compound No. 1-107:

1H-NMR (400.0 MHz, DMSO): δ = 8.499 (2.8); 8.408 (8.2); 8.406 (8.8); 8.395 (8.4); 8.393 (9.0);
7.620 (2.6); 7.616 (3.0); 7.602 (4.9); 7.597 (5.9); 7.587 (0.7); 7.582 (3.1); 7.578 (3.2); 7.552 (1.5);
7.547 (1.4); 7.538 (1.7); 7.533 (3.3); 7.531 (2.5); 7.529 (2.5); 7.526 (2.2); 7.518 (2.6); 7.516 (2.5);
7.513 (3.6); 7.508 (2.0); 7.499 (2.0); 7.495 (1.7); 7.422 (7.5); 7.419 (8.5); 7.409 (7.0); 7.406 (8.3);
7.379 (9.3); 7.377 (13.0); 7.298 (4.3); 7.288 (4.6); 7.286 (4.8); 7.277 (4.2); 7.273 (4.4); 7.269 (9.8);
7.250 (8.5); 5.756 (0.6); 4.470 (7.3); 4.456 (16.0); 4.441 (7.8); 3.665 (3.7); 3.651 (10.4);
3.637 (10.2); 3.622 (3.4); 3.324 (42.2); 2.676 (0.4); 2.671 (0.6); 2.667 (0.4); 2.542 (0.4); 2.525 (1.7);
2.511 (33.7); 2.507 (67.4); 2.502 (88.5); 2.498 (63.5); 2.493 (30.5); 2.334 (0.4); 2.329 (0.6);
2.325 (0.4); 0.146 (0.3); 0.008 (3.3); 0.000 (81.7); −0.009 (3.0); −0.150 (0.4)

Compound No. 1-108:

1H-NMR (400.0 MHz, DMSO): δ = 8.651 (2.0); 8.638 (3.9); 8.624 (2.0); 8.418 (8.5); 8.416 (9.4);
8.405 (8.8); 8.403 (9.7); 7.492 (4.2); 7.491 (3.6); 7.474 (8.6); 7.472 (8.5); 7.471 (8.2); 7.454 (3.9);
7.447 (4.7); 7.439 (5.0); 7.432 (7.1); 7.426 (9.3); 7.423 (9.8); 7.420 (11.4); 7.413 (11.7); 7.410 (10.6);
7.403 (3.4); 7.390 (16.0); 7.386 (12.2); 7.375 (6.1); 7.371 (14.5); 7.369 (15.1); 7.366 (10.1);
7.356 (1.4); 7.353 (1.2); 4.462 (7.3); 4.448 (16.0); 4.433 (7.8); 3.639 (3.9); 3.625 (11.0);
3.611 (10.7); 3.597 (3.5); 3.322 (36.0); 3.061 (0.3); 2.675 (0.5); 2.671 (0.7); 2.666 (0.5); 2.541 (0.5);
2.524 (2.2); 2.511 (42.8); 2.506 (87.0); 2.502 (115.4); 2.497 (83.3); 2.493 (40.4); 2.333 (0.5);
2.328 (0.7); 2.324 (0.5); 0.146 (0.4); 0.008 (4.2); 0.000 (110.6); −0.009 (4.3); −0.150 (0.5)

Compound No. 1-109:

1H-NMR (400.0 MHz, DMSO): δ = 8.642 (2.1); 8.629 (3.9); 8.615 (2.1); 8.418 (8.8); 8.416 (8.9);
8.405 (9.1); 8.403 (9.2); 7.654 (1.1); 7.650 (4.0); 7.647 (8.2); 7.632 (3.3); 7.627 (7.3); 7.440 (2.2);
7.437 (2.5); 7.425 (10.2); 7.422 (10.5); 7.419 (9.1); 7.412 (7.9); 7.409 (9.2); 7.403 (7.0); 7.400 (6.5);
7.375 (13.9); 7.373 (10.3); 7.368 (14.5); 7.366 (15.7); 7.351 (8.5); 7.348 (9.2); 7.331 (3.1);
7.326 (2.5); 5.756 (0.4); 4.462 (7.3); 4.448 (16.0); 4.434 (7.7); 3.634 (3.8); 3.620 (10.9);
3.606 (10.6); 3.591 (3.5); 3.323 (40.1); 2.676 (0.4); 2.671 (0.6); 2.667 (0.4); 2.541 (0.4); 2.524 (1.7);
2.511 (34.3); 2.506 (69.7); 2.502 (92.0); 2.497 (65.7); 2.493 (31.3); 2.333 (0.4); 2.329 (0.6);
2.324 (0.4); 1.989 (1.2); 1.193 (0.3); 1.175 (0.7); 1.157 (0.3); 0.146 (0.4); 0.008 (3.2);
0.000 (90.1); −0.009 (3.1); −0.150 (0.4)

TABLE 2-continued

Compound No. 1-110:

1H-NMR (400.0 MHz, DMSO): δ = 8.595 (2.3); 8.582 (4.5); 8.568 (2.3); 8.416 (9.5); 8.403 (9.6);
7.875 (7.5); 7.857 (7.6); 7.855 (7.7); 7.447 (3.1); 7.445 (3.3); 7.428 (7.7); 7.426 (8.7); 7.423 (9.3);
7.420 (9.5); 7.410 (11.8); 7.407 (13.3); 7.382 (14.3); 7.304 (6.9); 7.300 (7.8); 7.285 (5.6);
7.281 (5.7); 7.179 (3.9); 7.175 (3.9); 7.160 (6.4); 7.156 (6.2); 7.141 (3.4); 7.137 (3.2); 5.756 (2.0);
4.467 (7.3); 4.453 (16.0); 4.438 (7.8); 3.627 (3.9); 3.613 (11.1); 3.599 (10.7); 3.584 (3.6);
3.322 (46.0); 2.675 (0.5); 2.671 (0.7); 2.666 (0.5); 2.541 (0.4); 2.524 (2.1); 2.510 (40.7);
2.506 (81.8); 2.502 (108.2); 2.497 (78.5); 2.493 (38.3); 2.333 (0.5); 2.328 (0.7); 2.324 (0.5);
1.989 (0.7); 1.175 (0.4); 0.146 (0.5); 0.008 (3.8); 0.000 (101.6); −0.008 (4.1); −0.150 (0.5)

Compound No. 1-111:

1H-NMR (400.0 MHz, DMSO): δ = 8.951 (2.1); 8.938 (3.9); 8.925 (2.2); 8.416 (9.6); 8.403 (9.9);
7.543 (1.3); 7.526 (2.9); 7.522 (2.8); 7.509 (2.0); 7.505 (5.7); 7.501 (2.2); 7.488 (2.9); 7.484 (3.4);
7.467 (1.6); 7.431 (7.7); 7.428 (8.1); 7.418 (7.6); 7.415 (7.9); 7.351 (13.8); 7.181 (1.5); 7.173 (9.5);
7.154 (13.0); 7.133 (8.1); 7.125 (1.6); 4.443 (7.5); 4.429 (16.0); 4.414 (8.1); 3.661 (4.0);
3.647 (11.2); 3.633 (10.9); 3.619 (3.8); 3.324 (33.6); 2.676 (0.5); 2.672 (0.6); 2.667 (0.4);
2.525 (1.8); 2.511 (39.1); 2.507 (78.0); 2.502 (101.7); 2.498 (73.3); 2.494 (35.8); 2.334 (0.5);
2.329 (0.7); 2.325 (0.5); 1.259 (0.8); 1.175 (0.3); 0.146 (0.4); 0.008 (3.4);
0.000 (84.4); −0.008 (3.3); −0.149 (0.4)

Compound No. 1-112:

1H-NMR (400.0 MHz, DMSO): δ = 8.731 (2.1); 8.718 (4.1); 8.704 (2.2); 8.423 (9.3); 8.422 (9.0);
8.410 (9.5); 8.409 (9.3); 7.779 (5.1); 7.760 (6.8); 7.731 (2.2); 7.713 (5.8); 7.695 (4.3); 7.658 (4.1);
7.639 (5.2); 7.620 (1.9); 7.501 (6.2); 7.482 (5.3); 7.430 (8.4); 7.427 (9.0); 7.417 (8.1); 7.414 (8.7);
7.351 (10.0); 7.349 (13.6); 7.346 (9.0); 4.440 (7.3); 4.426 (16.0); 4.412 (7.8); 3.640 (3.9);
3.626 (10.9); 3.611 (10.6); 3.597 (3.6); 3.325 (31.0); 2.676 (0.4); 2.671 (0.5); 2.667 (0.4);
2.525 (1.6); 2.511 (30.2); 2.507 (60.5); 2.502 (79.3); 2.498 (56.5); 2.493 (27.2); 2.334 (0.4);
2.329 (0.5); 2.325 (0.4); 1.989 (0.9); 1.234 (0.4); 1.193 (0.4); 1.175 (0.8); 1.171 (0.9); 1.153 (1.6);
1.135 (0.8); 0.146 (0.3); 0.008 (3.2); 0.000 (79.0); −0.009 (2.8); −0.150 (0.3)

Compound No. 1-113:

1H-NMR (400.0 MHz, DMSO): δ = 8.841 (2.2); 8.827 (4.2); 8.814 (2.3); 8.471 (7.0); 8.466 (7.9);
8.459 (7.6); 8.454 (7.7); 8.444 (0.4); 8.431 (0.5); 8.420 (9.8); 8.419 (8.9); 8.408 (10.2); 8.406 (9.0);
8.266 (0.4); 8.260 (0.3); 7.878 (7.3); 7.873 (7.4); 7.859 (8.3); 7.855 (7.9); 7.831 (0.9); 7.811 (0.9);
7.499 (8.1); 7.487 (7.9); 7.481 (7.7); 7.469 (7.4); 7.431 (8.4); 7.428 (8.8); 7.418 (8.0); 7.415 (8.7);
7.400 (0.6); 7.376 (11.3); 7.374 (13.9); 7.371 (8.5); 7.163 (0.7); 5.756 (3.1); 4.519 (0.6); 4.506 (0.8);
4.493 (0.7); 4.468 (7.6); 4.454 (16.0); 4.440 (8.2); 4.056 (0.4); 4.038 (1.1); 4.020 (1.1); 4.003 (0.4);
3.659 (4.1); 3.645 (11.4); 3.631 (11.1); 3.617 (3.9); 3.325 (26.4); 3.241 (0.4); 3.236 (0.7);
3.223 (1.1); 3.209 (0.6); 2.989 (1.8); 2.676 (0.5); 2.672 (0.6); 2.667 (0.5); 2.542 (0.5); 2.511 (39.2);
2.507 (76.4); 2.503 (98.5); 2.498 (70.6); 2.494 (34.6); 2.334 (0.5); 2.329 (0.6); 2.325 (0.5);
1.989 (4.7); 1.236 (0.5); 1.193 (2.2); 1.175 (3.5); 1.158 (1.6); 1.148 (0.5); 1.130 (0.5); 0.146 (0.4);
0.008 (3.6); 0.000 (87.7); −0.009 (3.6); −0.150 (0.4)

Compound No. 1-114:

1H-NMR (400.0 MHz, DMSO): δ = 8.908 (2.2); 8.894 (4.2); 8.881 (2.2); 8.798 (5.2); 8.796 (5.5);
8.786 (5.4); 8.784 (5.5); 8.427 (9.2); 8.425 (9.3); 8.414 (9.4); 8.412 (9.5); 7.995 (4.8); 7.993 (5.0);
7.976 (5.9); 7.973 (5.8); 7.806 (0.5); 7.788 (5.8); 7.777 (5.5); 7.769 (4.7); 7.757 (4.5); 7.436 (8.4);
7.433 (9.0); 7.423 (8.1); 7.420 (8.7); 7.379 (0.4); 7.353 (13.9); 7.167 (0.3); 5.756 (2.8); 4.446 (7.5);
4.432 (16.0); 4.418 (8.0); 4.038 (0.6); 4.020 (0.7); 3.664 (4.0); 3.650 (11.1); 3.636 (10.7);
3.622 (3.6); 3.324 (45.1); 2.956 (0.7); 2.676 (0.6); 2.671 (0.8); 2.667 (0.6); 2.541 (0.5); 2.525 (2.3);
2.511 (48.8); 2.507 (99.3); 2.502 (131.2); 2.498 (94.1); 2.493 (45.2); 2.334 (0.6); 2.329 (0.8);
2.324 (0.6); 1.989 (2.8); 1.235 (0.5); 1.193 (0.8); 1.175 (1.5); 1.157 (0.8); 0.146 (0.6); 0.008 (4.7);
0.000 (132.3); −0.009 (4.9); −0.150 (0.6)

Compound No. 1-115:

1H-NMR (400.0 MHz, DMSO): δ = 8.803 (2.3); 8.789 (4.4); 8.776 (2.3); 8.434 (6.8); 8.429 (7.5);
8.422 (7.5); 8.416 (12.0); 8.414 (11.0); 8.402 (9.3); 8.401 (10.5); 8.390 (0.4); 8.065 (7.2);
8.060 (7.4); 8.046 (8.0); 8.041 (7.6); 7.514 (7.6); 7.502 (7.5); 7.495 (7.3); 7.483 (7.0); 7.430 (8.6);
7.427 (9.3); 7.417 (8.3); 7.414 (9.0); 7.338 (14.3); 7.336 (10.1); 5.757 (0.4); 4.460 (7.7);
4.446 (16.0); 4.432 (8.2); 3.668 (4.2); 3.654 (11.5); 3.640 (11.1); 3.626 (3.8); 3.324 (30.4);
2.948 (0.6); 2.676 (0.4); 2.672 (0.6); 2.667 (0.4); 2.542 (0.4); 2.525 (1.7); 2.512 (34.9); 2.507 (71.1);
2.503 (94.4); 2.498 (68.2); 2.494 (32.9); 2.334 (0.4); 2.330 (0.6); 2.325 (0.5); 1.989 (1.2);
1.193 (0.4); 1.176 (0.7); 1.158 (0.3); 0.146 (0.4); 0.008 (3.6); 0.000 (99.9); −0.009 (3.8); −0.150 (0.4)

Compound No. 1-116:

1H-NMR (400.0 MHz, DMSO): δ = 8.713 (2.0); 8.700 (3.8); 8.686 (2.1); 8.176 (11.3);
8.162 (11.6); 7.779 (4.9); 7.759 (6.6); 7.729 (2.1); 7.712 (5.6); 7.693 (4.2); 7.656 (4.0); 7.637 (5.1);
7.618 (1.9); 7.497 (6.0); 7.479 (5.1); 7.134 (7.9); 7.129 (8.3); 7.120 (7.7); 7.115 (8.1); 6.944 (12.0);
6.940 (11.4); 5.756 (4.0); 4.406 (7.3); 4.392 (16.0); 4.377 (7.9); 3.622 (3.9); 3.608 (11.0);
3.593 (10.7); 3.579 (3.6); 3.324 (13.7); 2.671 (0.4); 2.525 (1.2); 2.511 (23.1); 2.507 (46.7);
2.502 (61.5); 2.498 (44.3); 2.493 (21.5); 2.329 (0.4); 1.989 (0.6); 1.175 (0.3); 0.008 (2.5);
0.000 (63.8); −0.009 (2.3)

Compound No. 1-117:

1H-NMR (400.0 MHz, DMSO): δ = 8.921 (0.4); 8.890 (2.1); 8.877 (3.9); 8.863 (2.1); 8.795 (5.4);
8.784 (5.4); 8.180 (11.1); 8.171 (1.9); 8.166 (11.4); 8.157 (1.4); 7.990 (4.8); 7.971 (5.7); 7.788 (5.1);
7.776 (5.1); 7.768 (4.5); 7.756 (4.2); 7.505 (0.5); 7.175 (0.9); 7.155 (1.3); 7.140 (6.8); 7.135 (8.4);
7.126 (6.7); 7.121 (7.5); 6.948 (11.9); 6.944 (11.7); 5.757 (2.7); 4.413 (7.5); 4.399 (16.0);
4.391 (4.0); 4.385 (8.2); 4.057 (0.4); 4.039 (1.2); 4.021 (1.2); 4.003 (0.4); 3.647 (4.1); 3.633 (11.4);

TABLE 2-continued 3.619 (11.1); 3.605 (3.8); 3.325 (17.2); 2.945 (0.5); 2.672 (0.4); 2.525 (1.4); 2.512 (27.6);
2.507 (54.5); 2.503 (71.2); 2.498 (51.7); 2.494 (25.7); 2.334 (0.3); 2.330 (0.5); 1.990 (5.1);
1.236 (0.4); 1.193 (1.4); 1.175 (2.7); 1.158 (1.3); 0.146 (0.3); 0.008 (3.1);
0.000 (73.3); −0.009 (3.3); −0.150 (0.3)
Compound No. 1-118:

1H-NMR (400.0 MHz, DMSO): δ = 8.935 (1.9); 8.921 (3.5); 8.908 (2.0); 8.171 (11.1);
8.157 (11.4); 7.542 (1.3); 7.525 (2.9); 7.521 (2.7); 7.509 (2.0); 7.504 (5.6); 7.500 (2.2); 7.487 (2.8);
7.483 (3.4); 7.466 (1.5); 7.185 (1.1); 7.182 (1.6); 7.174 (9.4); 7.155 (12.3); 7.135 (13.9); 7.131 (9.7);
7.126 (2.5); 7.121 (7.9); 7.117 (8.0); 6.946 (11.9); 6.941 (11.4); 5.757 (6.9); 4.405 (7.6);
4.391 (16.0); 4.377 (8.1); 3.644 (4.0); 3.630 (11.2); 3.616 (10.9); 3.602 (3.7); 3.325 (30.6);
2.671 (0.4); 2.524 (1.3); 2.511 (23.2); 2.507 (46.6); 2.502 (61.3); 2.498 (44.3); 2.493 (21.6);
2.329 (0.4); 1.989 (1.0); 1.235 (0.3); 1.175 (0.5); 0.008 (2.3); 0.000 (57.9); −0.009 (2.3)
Compound No. 1-119:

1H-NMR (400.0 MHz, DMSO): δ = 8.587 (2.1); 8.573 (4.1); 8.559 (2.2); 8.171 (11.2);
8.158 (11.5); 7.875 (7.2); 7.856 (7.5); 7.447 (2.8); 7.445 (3.1); 7.428 (6.8); 7.426 (7.3); 7.409 (4.4);
7.407 (4.6); 7.303 (6.4); 7.299 (7.3); 7.284 (5.3); 7.280 (5.3); 7.179 (3.6); 7.175 (3.6); 7.160 (6.0);
7.156 (5.8); 7.141 (3.2); 7.137 (3.1); 7.128 (7.3); 7.123 (7.8); 7.114 (7.0); 7.109 (7.5); 6.980 (12.1);
6.976 (11.6); 5.756 (2.6); 4.434 (7.3); 4.420 (16.0); 4.405 (7.7); 3.609 (3.9); 3.595 (11.0);
3.580 (10.7); 3.566 (3.5); 3.323 (16.0); 2.671 (0.4); 2.510 (24.4); 2.506 (48.8); 2.502 (64.2);
2.497 (46.6); 2.493 (22.8); 2.329 (0.4); 1.989 (1.2); 1.193 (0.3); 1.175 (0.6); 1.157 (0.3); 0.008 (2.4);
0.000 (60.9); −0.008 (2.3)
Compound No. 1-120:

1H-NMR (400.0 MHz, DMSO): δ = 8.501 (2.9); 8.442 (7.0); 8.429 (7.1); 7.620 (2.5); 7.616 (3.0);
7.602 (4.9); 7.597 (6.0); 7.588 (0.8); 7.582 (3.1); 7.578 (3.3); 7.551 (1.5); 7.546 (1.5); 7.538 (1.7);
7.533 (3.2); 7.530 (2.6); 7.528 (2.5); 7.526 (2.3); 7.519 (2.6); 7.517 (2.6); 7.515 (2.6); 7.512 (3.6);
7.507 (2.0); 7.499 (2.0); 7.494 (1.7); 7.341 (5.3); 7.338 (5.6); 7.327 (5.3); 7.325 (5.4); 7.298 (4.3);
7.287 (4.6); 7.285 (4.9); 7.277 (4.3); 7.273 (4.5); 7.268 (9.2); 7.250 (8.0); 7.174 (10.0); 5.758 (0.4);
4.501 (7.4); 4.487 (16.0); 4.472 (7.9); 3.680 (3.8); 3.666 (10.5); 3.652 (10.3); 3.638 (3.5);
3.326 (12.2); 2.673 (0.4); 2.513 (20.6); 2.509 (41.4); 2.504 (54.7); 2.499 (40.4); 2.495 (20.3);
2.331 (0.3); 0.008 (2.3); 0.000 (53.7); −0.008 (2.6)
Compound No. 1-121:

1H-NMR (400.0 MHz, DMSO): δ = 8.652 (1.9); 8.638 (3.6); 8.625 (1.9); 8.451 (7.1); 8.438 (7.3);
7.492 (3.9); 7.473 (8.4); 7.471 (8.1); 7.453 (4.0); 7.446 (4.6); 7.438 (4.9); 7.431 (6.7); 7.427 (2.1);
7.418 (2.4); 7.411 (5.0); 7.403 (3.0); 7.390 (12.6); 7.389 (11.5); 7.385 (14.5); 7.373 (4.9);
7.370 (5.0); 7.366 (1.6); 7.354 (1.5); 7.351 (1.6); 7.344 (5.4); 7.342 (5.6); 7.331 (5.3); 7.329 (5.3);
7.158 (9.9); 5.757 (1.2); 4.493 (7.5); 4.479 (16.0); 4.464 (7.8); 4.039 (0.3); 4.021 (0.3); 3.654 (4.0);
3.640 (11.1); 3.626 (10.7); 3.612 (3.6); 3.324 (21.5); 2.676 (0.3); 2.672 (0.5); 2.667 (0.3);
2.525 (1.4); 2.512 (27.9); 2.507 (56.3); 2.503 (74.0); 2.498 (52.7); 2.493 (25.1); 2.334 (0.3);
2.329 (0.5); 1.989 (1.4); 1.193 (0.5); 1.176 (0.8); 1.158 (0.4); 0.146 (0.3); 0.008 (3.1);
0.000 (81.5); −0.009 (2.9); −0.150 (0.3)
Compound No. 1-122:

1H-NMR (400.0 MHz, DMSO): δ = 8.643 (2.1); 8.629 (4.0); 8.616 (2.2); 8.451 (7.3); 8.438 (7.5);
7.646 (7.7); 7.626 (7.4); 7.438 (2.0); 7.435 (2.3); 7.422 (2.6); 7.416 (7.4); 7.401 (6.2); 7.398 (6.2);
7.365 (15.8); 7.346 (12.7); 7.330 (8.4); 7.165 (10.7); 5.756 (0.5); 4.492 (7.4); 4.478 (16.0);
4.463 (7.9); 3.647 (4.0); 3.633 (11.2); 3.618 (10.8); 3.604 (3.7); 3.322 (31.3); 2.675 (0.5);
2.671 (0.7); 2.666 (0.6); 2.541 (0.6); 2.510 (45.2); 2.506 (89.9); 2.502 (118.8); 2.497 (87.2);
2.493 (43.7); 2.333 (0.6); 2.328 (0.8); 2.324 (0.6); 1.989 (0.5); 0.146 (0.5); 0.008 (4.4);
0.000 (105.6); −0.009 (4.6); −0.150 (0.5)
Compound No. 1-123:

1H-NMR (400.0 MHz, DMSO): δ = 8.602 (2.2); 8.588 (4.2); 8.575 (2.2); 8.452 (7.4); 8.439 (7.6);
7.876 (7.2); 7.858 (7.5); 7.856 (7.4); 7.446 (3.1); 7.444 (3.1); 7.428 (7.3); 7.425 (7.2); 7.409 (4.7);
7.407 (4.5); 7.343 (5.8); 7.340 (6.0); 7.329 (5.6); 7.327 (5.7); 7.306 (6.7); 7.302 (7.6); 7.287 (5.5);
7.283 (5.5); 7.180 (13.5); 7.177 (13.1); 7.161 (6.2); 7.157 (5.9); 7.142 (3.3); 7.138 (3.1); 5.756 (2.2);
4.498 (7.3); 4.483 (16.0); 4.469 (7.8); 3.641 (3.9); 3.626 (11.0); 3.612 (10.7); 3.598 (3.6);
3.323 (26.8); 2.676 (0.5); 2.671 (0.6); 2.667 (0.5); 2.542 (0.4); 2.524 (1.8); 2.511 (38.2);
2.507 (76.3); 2.502 (99.9); 2.498 (72.4); 2.494 (35.8); 2.334 (0.5); 2.329 (0.6); 2.325 (0.5);
1.989 (1.2); 1.193 (0.3); 1.175 (0.7); 1.158 (0.3); 0.146 (0.4); 0.008 (3.4);
0.000 (88.4); −0.008 (3.9); −0.150 (0.4)
Compound No. 1-124:

1H-NMR (400.0 MHz, DMSO): δ = 8.944 (1.2); 8.931 (2.2); 8.917 (1.2); 8.451 (4.6); 8.437 (4.7);
7.542 (0.9); 7.525 (1.9); 7.521 (1.7); 7.509 (1.2); 7.504 (3.7); 7.500 (1.3); 7.487 (1.8); 7.483 (2.2);
7.466 (1.0); 7.351 (3.5); 7.348 (3.6); 7.337 (3.4); 7.335 (3.4); 7.184 (0.7); 7.181 (1.0); 7.173 (6.2);
7.154 (7.8); 7.143 (6.8); 7.142 (7.0); 7.133 (5.6); 7.125 (1.0); 5.757 (16.0); 4.470 (4.8); 4.456 (10.0);
4.442 (5.1); 3.676 (2.5); 3.662 (7.0); 3.648 (6.7); 3.634 (2.3); 3.325 (19.0); 2.525 (0.7); 2.521 (1.1);
2.512 (16.2); 2.508 (33.4); 2.503 (44.5); 2.498 (31.8); 2.494 (15.1); 0.008 (1.6);
0.000 (47.6); −0.009 (1.6)
Compound No. 1-125:

1H-NMR (400.0 MHz, DMSO): δ = 8.723 (1.7); 8.710 (3.1); 8.696 (1.6); 8.456 (5.9); 8.442 (6.0);
7.778 (4.1); 7.759 (5.4); 7.729 (1.7); 7.711 (4.6); 7.692 (3.4); 7.656 (3.3); 7.637 (4.1); 7.618 (1.5);
7.502 (4.9); 7.483 (4.1); 7.347 (4.7); 7.345 (4.6); 7.334 (4.4); 7.332 (4.3); 7.177 (0.5); 7.136 (8.0);
7.135 (8.3); 5.757 (16.0); 4.485 (0.8); 4.470 (6.0); 4.456 (12.0); 4.442 (5.9); 4.057 (0.7); 4.039 (2.0);
4.021 (2.1); 4.004 (0.7); 3.655 (3.1); 3.641 (8.6); 3.627 (8.3); 3.613 (3.0); 3.326 (13.8); 2.512 (19.3);

TABLE 2-continued 2.508 (36.6); 2.503 (46.5); 2.499 (32.6); 2.494 (15.2); 1.990 (8.9); 1.194 (2.4); 1.176 (4.7);
1.158 (2.3); 0.008 (2.2); 0.000 (46.1); −0.009 (1.5)
Compound No. 1-126:

1H-NMR (400.0 MHz, DMSO): δ = 8.836 (1.2); 8.822 (2.3); 8.809 (1.2); 8.472 (4.8); 8.467 (5.2);
8.460 (5.7); 8.455 (9.4); 8.442 (4.7); 7.883 (4.9); 7.878 (5.1); 7.864 (5.7); 7.859 (5.3); 7.500 (5.5);
7.488 (5.3); 7.481 (5.1); 7.469 (5.0); 7.350 (3.4); 7.348 (3.5); 7.337 (3.3); 7.334 (3.3); 7.164 (5.9);
7.163 (6.5); 7.161 (5.7); 5.758 (16.0); 4.500 (4.7); 4.486 (9.6); 4.472 (4.9); 4.040 (0.8); 4.022 (0.8);
3.676 (2.5); 3.662 (6.8); 3.647 (6.6); 3.633 (2.2); 3.327 (9.4); 2.967 (1.1); 2.526 (0.6); 2.513 (10.6);
2.509 (21.4); 2.504 (28.1); 2.499 (19.9); 2.495 (9.3); 1.990 (3.4); 1.194 (0.9); 1.176 (1.9);
1.159 (0.9); 0.008 (1.3); 0.000 (34.2); −0.009 (1.1)
Compound No. 1-127:

1H-NMR (400.0 MHz, DMSO): δ = 8.897 (2.3); 8.883 (4.3); 8.870 (2.2); 8.796 (5.8); 8.784 (5.8);
8.460 (7.9); 8.446 (8.0); 7.999 (5.2); 7.982 (6.2); 7.979 (6.2); 7.788 (5.5); 7.776 (5.5); 7.769 (4.8);
7.757 (4.5); 7.354 (6.1); 7.352 (6.3); 7.341 (5.9); 7.339 (6.0); 7.139 (11.3); 5.758 (1.0); 4.477 (7.7);
4.463 (16.0); 4.449 (8.1); 4.039 (0.5); 4.021 (0.5); 3.680 (4.1); 3.666 (11.4); 3.652 (11.0);
3.638 (3.8); 3.326 (18.5); 2.673 (0.4); 2.525 (1.3); 2.512 (25.8); 2.508 (51.0); 2.503 (66.6);
2.499 (47.8); 2.495 (23.1); 2.330 (0.4); 1.990 (2.2); 1.194 (0.6); 1.176 (1.2); 1.158 (0.6); 0.008 (2.5);
0.000 (60.7); −0.008 (2.2)
Compound No. 1-128:

1H-NMR (400.0 MHz, DMSO): δ = 8.792 (2.3); 8.778 (4.4); 8.765 (2.4); 8.448 (8.1); 8.434 (13.1);
8.429 (7.5); 8.421 (7.0); 8.416 (6.8); 8.071 (6.7); 8.066 (6.8); 8.052 (7.4); 8.047 (7.0); 7.514 (7.1);
7.502 (7.0); 7.495 (6.8); 7.483 (6.5); 7.345 (6.4); 7.334 (7.3); 7.332 (6.2); 7.125 (11.5); 5.759 (2.4);
4.491 (7.9); 4.477 (16.0); 4.463 (8.4); 4.058 (0.5); 4.040 (1.4); 4.022 (1.4); 4.005 (0.5); 3.684 (4.3);
3.670 (11.6); 3.656 (11.2); 3.642 (3.9); 3.328 (15.8); 2.674 (0.3); 2.527 (1.0); 2.513 (21.5);
2.509 (42.8); 2.505 (56.0); 2.500 (40.6); 2.332 (0.3); 1.991 (5.9); 1.194 (1.6); 1.177 (3.1);
1.159 (1.5); 0.008 (2.1); 0.000 (53.5); −0.008 (2.3)
Compound No. 1-129:

1H-NMR (400.0 MHz, DMSO): δ = 9.132 (2.4); 9.118 (4.6); 9.105 (2.5); 8.685 (6.4); 8.681 (6.9);
8.674 (6.9); 8.669 (6.8); 8.436 (8.3); 8.423 (8.5); 8.201 (6.1); 8.196 (6.4); 8.181 (6.7); 8.177 (6.6);
7.514 (7.3); 7.502 (7.3); 7.494 (7.1); 7.482 (6.9); 7.341 (6.3); 7.339 (6.6); 7.328 (6.2); 7.326 (6.4);
7.164 (11.8); 5.759 (3.8); 4.525 (7.9); 4.511 (16.0); 4.497 (8.4); 4.041 (0.5); 4.023 (0.6); 3.700 (4.2);
3.686 (11.3); 3.672 (11.1); 3.658 (4.0); 3.331 (23.2); 2.676 (0.4); 2.529 (1.1); 2.516 (21.1);
2.511 (42.8); 2.507 (56.8); 2.502 (41.6); 2.498 (20.8); 2.333 (0.4); 1.992 (2.3); 1.196 (0.7);
1.178 (1.3); 1.160 (0.6); 0.008 (2.2); 0.000 (57.4); −0.009 (2.4)
Compound No. 1-130:

1H-NMR (400.0 MHz, DMSO): δ = 8.801 (1.3); 8.787 (2.5); 8.773 (1.3); 8.446 (4.3); 8.433 (4.4);
7.736 (1.2); 7.730 (1.9); 7.724 (1.9); 7.722 (1.9); 7.718 (1.7); 7.606 (1.6); 7.593 (9.3);
7.590 (13.6); 7.583 (16.0); 7.339 (3.3); 7.336 (3.3); 7.325 (3.2); 7.323 (3.2); 7.117 (6.1); 5.758 (1.4);
4.502 (4.1); 4.489 (8.2); 4.475 (4.3); 3.682 (2.2); 3.668 (5.9); 3.654 (5.7); 3.640 (2.0); 3.327 (9.1);
2.526 (0.5); 2.513 (10.4); 2.509 (21.2); 2.504 (28.1); 2.500 (20.3); 2.495 (9.7); 0.008 (1.1);
0.000 (29.8); −0.009 (1.1)
Compound No. 1-131:

1H-NMR (400.0 MHz, DMSO): δ = 8.502 (2.8); 8.050 (10.2); 8.043 (11.5); 7.982 (3.1);
7.976 (2.5); 7.961 (3.4); 7.956 (4.9); 7.950 (2.7); 7.936 (3.0); 7.929 (2.6); 7.616 (2.6); 7.612 (3.0);
7.598 (4.9); 7.593 (5.7); 7.578 (3.0); 7.574 (2.8); 7.551 (1.4); 7.546 (1.4); 7.538 (1.7); 7.533 (3.2);
7.530 (2.6); 7.519 (2.7); 7.512 (3.3); 7.507 (1.8); 7.498 (1.9); 7.494 (1.6); 7.298 (4.2); 7.289 (4.8);
7.287 (4.3); 7.277 (4.3); 7.270 (11.9); 7.250 (7.9); 4.495 (7.6); 4.480 (16.0); 4.466 (7.9); 3.677 (3.9);
3.662 (10.8); 3.648 (10.4); 3.634 (3.5); 3.326 (13.9); 2.513 (20.4); 2.508 (38.3); 2.504 (48.2);
2.499 (33.7); 2.495 (15.6); 0.008 (2.3); 0.000 (42.3); −0.009 (1.3)
Compound No. 1-132:

1H-NMR (400.0 MHz, DMSO): δ = 8.658 (2.0); 8.644 (3.7); 8.631 (2.0); 8.063 (10.6);
8.056 (12.0); 7.984 (3.1); 7.978 (2.6); 7.964 (3.3); 7.958 (4.9); 7.952 (2.9); 7.938 (3.1); 7.931 (2.6);
7.648 (4.0); 7.645 (6.3); 7.632 (2.0); 7.625 (8.3); 7.443 (2.1); 7.440 (2.3); 7.426 (2.9); 7.422 (6.8);
7.406 (6.2); 7.403 (5.7); 7.365 (13.6); 7.361 (7.4); 7.347 (10.4); 7.343 (5.9); 7.330 (3.2); 7.326 (2.4);
7.180 (0.4); 4.488 (7.6); 4.473 (16.0); 4.459 (7.8); 3.646 (4.0); 3.632 (11.1); 3.618 (10.7);
3.604 (3.6); 3.324 (21.5); 2.676 (0.3); 2.671 (0.5); 2.667 (0.3); 2.541 (0.3); 2.524 (1.6); 2.511 (28.2);
2.507 (55.8); 2.502 (72.8); 2.498 (52.3); 2.493 (25.2); 2.333 (0.3); 2.329 (0.5); 2.324 (0.3);
1.989 (0.3); 0.008 (2.9); 0.000 (70.2); −0.009 (2.5)
Compound No. 1-133:

1H-NMR (400.0 MHz, DMSO): δ = 8.953 (2.0); 8.940 (3.5); 8.926 (1.9); 8.056 (11.1);
8.050 (12.7); 7.985 (3.4); 7.979 (2.8); 7.965 (3.6); 7.959 (5.2); 7.953 (3.1); 7.939 (3.3); 7.932 (2.8);
7.540 (1.3); 7.523 (2.9); 7.519 (2.7); 7.506 (1.9); 7.502 (5.6); 7.498 (2.1); 7.485 (2.8); 7.481 (3.4);
7.464 (1.6); 7.177 (1.7); 7.169 (9.4); 7.150 (12.4); 7.129 (7.1); 7.121 (1.4); 7.125 (1.1); 4.468 (7.8);
4.454 (16.0); 4.440 (8.2); 4.266 (0.4); 4.039 (0.7); 4.021 (0.7); 3.675 (4.1); 3.661 (11.3);
3.647 (10.9); 3.633 (3.7); 3.327 (21.7); 2.950 (2.7); 2.525 (0.9); 2.512 (18.8); 2.507 (37.8);
2.503 (49.4); 2.498 (35.3); 2.494 (16.8); 2.330 (0.3); 1.990 (2.8); 1.194 (0.8); 1.176 (1.5);
1.158 (0.7); 0.008 (1.7); 0.000 (45.8); −0.008 (1.6)
Compound No. 1-134:

1H-NMR (400.0 MHz, DMSO): δ = 8.738 (1.0); 8.724 (1.9); 8.711 (1.0); 8.063 (5.9); 8.057 (6.7);
7.983 (1.9); 7.976 (1.6); 7.962 (2.0); 7.957 (2.6); 7.951 (1.7); 7.936 (1.9); 7.930 (1.7); 7.775 (2.5);
7.756 (3.3); 7.732 (1.1); 7.715 (2.8); 7.696 (2.0); 7.655 (2.0); 7.636 (2.5); 7.618 (0.9); 7.495 (3.0);

TABLE 2-continued 7.476 (2.5); 5.755 (16.0); 4.467 (3.7); 4.453 (7.9); 4.439 (3.9); 4.039 (0.7); 4.021 (0.7); 3.655 (2.0); 3.641 (5.4); 3.627 (5.2); 3.612 (1.8); 3.333 (54.2); 2.946 (1.7); 2.526 (0.5); 2.521 (0.7); 2.512 (8.3); 2.508 (17.0); 2.503 (22.4); 2.499 (16.0); 2.494 (7.5); 1.990 (3.3); 1.194 (0.9); 1.176 (1.8); 1.158 (0.9); 0.008 (1.0); 0.000 (27.6); −0.009 (0.9)
Compound No. 1-135:

1H-NMR (400.0 MHz, DMSO): δ = 8.850 (2.0); 8.836 (3.7); 8.823 (2.0); 8.470 (6.9); 8.465 (7.5); 8.458 (7.4); 8.453 (7.3); 8.064 (11.7); 8.058 (13.4); 7.989 (3.6); 7.982 (3.0); 7.968 (3.8); 7.962 (5.4); 7.956 (3.3); 7.942 (3.6); 7.936 (3.1); 7.866 (7.1); 7.861 (7.3); 7.847 (8.1); 7.842 (7.8); 7.501 (8.1); 7.489 (7.9); 7.482 (7.3); 7.470 (7.3); 5.755 (7.4); 4.493 (7.7); 4.479 (16.0); 4.465 (8.1); 3.672 (4.1); 3.658 (11.3); 3.644 (11.0); 3.630 (3.7); 3.333 (284.4); 2.676 (0.4); 2.672 (0.6); 2.667 (0.4); 2.525 (1.6); 2.512 (33.4); 2.507 (68.4); 2.503 (90.6); 2.498 (65.1); 2.494 (31.0); 2.334 (0.4); 2.330 (0.6); 2.325 (0.4); 0.146 (0.4); 0.008 (3.0); 0.000 (88.2); −0.009 (3.1); −0.150 (0.4)
Compound No. 1-136:

1H-NMR (400.0 MHz, DMSO): δ = 5.753 (16.0); 3.322 (1.6); 2.945 (0.5); 2.511 (1.2); 2.507 (2.4); 2.503 (3.1); 2.498 (2.2); 2.494 (1.1); 1.989 (0.5); 0.000 (3.2)
Compound No. 1-137:

1H-NMR (400.0 MHz, DMSO): δ = 8.806 (1.9); 8.792 (3.6); 8.779 (1.9); 8.433 (5.5); 8.428 (6.0); 8.421 (5.9); 8.416 (5.9); 8.059 (6.5); 8.054 (16.0); 8.047 (12.3); 8.040 (6.8); 8.035 (6.3); 7.985 (3.3); 7.978 (2.7); 7.964 (3.5); 7.959 (5.0); 7.952 (2.9); 7.938 (3.2); 7.932 (2.7); 7.516 (6.2); 7.503 (6.1); 7.497 (5.9); 7.485 (5.7); 5.757 (2.0); 4.484 (6.7); 4.470 (13.5); 4.456 (7.1); 3.683 (3.7); 3.669 (9.8); 3.655 (9.4); 3.641 (3.3); 3.330 (70.2); 2.526 (1.0); 2.513 (18.9); 2.509 (37.5); 2.504 (48.9); 2.500 (34.9); 2.495 (16.6); 1.236 (0.3); 0.008 (1.9); 0.000 (45.9); −0.008 (1.5)
Compound No. 1-138:

1H-NMR (400.0 MHz, DMSO): δ = 9.160 (1.0); 9.146 (1.8); 9.133 (1.0); 8.685 (2.7); 8.680 (2.9); 8.673 (2.9); 8.669 (2.8); 8.193 (2.6); 8.189 (2.6); 8.173 (2.8); 8.169 (2.7); 8.041 (5.2); 8.035 (5.1); 7.981 (1.6); 7.975 (1.3); 7.961 (1.7); 7.955 (2.5); 7.949 (1.4); 7.935 (1.6); 7.928 (1.3); 7.516 (3.2); 7.504 (3.1); 7.496 (3.1); 7.484 (3.0); 5.757 (16.0); 4.516 (3.3); 4.502 (6.7); 4.488 (3.5); 4.040 (0.9); 4.022 (1.0); 3.697 (1.7); 3.683 (4.7); 3.669 (4.6); 3.655 (1.6); 3.361 (0.3); 3.338 (83.1); 3.317 (0.4); 2.528 (0.5); 2.515 (11.0); 2.510 (22.1); 2.506 (29.0); 2.501 (20.8); 2.497 (10.0); 1.991 (4.1); 1.195 (1.1); 1.177 (2.1); 1.159 (1.1); 0.008 (1.1); 0.000 (29.4); −0.008 (1.1)
Compound No. 1-139:

1H-NMR (400.0 MHz, DMSO): δ = 8.822 (1.4); 8.809 (2.6); 8.796 (1.4); 8.052 (7.0); 8.045 (8.0); 7.977 (2.0); 7.971 (1.7); 7.956 (2.1); 7.951 (3.2); 7.945 (1.9); 7.931 (2.0); 7.924 (1.7); 7.731 (2.0); 7.722 (2.5); 7.714 (2.2); 7.614 (0.4); 7.604 (3.0); 7.589 (11.5); 7.581 (16.0); 7.574 (4.1); 5.757 (1.8); 4.498 (4.8); 4.484 (9.7); 4.470 (5.0); 3.677 (2.6); 3.663 (6.9); 3.649 (6.7); 3.635 (2.3); 3.331 (55.9); 2.526 (0.7); 2.512 (13.9); 2.508 (27.6); 2.504 (36.1); 2.499 (26.0); 2.495 (12.7); 0.008 (1.5); 0.000 (34.7); −0.008 (1.3)
Compound No. 1-140:

1H-NMR (400.0 MHz, DMSO): δ = 9.000 (2.0); 8.987 (3.7); 8.973 (1.8); 8.417 (0.4); 8.404 (0.4); 8.334 (2.4); 8.316 (4.0); 8.109 (13.6); 8.089 (16.0); 8.064 (10.8); 8.057 (11.9); 7.985 (3.4); 7.979 (2.9); 7.965 (3.7); 7.959 (4.9); 7.953 (3.0); 7.939 (3.4); 7.932 (2.8); 7.868 (3.2); 7.848 (4.9); 7.828 (2.3); 7.421 (0.6); 7.407 (0.5); 7.391 (0.3); 7.383 (0.5); 4.453 (0.9); 4.437 (6.8); 4.424 (13.4); 4.410 (7.0); 3.802 (0.5); 3.786 (0.5); 3.664 (3.5); 3.651 (9.4); 3.637 (9.0); 3.623 (3.4); 3.598 (0.5); 3.440 (0.4); 3.406 (0.5); 3.371 (0.6); 3.321 (428.7); 3.249 (0.3); 2.715 (0.3); 2.703 (0.4); 2.679 (2.4); 2.675 (4.8); 2.671 (6.6); 2.666 (4.7); 2.662 (2.4); 2.631 (0.5); 2.607 (0.7); 2.602 (0.7); 2.541 (4.6); 2.524 (20.4); 2.510 (385.3); 2.506 (769.5); 2.502 (1008.5); 2.497 (720.5); 2.493 (346.0); 2.337 (2.1); 2.333 (4.5); 2.328 (6.3); 2.324 (4.5); 1.808 (0.7); 1.351 (0.9); 1.335 (0.8); 1.298 (2.2); 1.259 (3.6); 1.234 (5.8); 1.187 (0.7); 1.158 (0.4); 1.139 (0.4); 1.117 (0.4); 1.096 (0.5); 1.078 (0.8); 1.060 (0.4); 0.884 (1.4); 0.868 (1.8); 0.854 (1.2); 0.836 (0.8); 0.807 (0.4); 0.146 (3.7); 0.008 (33.1); 0.000 (862.3); −0.008 (32.6); −0.039 (0.6); −0.150 (3.8)
Compound No. 1-141:

1H-NMR (400.0 MHz, DMSO): δ = 8.623 (2.1); 8.610 (4.0); 8.596 (2.1); 8.062 (11.2); 8.055 (12.7); 7.981 (3.3); 7.975 (2.8); 7.961 (3.5); 7.955 (5.2); 7.949 (3.0); 7.935 (3.3); 7.928 (2.9); 7.875 (7.1); 7.857 (7.2); 7.855 (7.3); 7.451 (2.9); 7.449 (3.1); 7.433 (6.9); 7.430 (7.2); 7.414 (4.4); 7.412 (4.4); 7.302 (6.5); 7.298 (7.4); 7.283 (5.4); 7.279 (5.4); 7.180 (3.7); 7.176 (3.7); 7.161 (6.0); 7.157 (5.8); 7.142 (3.2); 7.138 (3.0); 5.756 (1.9); 4.492 (7.3); 4.477 (16.0); 4.463 (7.7); 3.639 (3.8); 3.624 (10.9); 3.610 (10.6); 3.596 (3.5); 3.323 (14.9); 2.671 (0.4); 2.524 (1.2); 2.511 (25.4); 2.506 (51.0); 2.502 (67.1); 2.497 (48.5); 2.493 (23.6); 2.328 (0.4); 1.989 (1.1); 1.175 (0.6); 1.157 (0.3); 0.008 (2.3); 0.000 (59.5); −0.008 (2.4)
Compound No. 1-142:

1H-NMR (400.0 MHz, DMSO): δ = 8.949 (2.2); 8.936 (3.9); 8.923 (2.1); 7.999 (3.8); 7.979 (6.8); 7.960 (4.4); 7.540 (1.3); 7.523 (3.1); 7.519 (2.8); 7.502 (14.9); 7.484 (11.5); 7.464 (1.6); 7.176 (1.8); 7.169 (9.4); 7.149 (13.6); 7.142 (10.4); 7.129 (8.3); 7.120 (9.1); 4.419 (7.9); 4.405 (16.0); 4.391 (8.3); 3.680 (4.2); 3.666 (11.4); 3.652 (11.0); 3.638 (3.8); 3.327 (169.3); 3.299 (0.4); 2.676 (0.6); 2.672 (0.8); 2.667 (0.6); 2.542 (3.8); 2.511 (57.4); 2.507 (108.4); 2.503 (136.8); 2.498 (97.7); 2.334 (0.7); 2.329 (0.9); 2.325 (0.7); 2.075 (0.4); 1.235 (0.4); 0.000 (9.3); −0.009 (0.4)
Compound No. 1-143:

1H-NMR (400.0 MHz, DMSO): δ = 8.819 (1.3); 8.805 (2.4); 8.792 (1.3); 7.992 (2.2); 7.972 (3.8); 7.952 (2.5); 7.724 (2.0); 7.717 (2.0); 7.712 (1.8); 7.710 (1.9); 7.602 (1.2); 7.586 (14.2); 7.579 (16.0); 7.565 (0.7); 7.490 (5.6); 7.471 (5.2); 7.129 (4.7); 7.107 (4.5); 4.453 (4.3); 4.440 (8.8); 4.426 (4.6); 3.680 (2.3); 3.666 (6.2); 3.652 (6.0); 3.639 (2.1); 3.328 (154.4); 2.676 (0.5); 2.672 (0.7); 2.667 (0.5);

TABLE 2-continued 2.542 (2.4); 2.525 (2.3); 2.511 (44.4); 2.507 (87.7); 2.502 (113.5); 2.498 (81.1); 2.494 (39.0);
2.334 (0.5); 2.329 (0.7); 2.324 (0.5); 0.008 (0.4); 0.000 (9.0)
Compound No. 1-144:

1H-NMR (400.0 MHz, DMSO): δ = 8.840 (2.2); 8.827 (4.2); 8.813 (2.2); 8.430 (7.0); 8.425 (7.6);
8.418 (7.5); 8.413 (7.4); 7.998 (3.8); 7.978 (6.8); 7.958 (4.3); 7.806 (7.0); 7.802 (7.2); 7.788 (8.3);
7.783 (7.9); 7.511 (8.2); 7.500 (15.2); 7.493 (7.8); 7.481 (12.5); 7.162 (8.4); 7.141 (8.0); 4.451 (7.9);
4.437 (16.0); 4.423 (8.4); 3.671 (4.2); 3.657 (11.4); 3.643 (11.0); 3.630 (3.8); 3.326 (142.2);
2.676 (0.7); 2.671 (0.9); 2.667 (0.7); 2.542 (31.9); 2.511 (58.1); 2.507 (114.8); 2.502 (148.9);
2.498 (107.2); 2.494 (52.0); 2.334 (0.7); 2.329 (0.9); 2.325 (0.7); 2.075 (0.4); 1.235 (0.4);
0.008 (0.6); 0.000 (15.9); −0.008 (0.6)
Compound No. 1-145:

1H-NMR (400.0 MHz, DMSO): δ = 8.731 (2.2); 8.718 (4.1); 8.704 (2.3); 8.317 (0.6); 7.999 (3.8);
7.979 (6.7); 7.959 (4.4); 7.773 (5.4); 7.754 (7.2); 7.723 (2.2); 7.704 (6.0); 7.686 (4.5); 7.652 (4.4);
7.633 (5.4); 7.614 (2.0); 7.499 (16.0); 7.480 (14.4); 7.134 (8.2); 7.113 (7.8); 4.426 (7.6);
4.412 (15.9); 4.398 (8.2); 3.658 (4.0); 3.644 (11.1); 3.630 (10.8); 3.616 (3.8); 3.327 (113.5);
2.676 (0.6); 2.671 (0.8); 2.667 (0.6); 2.542 (4.4); 2.511 (53.9); 2.507 (104.2); 2.503 (134.5);
2.498 (97.8); 2.334 (0.6); 2.329 (0.8); 2.325 (0.6); 1.236 (0.3); 0.008 (0.5); 0.000 (12.9); −0.008 (0.6)
Compound No. 1-146:

1H-NMR (400.0 MHz, DMSO): δ = 9.149 (2.5); 9.136 (4.5); 9.123 (2.4); 8.680 (6.6); 8.676 (6.5);
8.668 (6.8); 8.664 (6.2); 8.317 (0.6); 8.207 (6.2); 8.203 (5.8); 8.188 (6.8); 8.184 (5.9); 7.994 (4.1);
7.974 (7.2); 7.954 (4.6); 7.504 (7.2); 7.493 (14.8); 7.484 (7.2); 7.475 (11.4); 7.157 (8.6); 7.136 (8.1);
4.475 (8.0); 4.462 (16.0); 4.448 (8.2); 3.702 (4.2); 3.688 (11.2); 3.674 (10.7); 3.661 (3.7);
3.328 (157.2); 2.677 (0.8); 2.673 (1.0); 2.668 (0.7); 2.543 (8.2); 2.508 (135.6); 2.504 (167.2);
2.499 (116.5); 2.335 (0.8); 2.330 (1.0); 2.326 (0.8); 1.235 (0.4); 0.008 (0.7);
0.000 (14.2); −0.009 (0.5)
Compound No. 1-147:

1H-NMR (400.0 MHz, DMSO): δ = 8.907 (2.3); 8.893 (4.2); 8.879 (2.2); 8.790 (5.8); 8.781 (5.6);
8.778 (5.6); 8.316 (0.6); 8.003 (4.3); 7.996 (5.5); 7.994 (5.7); 7.984 (7.6); 7.977 (6.7); 7.974 (6.5);
7.964 (4.6); 7.780 (5.6); 7.768 (5.5); 7.761 (4.8); 7.749 (4.6); 7.504 (10.1); 7.486 (9.4); 7.139 (8.6);
7.117 (8.1); 4.431 (8.0); 4.418 (16.0); 4.404 (8.5); 3.682 (4.3); 3.668 (11.4); 3.655 (11.0);
3.641 (3.8); 3.326 (229.8); 2.676 (0.9); 2.671 (1.2); 2.667 (0.9); 2.542 (45.6); 2.525 (4.3);
2.511 (74.3); 2.507 (147.4); 2.502 (192.3); 2.498 (137.6); 2.493 (66.2); 2.334 (0.9); 2.329 (1.2);
2.325 (0.9); 2.075 (0.4); 1.235 (0.5); 0.008 (0.7); 0.000 (19.1); −0.009 (0.7)
Compound No. 1-148:

1H-NMR (400.0 MHz, DMSO): δ = 15.589 (0.8); 8.801 (2.5); 8.790 (4.5); 8.775 (2.2); 8.519 (7.0);
8.514 (7.6); 8.506 (7.1); 8.502 (7.3); 8.450 (7.1); 8.446 (6.6); 8.431 (12.2); 8.426 (13.0); 8.420 (7.6);
8.415 (7.0); 8.315 (3.1); 7.779 (6.4); 7.774 (6.9); 7.760 (7.4); 7.755 (7.2); 7.524 (7.7); 7.512 (7.2);
7.505 (7.2); 7.493 (6.6); 7.272 (7.1); 7.260 (7.2); 7.252 (7.0); 7.240 (7.2); 5.752 (0.7); 4.628 (7.5);
4.615 (16.0); 4.601 (8.1); 4.337 (0.8); 3.672 (4.1); 3.657 (11.2); 3.643 (10.9); 3.629 (4.0);
3.589 (0.8); 3.487 (0.9); 3.441 (0.9); 3.412 (1.4); 3.400 (1.3); 3.388 (1.9); 3.326 (2283.0);
3.297 (4.0); 3.286 (2.9); 3.256 (1.6); 3.212 (0.8); 2.778 (0.9); 2.675 (8.1); 2.671 (10.5); 2.666 (8.4);
2.589 (1.8); 2.541 (87.6); 2.524 (41.6); 2.510 (692.7); 2.506 (1353.2); 2.502 (1751.1);
2.497 (1269.6); 2.493 (625.3); 2.462 (4.7); 2.432 (2.0); 2.375 (1.1); 2.333 (7.9); 2.328 (10.5);
2.324 (8.0); 2.074 (4.1); 1.298 (1.2); 1.289 (0.9); 1.275 (0.9); 1.259 (1.4); 1.235 (3.7); 0.854 (0.8);
0.000 (129.6); −0.008 (5.4); −0.017 (1.0); −0.148 (0.9); −2.639 (0.7); −3.149 (0.7); −3.644 (0.7)
Compound No. 1-149:

1H-NMR (400.0 MHz, DMSO): δ = 8.691 (2.3); 8.678 (4.0); 8.664 (2.2); 8.518 (6.7); 8.514 (7.7);
8.506 (7.2); 8.502 (7.6); 8.450 (7.4); 8.445 (6.8); 8.430 (7.8); 8.425 (6.8); 8.315 (1.0); 7.771 (5.4);
7.752 (7.1); 7.731 (2.3); 7.712 (6.0); 7.694 (4.4); 7.653 (4.2); 7.634 (5.3); 7.615 (2.0); 7.493 (6.3);
7.474 (5.3); 7.271 (7.6); 7.259 (7.3); 7.251 (7.3); 7.239 (7.1); 4.603 (7.6); 4.589 (16.0); 4.575 (8.0);
3.657 (3.9); 3.642 (11.2); 3.628 (11.0); 3.614 (3.7); 3.359 (0.9); 3.324 (442.5); 3.280 (0.4);
2.675 (2.3); 2.671 (3.1); 2.666 (2.2); 2.662 (1.1); 2.541 (36.7); 2.524 (10.2); 2.510 (197.3);
2.506 (393.3); 2.502 (514.3); 2.497 (372.4); 2.493 (183.9); 2.435 (0.6); 2.426 (0.7); 2.404 (0.4);
2.367 (0.5); 2.333 (2.4); 2.328 (3.3); 2.324 (2.5); 2.289 (0.3); 2.074 (0.3); 1.299 (0.3); 1.258 (0.4);
1.236 (1.2); 0.008 (1.9); 0.000 (57.7); −0.009 (2.5)
Compound No. 1-150:

1H-NMR (400.0 MHz, DMSO): δ = 8.903 (2.4); 8.891 (4.0); 8.878 (2.2); 8.508 (6.2); 8.504 (6.6);
8.495 (6.4); 8.492 (6.4); 8.446 (6.6); 8.442 (5.6); 8.427 (6.8); 8.422 (5.7); 8.315 (0.6); 7.533 (1.2);
7.517 (2.9); 7.513 (2.7); 7.496 (5.3); 7.479 (2.9); 7.475 (3.1); 7.458 (1.5); 7.269 (6.3); 7.257 (6.3);
7.249 (6.0); 7.237 (5.8); 7.163 (9.1); 7.143 (13.3); 7.123 (7.5); 7.114 (9.8); 4.602 (8.0); 4.588 (16.0);
4.574 (8.1); 3.677 (4.3); 3.663 (11.6); 3.649 (11.2); 3.635 (3.9); 3.415 (0.4); 3.327 (605.6);
3.265 (0.5); 2.670 (2.5); 2.591 (0.4); 2.583 (0.5); 2.541 (44.0); 2.506 (318.2); 2.502 (391.3);
2.498 (280.0); 2.329 (2.3); 2.074 (1.1); 1.258 (0.4); 1.236 (0.9); 0.000 (14.9)
Compound No. 1-151:

1H-NMR (400.0 MHz, DMSO): δ = 8.787 (1.5); 8.773 (2.9); 8.759 (1.5); 8.507 (4.5); 8.502 (5.4);
8.495 (4.9); 8.490 (5.2); 8.447 (5.1); 8.443 (4.6); 8.427 (5.4); 8.423 (4.6); 8.315 (0.4); 7.729 (2.0);
7.717 (2.8); 7.708 (2.6); 7.599 (4.7); 7.589 (6.6); 7.585 (8.6); 7.576 (16.0); 7.568 (3.9); 7.550 (0.6);
7.264 (5.1); 7.252 (5.1); 7.244 (5.0); 7.232 (4.9); 4.631 (5.1); 4.618 (10.1); 4.604 (5.2); 3.678 (2.7);
3.664 (7.2); 3.650 (7.0); 3.636 (2.5); 3.406 (0.3); 3.383 (0.7); 3.330 (412.2); 3.294 (0.5); 2.676 (1.0);
2.671 (1.3); 2.667 (1.0); 2.541 (20.0); 2.524 (6.4); 2.511 (89.8); 2.507 (173.2); 2.502 (222.8);
2.498 (158.9); 2.493 (76.6); 2.334 (1.1); 2.329 (1.4); 2.325 (1.0); 2.074 (0.6); 1.236 (0.5);
0.008 (0.3); 0.000 (7.9); −0.008 (0.3)

TABLE 2-continued

Compound No. 1-152:

1H-NMR (400.0 MHz, DMSO): δ = 9.110 (2.4); 9.097 (4.6); 9.084 (2.4); 8.680 (6.3); 8.676 (6.7); 8.668 (6.7); 8.664 (6.4); 8.493 (6.8); 8.489 (8.2); 8.481 (7.1); 8.476 (7.9); 8.451 (7.8); 8.447 (6.7); 8.431 (8.2); 8.427 (6.8); 8.315 (0.9); 8.162 (6.1); 8.158 (6.2); 8.143 (6.5); 8.138 (6.3); 7.515 (7.0); 7.503 (7.1); 7.495 (6.8); 7.483 (6.6); 7.266 (7.7); 7.254 (7.5); 7.246 (7.3); 7.234 (7.1); 4.648 (7.9); 4.634 (16.0); 4.620 (8.2); 3.697 (4.1); 3.683 (11.3); 3.670 (11.0); 3.655 (3.9); 3.593 (0.3); 3.533 (0.4); 3.495 (0.4); 3.457 (0.5); 3.439 (0.6); 3.424 (0.5); 3.383 (1.3); 3.329 (739.4); 3.280 (0.9); 3.260 (0.3); 3.247 (0.4); 2.995 (0.9); 2.711 (0.4); 2.676 (2.6); 2.671 (3.5); 2.667 (2.6); 2.630 (0.5); 2.610 (0.5); 2.598 (0.6); 2.542 (40.2); 2.511 (208.0); 2.507 (408.4); 2.502 (532.2); 2.498 (387.2); 2.457 (0.7); 2.421 (0.3); 2.333 (2.2); 2.329 (3.1); 2.074 (1.8); 1.259 (0.4); 1.235 (1.3); 1.117 (0.4); 1.100 (0.7); 0.008 (1.3); 0.000 (36.6); −0.008 (1.6)

Compound No. 1-153:

1H-NMR (400.0 MHz, DMSO): δ = 8.582 (2.8); 8.580 (2.8); 8.579 (2.8); 8.576 (2.8); 8.551 (0.9); 8.538 (1.6); 8.524 (0.9); 8.086 (2.0); 8.080 (1.9); 8.064 (2.1); 8.057 (2.0); 7.309 (16.0); 7.027 (3.5); 7.006 (3.3); 4.484 (3.4); 4.470 (7.3); 4.456 (3.6); 3.627 (1.8); 3.613 (5.1); 3.599 (4.9); 3.584 (1.7); 3.324 (24.1); 2.526 (0.7); 2.521 (1.0); 2.512 (14.6); 2.508 (30.1); 2.503 (39.8); 2.499 (28.0); 2.494 (12.9); 1.990 (0.5); 0.008 (2.0); 0.000 (60.1); −0.009 (1.8)

Compound No. 1-154:

1H-NMR (400.0 MHz, DMSO): δ = 8.559 (3.2); 8.556 (3.9); 8.553 (3.9); 8.551 (3.1); 8.532 (1.0); 8.518 (1.9); 8.505 (1.0); 8.397 (4.3); 8.392 (4.0); 8.315 (0.6); 7.284 (16.0); 6.573 (0.8); 4.581 (3.3); 4.567 (7.0); 4.553 (3.5); 3.653 (1.8); 3.639 (4.9); 3.625 (4.8); 3.611 (1.6); 3.321 (97.7); 2.946 (0.4); 2.676 (0.7); 2.671 (1.0); 2.666 (0.7); 2.662 (0.4); 2.541 (0.5); 2.524 (2.6); 2.520 (4.1); 2.511 (60.2); 2.507 (122.2); 2.502 (160.0); 2.497 (112.7); 2.493 (52.1); 2.333 (0.8); 2.329 (1.0); 2.324 (0.7); 2.320 (0.3); 0.146 (0.8); 0.020 (0.4); 0.008 (6.4); 0.000 (192.0); −0.009 (6.4); −0.014 (0.5); −0.150 (0.8)

Compound No. 1-155:

1H-NMR (400.0 MHz, DMSO): δ = 8.554 (2.1); 8.552 (2.1); 8.468 (0.5); 8.454 (1.0); 8.441 (0.5); 8.403 (2.4); 8.398 (2.1); 8.312 (1.5); 8.307 (1.6); 8.300 (1.6); 8.295 (1.6); 8.163 (1.6); 8.158 (1.6); 8.144 (1.7); 8.139 (1.5); 7.142 (1.6); 7.130 (1.6); 7.124 (1.6); 7.112 (1.5); 4.613 (1.7); 4.599 (3.6); 4.585 (1.8); 3.951 (16.0); 3.761 (1.0); 3.747 (2.6); 3.733 (2.5); 3.718 (0.9); 3.325 (2.3); 2.509 (12.7); 2.505 (16.2); 2.501 (11.7); 0.000 (3.3)

Compound No. 1-156:

1H-NMR (601.6 MHz, DMSO): δ = 8.640 (1.4); 8.630 (2.7); 8.621 (1.4); 8.555 (4.4); 8.553 (4.5); 8.365 (5.0); 8.361 (5.0); 7.465 (2.9); 7.452 (5.3); 7.431 (2.1); 7.428 (2.3); 7.419 (3.0); 7.416 (3.4); 7.406 (1.7); 7.403 (1.9); 7.370 (1.6); 7.368 (1.6); 7.358 (3.8); 7.356 (4.1); 7.346 (2.7); 7.344 (3.0); 7.338 (5.0); 7.334 (5.0); 7.325 (2.2); 7.322 (1.7); 5.756 (2.1); 5.526 (1.3); 5.515 (2.1); 5.508 (2.0); 5.505 (1.7); 5.497 (1.3); 4.036 (0.5); 4.024 (0.5); 3.638 (1.0); 3.629 (1.3); 3.621 (1.2); 3.615 (1.7); 3.606 (2.1); 3.598 (1.5); 3.528 (1.5); 3.517 (2.4); 3.507 (1.9); 3.494 (1.7); 3.484 (1.1); 3.320 (31.5); 2.523 (0.5); 2.520 (0.6); 2.517 (0.7); 2.508 (16.7); 2.505 (36.1); 2.502 (50.9); 2.499 (37.9); 2.496 (18.7); 2.386 (0.3); 1.989 (1.9); 1.507 (0.4); 1.496 (0.4); 1.388 (15.9); 1.378 (16.0); 1.256 (0.4); 1.245 (0.4); 1.187 (0.5); 1.176 (1.0); 1.164 (0.5); 0.005 (0.3); 0.000 (10.2); −0.006 (0.4)

Compound No. 1-157:

1H-NMR (601.6 MHz, DMSO): δ = 8.666 (2.7); 8.653 (2.7); 8.571 (3.6); 8.569 (4.5); 8.567 (4.5); 8.566 (3.7); 8.405 (5.2); 8.401 (5.1); 7.707 (2.0); 7.704 (3.5); 7.693 (3.2); 7.639 (1.0); 7.636 (1.2); 7.627 (3.1); 7.624 (3.3); 7.615 (4.6); 7.612 (3.0); 7.604 (2.8); 7.594 (1.0); 7.545 (2.9); 7.533 (2.2); 7.332 (2.0); 7.240 (4.4); 7.148 (2.3); 6.574 (0.3); 5.756 (1.4); 4.584 (2.4); 4.575 (3.0); 4.566 (3.1); 4.558 (3.2); 4.471 (0.6); 4.458 (1.3); 4.449 (1.3); 4.447 (1.5); 4.438 (1.2); 4.434 (0.9); 4.425 (0.7); 4.383 (3.6); 4.370 (2.6); 4.365 (3.2); 4.353 (2.4); 3.323 (20.3); 2.524 (0.4); 2.521 (0.4); 2.518 (0.4); 2.509 (11.9); 2.506 (26.4); 2.503 (37.5); 2.500 (27.2); 2.497 (12.9); 1.990 (0.5); 1.268 (16.0); 1.256 (16.0); 1.176 (0.3); 0.000 (10.1); −0.006 (0.4)

Compound No. 1-158:

1H-NMR (601.6 MHz, DMSO): δ = 8.557 (1.2); 8.556 (1.2); 8.405 (1.4); 8.401 (1.4); 8.384 (1.6); 7.658 (0.5); 7.654 (0.6); 7.643 (0.9); 7.590 (0.9); 7.587 (1.4); 7.580 (1.5); 7.575 (1.4); 7.572 (0.9); 7.499 (0.7); 7.489 (0.6); 7.484 (0.5); 7.252 (0.6); 7.159 (1.3); 7.067 (0.6); 4.664 (5.0); 3.320 (14.3); 2.508 (6.3); 2.505 (14.4); 2.502 (20.8); 2.499 (16.1); 2.496 (8.3); 1.467 (16.0); 0.000 (3.8)

Compound No. 1-159:

1H-NMR (601.6 MHz, DMSO): δ = 8.809 (1.3); 8.799 (2.6); 8.790 (1.4); 8.533 (4.2); 8.531 (4.2); 8.372 (5.1); 8.368 (5.0); 7.693 (2.7); 7.681 (3.6); 7.624 (1.6); 7.613 (3.3); 7.611 (3.4); 7.601 (2.2); 7.598 (2.1); 7.589 (2.0); 7.577 (3.0); 7.564 (1.3); 7.481 (3.2); 7.468 (2.6); 7.317 (2.0); 7.224 (4.5); 7.132 (2.2); 5.755 (1.8); 5.555 (1.2); 5.548 (1.4); 5.544 (2.0); 5.537 (1.9); 5.533 (1.5); 5.526 (1.2); 4.035 (0.7); 4.024 (0.6); 3.676 (1.0); 3.667 (1.3); 3.659 (1.2); 3.653 (1.6); 3.644 (1.8); 3.636 (1.4); 3.534 (1.4); 3.523 (2.1); 3.512 (1.9); 3.500 (1.7); 3.489 (1.2); 3.323 (137.5); 2.614 (0.5); 2.611 (0.4); 2.523 (0.7); 2.520 (0.8); 2.517 (0.8); 2.508 (24.2); 2.505 (53.8); 2.502 (76.3); 2.499 (55.6); 2.496 (26.5); 2.386 (0.5); 1.989 (2.8); 1.496 (0.5); 1.485 (0.6); 1.381 (15.9); 1.371 (16.0); 1.307 (0.4); 1.266 (0.4); 1.187 (0.8); 1.175 (1.5); 1.164 (0.8); 0.005 (0.4); 0.000 (15.6); −0.006 (0.6)

Compound No. 1-160:

1H-NMR (601.6 MHz, DMSO): δ = 8.814 (2.0); 8.801 (2.0); 8.765 (1.4); 8.752 (1.4); 8.639 (2.8); 8.635 (4.2); 8.632 (2.9); 8.555 (1.9); 8.553 (2.2); 8.551 (2.3); 8.545 (2.7); 8.544 (3.2); 8.542 (3.2); 8.393 (1.8); 8.391 (2.0); 8.389 (1.8); 8.387 (1.9); 8.379 (7.5); 8.375 (7.6); 8.327 (0.7); 8.323 (5.6); 8.319 (1.8); 8.315 (0.6); 8.311 (1.7); 8.308 (6.2); 8.304 (0.8); 8.265 (1.8); 8.263 (2.4); 8.261 (1.8); 8.252 (2.0); 8.250 (2.5); 8.248 (2.0); 8.051 (0.8); 8.047 (6.1); 8.044 (1.8); 8.036 (1.7); 8.033 (5.7);

TABLE 2-continued 8.029 (0.7); 7.790 (2.9); 7.776 (4.9); 7.763 (2.7); 5.755 (10.7); 4.613 (1.8); 4.604 (2.2); 4.595 (2.3); 4.592 (1.5); 4.587 (2.6); 4.584 (1.8); 4.575 (1.5); 4.566 (1.7); 4.523 (0.6); 4.511 (1.3); 4.499 (1.8); 4.489 (1.5); 4.478 (1.2); 4.467 (0.5); 4.445 (2.8); 4.433 (1.9); 4.428 (2.5); 4.423 (2.1); 4.415 (1.9); 4.410 (1.4); 4.406 (1.7); 4.393 (1.2); 4.047 (0.4); 4.036 (0.5); 4.024 (1.5); 4.012 (0.5); 3.324 (302.6); 2.618 (0.6); 2.615 (0.9); 2.612 (0.6); 2.542 (0.4); 2.524 (1.4); 2.521 (1.7); 2.518 (1.5); 2.509 (44.1); 2.506 (99.7); 2.503 (143.2); 2.500 (102.5); 2.497 (47.9); 2.390 (0.7); 2.387 (1.0); 2.384 (0.7); 1.989 (6.7); 1.382 (0.5); 1.371 (0.5); 1.303 (11.8); 1.292 (16.0); 1.281 (8.4); 1.270 (0.7); 1.259 (0.6); 1.235 (0.4); 1.188 (2.0); 1.176 (3.8); 1.171 (0.8); 1.164 (1.9); 1.160 (0.8); 1.069 (0.4); 1.059 (0.4); 0.005 (1.0); 0.000 (37.9); −0.006 (1.3)
Compound No. 1-161:

1H-NMR (601.6 MHz, DMSO): δ = 8.572 (1.0); 8.571 (1.3); 8.569 (1.3); 8.497 (1.6); 8.401 (1.4); 8.397 (1.4); 8.046 (1.1); 8.045 (1.1); 8.033 (1.2); 8.031 (1.1); 7.782 (0.6); 7.780 (0.5); 7.770 (1.3); 7.768 (1.2); 7.757 (0.8); 7.755 (0.7); 7.673 (0.7); 7.671 (0.7); 7.660 (0.9); 7.659 (0.9); 7.647 (0.6); 7.645 (0.6); 7.506 (1.1); 7.504 (1.1); 7.493 (1.1); 7.491 (1.0); 4.626 (5.0); 3.324 (19.6); 3.323 (25.1); 2.508 (6.9); 2.505 (15.3); 2.502 (21.4); 2.499 (15.7); 2.496 (7.6); 1.989 (0.6); 1.461 (16.0); 1.176 (0.3); 0.000 (3.2)
Compound No. 1-162:

1H-NMR (601.6 MHz, DMSO): δ = 8.887 (1.3); 8.877 (2.7); 8.868 (1.4); 8.565 (3.7); 8.563 (4.5); 8.561 (4.4); 8.367 (5.0); 8.363 (5.0); 8.322 (0.9); 8.024 (3.9); 8.022 (3.9); 8.010 (4.2); 8.009 (4.1); 7.968 (1.1); 7.965 (1.1); 7.774 (1.9); 7.772 (1.9); 7.762 (4.5); 7.760 (4.3); 7.749 (2.8); 7.747 (2.7); 7.690 (2.6); 7.687 (2.8); 7.676 (3.4); 7.675 (3.5); 7.664 (1.9); 7.661 (1.9); 7.513 (3.9); 7.511 (4.0); 7.500 (3.7); 7.498 (3.5); 7.008 (0.5); 5.755 (3.4); 5.504 (1.3); 5.494 (2.2); 5.486 (2.1); 5.475 (1.3); 4.809 (1.2); 4.801 (1.3); 3.862 (0.4); 3.636 (1.0); 3.627 (1.4); 3.618 (1.2); 3.613 (1.6); 3.604 (0.2); 3.595 (1.5); 3.530 (1.4); 3.519 (2.4); 3.509 (1.8); 3.496 (1.6); 3.486 (1.0); 3.424 (0.3); 3.411 (0.4); 3.402 (0.6); 3.393 (0.4); 3.340 (0.5); 3.325 (62.3); 3.324 (62.7); 3.297 (0.3); 2.615 (0.4); 2.524 (0.6); 2.521 (0.7); 2.518 (0.7); 2.509 (19.3); 2.506 (42.9); 2.503 (60.5); 2.500 (44.5); 2.497 (21.3); 2.387 (0.4); 1.989 (0.5); 1.391 (15.9); 1.380 (16.0); 1.134 (0.8); 1.090 (0.6); 1.079 (0.6); 1.070 (4.1); 1.059 (4.0); 0.000 (10.8); −0.006 (0.4)
Compound No. 1-163:

1H-NMR (601.6 MHz, DMSO): δ = 8.564 (4.0); 8.562 (4.9); 8.560 (4.6); 8.390 (5.2); 8.387 (4.7); 8.358 (2.1); 8.345 (2.2); 7.558 (1.5); 7.555 (1.7); 7.546 (2.8); 7.543 (3.2); 7.533 (1.8); 7.530 (1.9); 7.525 (1.0); 7.520 (1.1); 7.516 (2.0); 7.507 (1.6); 7.503 (1.9); 7.499 (1.0); 7.494 (1.1); 7.491 (0.9); 7.278 (2.3); 7.272 (3.1); 7.271 (2.7); 7.264 (2.8); 7.260 (7.6); 7.247 (5.1); 5.754 (0.5); 4.545 (2.3); 4.537 (2.9); 4.528 (3.0); 4.519 (3.4); 4.470 (0.7); 4.459 (1.4); 4.447 (1.6); 4.437 (1.3); 4.426 (0.8); 4.401 (3.9); 4.389 (2.5); 4.384 (3.2); 4.372 (2.2); 3.336 (138.9); 3.335 (159.7); 2.615 (0.3); 2.525 (0.5); 2.522 (0.6); 2.518 (0.6); 2.507 (37.8); 2.504 (51.7); 2.501 (37.0); 2.498 (17.3); 2.388 (0.3); 1.261 (16.0); 1.250 (15.9); 0.000 (9.5); −0.006 (0.4)
Compound No. 1-164:

1H-NMR (400.0 MHz, DMSO): δ = 8.738 (2.5); 8.725 (4.8); 8.711 (2.5); 8.541 (10.8); 8.534 (12.7); 8.454 (6.5); 8.446 (5.5); 8.434 (6.6); 8.427 (5.4); 7.782 (5.9); 7.763 (7.9); 7.735 (2.5); 7.717 (6.7); 7.698 (5.0); 7.661 (4.8); 7.642 (6.0); 7.623 (2.2); 7.527 (7.1); 7.508 (5.9); 6.574 (0.3); 5.756 (3.2); 4.533 (7.6); 4.519 (16.0); 4.505 (8.0); 3.657 (4.0); 3.643 (11.3); 3.629 (10.9); 3.615 (3.8); 3.324 (52.7); 2.676 (0.5); 2.671 (0.6); 2.667 (0.5); 2.541 (0.4); 2.524 (1.6); 2.507 (74.8); 2.502 (93.3); 2.498 (67.0); 2.333 (0.5); 2.329 (0.6); 2.325 (0.5); 1.185 (0.6); 1.167 (0.9); 1.150 (0.5); 0.008 (2.1); 0.000 (52.2); −0.008 (2.4)
Compound No. 1-165:

1H-NMR (400.0 MHz, DMSO): δ = 8.812 (5.7); 8.558 (4.4); 8.556 (4.4); 8.392 (5.2); 8.386 (4.8); 7.610 (3.5); 7.608 (3.5); 7.591 (4.2); 7.588 (4.0); 7.407 (1.2); 7.404 (1.3); 7.389 (3.6); 7.386 (3.7); 7.370 (3.2); 7.367 (3.0); 7.344 (2.3); 7.339 (3.0); 7.325 (2.9); 7.320 (3.7); 7.306 (1.5); 7.301 (1.6); 7.294 (4.5); 7.290 (3.5); 7.276 (3.0); 7.271 (2.5); 4.673 (16.0); 3.388 (0.4); 3.369 (0.4); 3.356 (1.0); 3.354 (1.1); 3.326 (471.3); 3.310 (1.4); 3.306 (1.4); 2.995 (0.3); 2.675 (1.3); 2.671 (1.8); 2.666 (1.3); 2.558 (0.4); 2.541 (4.2); 2.524 (5.1); 2.510 (110.1); 2.506 (215.5); 2.502 (278.7); 2.497 (198.1); 2.493 (93.6); 2.332 (1.2); 2.328 (1.6); 2.324 (1.2); 2.075 (0.4); 1.258 (0.4); 1.235 (1.1); 1.013 (2.0); 0.999 (5.3); 0.994 (6.3); 0.983 (3.1); 0.945 (1.0); 0.907 (3.1); 0.896 (6.0); 0.891 (5.4); 0.877 (1.8); 0.008 (2.4); 0.000 (62.1); −0.009 (2.2)
Compound No. 1-166:

1H-NMR (400.0 MHz, DMSO): δ = 8.972 (5.8); 8.528 (3.8); 8.526 (4.7); 8.523 (4.6); 8.520 (3.7); 8.405 (3.8); 8.401 (4.1); 8.393 (5.1); 8.389 (8.9); 8.384 (5.0); 7.986 (4.1); 7.981 (4.1); 7.967 (4.6); 7.962 (4.2); 7.483 (4.3); 7.470 (4.2); 7.464 (4.0); 7.452 (3.9); 4.651 (16.0); 4.446 (0.4); 3.421 (0.4); 3.412 (0.5); 3.406 (0.5); 3.384 (1.3); 3.369 (1.3); 3.336 (1222.1); 3.311 (3.4); 3.300 (1.6); 3.294 (1.2); 3.270 (0.4); 3.263 (0.3); 2.995 (0.4); 2.865 (0.3); 2.681 (0.6); 2.676 (1.4); 2.672 (1.9); 2.667 (1.3); 2.542 (8.1); 2.525 (4.2); 2.520 (7.5); 2.512 (111.5); 2.507 (226.5); 2.503 (296.2); 2.498 (208.2); 2.493 (96.0); 2.468 (1.2); 2.338 (0.7); 2.334 (1.3); 2.329 (1.9); 2.325 (1.3); 2.320 (0.6); 2.290 (0.4); 1.461 (0.3); 1.258 (0.4); 1.235 (1.0); 1.039 (2.2); 1.026 (5.9); 1.020 (6.4); 1.009 (3.0); 0.970 (0.4); 0.936 (0.4); 0.897 (2.9); 0.885 (6.0); 0.880 (5.9); 0.867 (2.1); 0.853 (0.4); 0.000 (7.1)
Compound No. 1-167:

1H-NMR (400.0 MHz, DMSO): δ = 9.107 (5.3); 8.532 (4.5); 8.530 (4.5); 8.393 (5.0); 8.388 (4.7); 7.512 (0.7); 7.495 (1.5); 7.491 (1.4); 7.474 (2.9); 7.457 (1.5); 7.453 (1.7); 7.436 (0.8); 7.139 (0.8); 7.132 (4.8); 7.112 (6.6); 7.092 (4.1); 7.084 (0.7); 4.657 (16.0); 3.394 (0.5); 3.371 (0.7); 3.328 (506.9); 2.675 (1.2); 2.671 (1.6); 2.666 (1.2); 2.567 (0.4); 2.564 (0.4); 2.541 (2.8); 2.524 (3.8); 2.510 (97.9); 2.506 (195.1); 2.502 (254.0); 2.497 (182.4); 2.493 (87.6); 2.333 (1.2); 2.329 (1.6);

TABLE 2-continued 2.324 (1.1); 1.472 (0.4); 1.235 (0.7); 1.038 (2.2); 1.024 (6.3); 1.020 (6.7); 1.008 (2.8); 0.863 (2.7); 0.850 (6.3); 0.846 (6.5); 0.832 (2.0); 0.008 (0.9); 0.000 (28.2); −0.008 (1.0)
Compound No. 1-168:

1H-NMR (400.0 MHz, DMSO): δ = 9.105 (5.0); 8.548 (3.6); 8.545 (3.5); 8.302 (2.1); 8.065 (2.4); 8.059 (2.4); 8.043 (2.5); 8.037 (2.5); 7.507 (0.7); 7.490 (1.5); 7.486 (1.4); 7.474 (1.1); 7.469 (2.9); 7.465 (1.1); 7.452 (1.5); 7.448 (1.7); 7.431 (0.8); 7.125 (0.8); 7.117 (4.8); 7.098 (6.2); 7.077 (4.1); 7.069 (0.7); 6.998 (4.1); 6.976 (4.0); 4.532 (16.0); 3.446 (0.5); 3.414 (0.7); 3.399 (1.0); 3.348 (594.6); 3.304 (0.9); 2.680 (0.4); 2.675 (0.6); 2.671 (0.4); 2.545 (4.3); 2.528 (1.6); 2.515 (36.3); 2.511 (73.3); 2.506 (96.2); 2.502 (68.7); 2.497 (32.7); 2.337 (0.4); 2.333 (0.6); 2.328 (0.4); 1.498 (0.9); 1.236 (0.9); 1.184 (1.3); 1.001 (2.1); 0.987 (5.9); 0.983 (6.4); 0.971 (2.9); 0.932 (0.3); 0.896 (0.3); 0.856 (3.0); 0.844 (6.0); 0.840 (6.0); 0.826 (1.9); 0.791 (0.5); 0.000 (8.2)
Compound No. 1-169:

1H-NMR (400.0 MHz, DMSO): δ = 8.907 (5.8); 8.566 (3.7); 8.563 (4.6); 8.561 (4.5); 8.558 (3.7); 8.401 (5.4); 8.396 (4.9); 7.746 (2.8); 7.727 (3.8); 7.700 (1.2); 7.682 (3.2); 7.663 (2.4); 7.633 (2.4); 7.615 (2.8); 7.596 (1.0); 7.413 (3.4); 7.394 (3.0); 4.648 (16.0); 3.412 (0.3); 3.400 (0.4); 3.391 (0.6); 3.380 (0.7); 3.372 (1.1); 3.353 (4.5); 3.334 (727.4); 3.312 (2.0); 3.292 (0.6); 2.676 (0.9); 2.671 (1.2); 2.667 (0.8); 2.542 (2.4); 2.511 (75.0); 2.507 (146.0); 2.502 (188.2); 2.498 (133.0); 2.493 (62.3); 2.471 (0.6); 2.338 (0.5); 2.333 (0.9); 2.329 (1.2); 2.325 (0.9); 1.234 (0.5); 1.010 (2.2); 0.997 (5.9); 0.992 (6.5); 0.980 (3.0); 0.942 (0.4); 0.874 (3.0); 0.863 (6.2); 0.858 (6.0); 0.844 (2.0); 0.008 (0.7); 0.000 (16.6); −0.008 (0.5)
Compound No. 1-170:

1H-NMR (400.0 MHz, DMSO): δ = 8.778 (6.4); 8.557 (4.5); 8.554 (4.7); 8.552 (4.2); 8.383 (4.8); 8.378 (4.6); 7.836 (4.3); 7.818 (4.4); 7.817 (4.4); 7.417 (1.9); 7.415 (2.0); 7.398 (4.4); 7.396 (4.4); 7.380 (2.7); 7.377 (2.7); 7.224 (3.4); 7.220 (4.0); 7.205 (3.0); 7.202 (3.1); 7.158 (2.5); 7.154 (2.3); 7.139 (3.8); 7.135 (3.4); 7.120 (2.1); 7.116 (1.9); 4.668 (16.0); 3.383 (158.4); 3.377 (132.9); 3.372 (120.8); 3.364 (158.6); 2.678 (0.3); 2.674 (0.5); 2.669 (0.3); 2.544 (0.9); 2.527 (1.0); 2.514 (27.3); 2.509 (55.4); 2.505 (72.5); 2.500 (51.2); 2.496 (23.7); 2.336 (0.4); 2.331 (0.5); 2.327 (0.3); 1.234 (0.5); 1.018 (1.9); 0.998 (6.6); 0.988 (3.4); 0.971 (0.9); 0.952 (1.0); 0.934 (3.4); 0.924 (6.2); 0.904 (1.8); 0.000 (3.8)
Compound No. 1-171:

1H-NMR (400.0 MHz, DMSO): δ = 8.993 (6.1); 8.566 (4.2); 8.564 (5.0); 8.561 (4.9); 8.558 (3.8); 8.412 (3.8); 8.407 (4.0); 8.400 (4.7); 8.395 (9.0); 8.389 (5.3); 7.731 (3.7); 7.726 (3.8); 7.712 (4.5); 7.708 (4.2); 7.492 (4.1); 7.480 (4.0); 7.474 (3.6); 7.462 (3.5); 4.667 (16.0); 3.550 (0.4); 3.469 (0.4); 3.448 (0.4); 3.434 (0.4); 3.424 (0.7); 3.413 (0.7); 3.407 (0.6); 3.393 (1.5); 3.388 (1.8); 3.382 (2.3); 3.366 (5.2); 3.341 (1438.6); 3.302 (1.4); 3.296 (1.2); 3.290 (0.9); 3.277 (0.9); 3.262 (0.6); 3.251 (0.4); 3.241 (0.5); 3.237 (0.4); 3.226 (0.4); 2.677 (1.3); 2.672 (1.8); 2.667 (1.3); 2.542 (9.2); 2.525 (4.5); 2.511 (119.1); 2.507 (227.9); 2.503 (287.3); 2.498 (204.3); 2.334 (1.3); 2.330 (1.8); 2.325 (1.3); 1.489 (0.7); 1.236 (0.7); 1.036 (2.0); 1.017 (6.7); 1.006 (3.1); 0.967 (0.6); 0.923 (3.0); 0.911 (6.4); 0.907 (6.1); 0.893 (1.9); 0.000 (2.2)
Compound No. 1-172:

1H-NMR (400.0 MHz, DMSO): δ = 8.995 (5.5); 8.557 (4.4); 8.554 (4.4); 8.446 (3.8); 8.442 (4.1); 8.434 (4.1); 8.430 (4.0); 8.397 (5.0); 8.392 (4.7); 7.802 (3.9); 7.798 (4.0); 7.784 (4.5); 7.779 (4.2); 7.471 (4.4); 7.459 (4.2); 7.452 (4.0); 7.440 (3.9); 4.670 (16.0); 3.652 (0.4); 3.634 (0.4); 3.616 (0.5); 3.583 (0.5); 3.572 (0.4); 3.558 (0.5); 3.549 (0.5); 3.533 (0.5); 3.523 (0.6); 3.515 (0.6); 3.497 (0.7); 3.483 (0.5); 3.472 (1.1); 3.439 (1.0); 3.424 (1.9); 3.407 (2.4); 3.375 (8.2); 3.342 (2847.4); 3.299 (2.3); 3.288 (1.9); 3.273 (1.3); 3.252 (1.0); 3.236 (0.8); 3.198 (0.4); 2.676 (2.8); 2.672 (3.7); 2.667 (2.7); 2.663 (1.4); 2.586 (0.4); 2.581 (0.4); 2.542 (8.8); 2.525 (10.4); 2.511 (222.0); 2.507 (449.0); 2.503 (589.2); 2.498 (417.5); 2.494 (194.9); 2.454 (0.5); 2.395 (0.4); 2.334 (2.7); 2.329 (3.6); 2.325 (2.6); 2.291 (0.7); 2.074 (1.4); 1.474 (0.5); 1.298 (0.5); 1.258 (0.6); 1.235 (1.4); 1.035 (2.2); 1.021 (5.5); 1.016 (6.4); 1.004 (3.0); 0.965 (0.5); 0.947 (0.4); 0.910 (2.9); 0.898 (6.0); 0.894 (5.7); 0.880 (1.9); 0.000 (1.5)
Compound No. 1-173:

1H-NMR (400.0 MHz, DMSO): δ = 8.898 (5.6); 8.581 (3.9); 8.580 (4.0); 8.578 (3.9); 8.087 (2.5); 8.081 (2.5); 8.065 (2.6); 8.059 (2.6); 7.742 (2.8); 7.723 (3.7); 7.683 (1.1); 7.665 (3.1); 7.647 (2.5); 7.627 (2.5); 7.609 (2.8); 7.590 (1.0); 7.380 (3.4); 7.362 (3.0); 7.009 (4.3); 6.987 (4.2); 4.528 (16.0); 3.330 (82.6); 2.542 (7.0); 2.525 (0.7); 2.512 (18.6); 2.507 (38.0); 2.503 (50.2); 2.498 (37.0); 0.976 (2.0); 0.961 (5.7); 0.957 (6.7); 0.946 (3.1); 0.908 (0.5); 0.900 (0.5); 0.862 (3.0); 0.850 (6.2); 0.846 (6.0); 0.832 (1.8); 0.000 (7.2)
Compound No. 1-174:

1H-NMR (400.0 MHz, DMSO): δ = 8.766 (6.4); 8.573 (4.0); 8.073 (2.7); 8.066 (2.6); 8.051 (2.8); 8.044 (2.8); 7.835 (4.3); 7.815 (4.5); 7.403 (1.9); 7.401 (1.9); 7.384 (4.3); 7.382 (4.2); 7.365 (2.7); 7.363 (2.5); 7.194 (3.3); 7.191 (4.0); 7.175 (3.0); 7.172 (3.2); 7.154 (2.5); 7.150 (2.1); 7.135 (3.8); 7.131 (3.3); 7.116 (2.0); 7.112 (1.7); 7.028 (4.6); 7.006 (4.4); 4.554 (16.0); 3.385 (73.7); 3.379 (75.1); 3.368 (67.2); 3.363 (84.2); 2.545 (1.3); 2.528 (0.5); 2.514 (13.2); 2.510 (26.7); 2.506 (34.9); 2.501 (24.8); 2.497 (11.8); 0.984 (1.9); 0.963 (6.6); 0.954 (4.5); 0.921 (4.5); 0.911 (6.2); 0.891 (1.8); 0.000 (5.0)
Compound No. 1-175:

1H-NMR (400.0 MHz, DMSO): δ = 8.983 (5.4); 8.580 (3.5); 8.578 (3.5); 8.576 (3.5); 8.407 (3.7); 8.402 (4.0); 8.395 (4.0); 8.390 (3.9); 8.079 (2.5); 8.072 (2.4); 8.057 (2.6); 8.050 (2.5); 7.721 (3.6); 7.716 (3.8); 7.702 (4.4); 7.697 (4.2); 7.477 (4.3); 7.465 (4.1); 7.458 (3.8); 7.446 (3.7); 7.020 (4.1); 6.998 (4.0); 4.548 (16.0); 3.384 (0.8); 3.376 (0.8); 3.370 (0.8); 3.337 (566.0); 3.308 (1.4); 2.676 (0.6); 2.672 (0.9); 2.667 (0.6); 2.542 (6.4); 2.525 (2.0); 2.511 (50.6); 2.507 (102.5);

TABLE 2-continued 2.502 (134.5); 2.498 (95.2); 2.493 (44.5); 2.334 (0.6); 2.329 (0.8); 2.325 (0.6); 1.235 (0.4);
1.000 (1.9); 0.981 (6.0); 0.970 (3.2); 0.944 (0.6); 0.933 (0.7); 0.907 (3.1); 0.896 (5.7); 0.877 (1.7);
0.000 (2.9)
Compound No. 1-176:

1H-NMR (400.0 MHz, DMSO): δ = 8.805 (5.4); 8.577 (3.5); 8.576 (3.5); 8.574 (3.5); 8.572 (3.5);
8.077 (2.5); 8.070 (2.4); 8.055 (2.6); 8.048 (2.5); 7.606 (3.4); 7.603 (3.3); 7.587 (4.2); 7.584 (3.9);
7.394 (1.2); 7.391 (1.3); 7.376 (3.6); 7.373 (3.7); 7.357 (3.4); 7.354 (3.0); 7.339 (2.5); 7.334 (3.2);
7.320 (3.0); 7.315 (3.6); 7.301 (1.4); 7.296 (1.3); 7.267 (4.2); 7.262 (3.8); 7.249 (3.0); 7.244 (2.7);
7.019 (4.2); 6.997 (4.0); 4.557 (16.0); 3.332 (74.8); 2.542 (1.2); 2.525 (0.5); 2.512 (13.4);
2.508 (27.2); 2.503 (35.5); 2.498 (25.2); 2.494 (11.8); 1.235 (0.4); 0.980 (1.8); 0.960 (6.0);
0.950 (3.3); 0.931 (0.8); 0.914 (0.8); 0.894 (3.2); 0.884 (5.7); 0.864 (1.7); 0.000 (5.9)
Compound No. 1-177:

1H-NMR (400.0 MHz, DMSO): δ = 8.991 (5.5); 8.577 (3.6); 8.573 (3.5); 8.442 (3.7); 8.437 (3.9);
8.430 (3.9); 8.425 (3.8); 8.082 (2.6); 8.076 (2.5); 8.060 (2.6); 8.054 (2.5); 7.791 (3.8); 7.787 (3.9);
7.773 (4.5); 7.768 (4.2); 7.458 (4.2); 7.445 (4.0); 7.439 (3.7); 7.427 (3.7); 7.016 (4.2); 6.994 (4.0);
4.553 (16.0); 3.384 (0.4); 3.374 (0.6); 3.339 (372.1); 3.307 (0.6); 3.299 (0.4); 2.677 (0.4);
2.672 (0.5); 2.668 (0.4); 2.542 (6.4); 2.525 (1.3); 2.512 (29.7); 2.508 (59.0); 2.503 (76.5);
2.499 (54.1); 2.494 (25.3); 2.334 (0.4); 2.330 (0.5); 2.325 (0.4); 1.001 (2.0); 0.986 (5.2); 0.982 (6.2);
0.971 (3.1); 0.933 (0.9); 0.895 (3.0); 0.884 (5.9); 0.879 (5.2); 0.865 (1.7); 0.000 (6.4)
Compound No. 1-178:

1H-NMR (400.0 MHz, DMSO): δ = 9.074 (5.5); 8.770 (3.0); 8.761 (2.9); 8.759 (2.9); 8.588 (3.7);
8.586 (3.7); 8.584 (3.6); 8.092 (2.6); 8.086 (2.5); 8.070 (2.6); 8.064 (2.5); 7.898 (2.5); 7.895 (2.6);
7.878 (3.3); 7.876 (3.2); 7.747 (3.0); 7.735 (2.9); 7.728 (2.4); 7.716 (2.3); 7.009 (4.2); 6.987 (4.1);
4.522 (16.0); 3.456 (0.4); 3.440 (0.5); 3.425 (0.5); 3.412 (0.9); 3.394 (1.4); 3.347 (833.5);
3.309 (1.5); 3.292 (0.5); 3.287 (0.5); 3.275 (0.3); 2.677 (0.8); 2.672 (1.0); 2.668 (0.7); 2.543 (5.1);
2.526 (2.5); 2.512 (61.4); 2.508 (121.1); 2.503 (156.1); 2.499 (110.0); 2.494 (51.1); 2.335 (0.7);
2.330 (1.0); 2.325 (0.7); 1.234 (0.4); 0.999 (2.1); 0.985 (5.6); 0.981 (6.3); 0.969 (3.0); 0.931 (0.5);
0.918 (0.4); 0.880 (3.0); 0.869 (6.0); 0.864 (5.6); 0.850 (1.8); 0.000 (1.3)
Compound No. 1-179:

1H-NMR (400.0 MHz, DMSO): δ = 9.080 (5.7); 8.776 (3.0); 8.766 (3.1); 8.571 (4.5); 8.568 (4.6);
8.404 (5.3); 8.399 (4.8); 7.908 (2.7); 7.891 (3.4); 7.764 (3.0); 7.752 (3.0); 7.745 (2.4); 7.733 (2.4);
4.641 (16.0); 3.644 (0.4); 3.620 (0.3); 3.604 (0.4); 3.591 (0.3); 3.575 (0.4); 3.560 (0.5); 3.542 (0.6);
3.496 (0.5); 3.479 (0.5); 3.446 (1.0); 3.409 (2.6); 3.390 (3.6); 3.344 (2699.8); 3.302 (3.8);
3.293 (2.7); 3.268 (1.0); 3.262 (1.2); 3.250 (0.8); 3.237 (0.6); 3.219 (0.9); 3.215 (0.9); 3.200 (0.5);
3.174 (0.5); 3.163 (0.5); 2.676 (2.3); 2.672 (3.2); 2.667 (2.4); 2.570 (0.5); 2.542 (4.5); 2.525 (8.7);
2.512 (198.0); 2.507 (396.8); 2.503 (515.9); 2.498 (365.8); 2.494 (171.0); 2.334 (2.4); 2.329 (3.2);
2.325 (2.4); 2.292 (0.7); 2.074 (0.6); 1.298 (0.4); 1.259 (0.5); 1.235 (1.2); 1.034 (2.2); 1.021 (6.0);
1.016 (6.5); 1.004 (3.0); 0.964 (0.4); 0.934 (0.3); 0.894 (2.9); 0.882 (6.2); 0.878 (6.0); 0.864 (1.9);
0.000 (5.9)
Compound No. 1-180:

1H-NMR (400.0 MHz, DMSO): δ = 8.984 (5.7); 8.553 (3.9); 8.551 (3.9); 8.549 (3.7); 8.406 (3.5);
8.401 (3.7); 8.393 (3.7); 8.389 (3.6); 8.080 (2.6); 8.074 (2.5); 8.058 (2.7); 8.052 (2.6); 7.981 (3.7);
7.976 (3.7); 7.962 (4.1); 7.957 (3.8); 7.474 (3.8); 7.462 (3.7); 7.455 (3.6); 7.443 (3.5); 6.990 (4.4);
6.968 (4.2); 4.536 (16.0); 3.343 (215.2); 3.317 (0.7); 2.998 (0.4); 2.544 (12.6); 2.513 (18.9);
2.509 (37.2); 2.505 (48.2); 2.500 (34.4); 2.496 (16.3); 1.236 (0.4); 1.007 (2.2); 0.993 (5.9);
0.988 (6.6); 0.977 (3.0); 0.938 (0.4); 0.918 (0.4); 0.879 (3.0); 0.868 (6.2); 0.863 (6.0); 0.849 (1.9);
0.000 (2.2)
Compound No. 1-181:

1H-NMR (400.0 MHz, DMSO): δ = 8.928 (2.3); 8.915 (4.4); 8.902 (2.3); 8.718 (8.4); 8.717 (8.9);
8.713 (9.4); 8.711 (8.5); 8.315 (0.7); 8.181 (7.4); 8.175 (7.5); 8.159 (7.6); 8.153 (7.7); 8.040 (6.7);
8.037 (6.6); 8.020 (7.7); 8.017 (7.3); 7.800 (3.1); 7.797 (3.1); 7.781 (8.0); 7.778 (7.5); 7.762 (5.6);
7.759 (5.0); 7.707 (4.8); 7.703 (5.3); 7.687 (6.1); 7.683 (6.2); 7.668 (7.3); 7.664 (7.8); 7.583 (7.6);
7.580 (7.4); 7.564 (6.5); 7.561 (6.0); 7.019 (10.0); 7.018 (9.5); 6.998 (9.6); 6.996 (9.1); 4.486 (7.5);
4.472 (16.0); 4.458 (8.0); 3.651 (4.0); 3.637 (11.1); 3.623 (10.8); 3.609 (3.7); 3.404 (0.4);
3.332 (826.1); 3.281 (0.4); 2.676 (1.5); 2.671 (2.0); 2.667 (1.6); 2.542 (12.8); 2.525 (4.9);
2.511 (122.7); 2.507 (243.2); 2.502 (316.1); 2.498 (234.6); 2.494 (118.7); 2.334 (1.5); 2.329 (2.0);
2.325 (1.5); 2.291 (0.5); 2.074 (0.8); 1.259 (0.4); 1.235 (1.4); 0.008 (0.7); 0.000 (19.8)
Compound No. 1-182:

1H-NMR (400.0 MHz, DMSO): δ = 8.917 (2.4); 8.903 (4.7); 8.889 (2.4); 8.799 (6.0); 8.790 (5.9);
8.788 (5.9); 8.545 (11.7); 8.537 (13.7); 8.458 (7.9); 8.450 (6.4); 8.438 (8.0); 8.431 (6.3); 8.315 (0.9);
7.997 (5.5); 7.980 (6.4); 7.978 (6.4); 7.798 (5.7); 7.786 (5.6); 7.778 (4.8); 7.767 (4.6); 4.537 (7.7);
4.523 (16.0); 4.509 (8.1); 3.682 (4.1); 3.668 (11.2); 3.654 (10.9); 3.640 (3.8); 3.396 (0.3);
3.329 (720.4); 2.680 (0.7); 2.676 (1.6); 2.671 (2.2); 2.667 (1.6); 2.542 (7.1); 2.525 (5.1);
2.511 (125.0); 2.507 (254.4); 2.502 (334.0); 2.498 (237.7); 2.493 (112.0); 2.338 (0.7); 2.334 (1.5);
2.329 (2.1); 2.324 (1.5); 2.290 (0.5); 2.074 (0.4); 1.259 (0.4); 1.236 (1.6); 0.008 (0.8);
0.000 (24.2); −0.008 (0.8)
Compound No. 1-183:

1H-NMR (400.0 MHz, DMSO): δ = 8.933 (2.2); 8.919 (4.4); 8.905 (2.2); 8.543 (11.5);
8.535 (13.4); 8.454 (7.3); 8.447 (6.0); 8.434 (7.3); 8.427 (5.9); 8.315 (0.8); 8.047 (6.7); 8.044 (6.8);
8.026 (7.8); 8.024 (7.5); 7.808 (3.0); 7.805 (3.1); 7.789 (7.8); 7.786 (7.6); 7.770 (5.5); 7.767 (5.0);
7.712 (4.7); 7.708 (5.3); 7.692 (5.8); 7.689 (6.2); 7.673 (3.1); 7.669 (3.0); 7.602 (7.6); 7.598 (7.4);
7.583 (6.5); 7.579 (6.0); 4.543 (7.3); 4.529 (16.0); 4.515 (7.7); 3.657 (3.9); 3.643 (11.0);

TABLE 2-continued 3.629 (10.7); 3.615 (3.6); 3.402 (0.4); 3.394 (0.5); 3.383 (0.8); 3.331 (1042.8); 3.299 (1.1);
2.680 (0.7); 2.676 (1.6); 2.671 (2.2); 2.667 (1.6); 2.662 (0.7); 2.542 (9.6); 2.525 (4.8); 2.520 (7.5);
2.511 (124.6); 2.507 (255.7); 2.502 (336.6); 2.498 (238.0); 2.493 (110.9); 2.338 (0.7); 2.334 (1.6);
2.329 (2.2); 2.324 (1.5); 2.320 (0.7); 2.291 (0.5); 2.074 (0.6); 1.259 (0.4); 1.235 (1.5); 0.008 (0.7);
0.000 (23.4); −0.009 (0.7)
Compound No. 1-184:

1H-NMR (400.0 MHz, DMSO): δ = 8.844 (2.4); 8.831 (4.5); 8.817 (2.3); 8.540 (12.1);
8.532 (13.7); 8.475 (7.8); 8.470 (8.5); 8.463 (8.6); 8.458 (9.2); 8.455 (9.3); 8.447 (6.7); 8.435 (8.3);
8.427 (6.4); 8.316 (0.7); 7.881 (8.1); 7.876 (8.3); 7.863 (9.3); 7.858 (8.8); 7.508 (9.0); 7.496 (8.7);
7.489 (8.3); 7.477 (8.1); 4.557 (7.9); 4.543 (16.0); 4.529 (8.3); 3.676 (4.2); 3.662 (11.5);
3.648 (11.1); 3.635 (3.8); 3.328 (618.8); 2.995 (0.6); 2.676 (1.5); 2.671 (2.0); 2.667 (1.5);
2.662 (0.7); 2.541 (21.5); 2.524 (5.3); 2.511 (119.4); 2.507 (237.8); 2.502 (310.4); 2.497 (223.1);
2.493 (106.2); 2.333 (1.4); 2.329 (2.0); 2.324 (1.4); 2.290 (0.5); 2.075 (0.8); 1.235 (1.5); 0.008 (1.2);
0.000 (32.7); −0.008 (1.1)
Compound No. 1-185:

1H-NMR (400.0 MHz, DMSO): δ = 8.709 (8.8); 8.704 (8.8); 8.703 (8.5); 8.615 (2.2); 8.601 (4.3);
8.588 (2.2); 8.168 (7.6); 8.162 (7.4); 8.146 (7.8); 8.140 (7.6); 7.874 (6.9); 7.872 (7.4); 7.854 (7.5);
7.852 (7.5); 7.446 (3.2); 7.443 (3.3); 7.427 (7.5); 7.425 (7.5); 7.408 (4.8); 7.406 (4.7); 7.300 (7.0);
7.296 (7.8); 7.281 (5.7); 7.277 (5.6); 7.178 (4.1); 7.174 (3.9); 7.159 (6.3); 7.155 (6.0); 7.140 (3.5);
7.136 (3.2); 7.029 (9.9); 7.028 (9.9); 7.007 (9.5); 7.006 (9.6); 4.499 (7.4); 4.484 (16.0); 4.470 (7.8);
3.637 (3.9); 3.623 (10.9); 3.609 (10.6); 3.595 (3.5); 3.329 (226.1); 2.676 (0.6); 2.671 (0.7);
2.667 (0.6); 2.541 (5.4); 2.524 (2.0); 2.511 (45.1); 2.507 (89.9); 2.502 (117.1); 2.498 (83.5);
2.493 (39.5); 2.333 (0.5); 2.329 (0.7); 2.324 (0.5); 1.235 (1.0); 0.008 (0.4); 0.000 (12.4); −0.008 (0.4)
Compound No. 1-186:

1H-NMR (400.0 MHz, DMSO): δ = 8.848 (2.4); 8.834 (4.5); 8.820 (2.3); 8.542 (11.2);
8.535 (12.8); 8.454 (8.0); 8.446 (6.8); 8.439 (8.5); 8.434 (16.0); 8.427 (12.5); 8.422 (8.5);
8.316 (0.8); 7.809 (7.7); 7.804 (7.8); 7.790 (9.2); 7.785 (8.5); 7.527 (8.8); 7.515 (8.6); 7.509 (7.8);
7.497 (7.8); 4.558 (7.5); 4.544 (15.3); 4.530 (7.8); 3.671 (4.0); 3.657 (10.8); 3.643 (10.4);
3.629 (3.6); 3.386 (0.4); 3.328 (689.4); 2.995 (0.9); 2.676 (1.7); 2.671 (2.2); 2.667 (1.6);
2.541 (25.8); 2.524 (5.9); 2.511 (137.1); 2.507 (269.1); 2.502 (344.8); 2.497 (243.6); 2.493 (113.3);
2.338 (0.8); 2.333 (1.7); 2.329 (2.2); 2.324 (1.6); 2.290 (0.5); 2.075 (0.8); 1.259 (0.4); 1.236 (1.8);
0.008 (1.3); 0.000 (34.5); −0.008 (1.1)
Compound No. 1-187:

1H-NMR (400.0 MHz, DMSO): δ = 8.622 (2.4); 8.608 (4.7); 8.595 (2.3); 8.537 (12.1);
8.529 (13.9); 8.445 (8.4); 8.438 (6.8); 8.425 (8.6); 8.418 (6.7); 8.315 (0.3); 7.880 (7.5); 7.878 (7.7);
7.860 (8.2); 7.858 (7.9); 7.454 (3.4); 7.451 (3.4); 7.435 (7.8); 7.432 (7.9); 7.416 (5.5); 7.414 (5.2);
7.332 (7.6); 7.328 (8.3); 7.313 (5.9); 7.309 (5.6); 7.185 (4.5); 7.180 (4.3); 7.166 (6.5); 7.161 (6.1);
7.146 (3.9); 7.142 (3.6); 4.556 (7.4); 4.541 (16.0); 4.527 (7.7); 3.644 (3.9); 3.630 (11.0);
3.616 (10.7); 3.601 (3.6); 3.358 (0.4); 3.329 (249.2); 3.303 (0.4); 2.676 (0.5); 2.671 (0.7);
2.667 (0.5); 2.541 (5.8); 2.524 (1.9); 2.511 (43.3); 2.507 (86.2); 2.502 (111.9); 2.498 (78.6);
2.493 (36.5); 2.333 (0.5); 2.329 (0.7); 2.324 (0.5); 1.235 (1.0); 0.008 (0.7); 0.000 (19.4); −0.009 (0.6)
Compound No. 1-188:

1H-NMR (400.0 MHz, DMSO): δ = 8.958 (2.0); 8.945 (3.7); 8.932 (2.0); 8.708 (8.9); 8.706 (9.2);
8.702 (9.4); 8.700 (8.6); 8.315 (0.6); 8.177 (8.6); 8.171 (8.3); 8.155 (8.9); 8.149 (8.7); 7.541 (1.5);
7.524 (3.2); 7.520 (2.7); 7.507 (2.1); 7.503 (6.0); 7.498 (2.1); 7.486 (2.8); 7.482 (3.5); 7.465 (1.6);
7.181 (1.2); 7.178 (1.6); 7.170 (10.1); 7.151 (12.7); 7.130 (8.4); 7.122 (1.4); 6.999 (10.5);
6.997 (10.1); 6.977 (10.2); 6.975 (9.9); 4.474 (7.8); 4.460 (16.0); 4.446 (8.3); 3.670 (4.0);
3.656 (11.1); 3.642 (10.7); 3.628 (3.7); 3.330 (653.3); 3.293 (0.4); 2.995 (0.6); 2.680 (0.6);
2.676 (1.2); 2.671 (1.6); 2.667 (1.1); 2.662 (0.5); 2.542 (78.4); 2.525 (3.8); 2.520 (6.1); 2.511 (90.9);
2.507 (183.7); 2.502 (239.2); 2.498 (167.5); 2.493 (77.4); 2.338 (0.5); 2.334 (1.1); 2.329 (1.5);
2.324 (1.1); 2.320 (0.5); 2.290 (0.4); 2.075 (0.5); 1.235 (1.2); 0.008 (0.5); 0.000 (16.2); −0.009 (0.5)
Compound No. 1-189:

1H-NMR (400.0 MHz, DMSO): δ = 8.949 (2.2); 8.935 (4.1); 8.922 (2.1); 8.526 (12.0);
8.519 (14.2); 8.451 (8.4); 8.443 (6.6); 8.431 (8.4); 8.423 (6.5); 8.315 (2.0); 7.541 (1.5); 7.524 (3.3);
7.520 (2.8); 7.508 (2.2); 7.503 (6.1); 7.499 (2.1); 7.487 (2.8); 7.482 (3.5); 7.466 (1.6); 7.180 (1.7);
7.172 (10.4); 7.153 (13.2); 7.132 (8.5); 7.124 (1.4); 4.533 (7.7); 4.519 (16.0); 4.505 (8.1);
3.679 (4.1); 3.665 (11.3); 3.651 (10.9); 3.637 (3.8); 3.489 (0.4); 3.463 (0.3); 3.445 (0.5); 3.434 (0.5);
3.405 (0.8); 3.385 (1.2); 3.378 (1.4); 3.359 (3.9); 3.329 (2501.7); 3.298 (2.1); 3.285 (1.2);
3.277 (1.0); 3.258 (0.5); 2.995 (0.5); 2.680 (1.9); 2.676 (4.1); 2.671 (5.5); 2.666 (3.9); 2.662 (1.8);
2.541 (39.3); 2.524 (13.6); 2.511 (329.8); 2.507 (660.9); 2.502 (858.1); 2.497 (603.0);
2.493 (279.9); 2.368 (0.3); 2.338 (1.9); 2.333 (4.1); 2.329 (5.5); 2.324 (3.9); 2.320 (1.8); 2.290 (1.0);
2.074 (1.7); 1.298 (0.7); 1.259 (1.0); 1.236 (4.2); 0.854 (0.4); 0.008 (1.7); 0.000 (54.8); −0.008 (1.7)
Compound No. 1-190:

1H-NMR (400.0 MHz, DMSO): δ = 8.816 (2.5); 8.803 (4.6); 8.789 (2.4); 8.707 (10.1); 8.702 (8.7);
8.701 (9.4); 8.433 (6.6); 8.428 (7.0); 8.420 (6.9); 8.416 (6.7); 8.316 (0.4); 8.181 (7.7); 8.175 (7.2);
8.159 (7.9); 8.153 (7.5); 8.062 (7.0); 8.058 (6.8); 8.044 (7.7); 8.039 (7.0); 7.512 (7.1); 7.500 (7.2);
7.494 (6.8); 7.481 (6.5); 6.988 (10.9); 6.966 (10.5); 4.491 (8.0); 4.477 (16.0); 4.463 (8.3);
3.676 (4.3); 3.662 (11.5); 3.648 (11.1); 3.634 (3.9); 3.330 (651.8); 3.294 (0.5); 2.676 (1.1);
2.671 (1.5); 2.667 (1.1); 2.542 (5.6); 2.511 (95.1); 2.507 (179.8); 2.502 (229.1); 2.498 (163.7);
2.494 (78.1); 2.333 (1.1); 2.329 (1.4); 2.325 (1.1); 2.075 (0.4); 1.235 (1.1); 0.000 (14.3); −0.008 (0.5)

TABLE 2-continued

Compound No. 1-191:

1H-NMR (400.0 MHz, DMSO): δ = 8.711 (8.6); 8.705 (8.7); 8.658 (2.1); 8.644 (4.0); 8.630 (2.1);
8.172 (6.3); 8.166 (6.1); 8.150 (6.5); 8.144 (6.3); 7.643 (6.6); 7.631 (2.1); 7.624 (8.1); 7.438 (2.0);
7.435 (2.1); 7.422 (2.5); 7.417 (7.1); 7.401 (6.1); 7.399 (5.7); 7.364 (15.1); 7.347 (11.2); 7.342 (6.4);
7.329 (2.8); 7.324 (2.0); 7.017 (10.0); 6.995 (9.6); 4.494 (7.4); 4.480 (16.0); 4.465 (7.9); 3.644 (3.9);
3.630 (10.9); 3.616 (10.6); 3.601 (3.6); 3.367 (0.3); 3.329 (251.6); 3.306 (0.6); 2.675 (0.7);
2.671 (0.9); 2.667 (0.6); 2.541 (1.9); 2.524 (2.1); 2.511 (53.3); 2.506 (105.4); 2.502 (136.7);
2.498 (97.4); 2.333 (0.6); 2.329 (0.9); 2.324 (0.6); 2.075 (0.5); 1.235 (1.0); 0.008 (0.4);
0.000 (12.2); −0.009 (0.4)

Compound No. 1-192:

1H-NMR (400.0 MHz, DMSO): δ = 8.653 (2.3); 8.640 (4.4); 8.626 (2.2); 8.539 (12.2);
8.531 (14.0); 8.450 (8.5); 8.443 (6.9); 8.431 (8.7); 8.423 (6.8); 8.316 (0.4); 7.652 (6.6); 7.650 (7.4);
7.633 (7.5); 7.630 (8.1); 7.444 (2.1); 7.442 (2.3); 7.425 (5.9); 7.423 (6.1); 7.408 (8.3); 7.405 (8.2);
7.394 (6.9); 7.389 (11.8); 7.375 (4.9); 7.371 (8.3); 7.366 (4.4); 7.354 (4.5); 7.352 (6.0); 7.349 (4.0);
7.346 (4.6); 7.334 (3.5); 7.329 (3.0); 4.553 (7.5); 4.538 (16.0); 4.524 (7.9); 3.652 (3.9); 3.638 (11.1);
3.624 (10.8); 3.610 (3.7); 3.326 (190.5); 2.676 (0.6); 2.671 (0.9); 2.666 (0.7); 2.541 (4.6);
2.524 (2.3); 2.519 (3.7); 2.511 (52.2); 2.506 (106.9); 2.502 (141.0); 2.497 (99.8); 2.493 (46.4);
2.333 (0.7); 2.329 (0.9); 2.324 (0.7); 2.320 (0.3); 1.235 (1.0); 0.008 (1.0); 0.000 (28.8); −0.009 (0.9)

Compound No. 1-193:

1H-NMR (400.0 MHz, DMSO): δ = 8.700 (7.9); 8.699 (7.9); 8.694 (8.1); 8.512 (2.9); 8.316 (0.4);
8.171 (6.9); 8.165 (6.5); 8.150 (7.1); 8.144 (6.7); 7.611 (2.6); 7.607 (2.9); 7.593 (4.9); 7.588 (5.8);
7.574 (3.1); 7.569 (3.0); 7.550 (1.5); 7.545 (1.4); 7.536 (1.7); 7.532 (3.2); 7.529 (2.5); 7.527 (2.3);
7.524 (2.0); 7.518 (2.6); 7.516 (2.5); 7.514 (2.5); 7.511 (3.4); 7.506 (1.8); 7.497 (1.9); 7.493 (1.6);
7.295 (4.1); 7.285 (4.8); 7.283 (4.6); 7.274 (4.2); 7.267 (10.2); 7.247 (8.1); 7.017 (9.3); 7.016 (8.8);
6.995 (8.9); 6.994 (8.5); 4.503 (7.5); 4.488 (16.0); 4.474 (7.8); 3.673 (3.7); 3.659 (10.4);
3.645 (10.1); 3.631 (3.4); 3.329 (341.2); 2.996 (0.4); 2.676 (0.9); 2.671 (1.2); 2.667 (0.9);
2.662 (0.4); 2.542 (12.7); 2.524 (4.2); 2.511 (78.2); 2.507 (149.2); 2.502 (189.1); 2.498 (132.4);
2.493 (61.2); 2.334 (0.9); 2.329 (1.2); 2.325 (0.9); 1.236 (1.0); 0.008 (0.6); 0.000 (14.0); −0.008 (0.4)

Compound No. 1-194:

1H-NMR (400.0 MHz, DMSO): δ = 8.519 (11.1); 8.511 (14.1); 8.495 (3.0); 8.446 (7.3);
8.438 (5.7); 8.426 (7.3); 8.418 (5.7); 8.316 (0.9); 7.629 (2.7); 7.624 (3.1); 7.611 (5.4); 7.606 (6.1);
7.591 (3.4); 7.587 (3.3); 7.552 (1.5); 7.547 (1.4); 7.538 (1.7); 7.534 (3.4); 7.531 (2.5); 7.529 (2.4);
7.526 (2.1); 7.520 (2.7); 7.516 (2.6); 7.513 (3.6); 7.508 (1.9); 7.499 (2.1); 7.495 (1.7); 7.301 (4.3);
7.289 (4.9); 7.286 (5.1); 7.280 (4.2); 7.276 (4.6); 7.273 (5.4); 7.270 (8.9); 7.255 (6.8); 7.251 (6.1);
4.556 (7.5); 4.542 (16.0); 4.528 (7.8); 3.675 (3.7); 3.661 (10.6); 3.647 (10.3); 3.633 (3.5);
3.387 (0.3); 3.328 (788.4); 3.291 (0.4); 2.676 (1.9); 2.671 (2.6); 2.667 (1.8); 2.662 (0.9);
2.541 (27.0); 2.525 (6.3); 2.511 (150.6); 2.507 (301.8); 2.502 (391.8); 2.498 (275.7); 2.493 (127.8);
2.338 (0.9); 2.333 (1.8); 2.329 (2.5); 2.324 (1.8); 2.290 (0.5); 2.075 (0.5); 1.259 (0.5); 1.235 (2.2);
0.008 (1.1); 0.000 (34.2); −0.008 (1.1)

Compound No. 1-195:

1H-NMR (400.0 MHz, DMSO): δ = 9.049 (6.1); 8.562 (4.7); 8.559 (4.7); 8.392 (5.3); 8.387 (5.0);
8.034 (3.7); 8.033 (3.8); 8.014 (4.2); 8.012 (4.1); 7.778 (1.6); 7.775 (1.6); 7.759 (4.1); 7.757 (3.9);
7.740 (2.8); 7.738 (2.6); 7.686 (2.4); 7.683 (2.6); 7.666 (3.3); 7.663 (3.4); 7.647 (1.6); 7.644 (1.5);
7.498 (3.9); 7.495 (3.9); 7.479 (3.5); 7.476 (3.3); 5.757 (0.5); 4.646 (16.0); 3.324 (40.8); 2.672 (0.4);
2.507 (50.0); 2.503 (64.4); 2.498 (46.4); 2.329 (0.4); 1.022 (2.0); 1.007 (5.9); 1.003 (6.7);
0.992 (3.1); 0.953 (0.5); 0.946 (0.5); 0.908 (3.1); 0.896 (6.4); 0.892 (6.0); 0.878 (1.9); 0.146 (0.4);
0.008 (3.2); 0.000 (73.2); −0.009 (2.6); −0.150 (0.3)

Compound No. 1-196:

1H-NMR (400.0 MHz, DMSO): δ = 9.048 (5.6); 8.579 (3.8); 8.083 (2.5); 8.076 (2.5); 8.061 (2.6);
8.054 (2.6); 8.027 (3.4); 8.025 (3.6); 8.007 (3.9); 8.005 (3.9); 7.761 (1.4); 7.758 (1.5); 7.742 (3.7);
7.740 (3.8); 7.723 (2.6); 7.721 (2.5); 7.680 (2.3); 7.677 (2.6); 7.661 (3.1); 7.657 (3.3); 7.641 (1.4);
7.638 (1.4); 7.479 (3.7); 7.475 (3.7); 7.460 (3.3); 7.456 (3.2); 7.020 (4.2); 6.998 (4.0); 5.757 (2.1);
4.529 (16.0); 3.323 (46.0); 2.675 (0.4); 2.671 (0.5); 2.667 (0.4); 2.524 (1.4); 2.511 (32.5);
2.506 (64.3); 2.502 (83.7); 2.498 (60.2); 2.493 (29.2); 2.333 (0.4); 2.329 (0.5); 2.324 (0.4);
0.987 (1.9); 0.967 (6.4); 0.957 (3.1); 0.928 (0.7); 0.920 (0.7); 0.891 (3.1); 0.880 (6.0); 0.861 (1.7);
0.146 (0.5); 0.008 (3.8); 0.000 (96.3); −0.008 (3.6); −0.150 (0.5)

Compound No. 1-197:

1H-NMR (400.0 MHz, DMSO): δ = 8.616 (1.4); 8.602 (2.9); 8.588 (2.1); 8.569 (4.1); 8.567 (4.9);
8.564 (4.9); 8.489 (0.4); 8.472 (0.4); 8.410 (0.9); 8.405 (0.8); 8.375 (5.6); 8.369 (5.4); 7.879 (0.8);
7.867 (4.4); 7.862 (1.0); 7.849 (4.6); 7.436 (2.1); 7.433 (1.8); 7.417 (4.3); 7.415 (4.3); 7.398 (2.7);
7.396 (2.6); 7.298 (0.6); 7.294 (0.7); 7.279 (0.5); 7.275 (0.5); 7.245 (3.9); 7.241 (4.5); 7.226 (3.5);
7.222 (3.5); 7.186 (0.5); 7.182 (0.5); 7.176 (2.5); 7.172 (2.3); 7.167 (0.8); 7.163 (0.8); 7.157 (3.8);
7.153 (3.5); 7.144 (0.5); 7.138 (2.0); 7.133 (1.8); 5.534 (1.3); 5.518 (2.2); 5.506 (2.1); 5.490 (1.3);
4.522 (0.4); 4.509 (0.5); 4.399 (0.6); 4.383 (0.6); 3.640 (0.9); 3.626 (1.3); 3.613 (1.1); 3.606 (1.8);
3.592 (2.4); 3.579 (1.5); 3.531 (1.6); 3.516 (2.6); 3.500 (1.9); 3.481 (1.6); 3.466 (1.0); 3.355 (561.6);
3.291 (0.4); 2.683 (0.4); 2.679 (0.6); 2.674 (0.4); 2.549 (45.2); 2.532 (1.8); 2.519 (36.8);
2.514 (74.7); 2.510 (98.4); 2.505 (70.9); 2.501 (34.6); 2.341 (0.5); 2.336 (0.6); 2.332 (0.5);
1.417 (16.0); 1.401 (15.9); 1.278 (2.0); 1.262 (2.2); 1.242 (1.4); 0.860 (0.4)

Compound No. 1-198:

1H-NMR (400.0 MHz, DMSO): δ = 8.805 (4.3); 8.792 (5.9); 8.770 (3.2); 8.592 (6.1); 8.589 (5.9);
8.421 (6.6); 8.416 (6.0); 7.969 (3.6); 7.950 (4.5); 7.805 (3.6); 7.793 (3.6); 7.786 (3.0); 7.774 (2.8);
4.541 (1.9); 4.530 (3.1); 4.517 (3.3); 4.506 (3.0); 4.453 (0.9); 4.436 (1.8); 4.419 (2.0); 4.407 (1.6);

TABLE 2-continued 4.400 (1.6); 4.390 (5.1); 4.373 (1.8); 4.366 (3.5); 4.348 (1.9); 3.405 (0.5); 3.352 (368.4); 2.683 (0.4); 2.679 (0.5); 2.674 (0.4); 2.549 (30.3); 2.514 (66.3); 2.510 (82.9); 2.505 (59.5); 2.341 (0.4); 2.336 (0.5); 2.332 (0.4); 1.269 (16.0); 1.253 (15.8)
Compound No. 1-199:

1H-NMR (400.0 MHz, DMSO): δ = 8.773 (1.0); 8.763 (1.0); 8.577 (1.5); 8.575 (1.5); 8.533 (1.7); 8.417 (1.6); 8.412 (1.5); 7.905 (0.9); 7.887 (1.1); 7.773 (0.9); 7.762 (0.9); 7.754 (0.7); 7.742 (0.7); 4.622 (5.2); 3.345 (93.4); 2.543 (10.8); 2.508 (19.0); 2.504 (24.0); 2.499 (17.7); 1.457 (16.0)
Compound No. 1-200:

1H-NMR (400.0 MHz, DMSO): δ = 8.882 (1.4); 8.868 (2.7); 8.854 (1.4); 8.785 (3.6); 8.775 (3.3); 8.773 (3.3); 8.575 (4.0); 8.572 (5.0); 8.569 (5.0); 8.567 (4.1); 8.380 (5.6); 8.375 (5.3); 7.930 (2.8); 7.928 (2.9); 7.911 (3.6); 7.909 (3.6); 7.777 (3.2); 7.765 (3.2); 7.757 (2.6); 7.745 (2.5); 5.499 (1.2); 5.487 (1.5); 5.482 (2.1); 5.471 (2.0); 5.466 (1.5); 5.455 (1.2); 3.697 (1.0); 3.685 (1.3); 3.682 (1.3); 3.671 (1.1); 3.662 (1.6); 3.650 (1.9); 3.647 (1.9); 3.636 (1.4); 3.545 (1.5); 3.529 (2.2); 3.513 (1.8); 3.494 (1.5); 3.479 (1.0); 3.405 (0.4); 3.346 (331.6); 3.302 (0.5); 2.673 (0.4); 2.543 (38.4); 2.526 (1.2); 2.513 (26.8); 2.509 (54.2); 2.504 (71.0); 2.499 (50.8); 2.495 (24.1); 2.335 (0.3); 2.331 (0.4); 2.326 (0.3); 1.384 (16.0); 1.368 (15.8); 1.264 (0.7); 1.248 (0.7); 1.235 (0.4)
Compound No. 1-201:

1H-NMR (400.0 MHz, DMSO): δ = 8.581 (5.6); 8.578 (5.6); 8.524 (2.8); 8.506 (2.8); 8.406 (6.3); 8.401 (5.9); 7.648 (3.5); 7.645 (4.1); 7.637 (1.2); 7.626 (5.8); 7.444 (1.6); 7.441 (1.6); 7.424 (4.4); 7.407 (4.0); 7.404 (3.8); 7.369 (1.8); 7.364 (4.7); 7.357 (5.4); 7.352 (6.2); 7.347 (5.1); 7.338 (3.6); 7.333 (3.4); 7.330 (2.5); 7.325 (1.3); 5.325 (0.3); 4.531 (1.4); 4.521 (3.1); 4.508 (3.3); 4.497 (2.1); 4.485 (0.5); 4.443 (0.8); 4.426 (1.6); 4.408 (1.9); 4.392 (4.4); 4.369 (3.8); 4.352 (1.7); 3.343 (544.6); 2.676 (0.6); 2.672 (0.8); 2.668 (0.6); 2.542 (6.7); 2.507 (97.0); 2.503 (125.3); 2.499 (90.2); 2.334 (0.6); 2.330 (0.8); 2.325 (0.6); 2.009 (0.6); 1.990 (0.6); 1.974 (0.3); 1.261 (15.2); 1.245 (16.0); 0.870 (0.3); 0.854 (0.8); 0.837 (0.3); 0.000 (0.4)
Compound No. 1-202:

1H-NMR (400.0 MHz, DMSO): δ = 8.649 (1.4); 8.635 (2.8); 8.621 (1.4); 8.578 (1.0); 8.562 (4.9); 8.559 (5.0); 8.526 (0.4); 8.507 (0.4); 8.406 (0.9); 8.401 (0.9); 8.371 (5.6); 8.366 (5.4); 7.649 (0.5); 7.646 (0.7); 7.628 (4.8); 7.610 (4.4); 7.608 (4.6); 7.422 (1.8); 7.419 (1.6); 7.403 (4.3); 7.400 (4.2); 7.385 (3.5); 7.382 (3.3); 7.369 (0.4); 7.365 (0.8); 7.356 (3.0); 7.351 (3.9); 7.337 (3.3); 7.332 (4.3); 7.318 (1.6); 7.313 (1.9); 7.308 (4.8); 7.304 (3.9); 7.290 (3.3); 7.285 (2.8); 5.531 (1.3); 5.514 (2.2); 5.503 (2.1); 5.499 (1.7); 5.487 (1.2); 4.521 (0.4); 4.509 (0.5); 4.393 (0.6); 4.370 (0.5); 3.645 (0.9); 3.632 (1.3); 3.618 (1.1); 3.610 (1.8); 3.596 (2.3); 3.584 (1.5); 3.529 (1.6); 3.514 (2.6); 3.498 (2.0); 3.479 (1.6); 3.464 (1.0); 3.398 (0.5); 3.379 (0.8); 3.345 (337.4); 2.677 (0.3); 2.673 (0.5); 2.668 (0.4); 2.543 (31.5); 2.526 (1.3); 2.512 (28.4); 2.508 (56.9); 2.504 (74.8); 2.499 (54.4); 2.331 (0.5); 1.398 (16.0); 1.382 (15.8); 1.262 (2.2); 1.246 (2.3); 1.236 (0.7); 0.000 (0.3)
Compound No. 1-203:

1H-NMR (400.0 MHz, DMSO): δ = 8.585 (5.7); 8.583 (5.6); 8.536 (2.9); 8.517 (2.8); 8.412 (6.1); 8.407 (5.8); 7.496 (3.1); 7.477 (7.1); 7.458 (2.2); 7.448 (3.6); 7.447 (3.5); 7.436 (3.8); 7.428 (2.5); 7.416 (2.5); 7.408 (1.0); 7.389 (12.5); 7.379 (8.5); 4.546 (1.8); 4.535 (3.0); 4.522 (3.2); 4.510 (2.9); 4.459 (0.9); 4.441 (1.7); 4.424 (1.9); 4.411 (1.5); 4.405 (1.4); 4.395 (4.9); 4.377 (1.7); 4.370 (3.6); 4.352 (1.9); 3.446 (0.4); 3.354 (733.6); 2.683 (0.7); 2.679 (0.9); 2.674 (0.7); 2.549 (10.5); 2.514 (108.5); 2.510 (140.4); 2.505 (101.7); 2.341 (0.7); 2.337 (0.9); 2.332 (0.6); 1.263 (16.0); 1.247 (16.0)
Compound No. 1-204:

1H-NMR (400.0 MHz, DMSO): δ = 8.921 (1.3); 8.907 (2.6); 8.893 (1.3); 8.829 (0.4); 8.810 (0.4); 8.571 (0.9); 8.569 (0.9); 8.549 (4.9); 8.546 (4.8); 8.402 (0.9); 8.397 (0.9); 8.370 (5.5); 8.365 (5.1); 7.527 (0.8); 7.520 (0.4); 7.510 (1.7); 7.506 (1.6); 7.498 (0.8); 7.493 (1.4); 7.489 (3.2); 7.472 (1.7); 7.468 (1.9); 7.451 (0.8); 7.166 (1.5); 7.154 (5.5); 7.145 (1.8); 7.135 (7.5); 7.114 (4.5); 7.106 (0.8); 5.499 (1.3); 5.488 (1.6); 5.483 (2.2); 5.472 (2.1); 5.468 (1.6); 5.456 (1.2); 4.502 (0.4); 4.489 (0.4); 4.478 (0.5); 4.384 (0.7); 4.360 (0.5); 3.663 (0.8); 3.650 (1.2); 3.637 (1.0); 3.628 (1.8); 3.615 (2.5); 3.602 (1.6); 3.577 (1.7); 3.562 (2.9); 3.546 (2.0); 3.527 (1.4); 3.511 (0.8); 3.403 (0.3); 3.347 (326.8); 3.313 (0.7); 2.673 (0.4); 2.543 (35.5); 2.526 (1.1); 2.513 (25.5); 2.508 (50.5); 2.504 (65.2); 2.500 (46.3); 2.495 (21.9); 2.331 (0.4); 1.373 (16.0); 1.357 (15.8); 1.257 (2.7); 1.241 (3.1); 0.000 (0.8)
Compound No. 1-205:

1H-NMR (400.0 MHz, DMSO): δ = 8.574 (1.4); 8.571 (1.4); 8.462 (1.6); 8.441 (1.2); 8.436 (1.2); 8.429 (1.2); 8.424 (1.2); 8.411 (1.5); 8.406 (1.4); 7.796 (1.1); 7.791 (1.1); 7.777 (1.2); 7.772 (1.2); 7.477 (1.2); 7.465 (1.2); 7.458 (1.1); 7.446 (1.0); 4.646 (5.1); 3.344 (120.2); 2.543 (11.1); 2.512 (11.4); 2.508 (21.7); 2.503 (27.7); 2.499 (19.9); 2.495 (9.5); 1.466 (16.0); 1.235 (0.5); 0.000 (0.5)
Compound No. 1-206:

1H-NMR (400.0 MHz, DMSO): δ = 8.820 (1.4); 8.806 (2.7); 8.792 (1.4); 8.581 (0.6); 8.578 (0.6); 8.576 (0.6); 8.566 (4.2); 8.563 (5.0); 8.561 (4.9); 8.471 (0.5); 8.466 (0.6); 8.458 (4.4); 8.454 (4.6); 8.446 (4.4); 8.442 (4.2); 8.410 (0.6); 8.404 (0.5); 8.377 (5.6); 8.371 (5.2); 7.851 (0.4); 7.846 (0.4); 7.832 (0.5); 7.828 (0.4); 7.820 (4.0); 7.815 (4.0); 7.801 (4.6); 7.796 (4.3); 7.506 (0.5); 7.493 (0.5); 7.487 (4.8); 7.475 (4.7); 7.468 (4.1); 7.456 (3.9); 5.528 (1.2); 5.516 (1.5); 5.511 (2.1); 5.500 (2.0); 5.495 (1.6); 5.484 (1.3); 4.389 (0.4); 3.683 (0.9); 3.671 (1.3); 3.668 (1.3); 3.657 (1.1); 3.648 (1.7); 3.636 (2.0); 3.634 (2.1); 3.622 (1.5); 3.548 (1.6); 3.533 (2.4); 3.516 (2.0); 3.497 (1.5); 3.482 (1.0); 3.428 (0.4); 3.396 (0.6); 3.347 (399.8); 3.229 (0.4); 2.677 (0.4); 2.673 (0.5); 2.668 (0.4); 2.543 (38.1); 2.526 (1.3); 2.513 (32.9); 2.508 (64.6); 2.504 (83.0); 2.499 (59.5); 2.495 (28.4);

TABLE 2-continued 2.335 (0.4); 2.331 (0.5); 2.326 (0.4); 1.396 (16.0); 1.381 (15.8); 1.271 (1.4); 1.255 (1.4); 1.235 (0.5);
0.000 (1.3)
Compound No. 1-207:

1H-NMR (400.0 MHz, DMSO): δ = 8.722 (3.2); 8.705 (3.1); 8.572 (7.1); 8.570 (6.9); 8.541 (6.0);
8.538 (5.9); 8.530 (6.3); 8.526 (5.8); 8.396 (7.5); 8.391 (7.1); 8.026 (5.7); 8.023 (5.3); 8.006 (6.3);
8.003 (5.6); 7.548 (5.9); 7.537 (5.7); 7.528 (5.4); 7.516 (5.3); 4.529 (0.5); 4.508 (3.3); 4.496 (3.5);
4.475 (5.0); 4.465 (3.6); 4.457 (3.3); 4.450 (6.5); 4.434 (4.1); 4.424 (2.0); 4.409 (0.6); 3.352 (404.1);
3.289 (0.3); 2.678 (0.4); 2.674 (0.5); 2.669 (0.4); 2.544 (33.5); 2.527 (1.4); 2.509 (64.5);
2.505 (83.3); 2.500 (59.9); 2.336 (0.4); 2.331 (0.5); 2.327 (0.4); 1.280 (16.0); 1.265 (14.8);
1.235 (0.8); 0.000 (1.0)
Compound No. 1-208:

1H-NMR (400.0 MHz, DMSO): δ = 8.566 (1.3); 8.563 (1.3); 8.497 (1.2); 8.494 (1.3); 8.486 (1.3);
8.482 (1.3); 8.433 (1.5); 8.399 (1.5); 8.393 (1.4); 7.987 (1.2); 7.984 (1.2); 7.967 (1.3); 7.964 (1.3);
7.506 (1.3); 7.494 (1.2); 7.485 (1.2); 7.474 (1.2); 4.659 (5.2); 3.352 (83.7); 2.544 (5.7); 2.514 (5.7);
2.509 (11.5); 2.505 (15.1); 2.500 (10.8); 2.496 (5.1); 1.485 (16.0)
Compound No. 1-209:

1H-NMR (400.0 MHz, DMSO): δ = 8.820 (1.3); 8.806 (2.5); 8.791 (1.3); 8.724 (0.3); 8.573 (0.8);
8.570 (0.8); 8.542 (5.4); 8.539 (5.3); 8.530 (1.1); 8.527 (1.0); 8.519 (4.4); 8.515 (4.6); 8.507 (4.6);
8.504 (4.5); 8.397 (0.8); 8.392 (0.8); 8.364 (5.3); 8.358 (5.0); 8.027 (0.7); 8.024 (0.7); 8.012 (4.4);
8.009 (4.6); 8.003 (1.0); 7.991 (4.9); 7.988 (4.6); 7.548 (0.8); 7.534 (4.9); 7.528 (0.9); 7.522 (4.6);
7.514 (4.4); 7.502 (4.3); 5.539 (1.3); 5.523 (2.2); 5.511 (2.0); 5.507 (1.7); 5.495 (1.2); 4.508 (0.3);
4.496 (0.4); 4.475 (0.5); 4.465 (0.3); 4.457 (0.3); 4.450 (0.6); 4.435 (0.4); 3.658 (0.6); 3.645 (0.9);
3.631 (0.8); 3.623 (2.1); 3.610 (2.9); 3.601 (2.5); 3.597 (2.3); 3.586 (3.4); 3.570 (2.1); 3.551 (1.1);
3.535 (0.7); 3.348 (352.4); 3.309 (0.5); 2.674 (0.4); 2.544 (27.8); 2.527 (1.4); 2.513 (25.6);
2.509 (51.2); 2.504 (66.7); 2.500 (47.2); 2.495 (22.2); 2.331 (0.4); 1.385 (16.0); 1.369 (15.8);
1.280 (1.6); 1.265 (1.5); 1.234 (0.4); 0.000 (0.8)
Compound No. 1-210:

1H-NMR (400.0 MHz, DMSO): δ = 9.084 (1.5); 9.070 (3.0); 9.056 (1.5); 8.909 (0.4); 8.891 (0.4);
8.679 (0.6); 8.675 (0.7); 8.663 (4.1); 8.660 (4.0); 8.652 (3.8); 8.648 (3.8); 8.545 (0.7); 8.494 (5.1);
8.492 (5.2); 8.383 (0.8); 8.378 (0.8); 8.353 (6.0); 8.348 (5.6); 8.157 (0.5); 8.153 (0.5); 8.137 (0.6);
8.133 (0.5); 8.085 (3.5); 8.081 (3.6); 8.066 (3.8); 8.062 (3.7); 7.513 (0.6); 7.501 (0.6); 7.493 (0.6);
7.484 (4.0); 7.472 (3.8); 7.464 (3.8); 7.453 (3.6); 5.569 (1.2); 5.558 (1.4); 5.552 (2.0); 5.542 (1.9);
5.536 (1.5); 5.525 (1.2); 4.594 (0.4); 4.579 (0.4); 4.568 (0.4); 4.408 (0.5); 4.383 (0.4); 3.681 (0.9);
3.668 (1.3); 3.656 (1.1); 3.646 (1.8); 3.633 (2.3); 3.621 (1.5); 3.571 (1.6); 3.555 (2.3); 3.538 (2.3);
3.519 (1.4); 3.503 (1.0); 3.415 (0.6); 3.347 (1079.8); 3.283 (0.8); 3.275 (0.6); 3.263 (0.5);
3.254 (0.4); 3.240 (0.3); 2.713 (0.4); 2.677 (0.9); 2.673 (1.2); 2.668 (0.9); 2.543 (81.4); 2.525 (3.3);
2.508 (151.9); 2.504 (198.3); 2.499 (144.5); 2.369 (0.4); 2.335 (1.0); 2.330 (1.3); 2.326 (1.0);
1.387 (16.0); 1.371 (15.9); 1.290 (2.1); 1.274 (2.0); 1.259 (0.4); 1.235 (1.3); 0.000 (0.5)
Compound No. 1-211:

1H-NMR (400.0 MHz, DMSO): δ = 8.579 (6.8); 8.577 (6.8); 8.481 (3.3); 8.463 (3.2); 8.404 (7.9);
8.399 (7.4); 7.874 (5.9); 7.872 (6.1); 7.854 (6.3); 7.852 (6.3); 7.452 (2.6); 7.449 (2.7); 7.433 (6.1);
7.431 (6.1); 7.414 (3.8); 7.412 (3.8); 7.291 (5.5); 7.287 (6.1); 7.272 (4.6); 7.268 (4.6); 7.179 (3.2);
7.174 (3.2); 7.159 (5.1); 7.155 (4.8); 7.140 (2.7); 7.136 (2.5); 4.535 (0.7); 4.522 (0.9); 4.513 (4.2);
4.501 (4.7); 4.491 (1.3); 4.479 (1.5); 4.430 (1.0); 4.413 (2.1); 4.393 (6.0); 4.376 (5.8); 4.359 (1.8);
3.417 (0.3); 3.331 (964.4); 3.293 (0.7); 3.283 (0.4); 2.995 (1.1); 2.675 (1.7); 2.671 (2.3); 2.667 (1.7);
2.541 (68.8); 2.524 (6.2); 2.511 (138.8); 2.506 (282.7); 2.502 (373.8); 2.497 (269.1); 2.493 (129.8);
2.367 (0.4); 2.338 (0.9); 2.333 (1.7); 2.329 (2.4); 2.324 (1.7); 1.298 (0.4); 1.271 (16.0); 1.255 (15.9);
1.235 (2.2); 0.000 (9.3); −0.009 (0.3)
Compound No. 1-212:

1H-NMR (400.0 MHz, DMSO): δ = 8.567 (1.4); 8.565 (1.4); 8.399 (1.6); 8.394 (1.5); 8.243 (1.7);
7.846 (1.2); 7.844 (1.3); 7.827 (1.3); 7.825 (1.3); 7.427 (0.6); 7.424 (0.6); 7.408 (1.3); 7.406 (1.3);
7.390 (0.8); 7.387 (0.8); 7.254 (1.2); 7.250 (1.3); 7.235 (1.0); 7.231 (1.0); 7.153 (0.7); 7.149 (0.7);
7.134 (1.1); 7.130 (1.0); 7.115 (0.6); 7.111 (0.6); 4.646 (5.2); 3.337 (21.6); 2.543 (5.1); 2.513 (3.3);
2.508 (6.7); 2.504 (8.8); 2.499 (6.4); 2.495 (3.1); 1.474 (16.0)

BIOLOGICAL EXAMPLES

Example 1

*Cooperia curticei* Test (COOPCU)

Solvent: dimethyl sulphoxide

To produce a suitable preparation of active compound, 10 mg of active compound are mixed with 0.5 ml of dimethyl sulphoxide, and the concentrate is diluted with Ringer solution to the desired concentration.

Vessels containing the active compound preparation of the desired concentration are populated with about 40 nematode larvae (*Cooperia curticei*).

After 5 days, the kill in % is determined. 100% means that all of the larvae have been killed; 0% means that none of the larvae have been killed.

In this test, for example, the following compounds of the Preparation Examples show an effect of 90% at an application rate of 100 ppm: 1-36.

In this test, for example, the following compounds of the Preparation Examples show an effect of 80% at an application rate of 100 ppm: 1-35, 1-45.

In this test, for example, the following compounds of the Preparation Examples show an effect of 100% at an application rate of 20 ppm: 1-1, 1-4, 1-28, 1-168, 1-170, 1-173.

In this test, for example, the following compounds of the Preparation Examples show an effect of 90% at an application rate of 20 ppm: 1-25, 1-27, 1-82, 1-164, 1-176, 1-178.

In this test, for example, the following compounds of the Preparation Examples show an effect of 80% at an application rate of 20 ppm: 1-26, 1-29, 1-48, 1-63, 1-78, 1-155, 1-169.

*Haemonchus contortus* Test (HAEMCO)

Solvent: dimethyl sulphoxide

To produce a suitable preparation of active compound, 10 mg of active compound are mixed with 0.5 ml of dimethyl sulphoxide, and the concentrate is diluted with Ringer solution to the desired concentration.

Vessels containing the active compound preparation of the desired concentration are populated with about 40 larvae of the red stomach worm (*Haemonchus contortus*).

After 5 days, the kill in % is determined. 100% means that all of the larvae have been killed; 0% means that none of the larvae have been killed.

In this test, for example, the following compounds of the Preparation Examples show an effect of 100% at an application rate of 20 ppm: 1-1, 1-2, 1-16, 1-18, 1-20, 1-22, 1-25, 1-26, 1-27, 1-28, 1-44, 1-46, 1-53, 1-155, 1-170, 1-173.

In this test, for example, the following compounds of the Preparation Examples show an effect of 90% at an application rate of 20 ppm: 1-4, 1-19, 1-34, 1-43, 1-45, 1-52, 1-63, 1-82, 1-164, 1-196, 1-168, 1-176.

In this test, for example, the following compounds of the Preparation Examples show an effect of 80% at an application rate of 20 ppm: 1-15, 1-23, 1-29, 1-33, 1-35, 1-36, 1-42, 1-57, 1-78, 1-167, 1-169, 1-195.

*Meloidogyne incognita* Test (MELGIN)

Solvent: 125.0 parts by weight of acetone

To prepare a suitable active compound preparation, 1 part by weight of active compound is mixed with the stated amount of solvent and the concentrate is diluted with water to the desired concentration.

Vessels are filled with sand, active compound solution, an egg/larvae suspension of the root-knot nematode (*Meloidogyne incognita*) and lettuce seeds. The lettuce seeds germinate and the plants develop. On the roots, galls are formed.

After 14 days, the nematicidal effect in % is determined by the formation of galls. 100% means that no galls have been found; 0% means that the number of galls on the treated plants corresponds to the untreated control.

In this test, for example, the following compounds of the Preparation Examples show, at an application rate of 20 ppm, an effect of 100%: 1-164, 1-170.

In this test, for example, the following compounds of the Preparation Examples show, at an application rate of 20 ppm, an effect of 90%: 1-49, 1-63, 1-133, 1-134, 1-141, 1-177, 1-189.

In this test, for example, the following compounds of the Preparation Examples show, at an application rate of 20 ppm, an effect of 80%: 1-18.

Example 2

*Haemonchus contortus* Test (HAEMCO)

Solvent: dimethyl sulphoxide

To produce a suitable preparation of active compound, 10 mg of active compound are mixed with 0.5 ml of dimethyl sulphoxide, and the concentrate is diluted with Ringer solution to the desired concentration.

Vessels containing the active compound preparation of the desired concentration are populated with about 40 larvae of the red stomach worm (*Haemonchus contortus*).

After 5 days, the kill in % is determined. 100% means that all of the larvae have been killed; 0% means that none of the larvae have been killed.

In this test, for example, the following compounds of the Preparation Examples show superior efficacy to the prior art: see table

*Cooperia curticei* Test (COOPCU)

Solvent: dimethyl sulphoxide

To produce a suitable preparation of active compound, 10 mg of active compound are mixed with 0.5 ml of dimethyl sulphoxide, and the concentrate is diluted with Ringer solution to the desired concentration.

Vessels containing the active compound preparation of the desired concentration are populated with about 40 nematode larvae (*Cooperia curticei*).

After 5 days, the kill in % is determined. 100% means that all of the larvae have been killed; 0% means that none of the larvae have been killed.

In this test, for example, the following compounds of the Preparation Examples show superior efficacy to the prior art: see table

TABLE 3

| Substance | Structure | Animal species | Concentration | % Activity | dat |
|---|---|---|---|---|---|
| 1.239 known from WO2009/012998 | 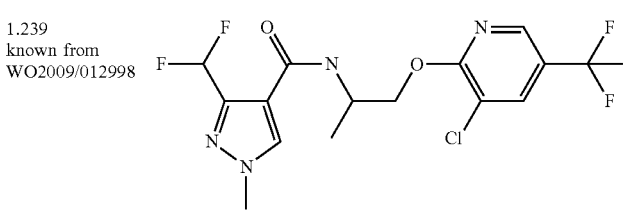 | HAEMCO COOPCU | 20 ppm 20 ppm | 0 0 | 5 dat 5 dat |

TABLE 3-continued

| Substance | Structure | Animal species | Concentration | % Activity | dat |
|---|---|---|---|---|---|
| 4-2 known from WO2012/118139 | 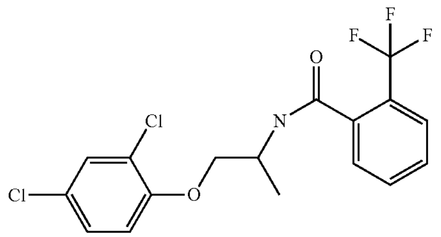 [SMILES: CC(COc1ccc(Cl)cc1Cl)NC(=O)c1ccccc1C(F)(F)F] | COOPCU | 20 ppm | 0 | 5 dat |
| 1-4 from Table 1 | 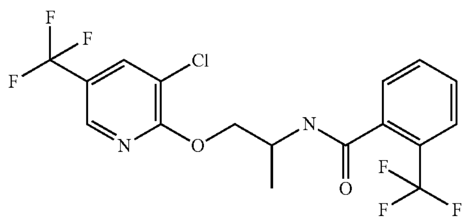 [SMILES: CC(COc1ncc(C(F)(F)F)cc1Cl)NC(=O)c1ccccc1C(F)(F)F] | HAEMCO COOPCU | 20 ppm 20 ppm | 90 100 | 5 dat 5 dat |

The invention claimed is:

1. A method for controlling endoparasites selected from the group consisting of helminths, nematodes, Pentastoma, and Acanthocephala in animals or humans comprising administering prophylactically and/or therapeutically to the animal or human a compound to thereby control said endoparasite, wherein the compound is a compound of formula (I)

(I)

where
Q represents the structural elements below, where n for each Q is in each case as defined below:

Q¹ : (M³)ₙ—thiophene—# with M⁴, n = 1-2

Q² : (M³)ₙ—thiophene—M⁴ with #, n = 1-2

Q³ : (M³)ₙ—furan—# with M⁴, n = 1-2

Q⁴ : (M³)ₙ—furan—M⁴ with #, n = 1-2

Q⁵ : isothiazole with M³, M⁴, #

Q⁶ : isoxazole with M³, M⁴, #

Q⁷ : isothiazole with M³, #, M⁴

-continued

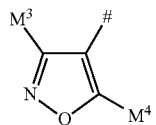

n = 1-3

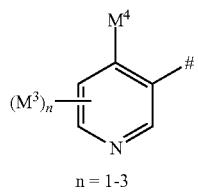

n = 1-3

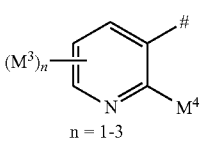

n = 1-3

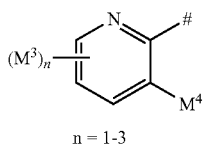

n = 1-2

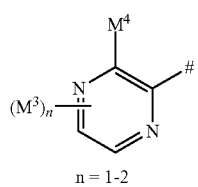

n = 1-2

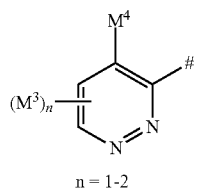

n = 1-2

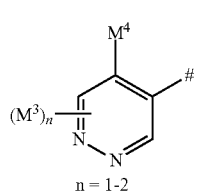

n = 1-2

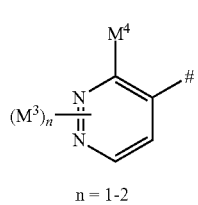

n = 1-2

Q⁸

Q¹⁰

Q¹¹

Q¹²

Q¹³

Q¹⁴

Q¹⁵

Q¹⁶

-continued

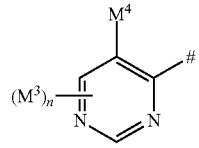

n = 1-2

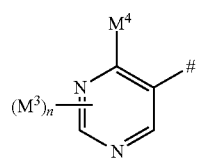

n = 1-2

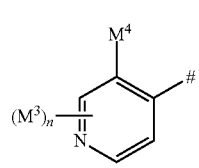

n = 1-3

Q¹⁷

Q¹⁸

Q¹⁹

Y represents hydrogen or represents optionally mono- or poly-$M^2$-substituted $(C_1-C_{10})$-alkyl, $(C_2-C_{10})$-alkenyl, $(C_2-C_{10})$-alkynyl, $(C_1-C_{10})$-haloalkyl, $(C_2-C_{10})$-haloalkenyl, $(C_2-C_{10})$-haloalkynyl, $(C_1-C_{10})$-alkoxy, $(C_2-C_{10})$-alkenyloxy, $(C_3-C_{10})$-alkynyloxy, $(C_3-C_{14})$-cycloalkyl-$(C_1-C_{10})$-alkyl or represents an optionally mono- or poly-$M^2$-substituted 3- to 14-membered cyclic group;

W represents oxygen or sulphur;

$L^2$ represents —C($R^{21}$, $R^{22}$)—;

$L^3$ represents —C($R^{31}$, $R^{32}$)—;

$M^1$, $M^2$ and $M^3$ each independently of one another represent hydrogen, halogen, cyano, nitro, OH, $(C_1-C_{10})$-alkyl, $(C_1-C_{10})$-haloalkoxy, $(C_1-C_{10})$-alkoxy, $(C_1-C_{10})$-haloalkoxy, $(C_1-C_{10})$-alkylthio, $(C_1-C_{10})$haloalkylthio, $(C_1-C_{10})$-alkylsulphonyl, $(C_1-C_{10})$-haloalkylsulphonyl, $(C_1-C_{10})$-alkylsulphanyl, $(C_1-C_{10})$-haloalkylsulphanyl or (3- to 14-membered cyclic group)-O—;

$M^4$ represents hydrogen, halogen, cyano, nitro, OH, $(C_1-C_{10})$-alkyl, $(C_1-C_{10})$-haloalkyl, $(C_1-C_{10})$-alkoxy, $(C_1-C_{10})$-haloalkoxy, $(C_1-C_{10})$-alkylthio, $(C_1-C_{10})$-haloalkylthio, $(C_1-C_{10})$-alkylsulphonyl, $(C_1-C_{10})$-haloalkylsulphonyl, $(C_1-C_{10})$-alkylsulphanyl, $(C_1-C_{10})$-haloalkylsulphanyl or (3- to 14-membered cyclic group)-O—;

k represents 1, 2 or 3;

$R^{21}$, $R^{22}$ each independently of one another represent hydrogen, halogen or optionally mono- or poly-$M^2$-substituted $(C_1-C_{10})$-alkyl, $(C_2-C_{10})$-alkenyl, $(C_2-C_{10})$-alkynyl, $(C_1-C_{10})$-haloalkyl, $(C_2-C_{10})$-haloalkenyl, $(C_2-C_{10})$-haloalkynyl, $(C_1-C_{10})$-alkoxy, $(C_1-C_{10})$-haloalkoxy, $(C_2-C_{10})$-alkenyloxy, $(C_3-C_{10})$-alkynyloxy, $(C_3-C_{14})$-cycloalkyl-$(C_1-C_{10})$-alkyl or represent an optionally mono- or poly-$M^2$-substituted 3- to 14-membered cyclic group; or $R^{21}$, $R^{22}$ together represent an optionally mono- or poly-$M^2$-substituted spiro-attached 3- to 14-membered carbo- or 3- to 10-membered heterocyclic group;

$R^{31}$, $R^{32}$ each independently of one another represent hydrogen, halogen or optionally mono- or poly-$M^2$- substituted (C₁-C₁₀)-alkyl, (C₂-C₁₀)-alkenyl, (C₂-C₁₀)-alkynyl, (C₁-C₁₀)-haloalkyl, (C₂-C₁₀)-haloalkenyl, (C₂-C₁₀)-haloalkynyl, (C₃-C₁₄)-cycloalkyl-(C₁-C₁₀)-alkyl or represent an optionally mono- or poly-M²-substituted 3- to 14-membered cyclic group;

R³¹, R³² together represent an optionally mono- or poly-M⁵-substituted spiro-attached 3- to 14-membered carbo- or 3- to 10-membered heterocyclic group;

M⁵ in each case independently of the others represents halogen, formyl, cyano, nitro, (C₁-C₁₀)-alkyl, (C₁-C₁₀)-haloalkyl, (C₂-C₁₀)-alkenyl, (C₂-C₁₀)-haloalkenyl, (C₂-C₁₀)-alkynyl, (C₂-C₁₀)-haloalkynyl, (C₁-C₁₀)-alkoxy, (C₁-C₁₀)-haloalkoxy, (C₂-C₁₀)-alkenyloxy, (C₂-C₁₀)-haloalkenyloxy, (C₃-C₁₀)-alkynyloxy, (C₃-C₁₀)-haloalkynyloxy, (C₁-C₁₀)-alkylthio, (C₁-C₁₀)-haloalkylthio, (C₂-C₁₀)-alkenylthio, (C₂-C₁₀)-haloalkenylthio, (C₃-C₁₀)-alkynylthio, (C₃-C₁₀)-haloalkynylthio, (C₁-C₁₀)-alkylsulphonyl, (C₁-C₁₀)-haloalkylsulphonyl, (C₂-C₁₀)-alkenylsulphonyl, (C₂-C₁₀)-haloalkenylsulphonyl, (C₃-C₁₀)-alkynylsulphonyl, (C₃-C₁₀)-haloalkynylsulphonyl, (C₁-C₁₀)-alkylsulphanyl, (C₁-C₁₀)-haloalkylsulphanyl, (C₂-C₁₀)-alkenylsulphanyl, (C₂-C₁₀)-haloalkenylsulphanyl, (C₃-C₁₀)-alkynylsulphanyl, (C₃-C₁₀)-haloalkynylsulphanyl, (C₁-C₁₀)-alkylcarbonyl, (C₁-C₁₀)-haloalkylcarbonyl, (C₂-C₁₀)-alkenylcarbonyl, (C₂-C₁₀)-haloalkenylcarbonyl, (C₂-C₁₀)-alkynylcarbonyl, (C₂-C₁₀)-haloalkynylcarbonyl, (C₁-C₁₀)-alkoxycarbonyl, (C₁-C₁₀)-haloalkoxycarbonyl, (C₂-C₁₀)-alkenyloxycarbonyl, (C₂-C₁₀)-haloalkenyloxycarbonyl, (C₃-C₁₀)-alkynyloxycarbonyl, (C₃-C₁₀)-haloalkynyloxycarbonyl, (C₁-C₁₀)-alkylcarbonyloxy, (C₁-C₁₀)-haloalkylcarbonyloxy, (C₂-C₁₀)-alkenylcarbonyloxy, (C₂-C₁₀)-haloalkenylcarbonyloxy, (C₂-C₁₀)-alkynylcarbonyloxy, (C₂-C₁₀)-haloalkynylcarbonyloxy, a 3- to 14-membered cyclic group;

and/or a salt, N-oxide and/or tautomeric form of a compound of the formula (I), except for the compounds N-[2-(pyridin-2-yloxy)ethyl]-4-(trifluoromethyl)nicotinamide:

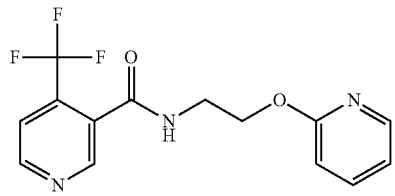 [SMILES: O=C(NCCOc1ccccn1)c1cnccc1C(F)(F)F]

and 4-(trifluoromethyl)-N-(2-{[5-(trifluoromethyl)pyridin-2-yl]oxy}ethyl)nicotinamide:

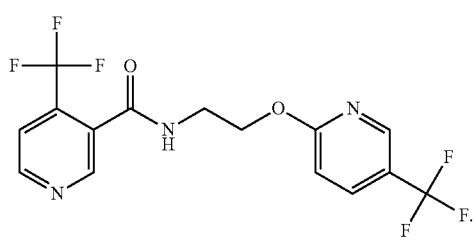 [SMILES: O=C(NCCOc1ccc(C(F)(F)F)cn1)c1cnccc1C(F)(F)F]

2. A method according to claim 1 where

Q represents the structural elements below, where n for each Q is in each case as defined below:

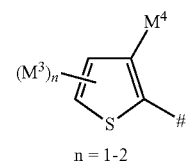

Q¹ n = 1-2

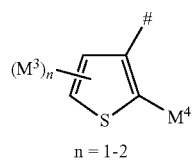

Q² n = 1-2

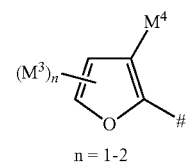

Q³ n = 1-2

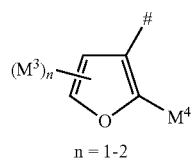

Q⁴ n = 1-2

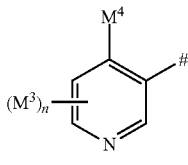

Q¹⁰ n = 1-3

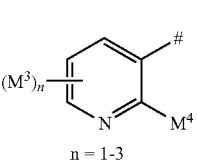

Q¹¹ n = 1-3

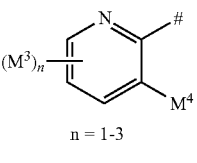

Q¹² n = 1-3

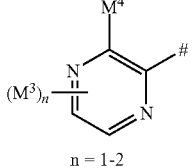

Q¹³ n = 1-2

Y represents hydrogen or represents optionally mono- or poly-M²-substituted (C₁-C₆)-alkyl, (C₂-C₆)-alkenyl, (C₂-C₆)-alkynyl, (C₁-C₆)-haloalkyl, (C₂-C₆)-haloalkenyl, $(C_2-C_6)$-haloalkynyl, $(C_1-C_6)$-alkoxy, $(C_2-C_6)$-alkenyloxy, $(C_3-C_6)$-alkynyloxy, $(C_3-C_{10})$-cycloalkyl-$(C_1-C_6)$-alkyl or represents an optionally mono- or poly-$M^2$-substituted 3- to 10-membered cyclic group;

W represents oxygen, $M^1$, $M^2$ and $M^3$ each independently of one another represent hydrogen, halogen, cyano, nitro, OH, $(C_1-C_6)$-alkyl, $(C_1-C_6)$-haloalkyl, $(C_1-C_6)$-alkoxy, $(C_1-C_6)$-haloalkoxy, $(C_1-C_6)$-alkylthio, $(C_1-C_6)$-haloalkylthio, $(C_1-C_6)$-alkylsulphonyl, $(C_1-C_6)$-haloalkylsulphonyl, $(C_1-C_6)$-alkylsulphanyl, $(C_1-C_6)$-haloalkylsulphanyl, $(C_3-C_{14})$-cycloalkyl-O—, $(C_3-C_{14})$-cycloalkenyl-O—, $(C_6-C_{14})$-aryl-O—, halogenated $(C_3-C_{14})$-cycloalkyl-O—, halogenated $(C_3-C_{14})$-cycloalkenyl-O—, halogenated $(C_6-C_{14})$-aryl-O—, where, if Q corresponds to $Q^{11}$, $M^3$ is not $(C_1-C_4)$-haloalkyl in position 4 at the pyridyl;

$M^4$ represents hydrogen, halogen, cyano, nitro, OH, $(C_1-C_6)$-alkyl, $(C_1-C_6)$-haloalkyl, $(C_1-C_6)$-alkoxy, $(C_1-C_6)$-haloalkoxy, $(C_1-C_6)$-alkylthio, $(C_1-C_6)$-haloalkylthio, $(C_1-C_6)$-alkyl sulphonyl, $(C_1-C_6)$-haloalkylsulphonyl, $(C_1-C_6)$-alkylsulphanyl, $(C_1-C_6)$-haloalkylsulphanyl, $(C_3-C_{14})$-cycloalkyl-O—, $(C_3-C_{14})$-cycloalkenyl-O—, $(C_6-C_{14})$-aryl-O—, halogenated $(C_3-C_{14})$-cycloalkyl-O—, halogenated $(C_3-C_{14})$-cycloalkenyl-O—, halogenated $(C_6-C_{14})$-aryl-O—, where, if Q corresponds to $Q^{10}$, $M^4$ is not $(C_1-C_4)$-haloalkyl;

k represents for 2;

$R^{21}$, $R^{22}$ each independently of one another represent hydrogen, fluorine or optionally mono- or poly-$M^2$-substituted $(C_1-C_6)$-alkyl, $(C_2-C_6)$-alkenyl, $(C_2-C_6)$-alkynyl, $(C_1-C_6)$-haloalkyl, $(C_2-C_6)$-haloalkenyl, $(C_2-C_6)$-haloalkynyl, $(C_1-C_6)$-alkoxy, $(C_1-C_6)$-haloalkoxy, $(C_2-C_6)$-alkenyloxy, $(C_3-C_6)$-alkynyloxy, $(C_3-C_6)$-cycloalkyl-$(C_1-C_6)$-alkyl or represent an optionally mono- or poly-$M^2$-substituted $(C_3-C_{14})$-carbocyclic group; or $R^{21}$, $R^{22}$ represents $C(R^{21}, R^{22})$ as spiro-$C(CH_2—CH_2)$;

$R^{31}$, $R^{32}$ each independently of one another represent hydrogen, fluorine or optionally mono- or poly-$M^2$-substituted $(C_1-C_6)$-alkyl, $(C_2-C_6)$-alkenyl, $(C_2-C_6)$-alkynyl, $(C_1-C_6)$-haloalkyl, $(C_2-C_6)$-haloalkenyl, $(C_2-C_6)$-haloalkynyl, $(C_1-C_6)$-alkoxy, $(C_1-C_6)$-haloalkoxy, $(C_2-C_6)$-alkenyloxy, $(C_3-C_6)$-alkynyloxy, $(C_3-C_6)$-cycloalkyl-$(C_1-C_6)$-alkyl or represent an optionally mono- or poly-$M^2$-substituted $(C_3-C_{14})$-carbocyclic group; or $R^{31}$, $R^{32}$ represents $C(R^{31}, R^{32})$ as spiro-$C(CH_2—CH_2)$.

3. A method according to claim 1 where

Q represents the structural elements below, where n for each Q is in each case as defined below:

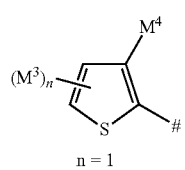

$Q^1$ n = 1

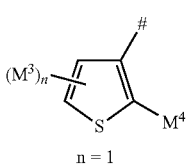

$Q^2$ n = 1

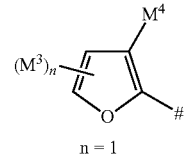

$Q^3$ n = 1

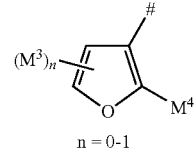

$Q^4$ n = 0-1

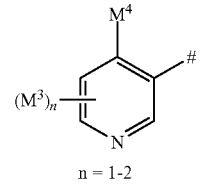

$Q^{10}$ n = 1-2

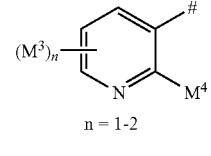

$Q^{11}$ n = 1-2

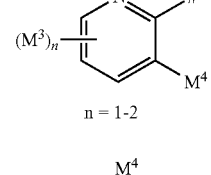

$Q^{12}$ n = 1-2

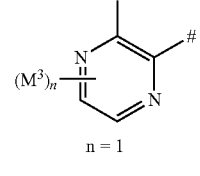

$Q^{13}$ n = 1

Y represents hydrogen or represents optionally mono- or poly-$M^2$-substituted $(C_1-C_4)$-alkyl, $(C_2-C_4)$-alkenyl, $(C_3-C_4)$-alkynyl, $(C_1-C_4)$-haloalkyl, $(C_2-C_4)$-haloalkenyl, $(C_3-C_4)$-haloalkynyl, $(C_1-C_4)$-alkoxy, $(C_2-C_4)$-alkenyloxy, $(C_3-C_4)$-alkynyloxy, $(C_3-C_6)$-cycloalkyl-$(C_1-C_4)$-alkyl or represents an optionally mono- or poly-$M^2$-substituted $C_3$- to $C_6$-membered carbocyclic group;

$M^1$, $M^2$ and $M^3$ represent hydrogen, halogen, cyano, nitro, OH, $(C_1-C_4)$-alkyl, $(C_1-C_4)$-haloalkyl, $(C_1-C_4)$-alkoxy, $(C_1-C_4)$-haloalkoxy, $(C_1-C_4)$-alkylthio, $(C_1-C_4)$-haloalkylthio, $(C_1-C_4)$-alkyl sulphonyl, $(C_1-C_4)$-haloalkylsulphonyl, $(C_1-C_4)$-alkylsulphanyl, $(C_1-C_6)$-haloalkylsulphanyl, $(C_3-C_{14})$-cycloalkyl-O—, $(C_3-C_{14})$-cycloalkenyl-O—, $(C_6-C_{14})$-aryl-O—, halogenated $(C_3-C_{14})$-cycloalkyl-O—, halogenated $(C_3-C_{14})$-cycloalkenyl-O—, halogenated $(C_6-C_{14})$-aryl-O—, where, if Q corresponds to $Q^{11}$, $M^3$ is not $(C_1-C_4)$-haloalkyl in position 4 at the pyridyl;

$M^4$ in each case independently of the others represents hydrogen, halogen, cyano, nitro, OH, $(C_1-C_4)$-alkyl, $(C_1-C_4)$-haloalkyl, $(C_1-C_4)$-alkoxy, $(C_1-C_4)$-haloalkoxy, $(C_1$-$C_4)$-alkylthio, $(C_1$-$C_4)$-haloalkylthio, $(C_1$-$C_4)$-alkylsulphonyl, $(C_1$-$C_4)$-haloalkylsulphonyl, $(C_1$-$C_4)$-alkylsulphanyl, $(C_1$-$C_6)$-haloalkylsulphanyl, $(C_3$-$C_{14})$-cycloalkyl-O—, $(C_3$-$C_{14})$-cycloalkenyl-O—, $(C_6$-$C_{14})$-aryl-O—, halogenated $(C_3$-$C_{14})$-cycloalkyl-O—, halogenated $(C_3$-$C_{14})$-cycloalkenyl-O—, halogenated $(C_6$-$C_{14})$-aryl-O—, where, if Q corresponds to $Q^{10}$, $M^4$ is not $(C_1$-$C_4)$-haloalkyl;

k represents 1;

$R^{21}$, $R^{22}$ each independently of one another represent hydrogen, fluorine or optionally mono- or poly-$M^2$-substituted $(C_1$-$C_4)$-alkyl, $(C_2$-$C_4)$-alkenyl, $(C_2$-$C_4)$-alkynyl, $(C_1$-$C_4)$-haloalkyl, $(C_2$-$C_4)$-haloalkenyl, $(C_2$-$C_4)$-haloalkynyl, $(C_1$-$C_6)$-alkoxy, $(C_1$-$C_4)$-haloalkoxy, $(C_2$-$C_4)$-alkenyloxy, $(C_3$-$C_4)$-alkynyloxy, $(C_3$-$C_4)$-cycloalkyl-$(C_1$-$C_4)$-alkyl, $(C_3$-$C_8)$-cycloalkyl or halogenated $(C_3$-$C_8)$-cycloalkyl;

$R^{31}$, $R^{32}$ each independently of one another represent hydrogen, fluorine or optionally mono- or poly-$M^2$-substituted $(C_1$-$C_4)$-alkyl, $(C_2$-$C_4)$-alkenyl, $(C_2$-$C_4)$-alkynyl, $(C_1$-$C_4)$-haloalkyl, $(C_2$-$C_4)$-haloalkenyl, $(C_2$-$C_4)$-haloalkynyl, $(C_1$-$C_6)$-alkoxy, $(C_1$-$C_4)$-haloalkoxy, $(C_2$-$C_4)$-alkenyloxy, $(C_3$-$C_4)$-alkynyloxy, $(C_3$-$C_4)$-cycloalkyl-$(C_1$-$C_4)$-alkyl or represent an optionally mono- or poly-$M^2$-substituted $(C_3$-$C_8)$-cycloalkyl or halogenated $(C_3$-$C_8)$-cycloalkyl.

4. A method according to claim 1, wherein the compound of formula (I) and/or a salt, N-oxide and/or tautomeric form thereof according to claim 1 and one or more auxiliaries are administered.

5. A method according to claim 1, wherein the endoparasite is Monogena, cestodes, or trematodes.

6. A method according to claim 1, wherein the endoparasite is Platyhelmintha.

7. A method according to claim 1, wherein the endoparasite is a helminth.

8. A method according to claim 3, wherein Q is Q1 or Q2.

9. A method according to claim 3, wherein Q is Q3 or Q4.

10. A method according to claim 3, wherein Q is Q10, Q11, or Q12.

11. A method according to claim 3, wherein Q is Q13.

* * * * *